US010632432B2

(12) United States Patent
Wilson et al.

(10) Patent No.: US 10,632,432 B2
(45) Date of Patent: Apr. 28, 2020

(54) SECURE PORTABLE, ON-DEMAND, MICROFLUIDIC MIXING AND DISPENSING DEVICE

(71) Applicant: ALTOPA, INC., Vashon, WA (US)

(72) Inventors: Matt Wilson, Vashon, WA (US); Jon Whalen, Vashon, WA (US); Todd Wilson, Delray Beach, FL (US); Pete Crawford, Bend, OR (US); Scott Eric Liddle, Raleigh, NC (US); Keith Gausmann, Cary, NC (US); Jaysun Giesler, Cary, NC (US); Nathan Thomas Luck, Apex, NC (US); Nicole Kaylor Wicker, Raleigh, NC (US); Jon Collette, Issaquah, WA (US)

(73) Assignee: Altopa, Inc., Vashon, WA (US)

( * ) Notice: Subject to any disclaimer, the term of this patent is extended or adjusted under 35 U.S.C. 154(b) by 0 days.

(21) Appl. No.: 16/157,504

(22) Filed: Oct. 11, 2018

(65) Prior Publication Data

US 2019/0105619 A1 Apr. 11, 2019

Related U.S. Application Data

(63) Continuation of application No. PCT/US2017/027064, filed on Apr. 11, 2017.

(60) Provisional application No. 62/446,779, filed on Jan. 16, 2017, provisional application No. 62/412,626, filed on Oct. 25, 2016, provisional application No. 62/321,161, filed on Apr. 11, 2016.

(51) Int. Cl.
*B01F 13/00* (2006.01)
*G16H 40/63* (2018.01)
*B01F 13/10* (2006.01)
*A61J 1/20* (2006.01)
*B01F 15/00* (2006.01)
*B01F 15/02* (2006.01)

(52) U.S. Cl.
CPC .............. *B01F 13/0079* (2013.01); *A61J 1/20* (2013.01); *B01F 13/0059* (2013.01); *B01F 13/1063* (2013.01); *B01F 13/1066* (2013.01); *B01F 15/00253* (2013.01); *B01F 15/00305* (2013.01); *B01F 15/00311* (2013.01); *B01F 15/00357* (2013.01); *B01F 15/026* (2013.01); *B01F 15/0246* (2013.01); *G16H 40/63* (2018.01)

(58) Field of Classification Search
CPC .................................................. B01F 13/0067
USPC .................................. 222/132, 145.5, 145.6
See application file for complete search history.

(56) References Cited

U.S. PATENT DOCUMENTS

| D245,060 S | 7/1977 | Hauenstein |
|---|---|---|
| 4,049,161 A | 9/1977 | Kohl |
| 4,511,091 A | 4/1985 | Vasco |
| D284,538 S | 7/1986 | Friz |
| D327,695 S | 7/1992 | Edstrom |
| D327,895 S | 7/1992 | Edstrom |
| D349,506 S | 8/1994 | Caruso et al. |
| D366,808 S | 2/1996 | Newnan |
| D367,797 S | 3/1996 | Hauser, II et al. |
| D373,046 S | 8/1996 | Newnan |
| 5,848,735 A | 12/1998 | Eddy et al. |
| D408,207 S | 4/1999 | Bourke |
| D444,986 S | 7/2001 | Smith et al. |
| D450,731 S | 11/2001 | Papaikonomou et al. |
| D472,253 S | 3/2003 | Reedy et al. |
| D474,111 S | 5/2003 | Lazaris |
| D474,280 S | 5/2003 | Niedbala et al. |
| D479,086 S | 9/2003 | Rivard et al. |
| D485,566 S | 1/2004 | Ledingham et al. |
| D489,215 S | 5/2004 | Honan et al. |
| D499,599 S | 12/2004 | Morrison |
| D544,299 S | 6/2007 | Schaffeld et al. |
| D549,755 S | 8/2007 | Wietgrefe et al. |
| D553,897 S | 10/2007 | De' Longhi |
| D554,930 S | 11/2007 | Lavy |
| D556,226 S | 11/2007 | Jennings et al. |
| D558,504 S | 1/2008 | Ben-Shlomo et al. |
| D564,378 S | 3/2008 | Kaushal et al. |

(Continued)

FOREIGN PATENT DOCUMENTS

| WO | WO-2009032938 A2 | 3/2009 |
|---|---|---|
| WO | WO-2015028815 A1 | 3/2015 |

(Continued)

OTHER PUBLICATIONS

International Search Report and Written Opinion dated Sep. 18, 2017, for International Application No. PCT/US2017/027064, 12 pages.

(Continued)

*Primary Examiner* — David L Sorkin
(74) *Attorney, Agent, or Firm* — Cooley LLP

(57) ABSTRACT

A dispensing device, comprising a plurality of microfluidic pumps, microfluidic valves, and a microfluidic mixer chip, for receiving and mixing microfluidic amounts of a plurality of fluids having differing viscosities, is disclosed. The device includes a plurality of pathways for moving fluids from associated reservoirs to the microfluidic mixer chip. A mix controller controls the microfluidic pumps and valves so that the fluids, having different viscosities, can be accurately mixed at specified microfluidic amounts or volumes according to a specified microfluidic recipe, and the microfluidic mixture dispensed from the device. The device can be in communication with a software application implemented on a mobile compute device, such as a smartphone, and receive instructions for implementing the specified microfluidic recipe from the software application such that the operation of device components is at the direction of the software application executed on the mobile compute device.

14 Claims, 134 Drawing Sheets

(56) References Cited

U.S. PATENT DOCUMENTS

| | | | |
|---|---|---|---|
| D564,924 S | 3/2008 | Kaushal et al. | |
| D569,526 S | 5/2008 | Duffy et al. | |
| D584,097 S | 1/2009 | Lam | |
| D597,605 S | 8/2009 | Davis | |
| D611,289 S | 3/2010 | de Visser | |
| D612,503 S | 3/2010 | Johnston et al. | |
| D629,907 S | 12/2010 | Boessneck et al. | |
| D639,836 S | 6/2011 | Van Cuijk et al. | |
| 8,008,091 B2 | 8/2011 | Higashino et al. | |
| D645,971 S | 9/2011 | Taylor et al. | |
| D647,398 S | 10/2011 | Winkler | |
| D650,090 S | 12/2011 | Odeh | |
| D650,091 S | 12/2011 | Odeh | |
| D650,911 S | 12/2011 | Odeh | |
| 8,162,210 B2 | 4/2012 | McInerney et al. | |
| 8,181,822 B2 * | 5/2012 | Doelman | B67D 1/0082 222/1 |
| 8,206,025 B2 | 6/2012 | Natarajan | |
| 8,240,513 B2 | 8/2012 | Voskuil et al. | |
| 8,256,647 B2 | 9/2012 | Engels et al. | |
| 8,297,482 B2 | 10/2012 | Hill | |
| D670,133 S | 11/2012 | Caswell et al. | |
| D675,335 S | 1/2013 | Feuerabend et al. | |
| 8,353,690 B2 | 1/2013 | Hogan et al. | |
| D681,231 S | 4/2013 | Steinhauer et al. | |
| D681,232 S | 4/2013 | Benarieh et al. | |
| D682,432 S | 5/2013 | Khan et al. | |
| D684,457 S | 6/2013 | Salow et al. | |
| D684,614 S | 6/2013 | Bergamini | |
| D684,615 S | 6/2013 | Bergamini | |
| 8,467,981 B2 | 6/2013 | Mukherjee et al. | |
| 8,496,032 B2 | 7/2013 | Miller et al. | |
| 8,517,596 B2 | 8/2013 | Natarajan | |
| D689,169 S | 9/2013 | Engels | |
| D689,193 S | 9/2013 | Shinohara et al. | |
| D698,038 S | 1/2014 | Davis et al. | |
| 8,672,532 B2 * | 3/2014 | Jovanovich | B01F 11/0045 366/181.5 |
| 8,783,516 B2 | 7/2014 | Baak et al. | |
| D710,642 S | 8/2014 | Broen et al. | |
| D713,666 S | 9/2014 | Van Baelen | |
| D714,847 S | 10/2014 | Broen et al. | |
| D718,462 S | 11/2014 | Cook et al. | |
| D719,404 S | 12/2014 | Manly et al. | |
| D720,180 S | 12/2014 | Manly et al. | |
| D721,247 S | 1/2015 | Manly et al. | |
| D721,248 S | 1/2015 | Manly et al. | |
| D722,463 S | 2/2015 | Manly et al. | |
| D723,317 S | 3/2015 | Manly et al. | |
| 9,022,039 B2 | 5/2015 | Hearn | |
| D731,662 S | 6/2015 | Khan et al. | |
| D736,552 S | 8/2015 | Shen et al. | |
| D737,625 S | 9/2015 | Caswell et al. | |
| D737,702 S | 9/2015 | Selberg et al. | |
| D738,153 S | 9/2015 | Brook | |
| 9,120,067 B2 | 9/2015 | Miyata et al. | |
| 9,140,597 B2 | 9/2015 | Mukherjee et al. | |
| D742,170 S | 11/2015 | Kunz | |
| D742,687 S | 11/2015 | Kunz | |
| D743,727 S | 11/2015 | Cha et al. | |
| D743,728 S | 11/2015 | Tomasson et al. | |
| D743,729 S | 11/2015 | Tomasson et al. | |
| 9,174,179 B2 | 11/2015 | Bertucci et al. | |
| D749,674 S | 2/2016 | Ibbett | |
| D750,412 S | 3/2016 | Gagnon et al. | |
| 9,271,528 B2 | 3/2016 | Liu | |
| D762,750 S | 8/2016 | Jiang et al. | |
| D762,860 S | 8/2016 | He et al. | |
| D763,614 S | 8/2016 | Han et al. | |
| 9,474,725 B1 | 10/2016 | Reillo et al. | |
| D773,684 S | 12/2016 | Ketterer et al. | |
| D775,364 S | 12/2016 | Ray et al. | |
| D781,930 S | 3/2017 | Ward | |
| D783,178 S | 4/2017 | Mead et al. | |
| D784,549 S | 4/2017 | Brooks et al. | |
| D789,198 S | 6/2017 | Ngo et al. | |
| D791,846 S | 7/2017 | Zhang | |
| D792,165 S | 7/2017 | Cauwood et al. | |
| 9,730,911 B2 | 8/2017 | Verzura et al. | |
| 9,745,182 B2 | 8/2017 | Hogan | |
| D802,992 S | 11/2017 | Wilson et al. | |
| D816,771 S | 5/2018 | Kobe | |
| D822,154 S | 7/2018 | Lee | |
| D825,245 S | 8/2018 | McConnell et al. | |
| D829,061 S | 9/2018 | King et al. | |
| D830,430 S | 10/2018 | Sherman et al. | |
| D831,400 S | 10/2018 | Han et al. | |
| D834,870 S | 12/2018 | Steiner | |
| 2006/0280029 A1 | 12/2006 | Garstecki et al. | |
| 2007/0258849 A1 | 11/2007 | Kent | |
| 2008/0264518 A1 | 10/2008 | Collins | |
| 2010/0276452 A1 | 11/2010 | Vesborg et al. | |
| 2011/0264285 A1 | 10/2011 | Mattos, Jr. et al. | |
| 2012/0035761 A1 | 2/2012 | Tilton et al. | |
| 2012/0123588 A1 | 5/2012 | Cloran et al. | |
| 2012/0128549 A1 | 5/2012 | Zhou et al. | |
| 2012/0167906 A1 | 7/2012 | Gysland | |
| 2012/0248137 A1 | 10/2012 | Baak et al. | |
| 2012/0248147 A1 | 10/2012 | Krom et al. | |
| 2012/0250451 A1 | 10/2012 | Post et al. | |
| 2013/0061981 A1 | 3/2013 | Bragg et al. | |
| 2013/0231774 A1 | 9/2013 | Tilton et al. | |
| 2014/0166028 A1 | 6/2014 | Fuisz et al. | |
| 2015/0053719 A1 | 2/2015 | Hogan | |
| 2015/0083146 A1 | 3/2015 | Goldman et al. | |
| 2015/0157053 A1 | 6/2015 | Mayor | |
| 2015/0247786 A1 | 9/2015 | Parker et al. | |
| 2015/0336689 A1 | 11/2015 | Brown et al. | |
| 2016/0038940 A1 | 2/2016 | Babcock | |
| 2016/0073677 A1 | 3/2016 | Kappel et al. | |
| 2016/0153433 A1 | 6/2016 | Hogan | |
| 2016/0200463 A1 | 7/2016 | Hodges et al. | |
| 2016/0250270 A1 | 9/2016 | Wendschuh et al. | |
| 2016/0310443 A1 | 10/2016 | Reillo et al. | |
| 2016/0367479 A1 | 12/2016 | Reillo et al. | |
| 2016/0374515 A1 | 12/2016 | Stuart et al. | |
| 2017/0020945 A1 | 1/2017 | Reillo et al. | |
| 2017/0233114 A1 | 8/2017 | Christensen et al. | |
| 2017/0266153 A1 | 9/2017 | Levy et al. | |
| 2019/0062144 A1 * | 2/2019 | Greenbaum | G07F 17/0092 |

FOREIGN PATENT DOCUMENTS

| | | |
|---|---|---|
| WO | WO-2017100062 A1 | 6/2017 |
| WO | WO-2017100063 A2 | 6/2017 |
| WO | WO-2017100369 A1 | 6/2017 |

OTHER PUBLICATIONS

Office Action dated May 7, 2018, for Canadian Design Application No. 179163, 2 pages.

Office Action dated Aug. 13, 2018, for Israel Design Application No. 61508, 2 pages.

Office Action dated Sep. 19, 2018, for Canadian Design Application No. 175984, 1 page.

Office Action dated Sep. 19, 2018, for Canadian Design Application No. 179163, 1 page.

Oblend Altopa Personalized Tinctures at CES 2018, posted Jan. 10, 2018 [online] 03:49, retrieved Jan. 15, 2019, retrieved from internet, <https://www.youtube.com/watch?v=WdDO-yi6mAO>.

Meet Oblend, the canna-tech that lit it up at CES 2018, posted Jan. 18, 2018 [online], retrieved Jan. 15, 2019, retrieved from internet, <https://dgit.com/oblend-at-home-dispensary-54056/>.

Oblend lets you create blended massage oils, extracts at home, posted Jan. 16, 2018 [online] 01:04, retrieved Jan. 15, 2019, retrieved from internet, <https://www.youtube.com/watch?v=faHlgq4DNbe>.

* cited by examiner

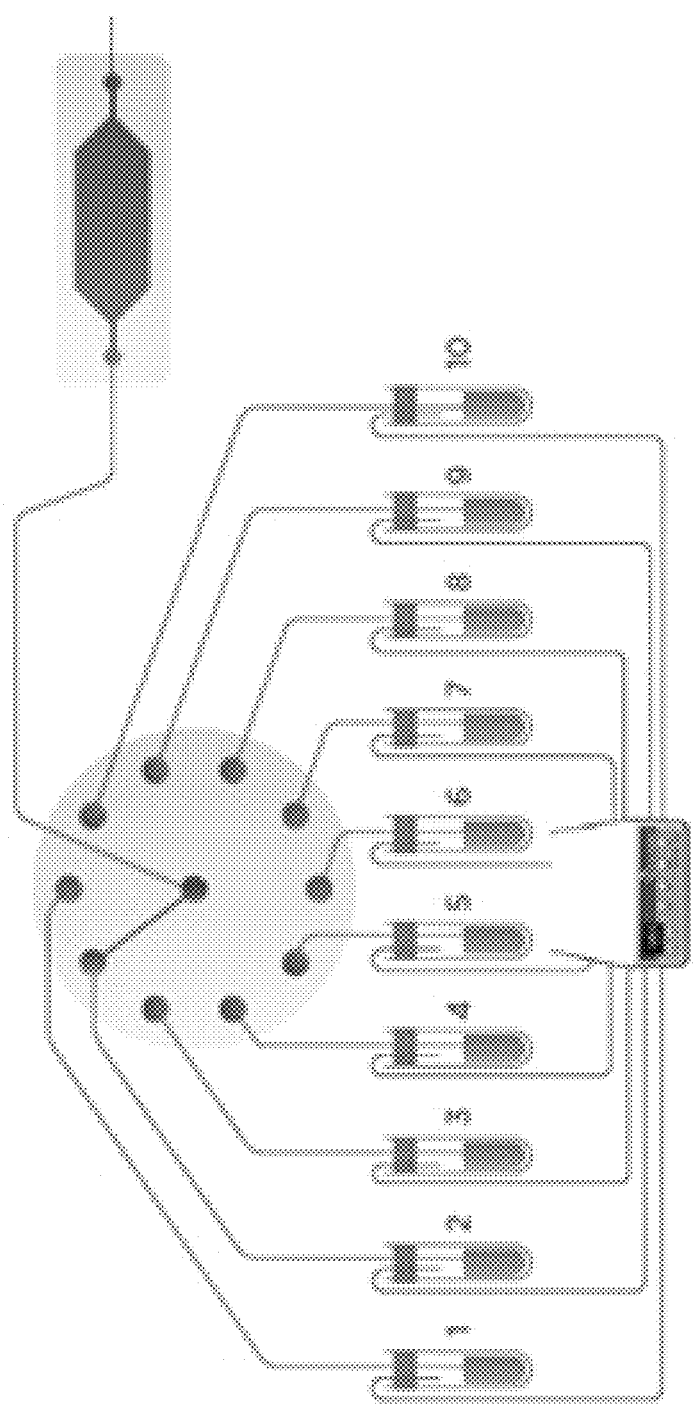

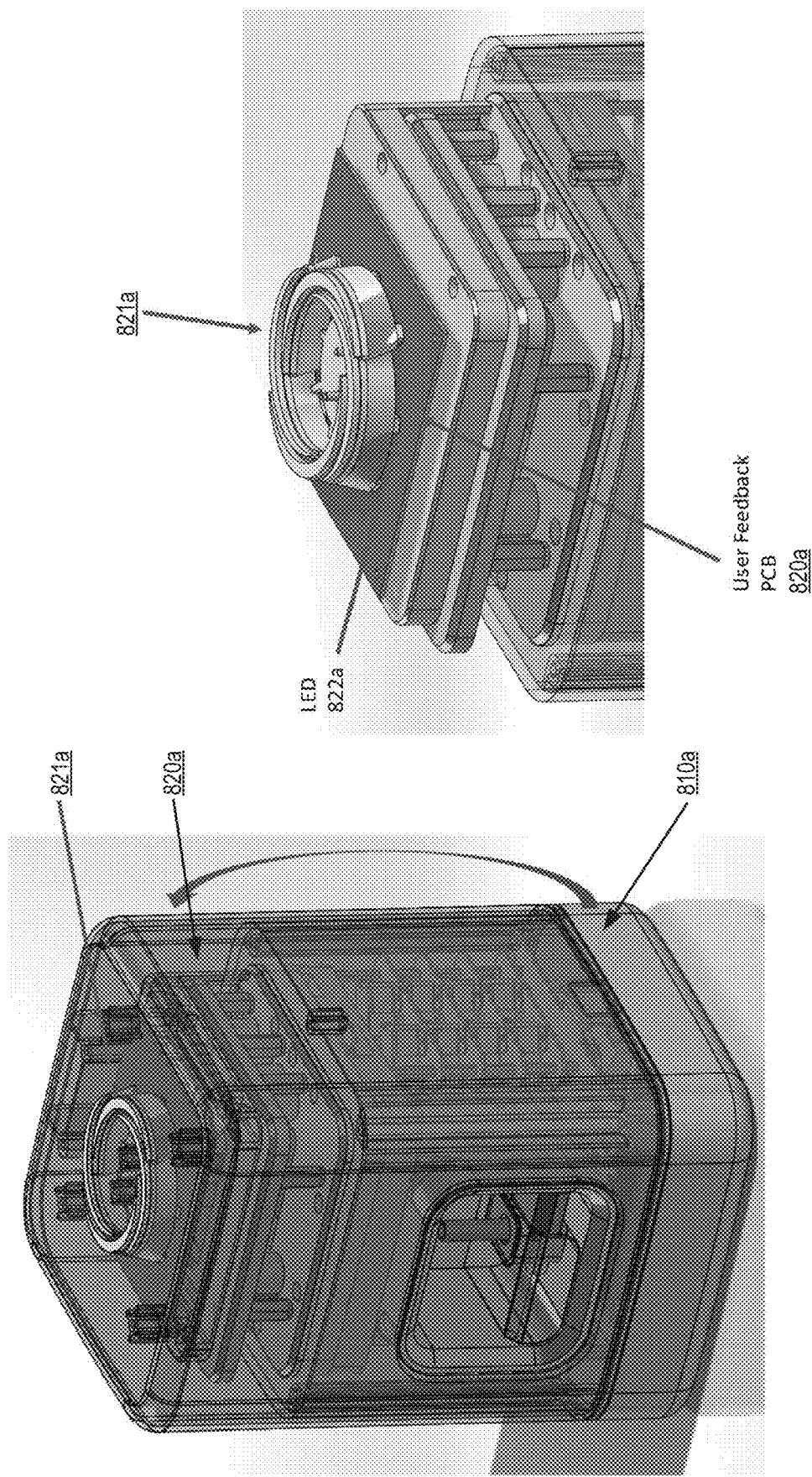

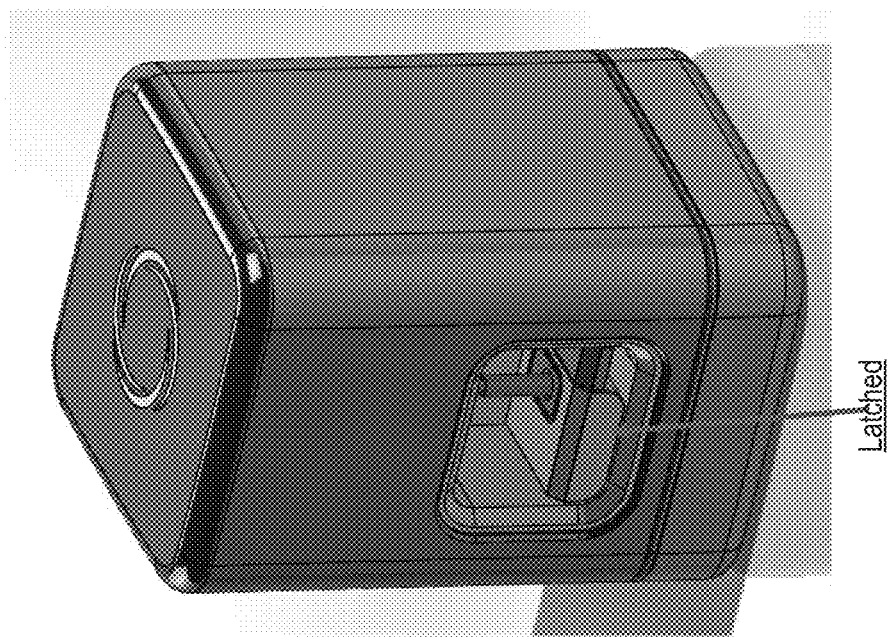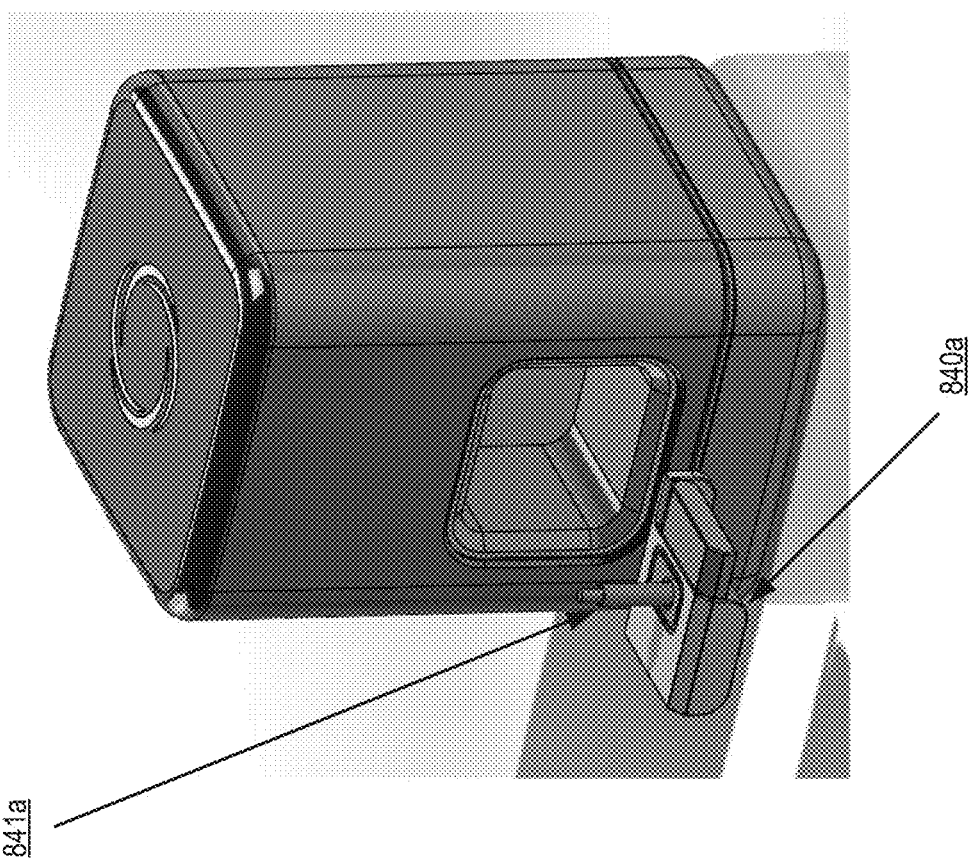
Fig. 8E

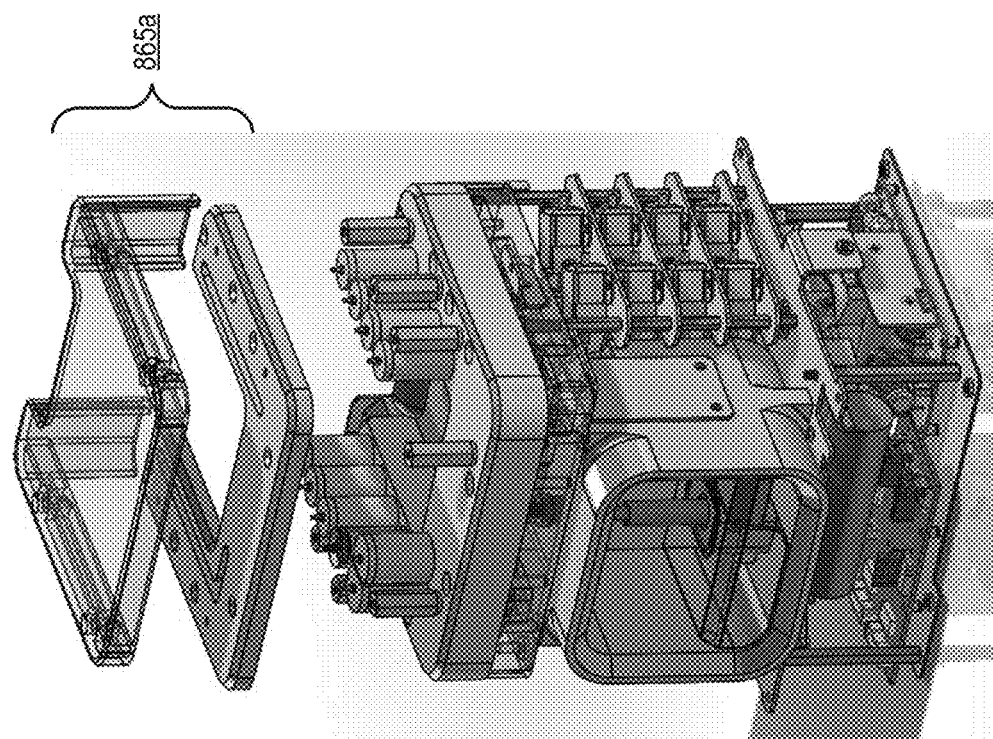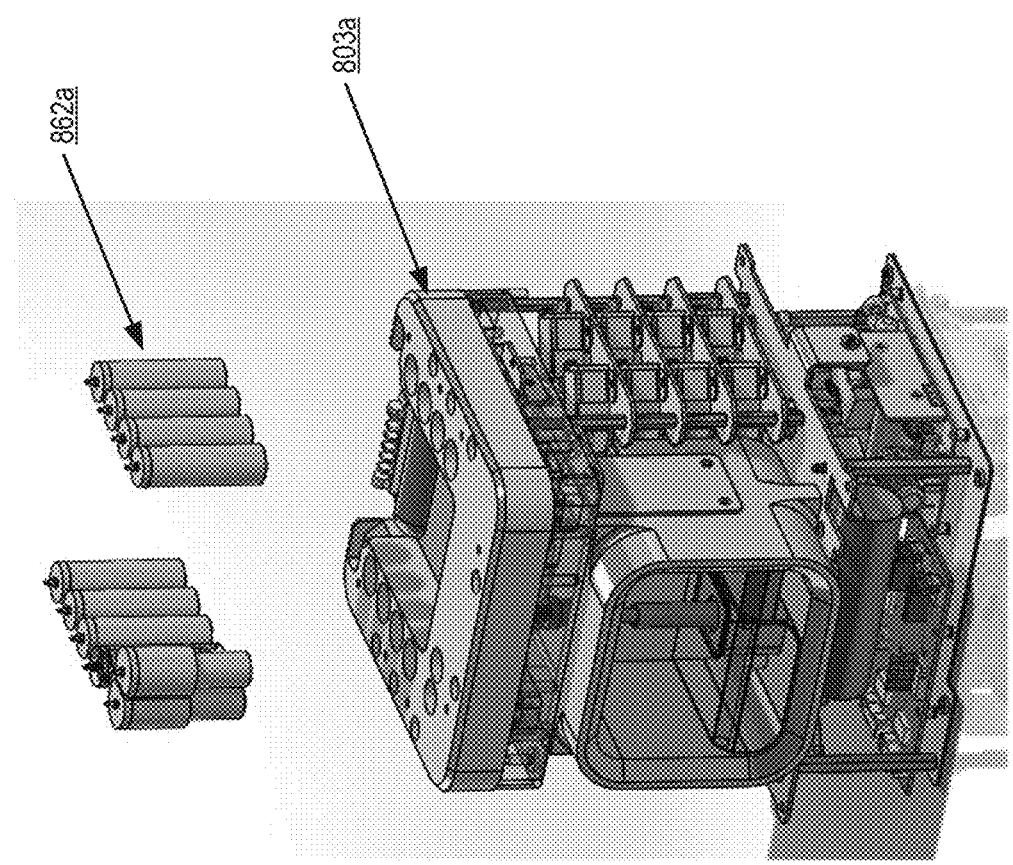
Fig. 8H

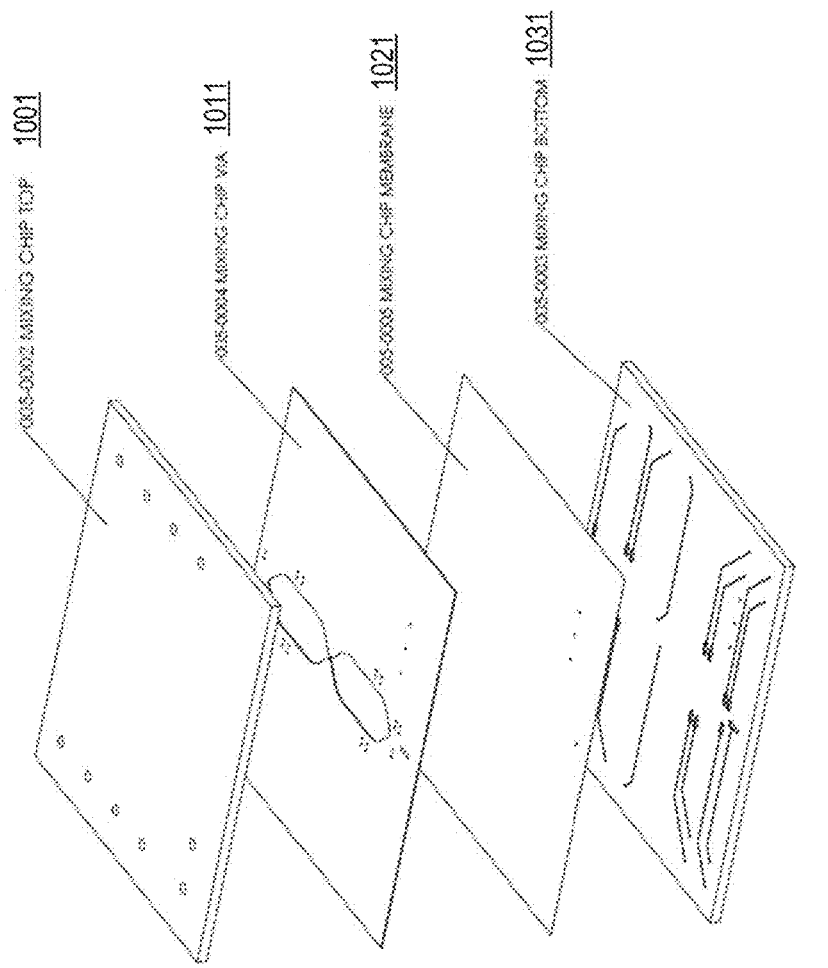
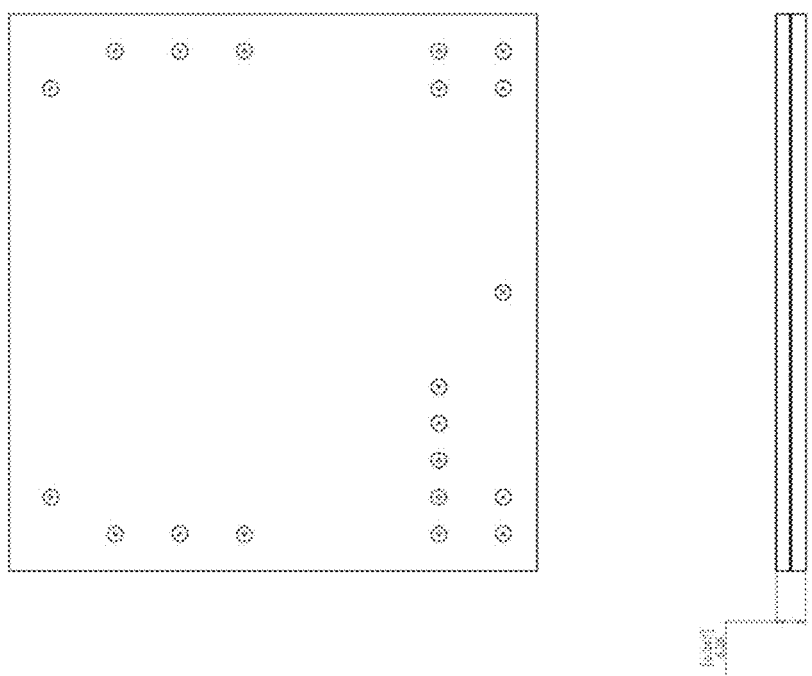
Fig. 10

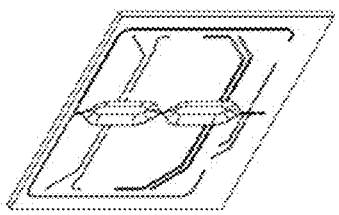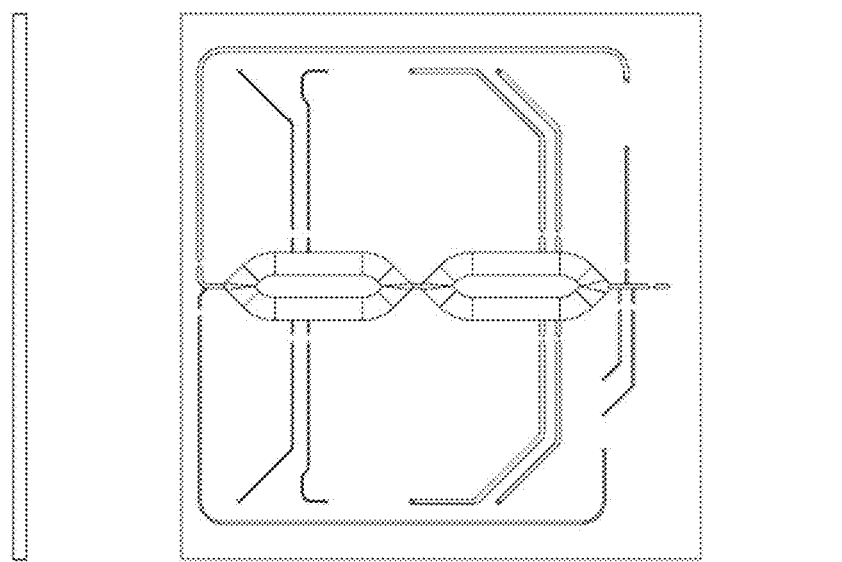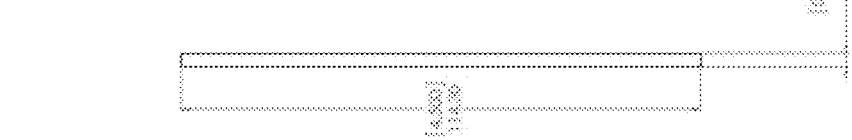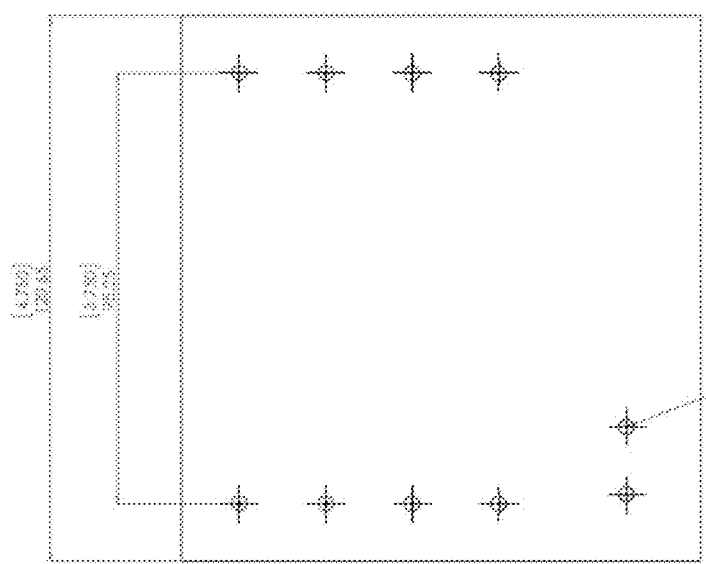
Fig. 10A

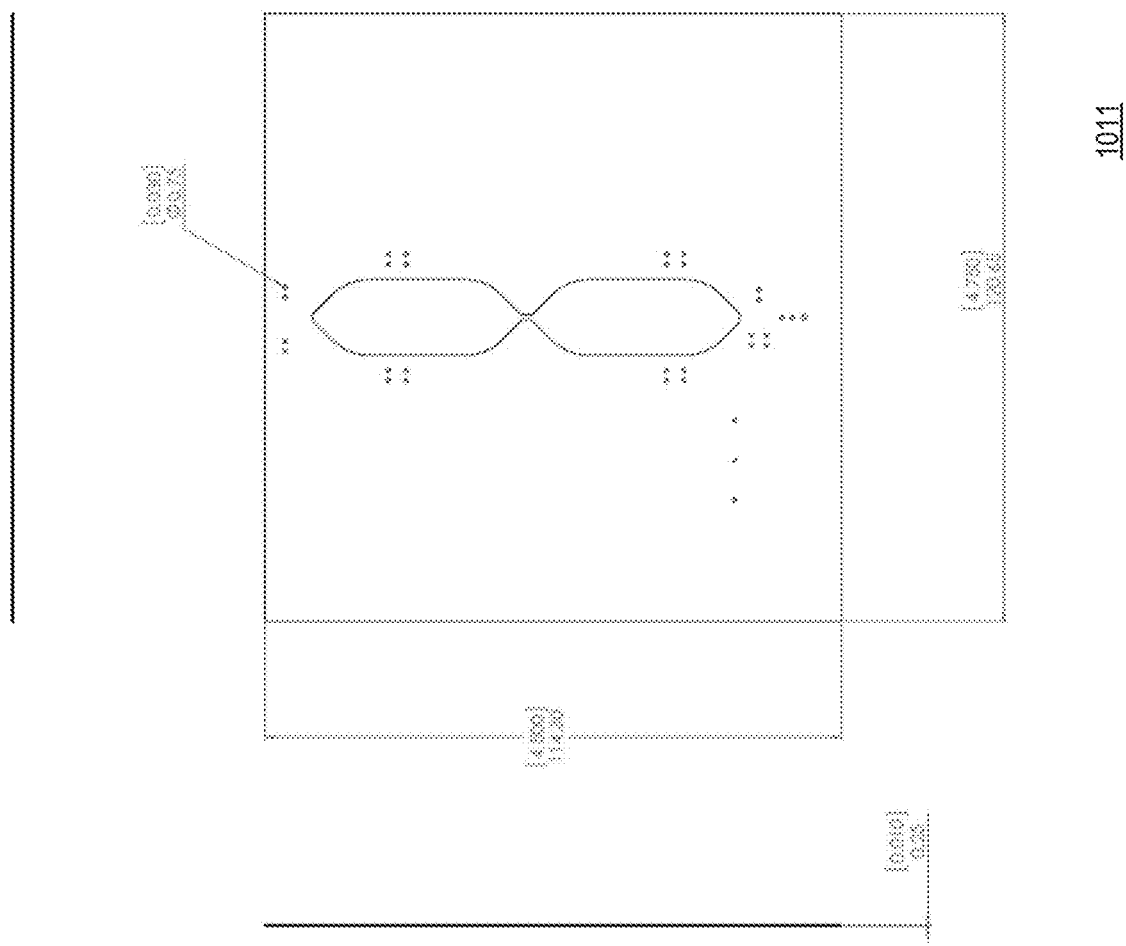
Fig. 10B

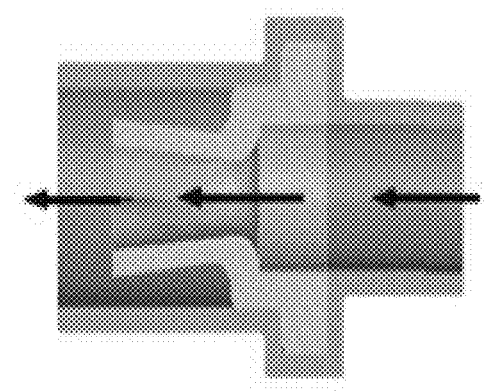
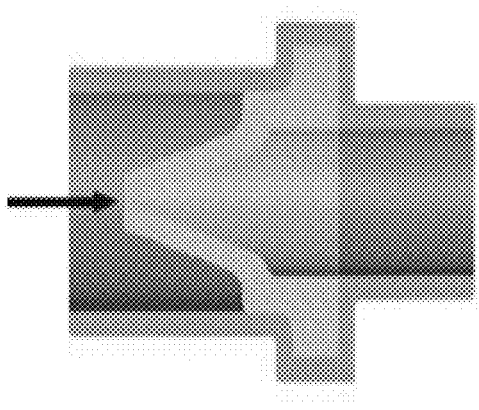
Fig. 12B

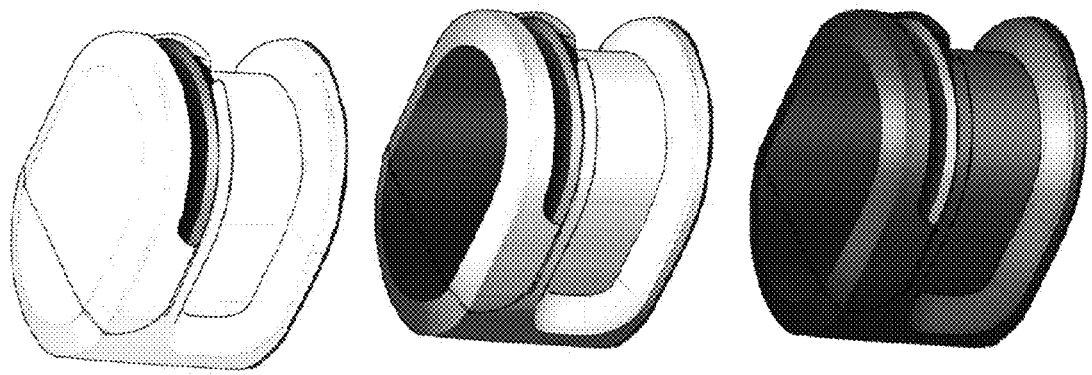
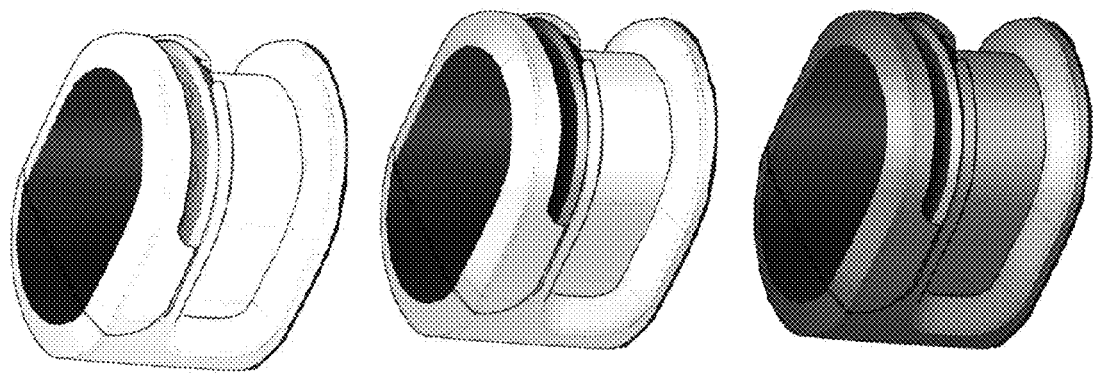
Fig. 18A

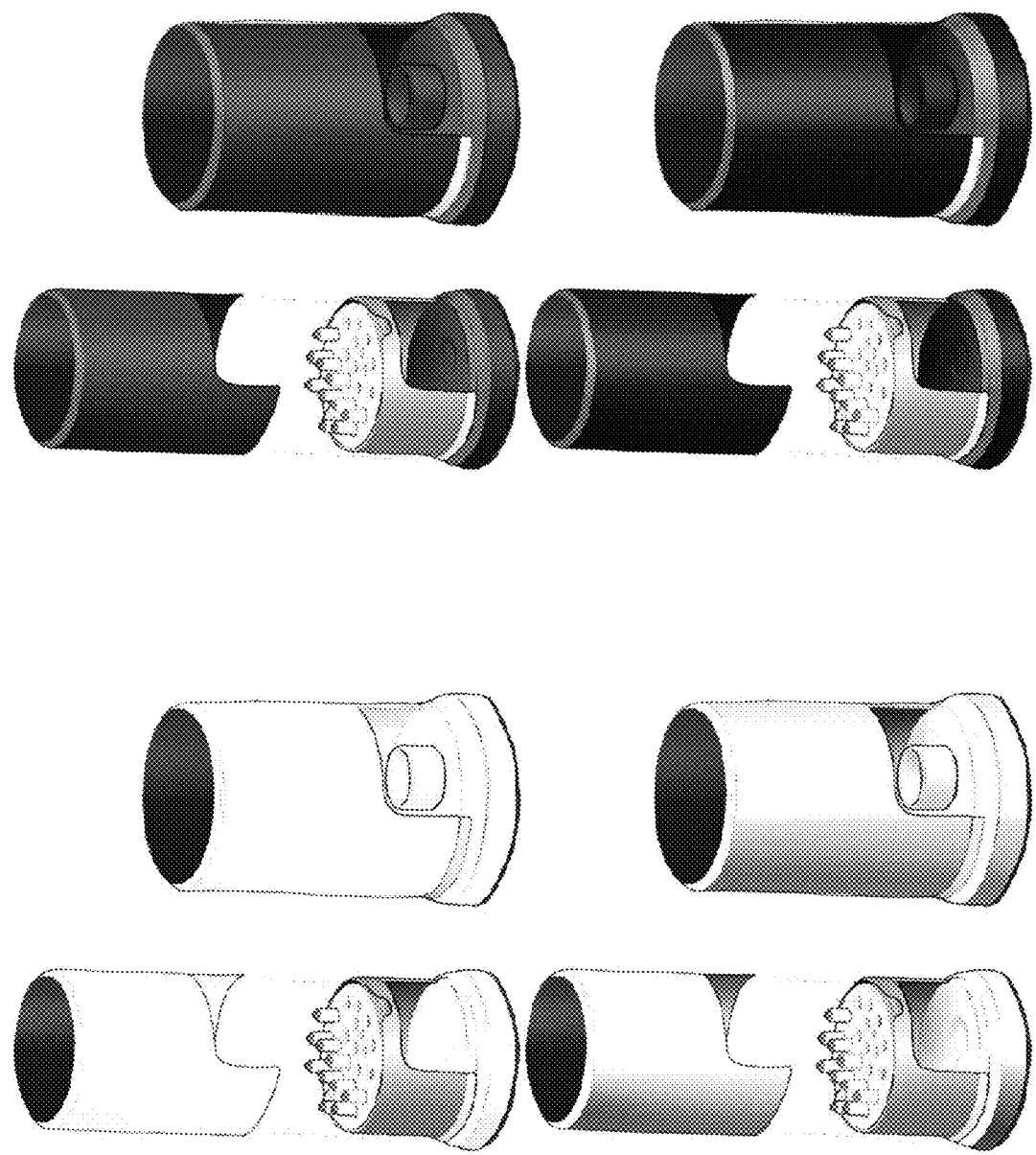

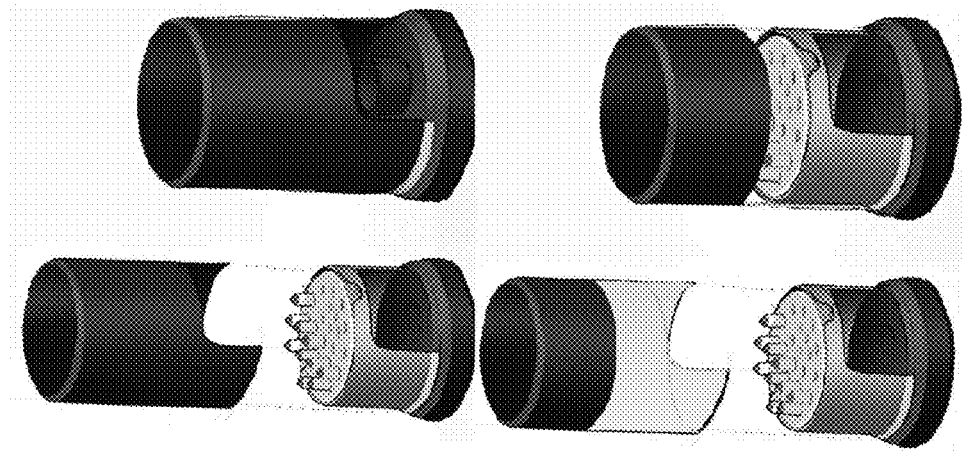
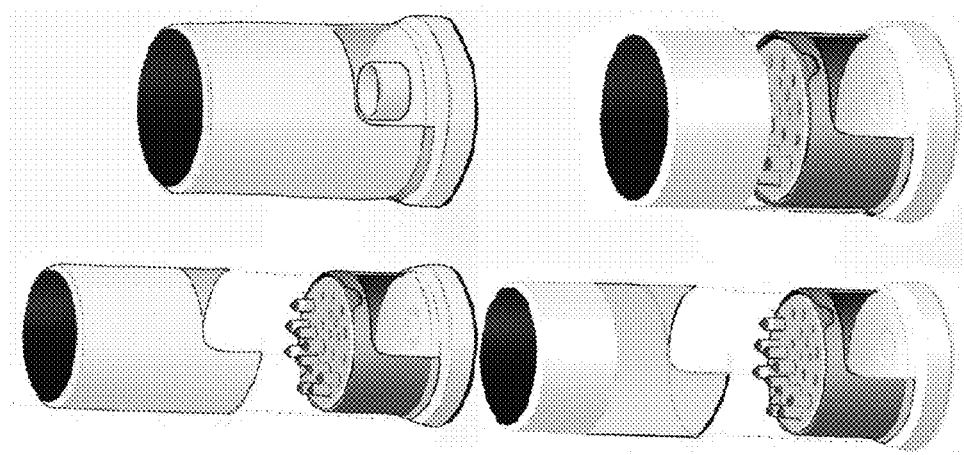
Fig. 18D

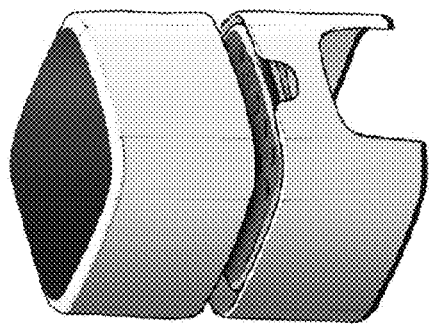
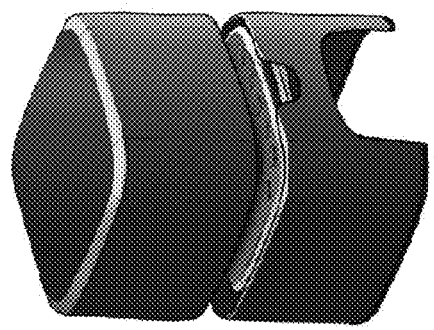
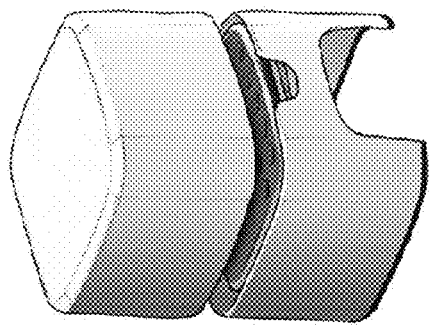
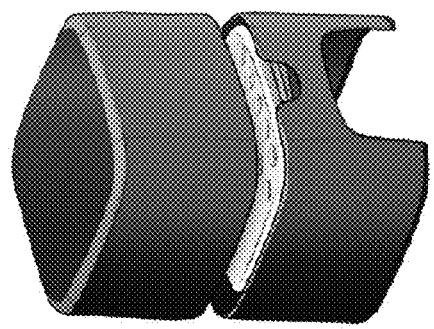
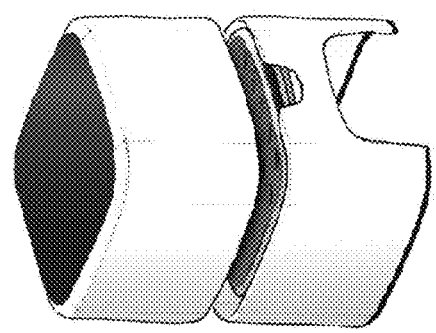
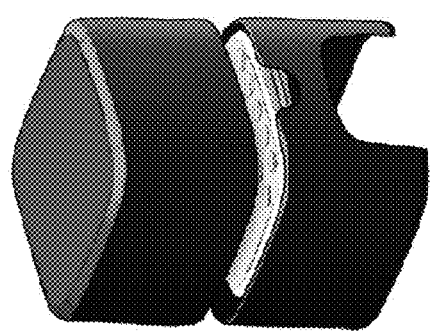
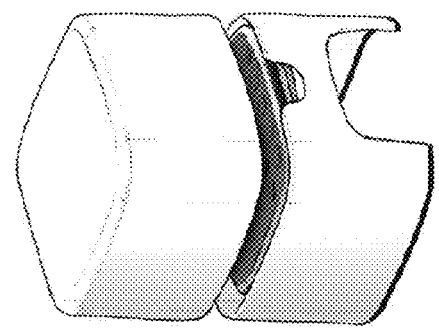
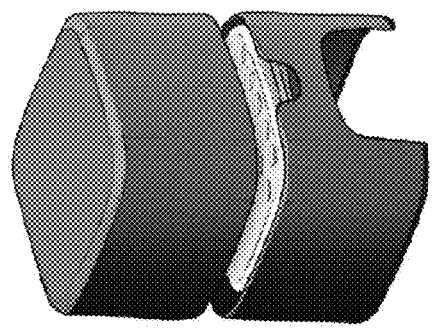
Fig. 19A Fig. 22 Exemplary Clip-in Fluid Cartridge

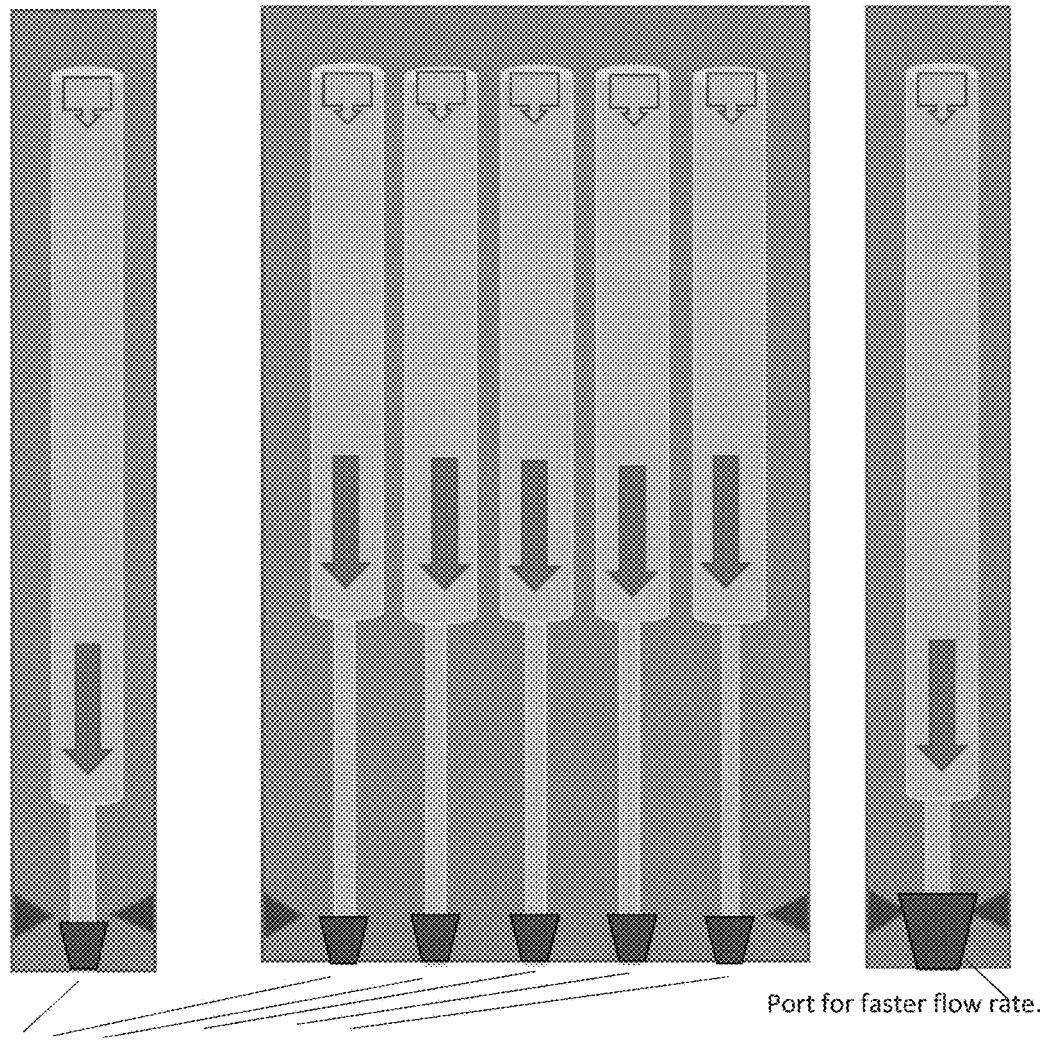

Port for faster flow rate.

Micro-chip embedded in the dispensing end of the cartridge tells the OBD what the contents of the cartridge is and how much is left, expiration date, etc.

Variations on a fluid reservoir cartridge; single or multi-cartridges are filled with terpenes, Cannabinoids, or other fluids and can be plugged into the OBD. Single cartridges can, in some embodiments, use a twist-lock or Luar connection.

Cartridges are configured/designed to handle specific fluid viscosities and flow volumes.

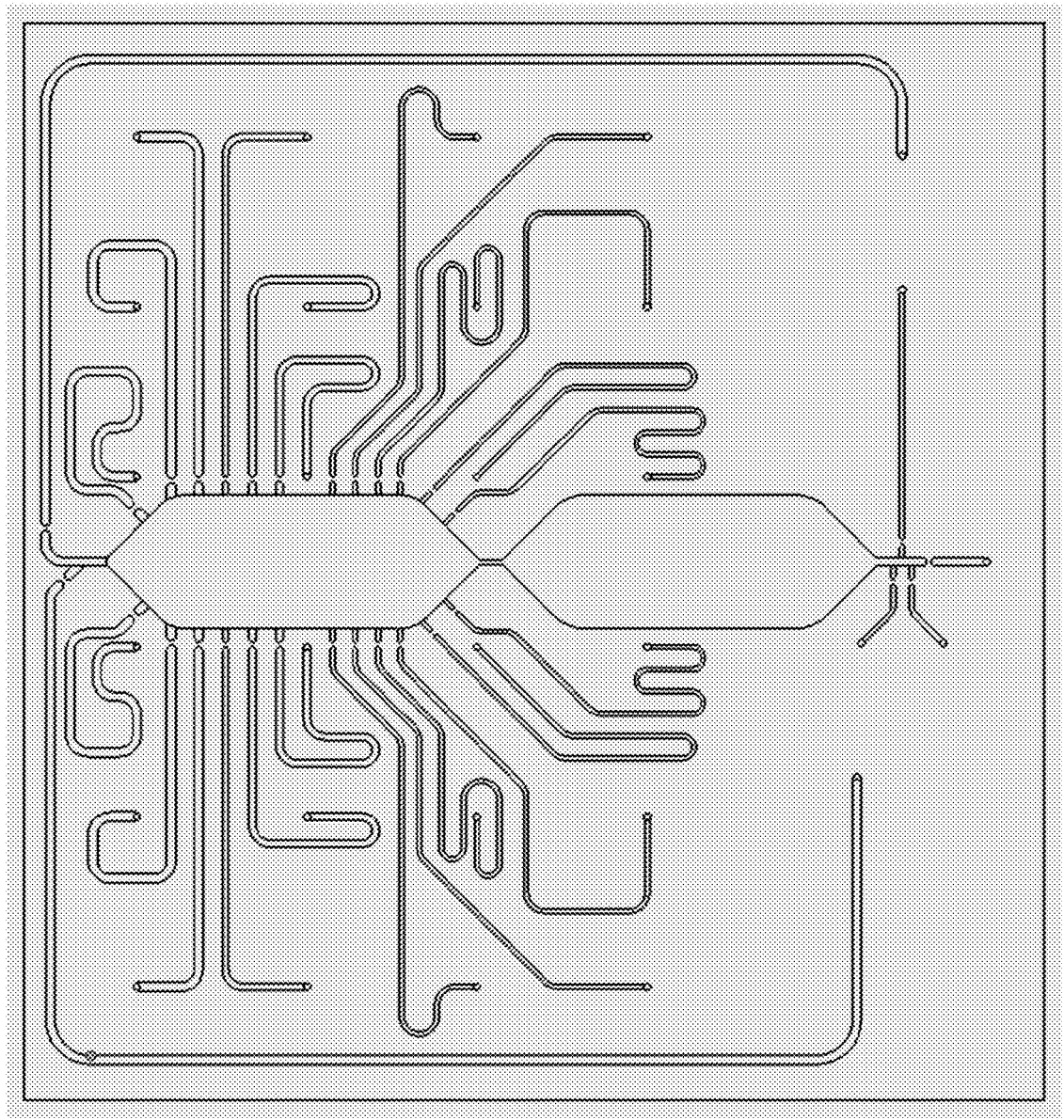
Fig. 23A - Example Valved Chip Fluidic Side

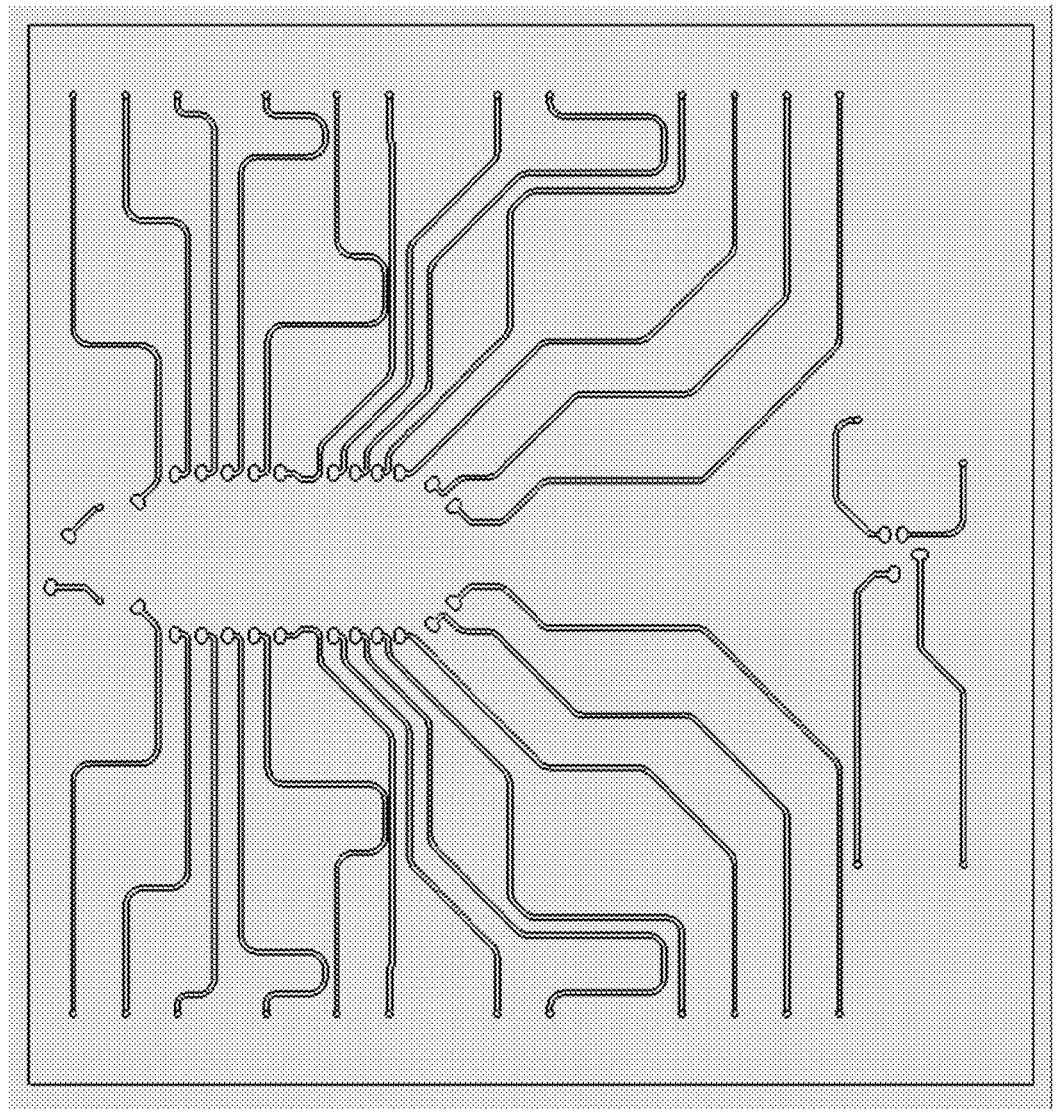
Fig. 23B - Example Valved Chip Pneumatic Side

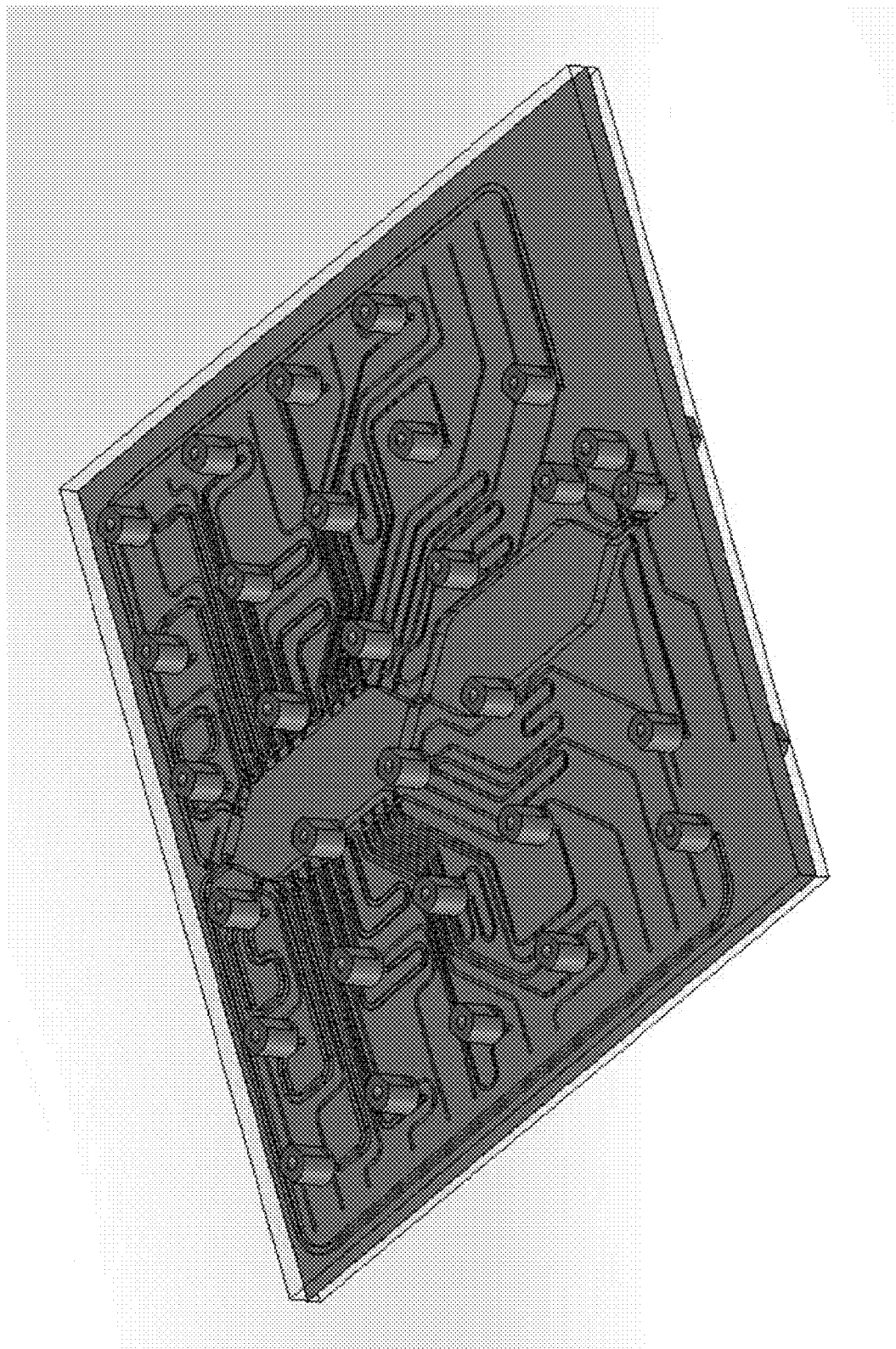
Fig. 23C - Example Valved Chip Fluidic Side

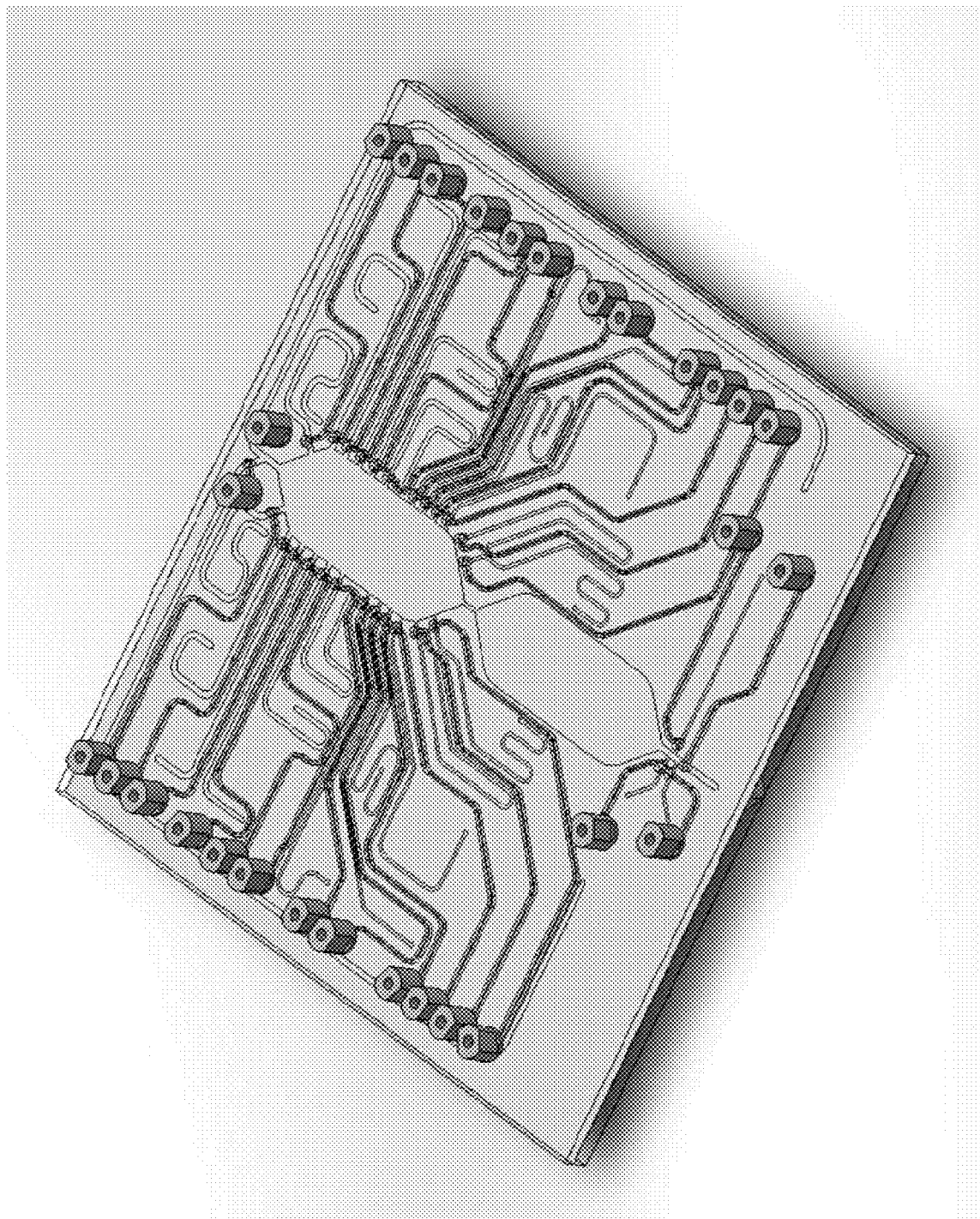
Fig. 23D - Example Valved Chip Pneumatic Side

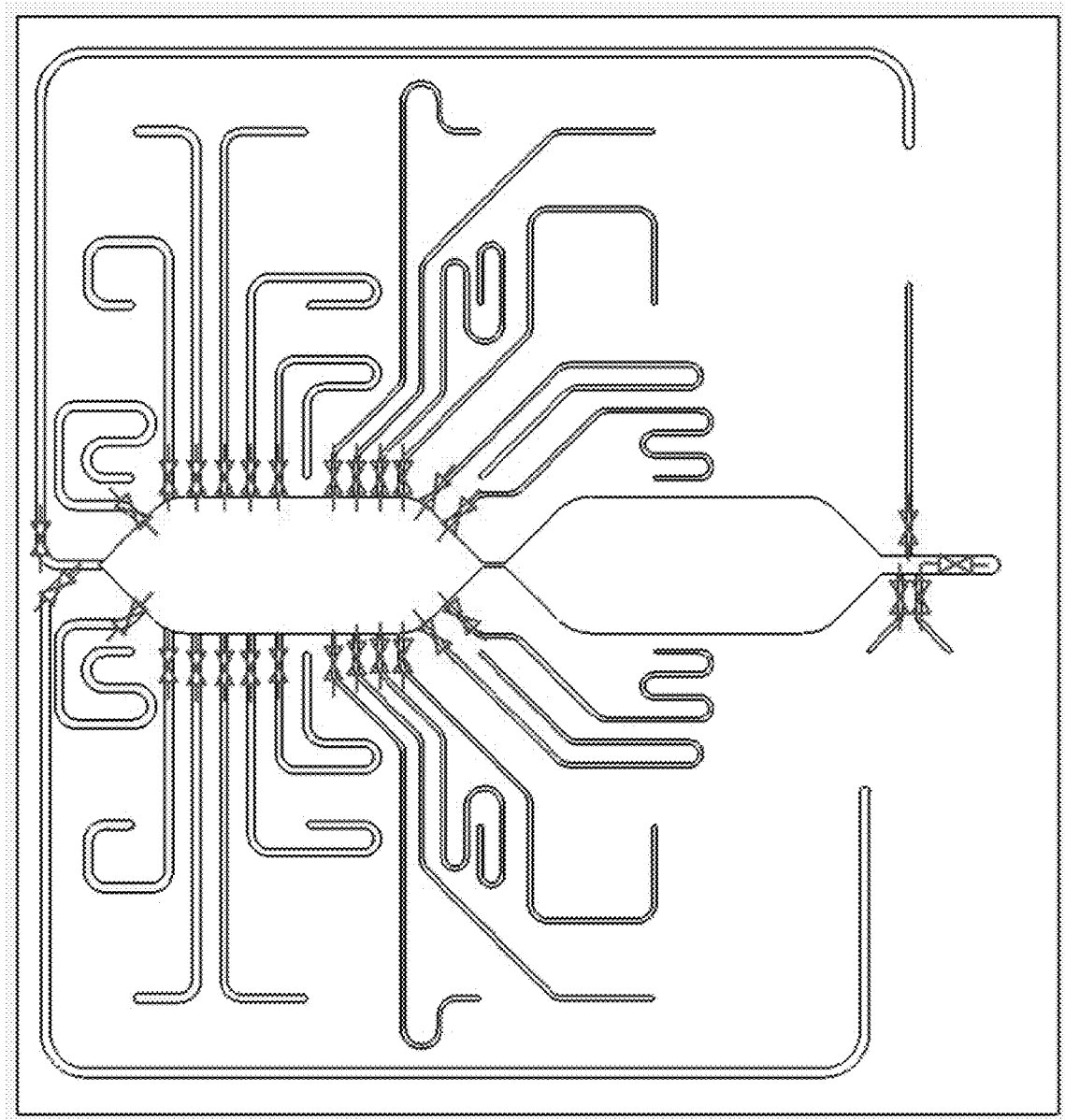
Fig. 23E - Example Valved Chip Design

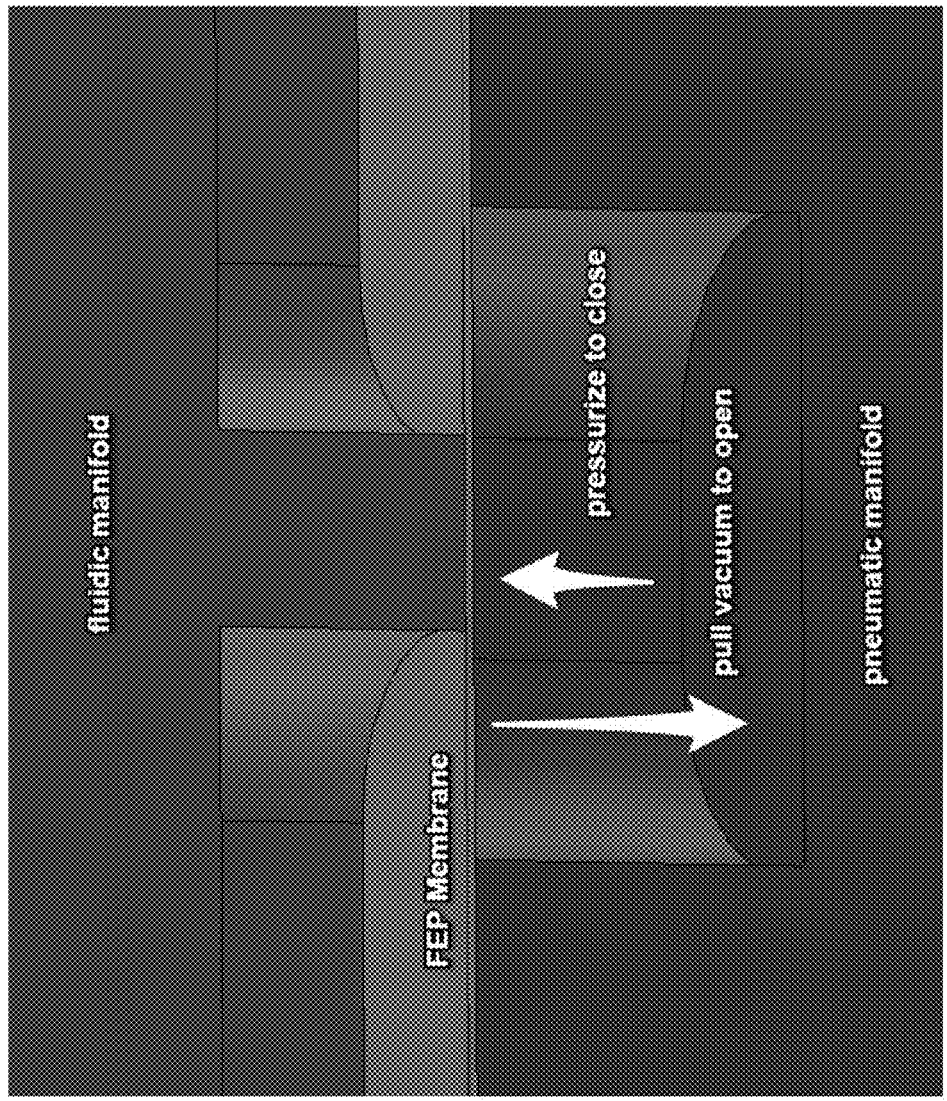
Fig. 23F - Example Valved Cross Section

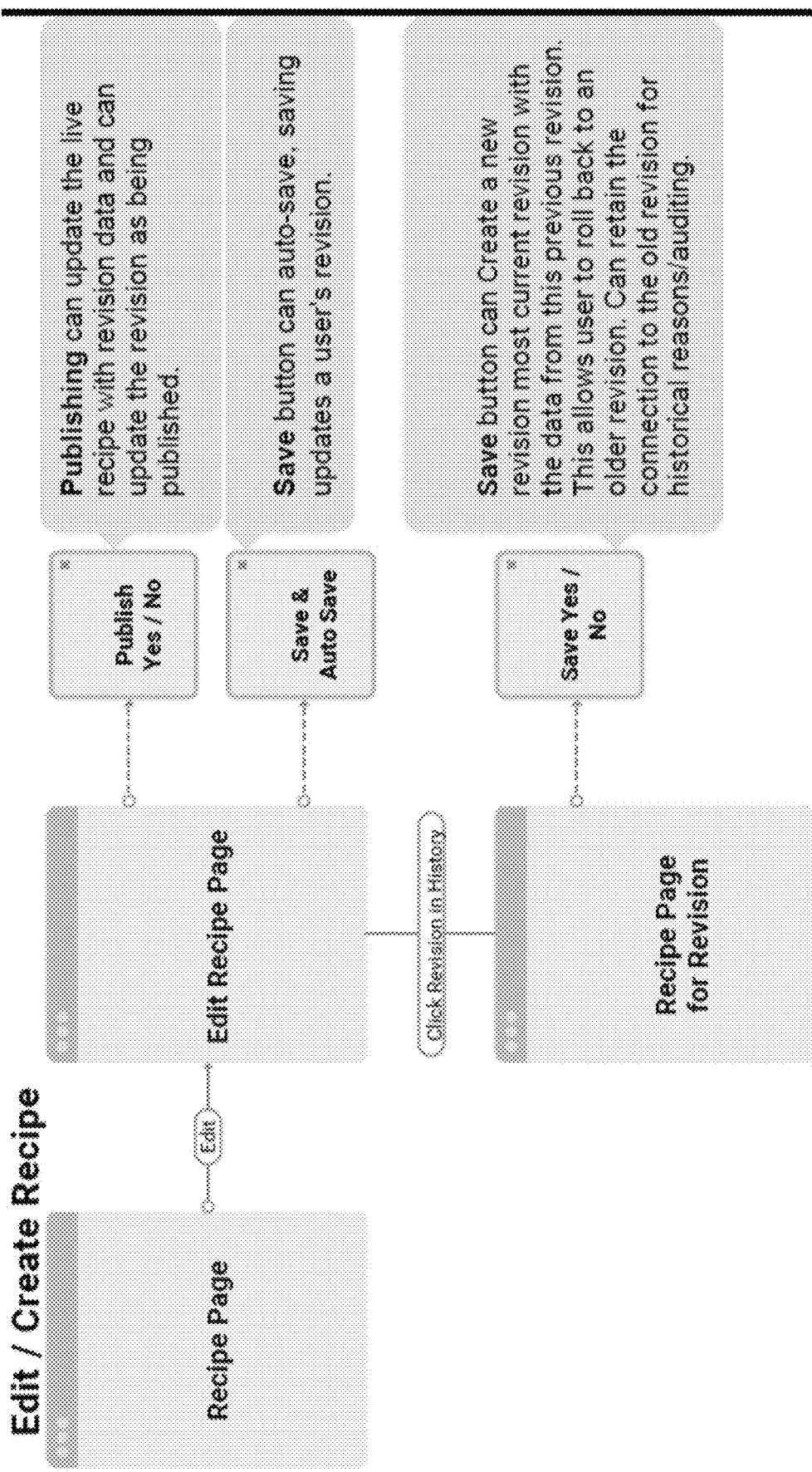
Fig. 30D - Example Edit / Create Recipe Flow

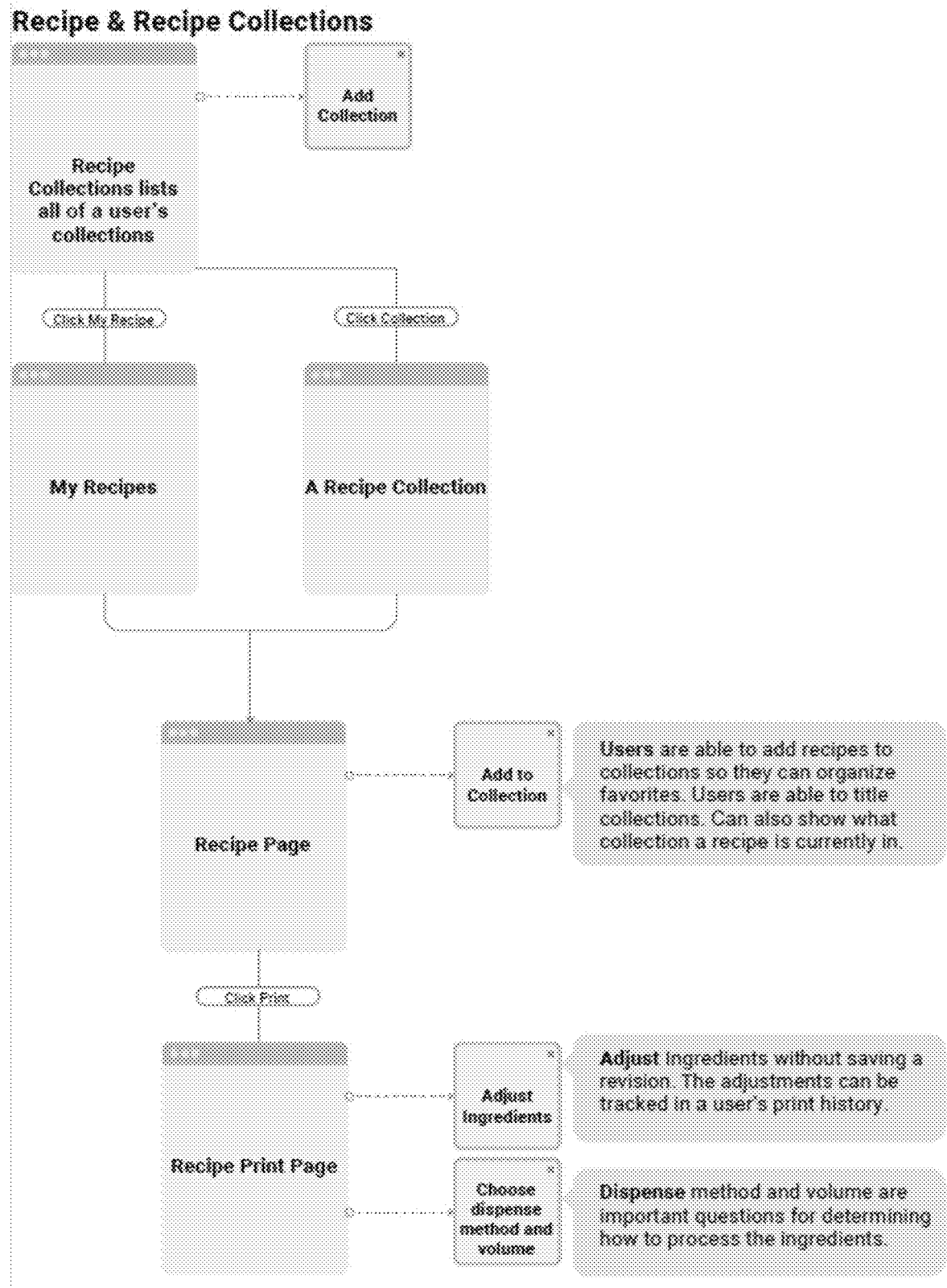
Fig. 30E - Example Recipe and Collection

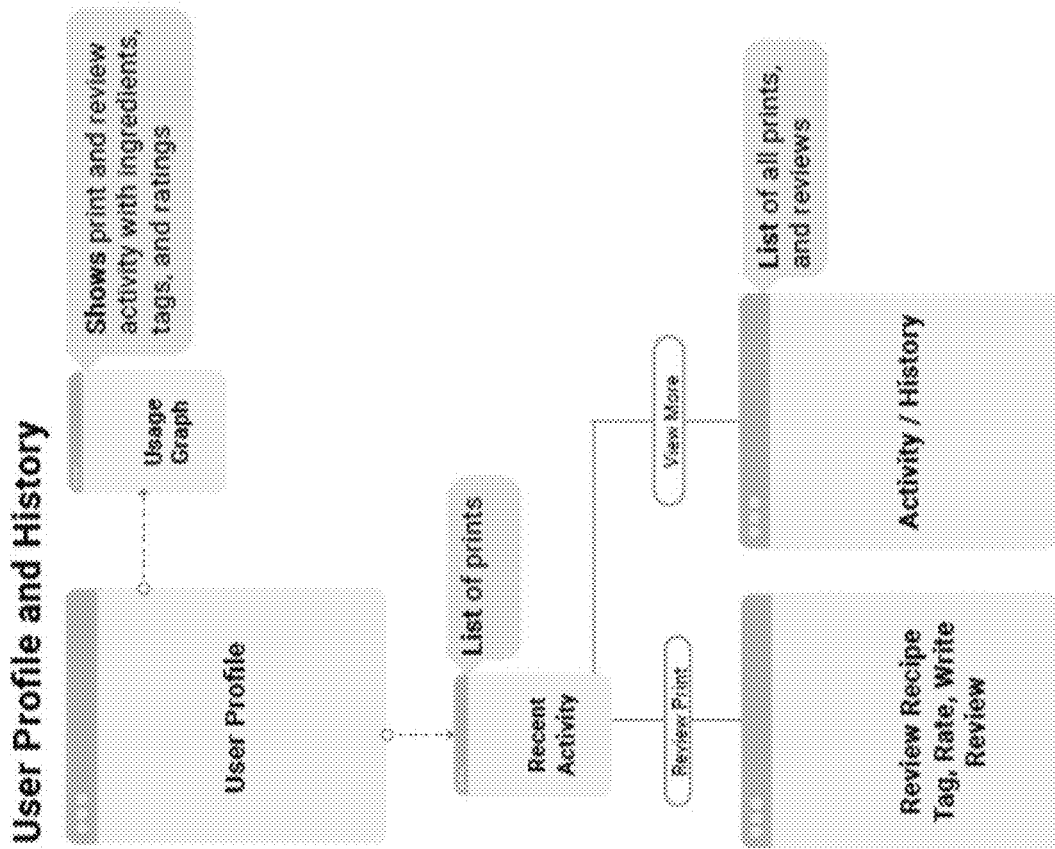
Fig. 30F - Example User Profile and History

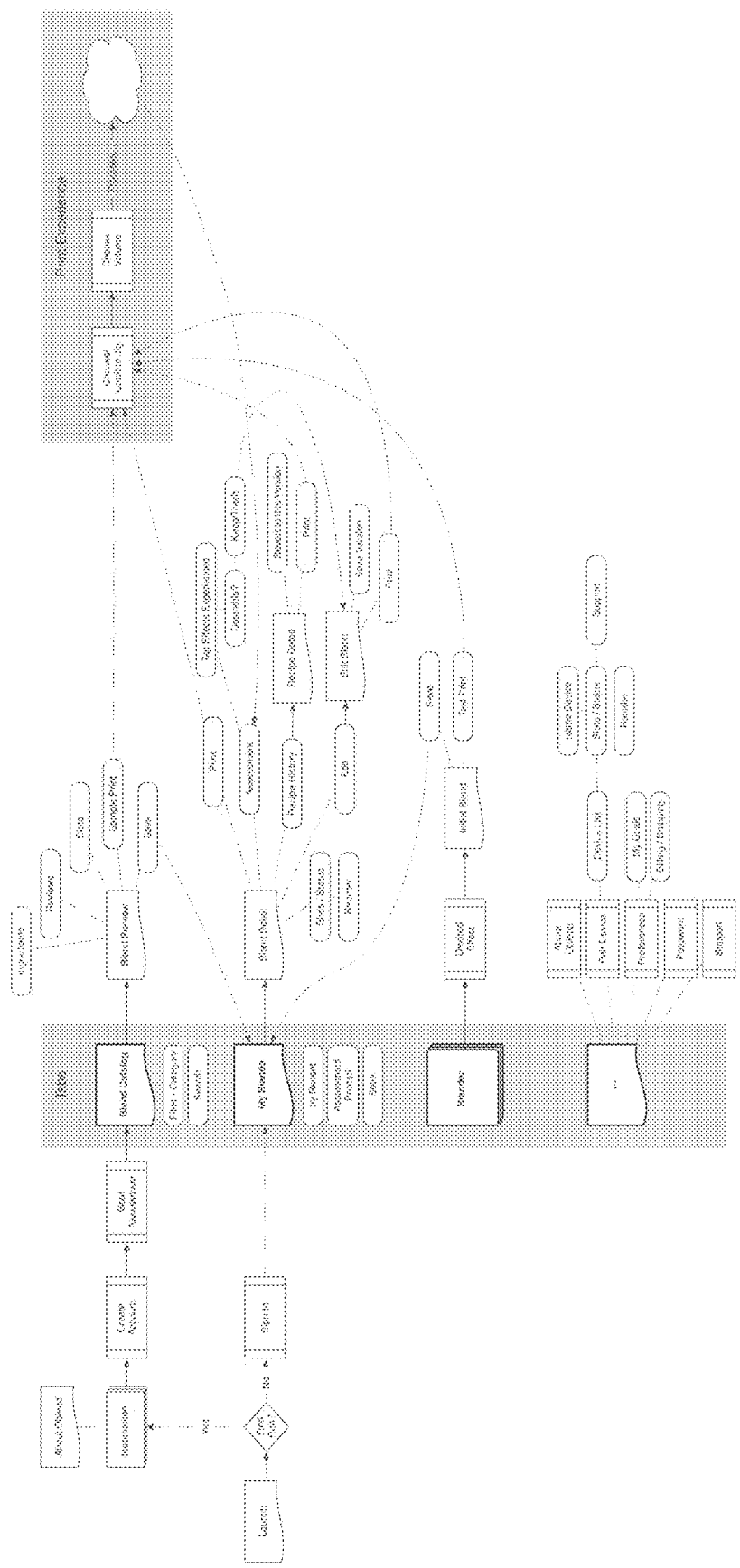
Fig. 30G - Example OBD mobile application architecture

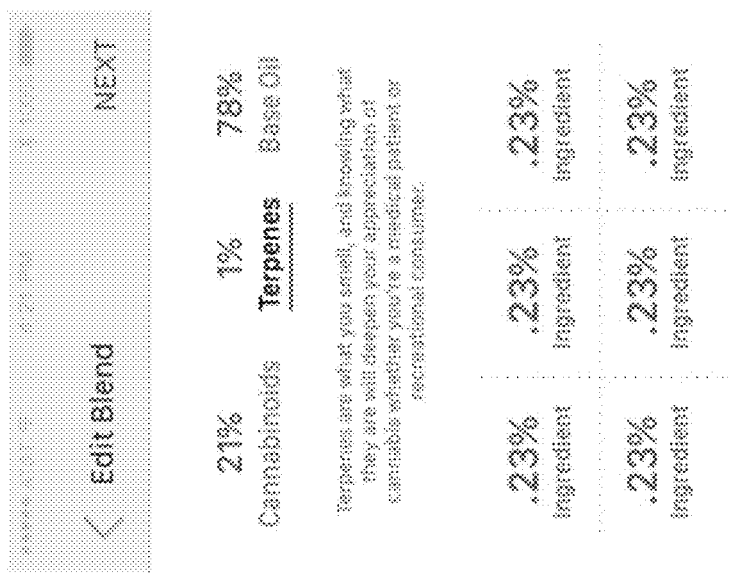
Fig. 30M
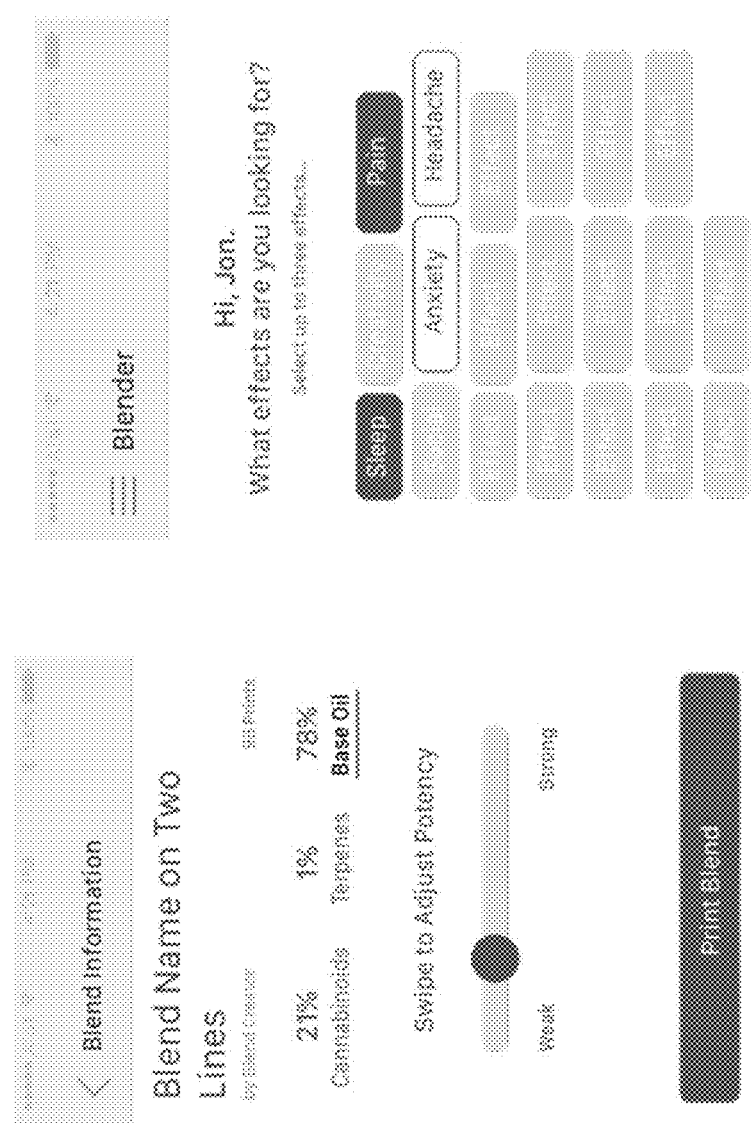
Fig. 30L
Fig. 30K

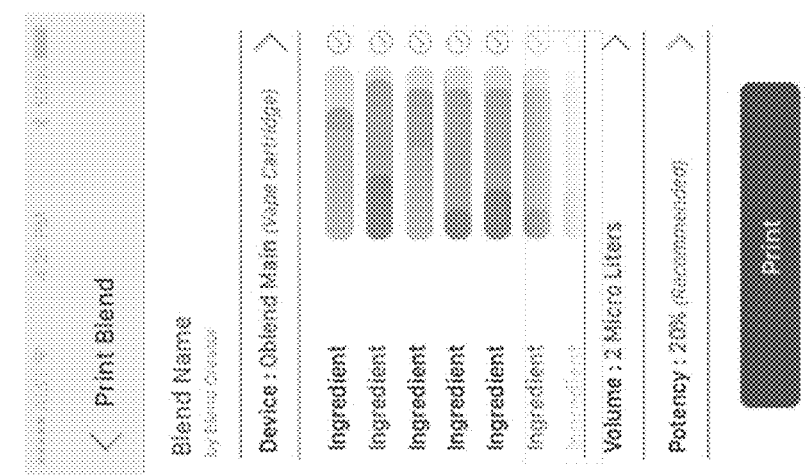
Fig. 30P
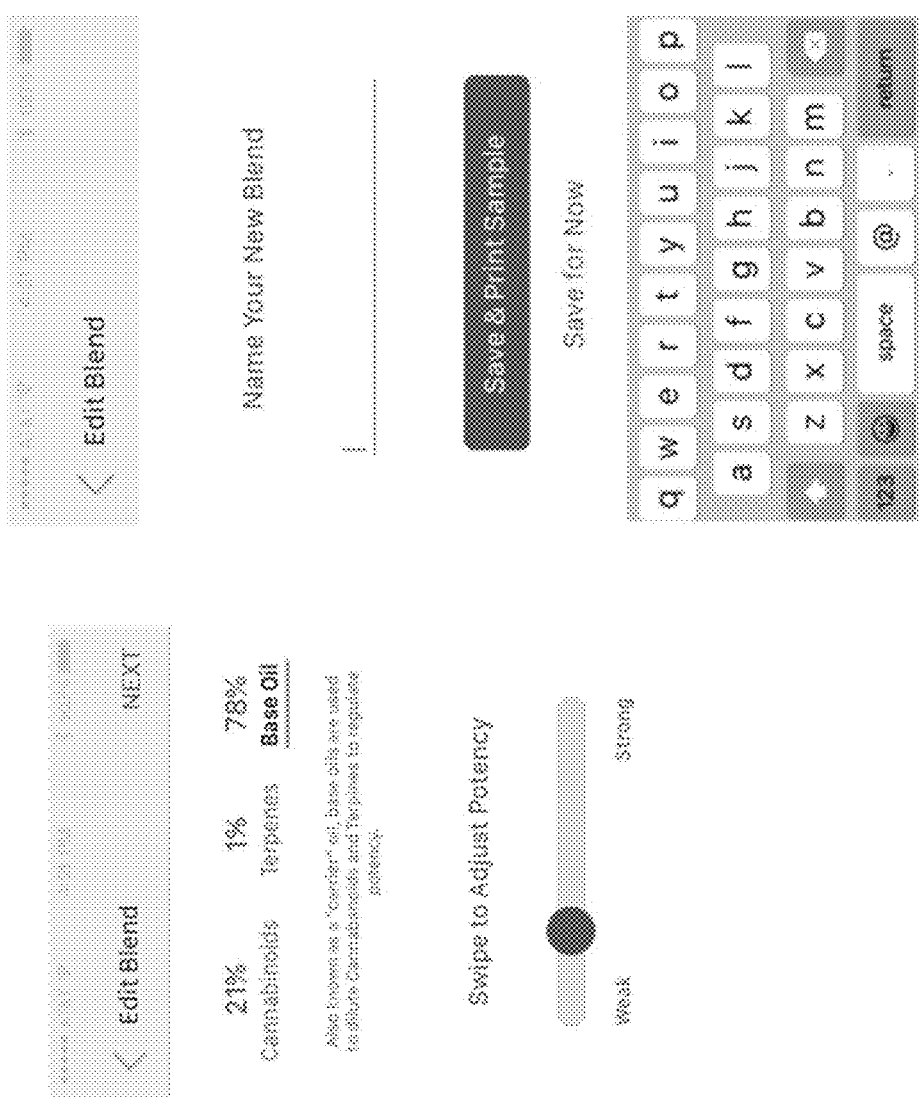
Fig. 30O
Fig. 30N

| | THC | CBD | CBG | THCV | CBDV | CBN | CBC | CBLA | terpinolene | linalool | phytol | beta myrcene | citronellol | caryophylene oxide | alpha pinene | limonene | beta caryophyllene | humulene | Total | Base Oil |
|---|---|---|---|---|---|---|---|---|---|---|---|---|---|---|---|---|---|---|---|---|
| SD | 17.726 | 0.094 | 0.561 | 0.176 | 0 | 0.03 | 0.03 | 0.442 | 0.339 | 0.147 | 0.073 | 0.223 | 0.234 | 0 | 0.037 | 0.201 | 0.357 | 0.395 | 20.448 | 78.392 |
| BD | 17.273 | 0.066 | 0.226 | 0.087 | 0.06 | 0.038 | 0.065 | 0.063 | 0.166 | 0.057 | 0.223 | 0.622 | 0 | 0 | 0.012 | 0.596 | 0.147 | 0.204 | 20.118 | 79.817 |
| OSC | 18.12 | 0.066 | 0.777 | 0.106 | 0.009 | 0.047 | 0.145 | 0.312 | 0.118 | 0.128 | 0.365 | 0.204 | 0 | 0 | 0.032 | 0.197 | 0.317 | 0.566 | 21.945 | 76.056 |
| Chindog | 18.211 | 0.082 | 0.531 | 0.156 | 0.004 | 0.031 | 0.075 | 0.32 | 0.115 | 0.086 | 0 | 0.408 | 0 | 0 | 0.02 | 0.241 | 0.257 | 0.85 | 21.857 | 78.143 |
| Sativa | 18.166 | 0.051 | 1.002 | 0.062 | 0.001 | 0.02 | 0.038 | 0.246 | 0.206 | 0.291 | 0 | 0.726 | 0.133 | 0 | 0 | 0.345 | 0.367 | 0.347 | 21.088 | 78.612 |
| Hybrid | 17.968 | 0.066 | 0.621 | 0 | 0 | 0.016 | 0.059 | 0.275 | 0.065 | 0.333 | 0 | 0.463 | 0.07 | 0 | 0 | 0.164 | 0.409 | 0.484 | 21.239 | 78.761 |
| Indica | 17.212 | 0.062 | 0.469 | 0.172 | 0 | 0.044 | 0.057 | 0.263 | 0.072 | 0.488 | 0 | 0.392 | 0 | 0 | 0 | 0.335 | 0.136 | 0.477 | 20.533 | 79.467 |
| AVG | 17.9523 | 0.0769 | 0.5656 | 0.1091 | 0.0134 | 0.0323 | 0.0859 | 0.2554 | 0.1314 | 0.1967 | 0.084 | 0.4336 | | 0.029 | 0.0144 | 0.2974 | 0.2604 | 0.4216 | 21.32797 | 78.67243 |
| Potency Multiplier | 3.5 | | | | | | | | | | | | | | | | | | | |
| Potency Percentage | 62.833 | 0.269 | 1.9795 | 0.382 | 0.047 | 0.1113 | 0.3005 | 0.894 | 0.46 | 0.6885 | 0.294 | 1.5175 | 0.1915 | | 0.0505 | 1.041 | 0.9115 | 1.4755 | | |

Vape Cartridge Size and amounts of each ingredient by µl

| | | | | | | | | | | | | | | | | | | | | |
|---|---|---|---|---|---|---|---|---|---|---|---|---|---|---|---|---|---|---|---|---|
| 100µl | 62.833 | 0.269 | 1.9795 | 0.382 | 0.047 | 0.1113 | 0.3005 | 0.894 | 0.46 | 0.6885 | 0.294 | 1.5175 | 0.1915 | | 0.0505 | 1.041 | 0.9115 | 1.4755 | 74.6466 | 25.3535 |
| 300µl | 188.499 | 0.807 | 5.9385 | 1.146 | 0.141 | 0.339 | 0.9015 | 2.682 | 1.38 | 2.0655 | 0.882 | 4.5525 | 0.3045 | | 0.1515 | 3.123 | 2.7345 | 4.4265 | 223.9395 | 76.0605 |
| 500µl | 314.165 | 1.345 | 9.8975 | 1.911 | 0.235 | 0.565 | 1.5025 | 4.47 | 2.3 | 3.4425 | 1.47 | 7.5875 | 0.5075 | | 0.2535 | 5.205 | 4.5575 | 7.3775 | 373.2325 | 126.7675 |

Number of formulas produced from a 3ml cartridge

| 10µl Vape | 47.74561 | 1152.42 | 1515.534 | 7853.403 | 63824.79 | 26946.67 | 9983.361 | 3355.705 | 8521.739131 | 4357.298 | 10204.08 | 1976.936 | 29550.15625 | 59405.94059 | 2881.344 | 3291.27811 | 2368.088708 | 2013.20400 | 118.3326 | |
| 30µl Vape | 15.9152 | 3717.472 | 6051.781 | 2617.801 | 21276.6 | 8849.556 | 3327.767 | 1118.668 | 2173.913043 | 1452.433 | 3401.361 | 658.9786 | 9852.218749 | 18601.86017 | 960.6448 | 1097.0827 | 776.0862358 | 677.79638 | 36.44208 | |
| 50µl Vape | 9.549132 | 2230.483 | 3031.068 | 1870.681 | 12765.96 | 5309.735 | 1996.672 | 671.1409 | 1304.347826 | 871.4897 | 2040.816 | 395.3871 | 5911.330648 | 11881.18812 | 676.3686 | 598.26659 | 466.6577416 | 406.641816 | 23.66533 | |

Fig. 30W

Example OBD Start Sequence

Example OBD Mix State Processes

Example OBD Mix State Control

Example OBD Tablet/Phone Application Process 2

SECURE PORTABLE, ON-DEMAND, MICROFLUIDIC MIXING AND DISPENSING DEVICE

This application is a continuation of International Patent Application Number PCT/US2017/027064, filed Apr. 11, 2017 and titled "Secure Portable, On-Demand, Microfluidic Mixing and Dispensing Device," which in turn claims priority to and benefit of: U.S. Provisional Application Ser. No. 62/321,161, filed Apr. 11, 2016; U.S. Provisional Application Ser. No. 62/412,626, filed Oct. 25, 2016; and U.S. Provisional Application Ser. No. 62/446,779, filed Jan. 16, 2017; the entire contents of each of the aforementioned applications are expressly incorporated by reference herein in their entireties for all purposes.

This application may contain material that is subject to copyright, mask work, and/or other intellectual property protection. The respective owners of such intellectual property have no objection to the facsimile reproduction of the disclosure by anyone as it appears in published Patent Office file/records, but otherwise reserve all rights.

BACKGROUND

Electric home appliances have automated repetitive tasks previously done manually. For example, electric kitchen mixers can replace stirring, whisking, and beating. Stand mixers, using a dough hook, can be used to knead bread. Electric kitchen mixers with a variety of speeds allow users to have more control over the mixing/blending process and the development of the mixtures.

SUMMARY

Embodiments of the present disclosure of SECURE PORTABLE, ON-DEMAND, MICROFLUIDIC MIXING AND DISPENSING DEVICE (hereinafter "OBD") include, by way of non-limiting example, a device configured for portable, on-demand, app-controlled (IoT), microfluidic mixing and dispensing, as well as microfluidic oil and fluid blending for vaping, transdermal patches, capsules, vitamins, aroma therapy, scents, perfumes, topicals, sublinguals, nutraceuticals, beverages, entertainment, food, pharmacies, and clinical research and trials.

Some embodiments include a device comprising a plurality of microfluidic pumps, microfluidic valves, at least one heater, a microfluidic mixer chip and/or multiple microfluidic chips configured to receive and mix microfluidic amounts of a plurality of fluids having different viscosities from one another is disclosed. Some embodiments include multiple microfluidic chips such that one microfluidic chip or array of microfluidic chips can handle a first set of fluids and a second microfluidic chip or set of microfluidic chips can process a second set of fluids. The device includes a plurality of pathways defined therein for moving each of the plurality of fluids from a respective tank or reservoir to the microfluidic mixer chip. A mix controller is configured to control the microfluidic pumps, valves, and at least one heater so that the fluids having different viscosities can be accurately mixed at specified microfluidic amounts or volumes according to a specified microfluidic recipe, and the microfluidic mixture dispensed from the device. The device can be in communication with a software application implemented on a mobile compute device, such as a smartphone, and receive instructions for implementing the specified microfluidic recipe from the software application such that the operation of device components is at the direction of the software application executed on the mobile compute device.

Some embodiments include a microfluidic cannabinoid mixer system, comprising: a blend application implemented on a mobile compute device and a microfluidic mixer device. The microfluidic mixer device includes, a microfluidic mixer device housing, at least one microfluidic pump, at least one microfluidic valve, a microfluidic dispenser, and a microfluidic mixer chip configured to receive and mix a microfluidic amount of a first cannabinoid oil, a microfluidic amount of at least one second cannabinoid oil, and a microfluidic amount of an at least one terpene to form a microfluidic cannabinoid mixture, the first cannabinoid oil and the second cannabinoid oil each having a viscosity different from a viscosity of the at least one terpene. Some embodiments can be configured to only include cannabinoids. The microfluidic mixer device includes a plurality of fluid pathways defined therein, including a fluid pathway providing fluid communication from a first cannabinoid canister containing the first cannabinoid oil to the microfluidic mixer chip, a fluid pathway providing fluid communication from a second cannabinoid canister containing the second cannabinoid oil to the microfluidic mixer chip, a fluid pathway providing fluid communication from a terpene canister containing the at least one terpene to the microfluidic mixer chip, and a fluid pathway providing fluid communication from the microfluidic mixer chip and a microfluidic dispenser, the microfluidic dispenser configured to receive the microfluidic mixture from the microfluidic mixer chip and dispense the microfluidic mixture from the device. The microfluidic mixer device also includes a microfluidic mixer chip heater configured to heat the microfluidic mixer chip and/or a canister heater configured to heat at least one of the first cannabinoid canister, the second cannabinoid canister, and/or the terpene canister. The microfluidic mixer device includes a mix controller in communication with the blend application implemented on the mobile compute device, and configured to, based on instructions received from the blend application, control each of the at least one microfluidic pump, the at least one microfluidic valve, the microfluidic mixer chip heater, and the canister heater, such that: (1) a microfluidic amount specified by the instructions from the blend application of the first cannabinoid oil is delivered to the microfluidic mixer chip, (2) a microfluidic amount specified by the instructions from the blend application of the second cannabinoid oil is delivered to the microfluidic mixer chip, (3) a microfluidic amount specified by the instructions from the blend application of the at least one terpene is delivered to the microfluidic mixer chip, (4) the microfluidic mixer chips mixes the first cannabinoid oil, the second cannabinoid oil, and the at least one terpene to form the microfluidic mixture, and (5) the microfluidic mixture is dispensed from the microfluidic dispenser. In some embodiments, there is a base or carrier fluid or material into which the microfluidic mixtures are added, e.g., a base oil, and the strength of a particular blend can be determined by the amount of the base or carrier percentage. Although discussed in terms of mixing of fluids occurring in a microfluidic mixer chip, it is to be understood that some embodiment of the OBD, the microfluidic mixer chip (mixer chip, or chip) can instead accurately microfluidically meter and dispense the fluids (i.e., not actively mix the fluids together in the chip) and the mixing can occur in the a collection vessel such as a vial, vape cartridge, bowl, etc.

It should be appreciated that all combinations of the concepts discussed herein and detailed below (provided such concepts are not mutually inconsistent) are contemplated as being part of the inventive subject matter disclosed herein. In particular, all combinations of subject matter appearing in this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 2A and 2B illustrate aspects of a pressure-driven pneumatic OBD with rotary valve control according to some embodiments of the disclosure;

FIG. 8D provides an overview of system feedback for some embodiments of the OBD;

FIG. 8E and FIG. 8F provide an overview of microfluidic mixture dispensing for some embodiments of the OBD;

FIG. 8H provides an overview of inserting and/or replacing fluid vials for some embodiments of the OBD;

FIGS. 12B and 12C illustrate valving for some embodiments according to the disclosure;

FIGS. 14A to 19B provide designs and configurations for some OBD embodiments according to the disclosure;

FIGS. 21 and 22 provide example configurations for some embodiments of the OBD according to the disclosure;

FIGS. 23A to 23F provide details for example OBD chips according to some embodiments of the disclosure;

FIG. 27I shows an embodiment of the OBD in a base and middle housing;

DETAILED DESCRIPTION

Figure 1A:
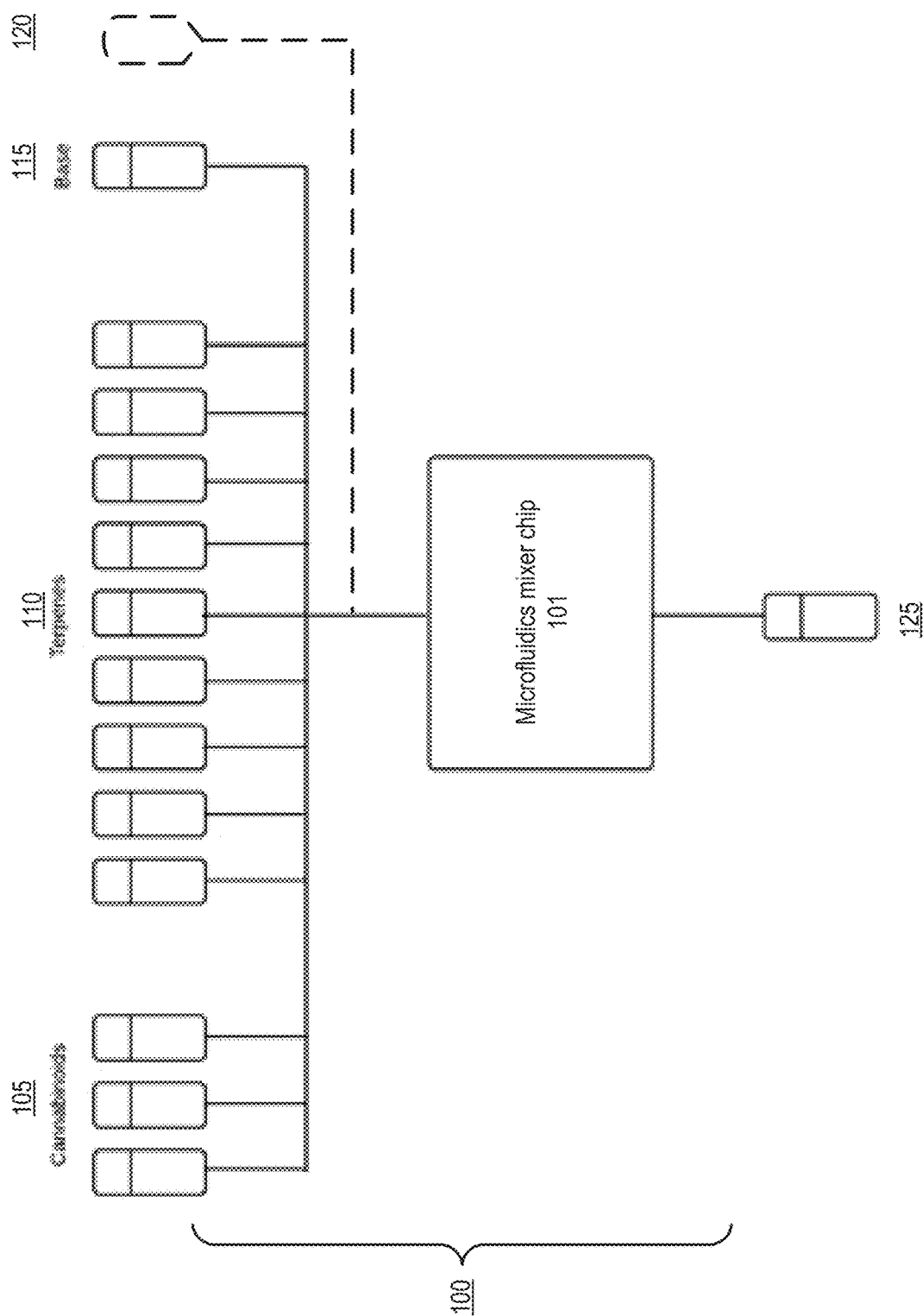
FIGS. 1A-1C illustrates aspects of embodiments of the OBD according to the disclosure.

Following below are more detailed descriptions of various concepts related to, and embodiments of, SECURE PORTABLE, ON-DEMAND, MICROFLUIDIC MIXING AND DISPENSING DEVICE (hereinafter "OBD"). It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Embodiments of the present disclosure include, by way of non-limiting example, a microfluidic chip and apparatus configured for portable, on-demand, app-controlled (IoT), microfluidic mixing and dispensing, as well as microfluidic oil blending for vaping, aroma therapy, scents, entertainment, and food.

In some embodiments, the OBD comprises a device that can store, mix to specific ratios in microliter quantities, and dispense a blend of fluids, on demand, to be ingested, vaped, inhaled, applied to the body, taken sublingually, etc. Embodiments of the OBD can be Internet-connected and controlled manually (e.g., via touch-screen and/or by a smartphone app), to produce a custom mixture or recipe using of the available onboard fluids.

Implementations of the OBD may be provided for the medical and/or cannabis industry for use in producing blends of, by way of non-limiting example, cannabinoid oils, terpenes, terpinoids, flavonoids, cannaflavins, various bases (such as propylene glycol, vegetable glycerin, etc.), and/or "flavors," for recreational and medicinal use in vaping, eating, aroma therapy, skin care, and/or the like.

In some embodiments, the OBD can produce "Microvape" (e.g., 0.1 mL or less) for a user that wants a small (e.g., 30 puff) vape.

The OBD can also be used in the aromatherapy industry for customized blending of various aromatherapy oils to obtain varying effects not possible in single oil solutions. Also, in cooking, the OBD can be utilized to create customized blends of cooking oils with terpenes, esters, essential oils, etc., to manipulate the subtle flavorings in the oil and subsequently the foods. Combining various skin care lotions with different terpenes is another of the numerous applications of the OBD. In some embodiments, the OBD can also be used for entertainment purposes, for example, by connecting the OBD and/or associated component (e.g., via a home network) to televisions, creating scents in public areas such as hotels or bars or different rooms within the home, computers gaming consoles, and/or VR devices and content, such as the OCULUS RIFT. The OBD (and/or associated components that use output from the OBD) can produce aromas that match the content being viewed on these devices. Accordingly, it could also be utilized in public places, such as movie theaters, hotels, bars, to blend and provide particular smells. The OBD could also be used in the beverage industry in formulating consumables with certain flavors, smells, and/or other attributes (health, recreation, and/or medical purposes).

In some embodiments, the OBD is a commercial device for creating custom blends of components (e.g., oils, waxes, flavors, etc.; generally referred to hereafter as "liquids" with the understanding that some may not be liquid at room temperature) for a diverse range of volumes (e.g., 0.1 nanoliters to 1 microliters, 0.01 microliters to 1 milliliter, 1 microliters to 10 milliliters, 100 microliters to 1 milliliter, etc.). Some implementations of the OBD are configured for cannabis extract and related markets, and provide users with the ability to mix chemical components found in cannabis, including cannabinoids and terpenes, and a base (e.g., propylene glycol, vegetable glycerin, a terpene blend, and/or the like). The OBD can include and/or be configured to utilize cartridges containing a set of mixing fluids/components. In some embodiments, some or all of the fluids/components may be safety restricted (i.e., the OBD will only accept cartridges/containers that satisfy a specified authentication or source verification), while in additional or alternative embodiments, the OBD can be configured to allow a user or other party to fill/refill cartridges with specified or custom fluids, such as flavoring agents. In some embodiments, fluid cartridges can include a memory device component that can be read by the OBD to identify key information about the contents (e.g., fluid), including volume, viscosity, fill date/shelf life, etc. For user safety, some embodiments of the OBD can be configured to restrict or limit the types of additives/fluids that users can utilize to fill/refill a cartridge/container. Such limitations may be based on the amount to be added (either to the cartridge and/or to the end product), shelf life, viscosity, and/or the like. In some embodiments, the OBD can receive user input regarding additives/fluids through a mobile app. In some embodiments, cartridges/tanks/reservoirs are configured for secure/attach to an OBD, such as by a secure fitting, including a Luer taper fittings (Luer-locking and/or Luer-slipping), compression fittings, flare fittings, screw fittings, flange fittings, etc.

Embodiments of the OBD utilize microfluidic technologies in a compact, consumer-oriented commercial device to meter, mix, and dispense fluids in highly accurate, ultra-small amounts/volumes (including µL, nL, pL, and/or fL amounts, depending on the implementation and embodiment—generally referred to herein as "microfluidic amounts"), and do so in a way that that is repeatable.

Embodiments of the OBD meter, mix, and dispense a custom mixture of a plurality of fluids/components. By way of non-limiting example, one implementation is configured to mix up to 24 fluids (e.g., four cannabinoids, one base, one user-filled cartridge, and a blend of terpenes and flavonoids) with a total volume ranging from 100 microliters to 1 milliliter in approximately one minute.

The OBD can meter as little as 0.1 microliter, 0.01 microliter, 1 nanoliter, or 0.1 nanoliters of a single fluid into an overall mixture. In some instances, the OBD is configured to keep dead volume to a minimum and thus provide efficient use of resources (e.g., cannabinoids which can be expensive, and/or other compounds that may have a short effective life once removed from their storage environment), and to reduce areas where cross contamination could occur to disposable or replaceable components. It is to be understood that the discussion of cannabinoids and oils herein is illustrative, and numerous other liquids can be utilized additionally or alternatively, including alcohols, organics, polar and non-polar solvents and liquids, propylene glycol, vegetable glycerin, medicines/pharmaceuticals, nicotine, extracts, etc.

Functions of the microfluidic system in the OBD include: (1) metering controlled volumes of each fluid, (2) transporting fluid through the OBD, and (3) mixing the fluids. To handle the small volumes, some embodiments of the OBD use an array of small bore tubing. Other embodiments use one or more microfluidic chips with enclosed channels in order to provide efficient and hygienic components, and so can be replaced/recycled as needed. A number of methods and materials can be used to produce microfluidic chips according to the disclosure, and the methods and materials can be selected based on application, production capacity, cost, and/or complexity. Non-limiting examples of materials and production methods are provided below.

Silicon: Some embodiments utilize silicon. For some applications of the disclosure, silicon provides a versatile material for creating microfluidic and microelectromechanical devices due to its electrical and thermal conductivity and the ability to create complex features and devices through additive and subtractive processes. Silicon can also be scaled to large production volumes, but can be limited to applications having relatively lower flow rates, e.g., particularly if using piezo-driven pumps built into the silicon chip. In some instances, features of silicon, such as brittleness and/or appearance, may not be desired.

Glass: Some embodiments of the disclosure utilize glass. Glass can be used to create microfluidic channels and devices using etching processes. For some applications, glass can provide better thermal conductivity than polymers, can be easily coated, and is recyclable. However, for some applications, glass can be relatively more expensive than polymer (e.g., particularly in high volumes), and some manufacturing methods for glass microfluidics do not scale easily.

PDMS: Some embodiments of the disclosure utilize polydimethylsiloxane (PDMS) and/or like materials. Use of a flexible, cast elastomer, such as PDMS, allows for the incorporation of components, such as pumps and valves, directly into a chip according to the disclosure. Using soft lithography processes with a material such as PDMS, microfluidics according to the disclosure can be produced quickly. Materials such as PDMS can also bond to materials such as glass, and, in some embodiments, can thus be used to produce closed microchannels. Some designs utilizing PDMS may be configured for low aspect ratios which limit fluid flow rates.

Injection Molded Polymers: Some embodiments of the disclosure utilize injection molded polymers. Injection molding provides a cost-effective method for producing large volumes of microfluidic devices according to the disclosure. A wide variety of plastic resins can be used, depending on the implementation, and material(s) suited to the particular design/configuration are selected to meet particular specifications of an embodiment, such as fluid contact angle, permeability, and pH tolerance. Some embodiments may be configured from multiple materials and/or material types, and/or components moved off the chip, for example, in some embodiments, complex components, such as pumps and valves, may be moved off-chip for micro-injection molded microfluidics.

Materials for the OBD, including but not limited to those noted above, can be configured to be appropriate for particular applications of the OBD. The OBD and/or components thereof (e.g., valves, connectors, pathways, etc.) are configured to be non-reactive or resistant to corrosive or otherwise reactive ingredients (e.g., made of or coated with non-reactive or resistant materials). For example, the OBD or portions thereof can be configured for handling terpenes, such as limonene, that could act as a solvent for certain materials, such as materials generally used for making laminated chips with laser cut or machined layers, or adhesives used to bond different layers together to create integrated valving in chips. Some embodiments of the OBD utilize materials and/or adhesives that are resistant to terpenes and other ingredients/oils. Some embodiments utilize alternative bonds/bonding methods, such as heat bonding, ultrasonic welding, and solvent bonding that are resistant to terpenes and other ingredients/oils. Various materials can be utilized for the OBD, and while some embodiments of the OBD are configured to be formed from a single source/material, in some embodiments, various materials are utilized for one or more of the rigid and/or elastomeric components of the OBD. For example, elastomeric components of the OBD can utilize fluoroelastomers or Teflon in PTFE, FEP, or PFA form. Additional details for configuring materials for some embodiments of the OBD can be found in U.S. Pat. App. Pub. No. 2016/0250639, and "Solvent resistant microfluidic platform for complete SiFA-based PET tracer synthesis" Rensch et al., J Nucl Med May 2014 vol. 55 No. Supplement 1 1247; the entirety of each of the aforementioned documents is herein expressly incorporated by reference for all purposes.

In some embodiments, one or more fluid pumps and/or active valves are configured to be and/or located within permanent components of an OBD and/or in replaceable fluid cartridges.

For metering and transport, a variety of pumping and valving components can be utilized. Some examples with non-limiting example configurations are provided below.

Piezoelectric-Driven Diaphragm Pump: Piezoelectric pumps can be utilized in a variety of configurations for the OBD. Piezoelectric pumps can be situated between the fluid cartridge and the mixer chip and used to meter fluid into the mixing path. This provides a direct way of controlling fluid flow with low lag time due to system elasticity and pressure drop. In some such embodiments, a separate pump is provided for each fluid cartridge. Such embodiments can be configured to address issues resulting from a pump diaphragm being in direct contact with a fluid to reduce or avoid residue buildup inside the pump or cross-contamination between fluids (e.g., using a materials or coating that do not accumulate buildup and/or utilizing a cleaning-cycle within the OBD).

Some embodiments can use a direct pumping configuration using piezo micropumps where one or more micropumps are built directly into the fluid cartridge(s). Such embodiments can reduce or eliminate the possibility for cross-contamination.

Pressure-Driven Microfluidics: Some embodiments can additionally or alternatively use diaphragm pumps (whether piezo-driven or cam-driven) to pneumatically pressurize the fluid cartridges, creating a pressure-driven system. Each fluid cartridge could still have its own pump, but the pump would only be in contact with air as it pressurized the fluid cartridge through a port in the top. The differential pressure between the fluid cartridge and the mixer chip would cause fluid to flow at a controlled rate directly related to the pump pressure and could be stopped by removing the drive voltage to the pump. Use of diaphragm pumps can prevent backflow as the diaphragm is sealed when the pump is off.

Some embodiments use a single pump to pressurize a pressure chamber, and use valve(s) to apply and release pneumatic pressure to each fluid cartridge individually. By maintaining a constant (or relatively constant) pressure inside the chamber, such embodiments can provide for improved control. The same pump and pressure chamber can be used to transport the fluids within the mixer chip to produce a continuous flow system that uses air or other gas (e.g., nitrogen) as the carrier. Such embodiments can also be configured to allow for the use of air or other gas to purge the mixer chip (and/or the entire flow path of the system) at the completion of each use cycle, and thereby improve safety, reliability, and prolong the service life of the mixer chip. It is to be understood that generally, when air is referred to in the context of some example embodiments, other or additional embodiments may be configured to use a gas or mixtures of gasses different from atmospheric air. For example, some embodiments can be closed loop systems that include non-reactive gas or gasses therein, depending on the liquids/ingredients being processed (e.g., nitrogen can be used for terpenes).

Syringe Pump: Some embodiments of the disclosure utilize one or more syringe pumps. A syringe pump can be used to dispense fluid from each cartridge into the mixer chip. In some embodiment, a single syringe pump is used for all of the cartridges along with a carousel to index each cartridge into place. Such embodiments can be configured with precision motors, e.g., one for the syringe pump and another for the carousel, to achieve a balance of speed and precision using a single mechanical pump, and avoid the potential for metering error caused by flow pulsations.

Peristaltic Pump: Some embodiments of the disclosure utilize one or more peristaltic pumps. Some such embodiments include a permanent (or semi-permanent) tubing set that is contacted by rollers that force fluid through the system. Peristaltic pumps provide high accuracy, and the tubing set can be configured to be replaced periodically as it wears over time.

The pump (or pumps) can be selected for the particular application and implementation of the OBD. For example, a pressure-driven system has a variety of benefits, as discussed above, and may be preferred for some embodiments, depending on precision and size parameters. As another example, a direct fluid-driven piezo pump provides high accuracy, but may not be suitable for some embodiments that have a relatively high flow rate. Depending on the embodiment, the pump or pumps can be integrated as part of the OBD (either permanent or semi-permanent), and/or integrated into the fluid cartridge(s). The OBD can be configured to clean, purge, and/or sterilize the system, including cleaning a pump diaphragm after it has come into contact with fluids.

The OBD can utilize a variety of methods and mechanisms to provide mixing, including passive microfluidic mixing and active microfluidic mixing. Passive mixing can be provided with OBD systems having tortuous paths configured into the mixer chip that can take a variety of shapes, including zigzags, delta patterns, obstructions, and/or orifices. Active mixing can be provided with OBD systems that utilize the application of an external energy source to achieve mixing, such as acoustic waves, magnetic stir bars, thermal energy, and/or electrical fields. The methods and mechanisms used can be configured based on the application(s), for example, temperature changes may have undesirable effects on some liquids, such as cannabis extracts, and electrical fields may be most effective on polar molecules as in water-based solutions (and may not be as effective for other less-polar or non-polar fluids utilized in some applications).

FIG. 1A provides an example overview of one implementation of the OBD 100 configured to meter, mix, and dispense fluids according to the disclosure. Such embodiments can include additional components discussed in the disclosure, such as a wireless communications interface, housing, heaters, etc. A variety of housing materials can be used, including plastic, metal, anodized metal, glass, etc., and some housings can be configured with removable sections or skins. The illustrated embodiment includes an array of liquid vials containing a combination of cannabinoids 105, terpenes 110, and bases 115. A user-filled vial 120 can also be included, depending on the implementation.

The cannabinoids 105, terpenes 110, and base 115 tanks/vials/cartridges are loaded/attached to (i.e., put in fluid communication with) the OBD 100 and the contents thereof received into the OBD 100 and mixed in a microfluidics mixer chip 101. The mixed fluids are dispensed via an outlet and/or dispenser to a vial 125 or other receptacle that can be changed per use. The microfluidics mixer chip 101 can, in some embodiments, include multiple mixer components/paths for mixing, depending on the fluids and/or amount thereof to be mixed.

Figure 1B:
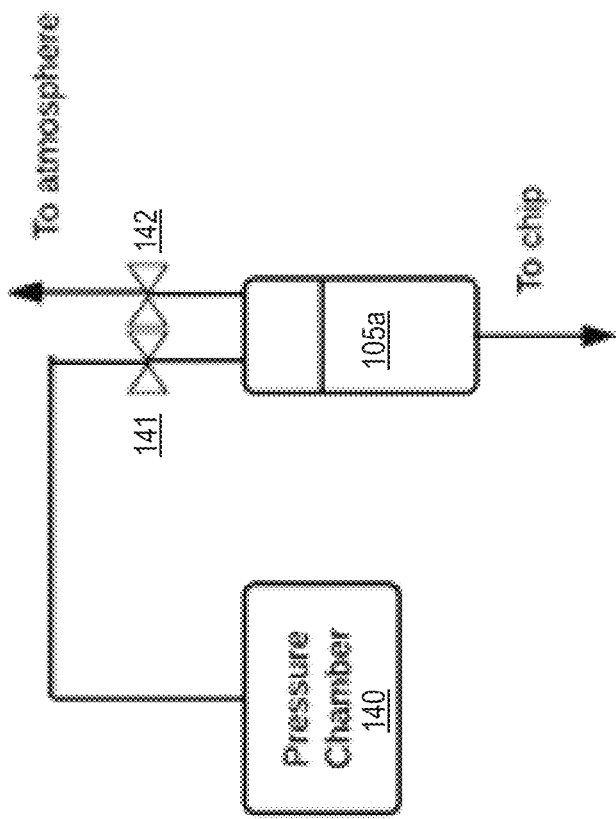
Figure 1C:
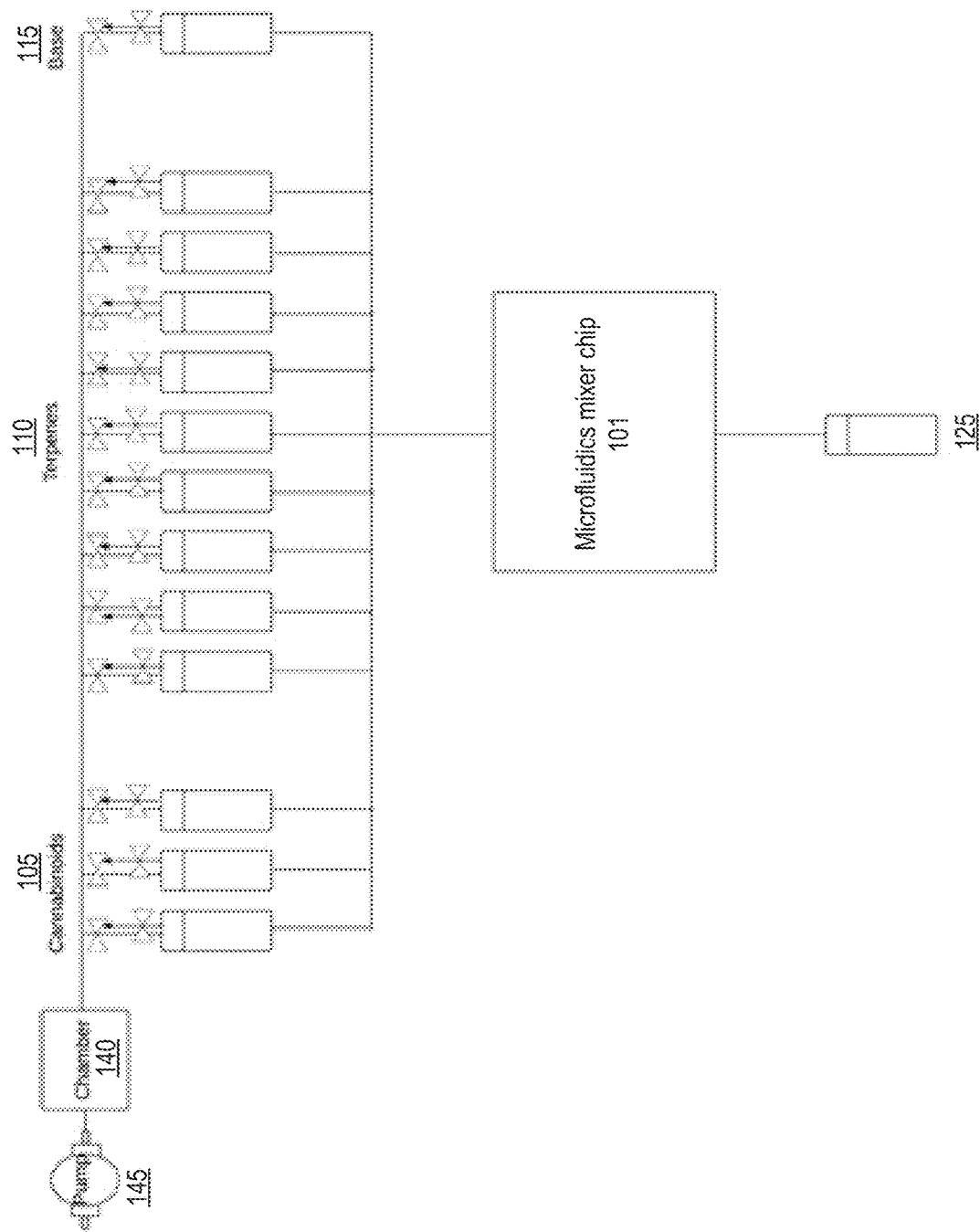

In some embodiments, fluids are moved using one or more diaphragm pumps, which can draw in a gas or fluid and forces it out due to the movement of the diaphragm. Piezo-electric diaphragm pumps can create a deformity in the diaphragm used to move the gas or fluid by applying a voltage. A variety of configurations using such pumps can be utilized for moving the fluids, depending on the embodiment. For example, a piezo-electric pump can be used to create a pressure chamber and provide a pneumatic mechanism in which the pump only pushes air into the chamber and is not in contact with the fluid. The pressure chamber can then be directed to different tanks. In some implementations, each tank can be configured with two, two-way solenoid valves that connect directly to a port on the top of the fluid tank. By controlling the solenoid valves, pressure can be applied or relieved from each fluid tank, thereby controlling the flow of fluid from the tank into the mixer chip. FIG. 1B is a diagram illustrating the pressure chamber 140 connected to a tank 105a having solenoid valves 141, 142. FIG. 1C shows a diagram illustrating single pressure chamber 140 and pump 145 incorporated into an OBD system, and where the fluid tanks in the system include two, two-way solenoid valves.

Some implementations may be configured with a single diaphragm pump, while other implementations can utilize more than one pump, and as such, may not utilize the two, two-way solenoids for each tank (and/or may reduce the number of solenoids based on using pumps for a subset of tanks). In some instances, the pressure in the chamber can be varied based on the total amount of fluid being dispensed. For example: if a smaller total volume of fluid, such as 100 microliters, is being mixed then the pressure is set to a lower level. The fluid will flow at a slower rate, providing increased control over the dispense volume. If a larger amount of fluid, such as one milliliter, is being mixed then the pressure can be set to a relatively higher level, increasing the flow rate so the user does not have to wait an extended period of time for the product. Depending on the embodiment and implementation, the percent error on the accuracy for the larger fluid and greater pressure can be comparable to that of the smaller fluid with lesser pressure.

Such pressure-driven embodiments can be configured based on the viscosities of each of the fluids (e.g., by determination when a tank is inserted and/or by providing/requiring tanks that have fluids of known viscosity). As pressure is applied to the fluid for a controlled amount of time through a microfluidic path of known dimensions, a known volume will be dispensed.

Figure 2B:
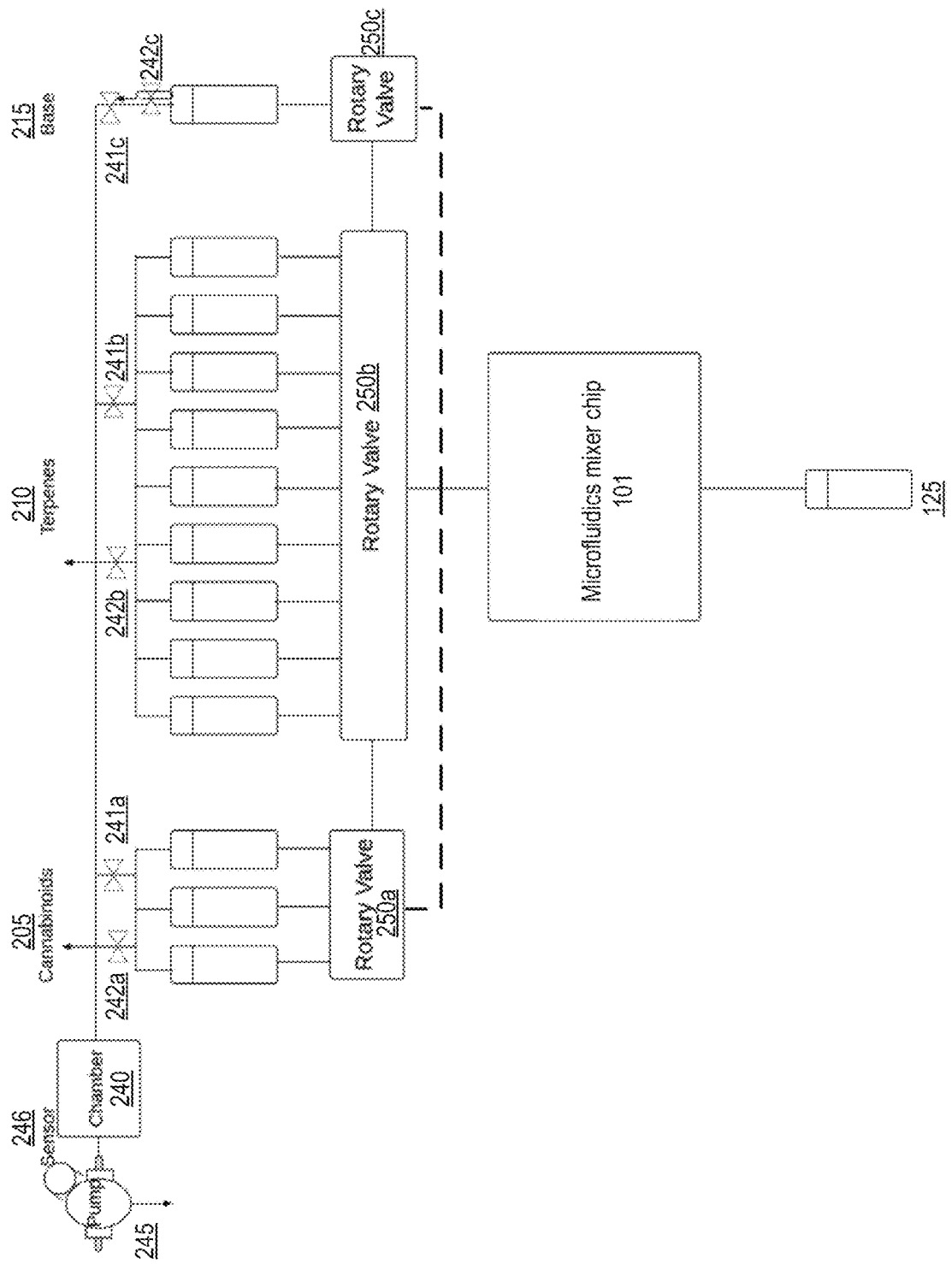

FIG. 2A illustrates a pressure-driven pneumatic system with rotary valve control according to some embodiments of the OBD. Such embodiments can include one or more rotary valves (e.g., in a mixer chip), and thereby reduce the number of valves (e.g., relative to the embodiment illustrated in FIG. 1C) required for a pressure-driven system. In some implementations of such embodiments, one, some, or each rotary valve is controlled by a servo or stepper motor in the OBD. As the OBD turns the rotary valve to a specific position, a single fluid can flow from its respective tank to the mixing chamber while obstructing all other fluid paths, as shown in the figure. FIG. 2B illustrates a pneumatic pressure-driven OBD system with rotary valves. In some embodiments, to address viscosity differences between the fluids (e.g. the viscosity difference between cannabinoids and terpenes), such a rotary valve may be provided based on groups of fluids with relatively similar viscosities (e.g., a terpenes group and a cannabinoids group). As shown in FIG. 2B, the OBD includes a pump 245, pressure chamber 240, and sensor 246, along with separate rotary valves for groups of liquids (i.e., a rotary valve 250a for cannabinoids group of tanks 205, with a two, two-way solenoids 241a, 242a for that group; similarly for the terpenes group of tanks 210 and base tank 215). Such embodiments can be configured so that each group has its own rotary valve (e.g., 250a, 250b, 250c), each with a different channel size to meet the various flow requirements for that group. The rotary valves can be connect to each other and/or connected directly to the microfluidics mixer chip 101. Table 1 below provides example viscosities of ingredients that are utilized in some embodiment of the OBD, along with their respective temperature sensitivities.

TABLE 1

| Sample | Viscosity @ 60 C. | Viscosity @ 70 C. | Sensitivity (%/C) |
| --- | --- | --- | --- |
| CBD 80% | 124.40523 | 67.07008 | 4.6 |
| CBG 80% | 46.08678 | 28.9006 | 3.7 |
| THC 80% | 582.98408 | 219.13165 | 6.2 |
| PEG | 13.20703 | 9.97539 | 2.4 |
| PG | 8.68223 | 6.10031 | 3.0 |
| Bisabolene | 1.50375 | 1.29836 | 1.4 |
| L-Borneol | 3.35655 | 2.30842 | 3.1 |
| delta-3-Carene | 0.72011 | 0.63903 | 1.1 |
| beta-Caryophyllene | 3.02548 | 2.49506 | 1.8 |
| 1-8-Cineole | 1.39024 | 1.18889 | 1.4 |
| Citronellol | 3.13805 | 2.43081 | 2.3 |
| d-Limonene | 0.59933 | 0.54232 | 1.0 |
| Linalool | 1.44909 | 1.17585 | 1.9 |
| Myrcene | 249.1163 | 221.55281 | 1.1 |
| Nerolidol | 3.44688 | 2.68387 | 2.2 |
| trans beta-Ocimene | 0.6227 | 0.55306 | 1.1 |
| alpha-Pinene | 0.82406 | 0.72887 | 1.2 |
| beta-Pinene | 0.96999 | 0.85135 | 1.2 |
| alpha-Terpinene | 0.59094 | 0.53321 | 1.0 |
| Terpinolene | 0.72378 | 0.64495 | 1.1 |
| alpha-Terpineol | 4.39011 | 3.02056 | 3.1 |

Figure 3A:
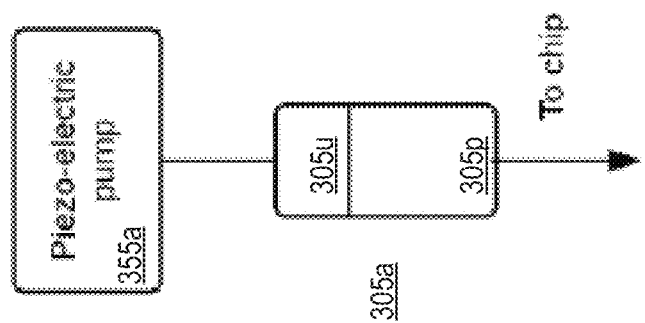
FIGS. 3A and 3B illustrate aspects of pneumatic volume-driven OBD according to some embodiments of the disclosure.
Figure 3B:
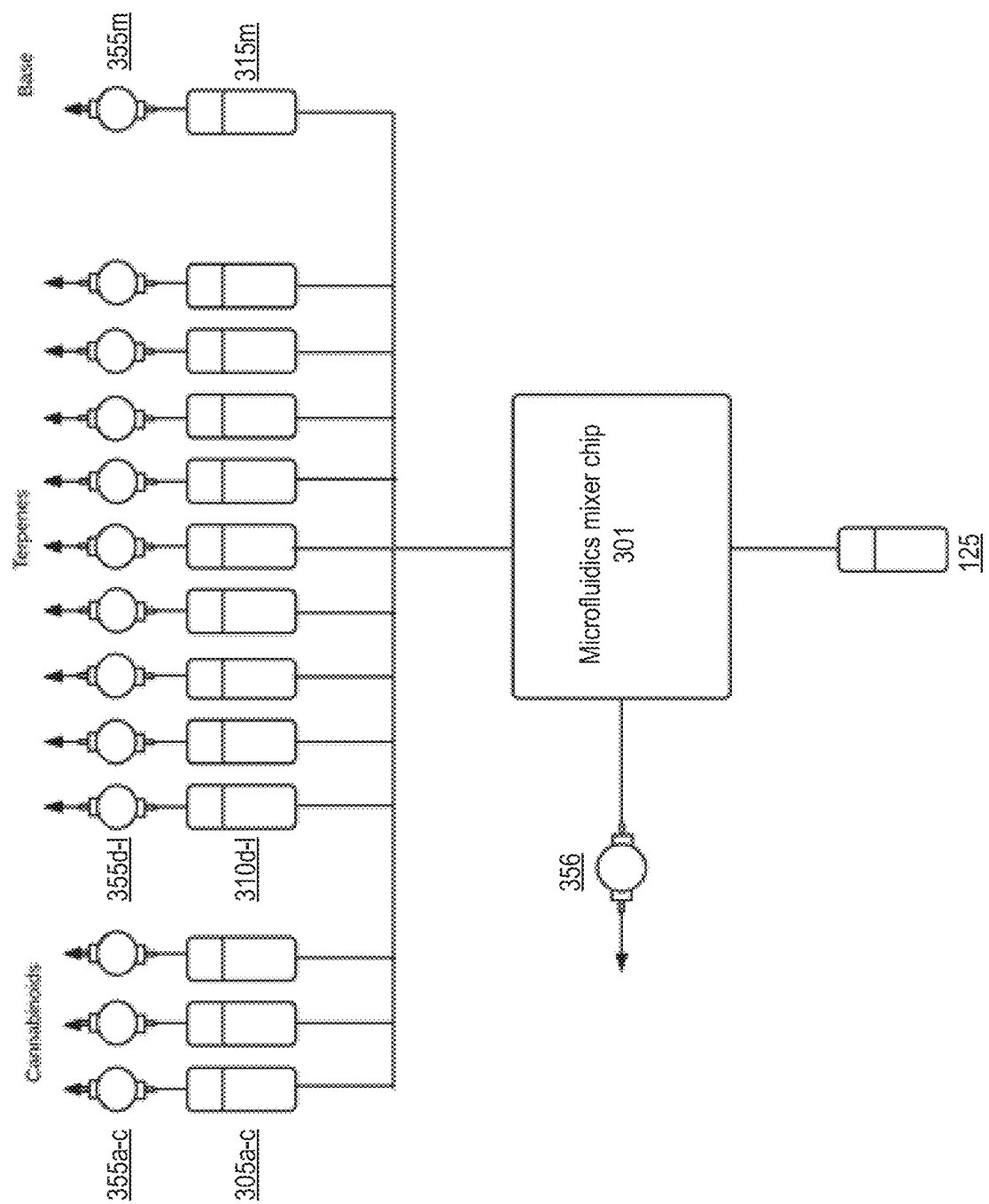

Some embodiments of the OBD include pneumatic volume-driven micropump(s). Such embodiments of the OBD can include a separate pump for each tank, and can utilize different pressures to be used to different fluids from their respective tanks. Such embodiments can in turn provide for the flow rates of fluids with different viscosities to be closer to one another and therefore facilitate coordinating the timing of the meeting of fluids/groups of fluids, in the mixing chamber and/or prior to entry into the mixing chamber. Additionally, multiple pumps can be run simultaneously and reduce the overall dispense time. FIG. 3A shows an example pneumatic volume-driven configuration using separate pump for some embodiments of the OBD. Following the configuration shown in FIG. 3A, a pump 355 can be situated above the fluid tank 305a and pumps air (and/or another gas, such as nitrogen) into the upper portion 305u of the tank, causing fluid to flow through a port 305p on the bottom of the tank to the mixer chip. In such an embodiment, since only air/gas would be flowing through the pump, the potential for cross-contamination between fluids and the potential for residual buildup within the body of the pump is reduced or eliminated. FIG. 3B illustrates pneumatic volume-driven OBD system with separate pumps 355a-m for each tank in the groups of cannabinoids tanks 305a-c, terpenes tanks 310d-1, and base tank 315m. A pump 356 (or multiple pumps) can also be provided for the microfluidics mixer chip 301. Each pump can be controlled to infuse a controlled volume of air or other gas into the respective fluid tank. The pressure in the tank rises and causes fluid to flow from the port in the bottom of the tank. As it does, the pressure in the tank will decay until it reaches equilibrium. Such embodiments can be configured to handle variable fluid flow rates resulting from such volume-based pumping (i.e., the fluid flow rate will not be constant because the pressure is changing over time).

Figure 4A:
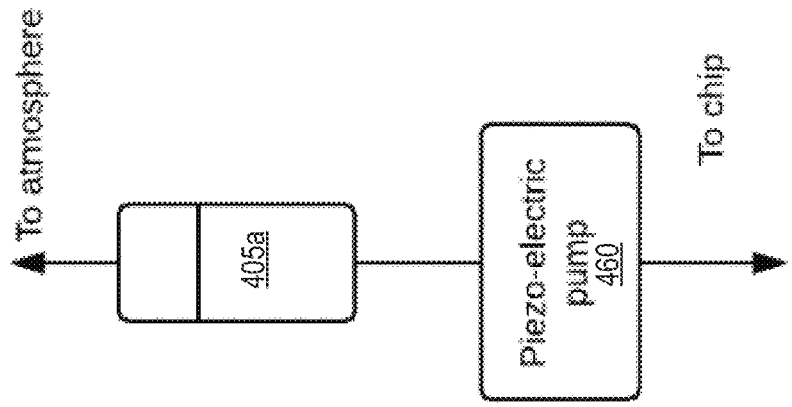
FIGS. 4A and 4B illustrate aspects of fluidic volume-driven OBD according to some embodiments of the disclosure.
Figure 4B:
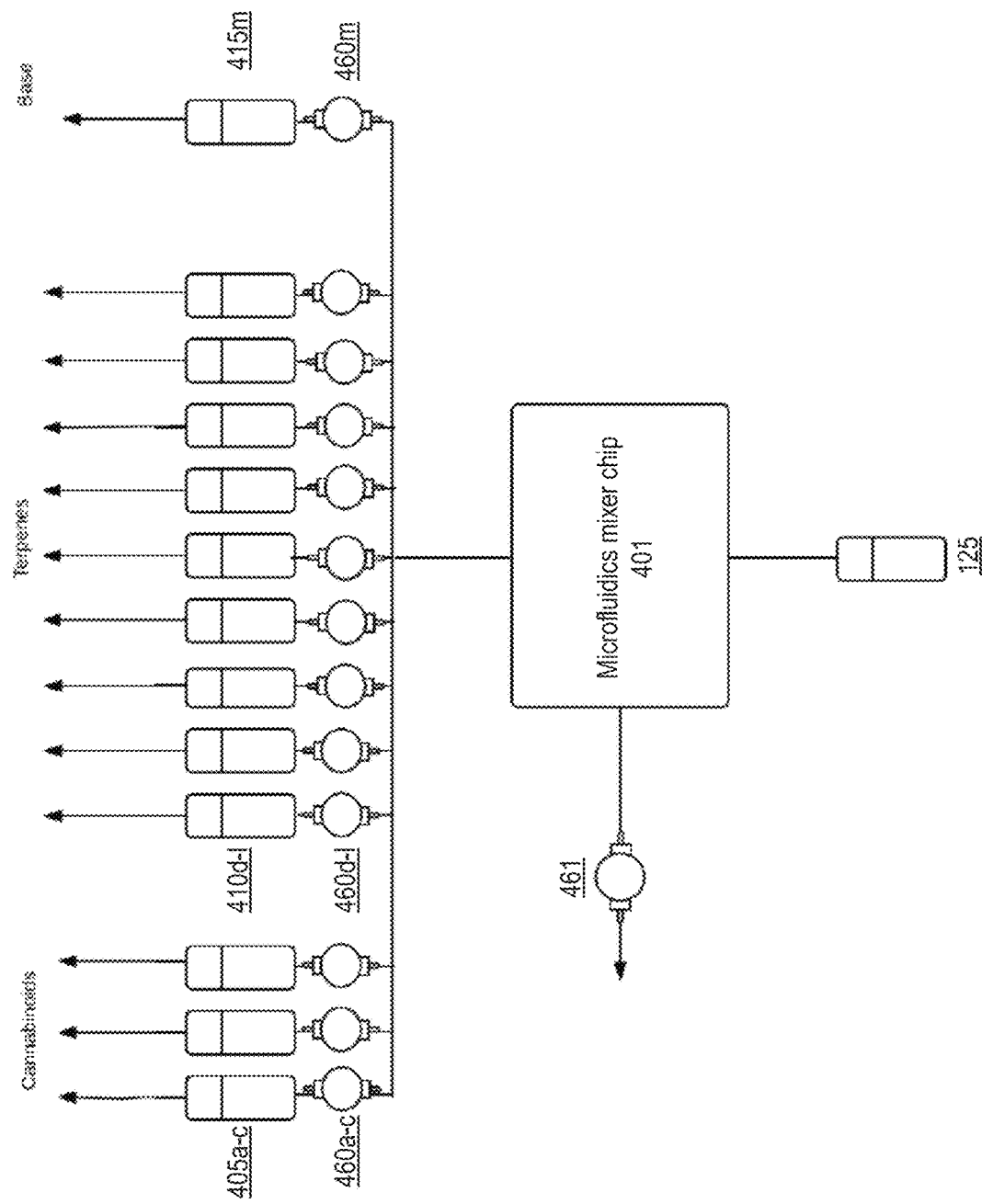

In some embodiments, the OBD is configured with one or more fluidic volume-driven micropumps, such as illustrated in FIG. 4A. In such embodiments, a pump 460 is in direct contact with the fluid from the tank 405a. Although illustrated with the tank 405a open to (i.e., in fluid communication with) the atmosphere, some embodiments can provide an inert/sterile alternative for one, some or all tanks, such as nitrogen gas. Such implementations can be configured to exposure to the atmosphere (which could contaminate and/or cause degradation of certain fluids), and/or to provide security (i.e., so no fluids could unintentionally leave the OBD if it is tipped over, etc.). Depending on the implementation, the pump can be integrated in to the tank design, or the pump can be a permanent/semi-permanent component in the OBD, and in either implementation, fluid is processed/forced through the pump 460. In configurations where pump is permanent/semi-permanent, the OBD can be configured with a cleaning/cleansing cycle to clear/remove residual fluid from the pump periodically (e.g., when swapping/changing out tanks). For embodiments where a pump is integrated into the fluid tank, the pump can be disposed of/recycled as fluids/fluid tanks are changed out. In the case of a permanent/semi-permanent pump, the OBD can be configured to purge the dead volume and any residual fluid from the system when changing fluid tanks, such as by running the pump when the fluid cartridge is removed to pump air (or other fluid/gas, such as nitrogen, water, dilute H2O2, H2O/EtOH mixture, etc.) through the line and thereby clean it out. Additionally or alternatively, the OBD can provide a clean or rinse cycle/setting in which sterile/non-toxic fluids are run through the OBD. Such a configuration can include one or more cleaning cartridges, and such cleaning cartridges can be configured for general use (i.e., cleaning the whole system) or for cleaning a particular liquid (e.g., for cleaning a cannabinoids pump, the cartridge includes a liquid (e.g., EtOH) configured to remove high viscosity liquid buildup from a cannabinoids path and pump). FIG. 4B illustrates a fluidic volume-driven OBD system with micropumps 460a-m for each tank in the group of cannabinoids tanks 405a-c, terpenes tanks 410d-1, and base tank 415*m*. In some embodiments, the base tank 415*m* and micropump 460*m* can be used to dispense the product, while in some embodiments, a separate pump 461 (or multiple pumps) can additionally or alternatively be provided for the microfluidics mixer chip 401 (to dispense the mixture and/or to clean the chip).

Although the above discussion addresses various methods and configurations as separate embodiments, it is to be understood that the disclosed methods and configurations can be used together in some embodiments of the OBD. For example, some embodiments can utilize pressure-driven pneumatics with rotary valve control in concert with fluidic volume-driven micropumps. While some aspects and features of the OBD are discussed in the context of particular embodiments for brevity and to facilitate understanding of the OBD, it is to be understood that such aspects and features are not limited to those particular embodiments. For example, if a feature or component were discussed in the context of an embodiment having pressure-driven pneumatics with solenoid valve control, it is to be understood that the disclosure includes that feature or component applied to an embodiment having volume-driven pneumatics with micropumps.

Figure 5:
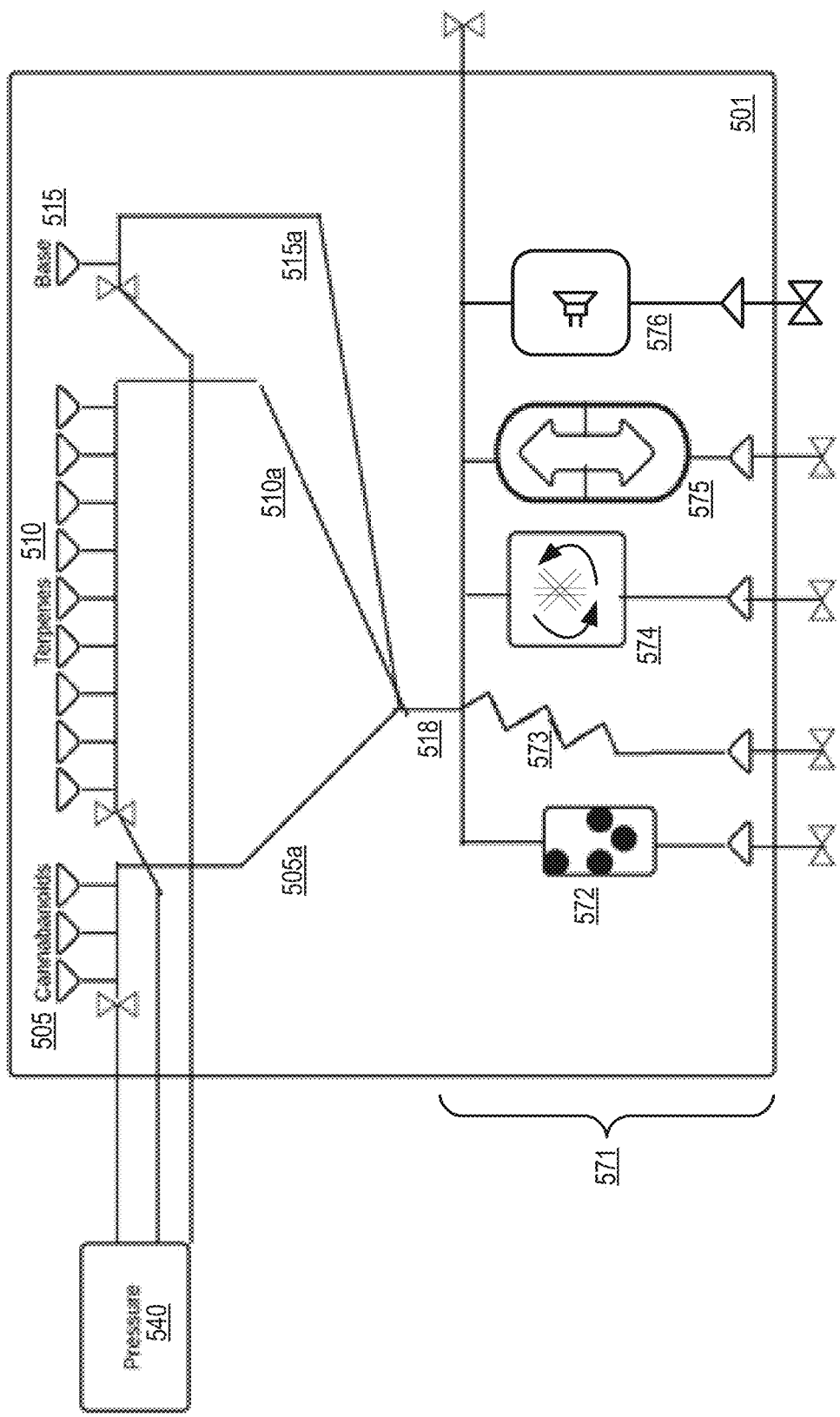
FIG. 5 is an overview of an OBD having pressure-driven pneumatics with solenoid control for a microfluidics mixer chip according to some embodiments of the disclosure.

FIG. 5 provides an overview of an embodiment of the OBD having pressure-driven pneumatics (e.g., via a pressure tank 540) with solenoid control for a microfluidics mixer chip 501. In this embodiment, the cannabinoids 505 are joined together in a group/channel 505*a* and the terpenes 510 are joined together in a group/channel 510*a*, creating three groups of fluids (505*a*, 510*a*, and the base 515*a*), with the only dead volume being that which exists in the fluid path from each tank prior to joining the main group/channel 518. The fluids then all flow towards the mixing region 571 at the same time. Since microfluidic mixing can be complicated for certain fluids, particularly fluids that have laminar flow, streamlined in the forward direction parallel to the channels, and some types of mixing microfluidics can create chaotic or potentially turbulent flow, a OBD can be configured to provide a variety of mixers/mixing options, each of which can be controlled or valved, so that, depending on the mixture/fluids, the correct mixer(s)/mixing option(s) can be utilized at the correct time(s). The fluid(s) continue down the designated mixing region(s) and are then directed to an output container. One or more passive mixers/mixing regions and/or chambers for active mixing/mixers can be incorporated into one microfluidic mixer chip. Passive mixing regions can include a region with barriers built-in the passage throughout 572, a zig-zag type mixer 573 (see also FIG. 9A), etc. (e.g., as illustrated by the microfluidic mixer chip of FIG. 9B). The barriers in 572 cause the fluids to move in a turbulent manner, and overall, forces different fluids to mix together. The zig-zag pattern mixer 573 can also cause turbulent flow and mixing. Either or both can be utilized, depending on the application/implementation, and configured to provide proper timing of the different fluids so that they reach the mixing area at the same (or substantially the same) time. Such passive mixers can have the benefit of being built into a OBD chip with no additional features (e.g., wiring) required to be added, and also may not require additional outside energy, such as electricity.

Figure 6A:
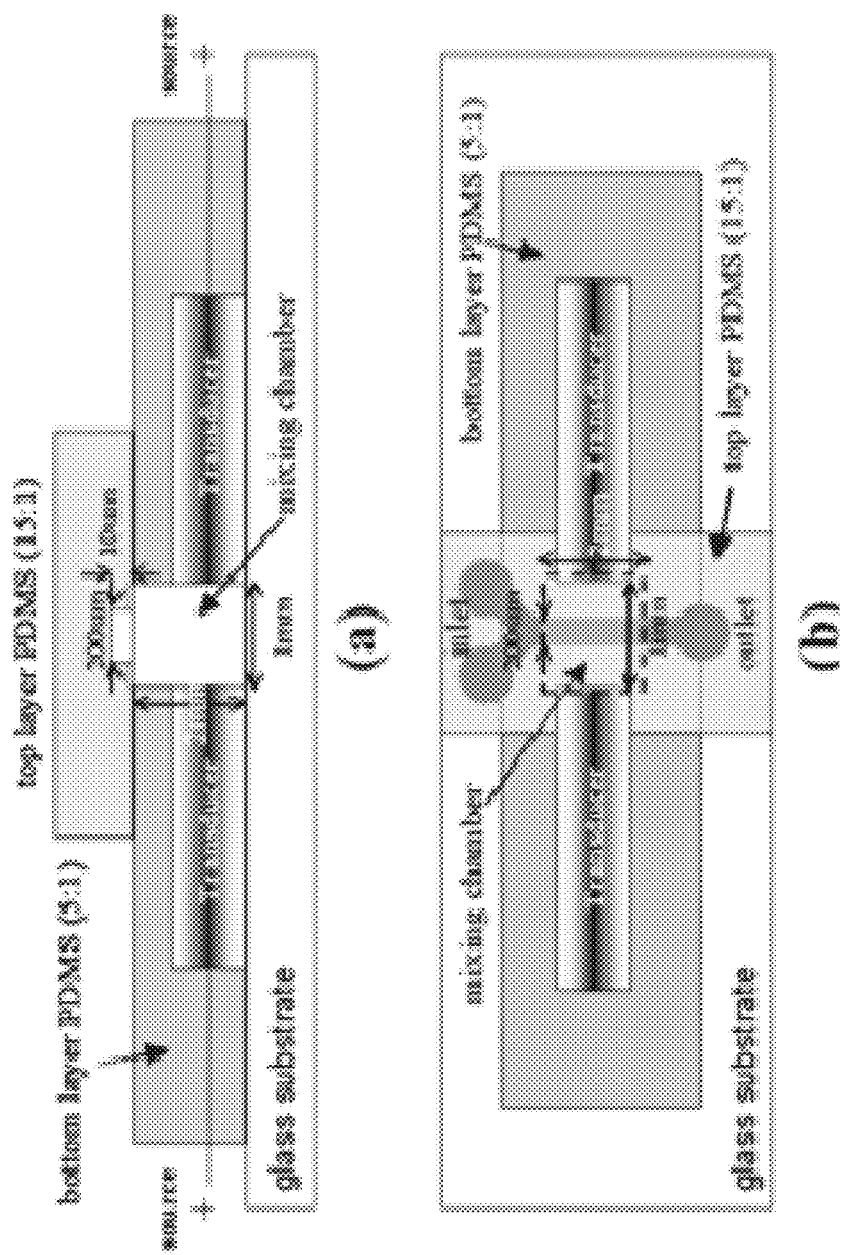
FIG. 6A illustrates aspects of embodiments of the OBD in which transducers are aligned perpendicularly around a chamber, according to the disclosure.

In some embodiments, active mixers/active mixing regions are additionally or alternatively included. Such active mixers can, for some implementations, provide more coherent/comprehensive mixing of certain fluids when compared to passive mixers. Active mixers/active mixing regions include ultrasonic wave mixing/mixers 576 and/or magnetic stirring 574. In some instances, ultrasonic wave mixing is conducted using one or more piezoelectric transducers that generate the ultrasonic waves by rapidly expanding and contracting when electrical voltage is applied. The configuration of such ultrasonic mixers can be changed depending on the implementation. As an example, the transducers can be placed such that they are aligned perpendicularly outside the chamber, as shown in FIG. 6A. The transducers in FIG. 6A are on both sides of the channel and point into the mixing region, causing mixing perpendicular to the flow of fluid and creating effective mixing. Alternatively, or additionally, a magnetic stirring mixer 574 can be provided, such as by a small stir bar disposed inside a built-in mixing region. An alternative can include a plurality of tiny magnetic beads inside such a region, either alone or in addition to a larger stir bar. A magnetic field is created by conductors, and the OBD can utilize a miniature magnetic stir plate, or conductors can be integrated into the design of the microfluidic mixer chip and/or OBD, and/or conductors could be embedded in a substrate below the channel Another active mixing region/active mixer option can utilize opening different valves to force fluid back and forth in a region 575 with a middle/central aperture (e.g., resembling an hourglass shape) that facilitates the mixing (e.g., see also the microfluidic mixer chip illustrated in FIG. 9C).

The OBD can include one or more heaters/heating elements, and such heaters and heating controlled by the OBD. In some implementations, individual paths or portions thereof in a microfluidic mixer chip can be heated based on the fluid specified for that path (e.g., a path configured to carry a substance that is wax-like at room temperature can include a heater, while a path that is configured to carry a low viscosity fluid may not include a heater). Alternatively or additionally, the OBD can be configured to heat tanks/cartridges (or a subset thereof) prior to entry of the fluid into the OBD or microfluidic mixer chip. Some embodiments can include heaters for certain tanks, while other embodiments can utilize tanks that include a heater or heat element therein. Additionally or alternatively, the microfluidic mixer chip can be heated by the OBD to facilitate measuring and mixing the different fluids.

Figure 6B:
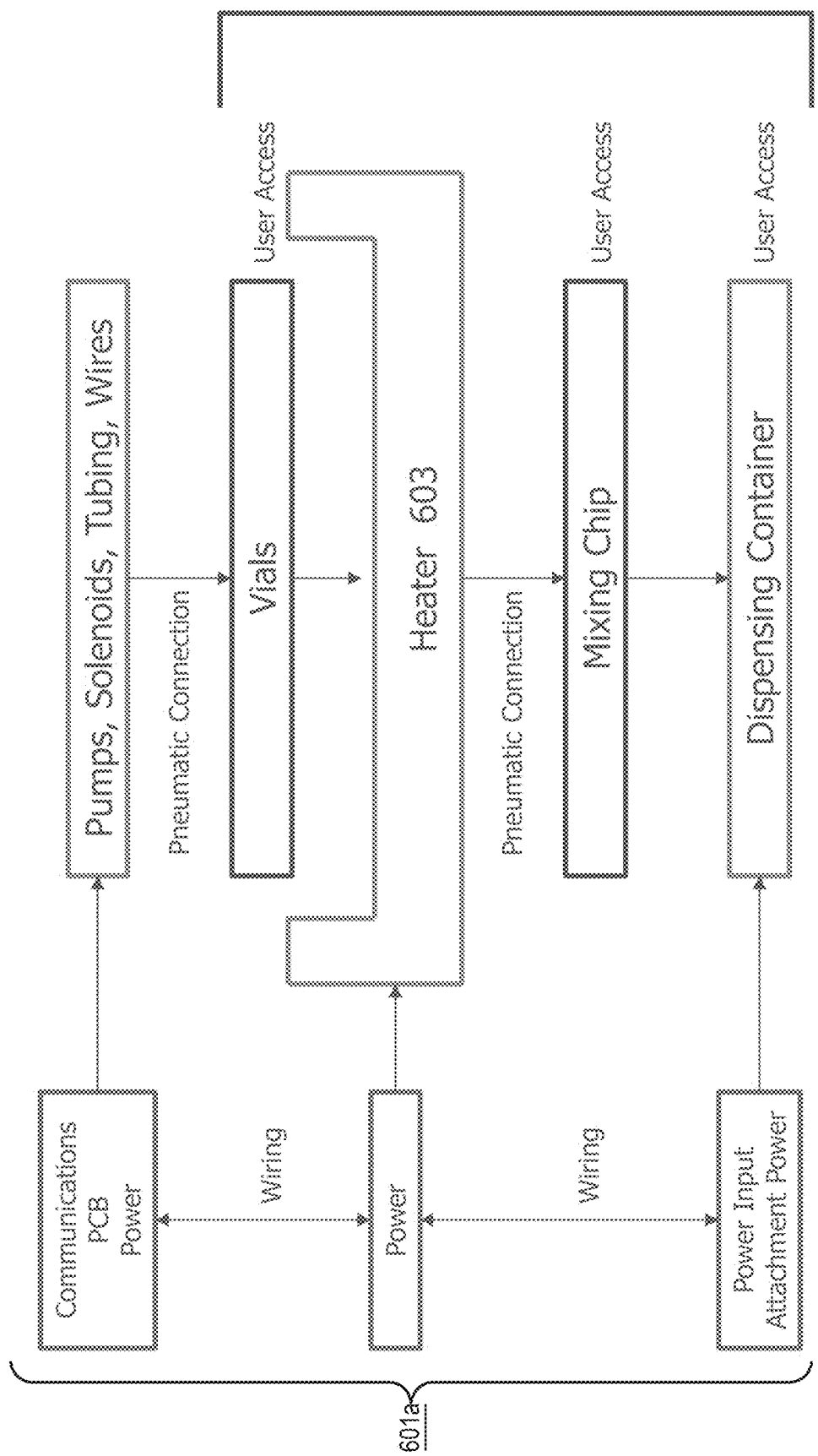
FIGS. 6B and 6C provide example OBD structures for some embodiments according to the disclosure.
Figure 6C:
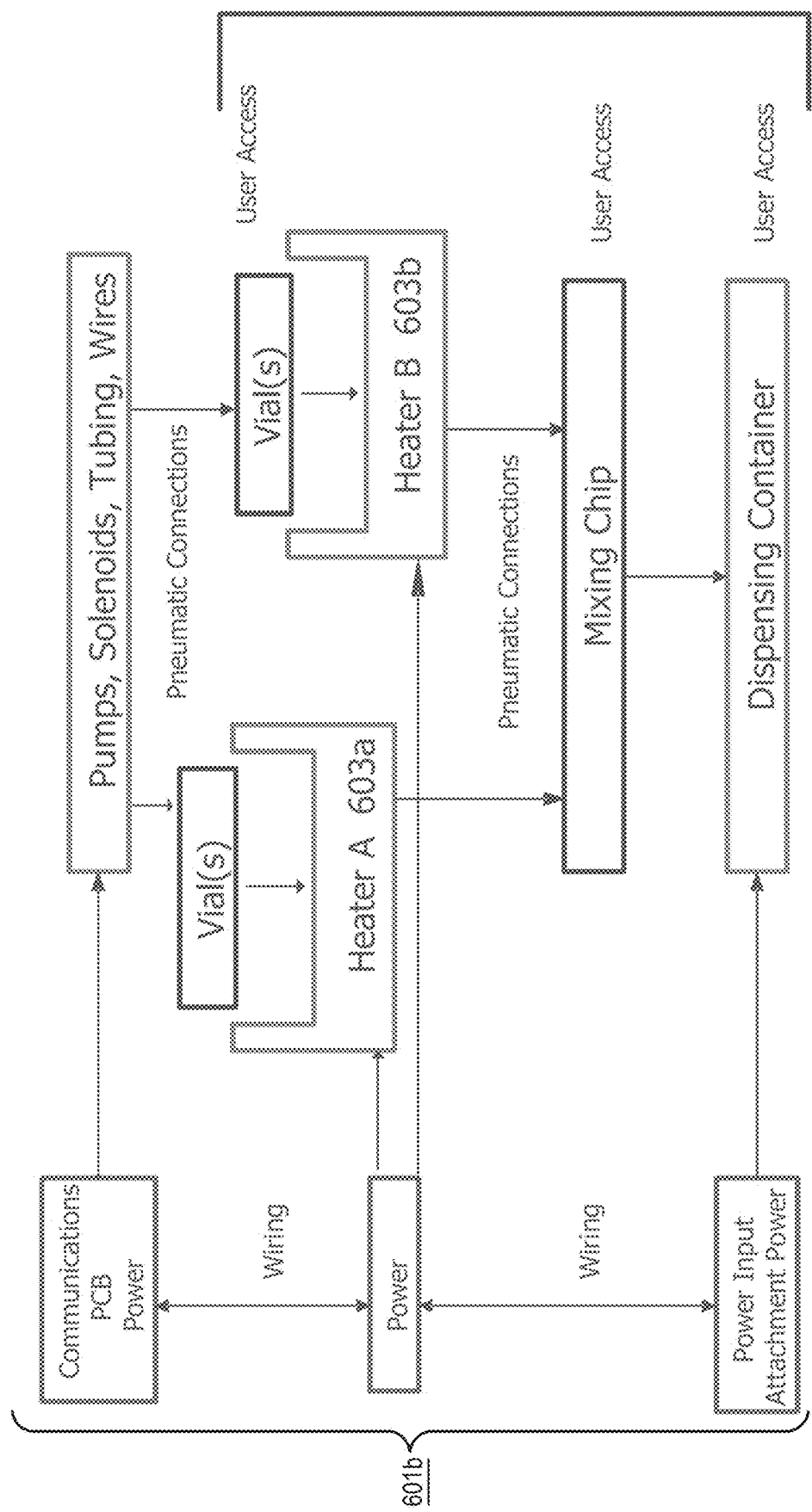

FIG. 6B and FIG. 6C provide example OBD system structures according to some embodiments. The embodiment illustrated in FIG. 6B, the OBD system 601*a* utilizes a single heater 603 to heat the vials/tanks/cartridge(s). In the embodiment illustrated in FIG. 6C, the OBD system 601*b* utilizes two heaters, 603*a*, 603*b*, to heat different groups/sets of vials/tanks/cartridge(s), and can be used to set different heats for different components/regions of the system, and/or to set one or more heat gradients or heat differentials within the OBD system 601*b*. It is to be understood that, depending on the implementation and/or embodiment, heaters can be provided for each vial, a set of vials, one or more flow paths, one or more regions, or a combination thereof, depending on the particular use and/or configuration.

Figure 7A:
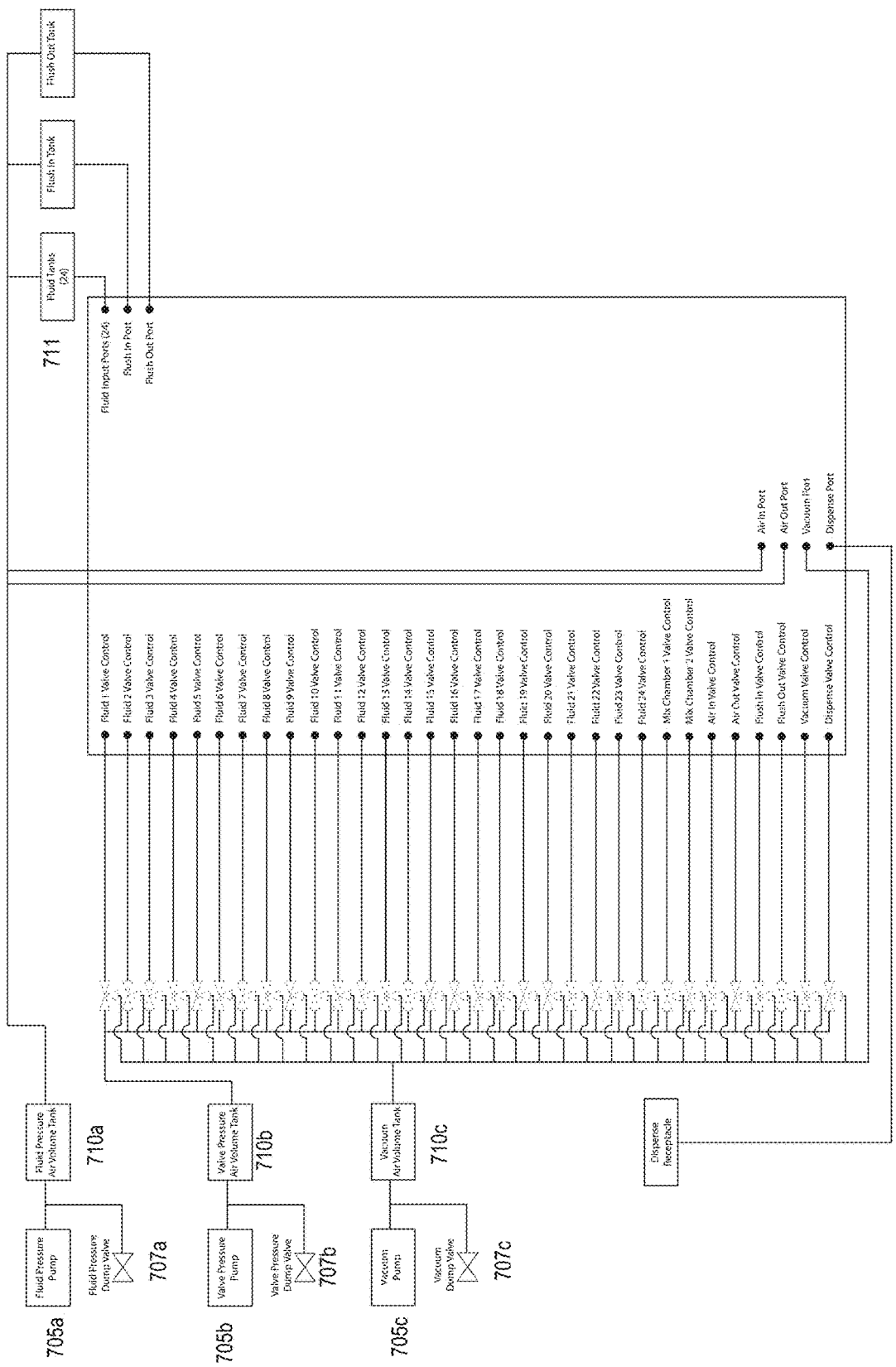
FIG. 7A provides an example fluidics diagram for some embodiments of the OBD.

FIG. 7A provides an example fluidics diagram for some embodiments of the OBD. As shown, each of the pumps (including fluid pressure pump 705*a*, valve pressure pump 705*b*, vacuum pump 705*c*), dump valves (including fluid pressure dump valve 707*a*, valve pressure dump valve 707*b*, vacuum dump valve 707*c*), and solenoid valves is independently controlled (e.g., by a mix board/mix controller/mixer controller). For example, in some embodiments, the general process is that the valve pressure air volume tank 710*b* is pressurized to a specific level (e.g., controlled by the fluid pressure pump 705*a* and dump valve 707*a*) sufficient to close the valves. Each of the valves can be configured to normally be closed such that when the solenoid is not powered the pressure from the air volume tank is applied to the valve, closing it. The fluid pressure air volume tank 710*a* is pressurized to a specific level and that pressure is applied to all of the fluid tanks 711. As the three-way solenoid associated with a tank is opened, the pressure applied to that tank causes fluid to flow at a known rate into the mixing chamber. There can also be several accessory valves (each controlled by its own three-way solenoid) that control other functions, such as opening the dispense port, introducing pressurized air at the inlet or outlet of the mixing chamber, introducing a flushing fluid at the inlet or outlet of the mixing chamber, pulling a vacuum on the outlet of the mixing chamber, and/or causing the membrane at the base of each mixing chamber to inflate, thereby evacuating the contents of that mixing chamber.

Figure 7B:
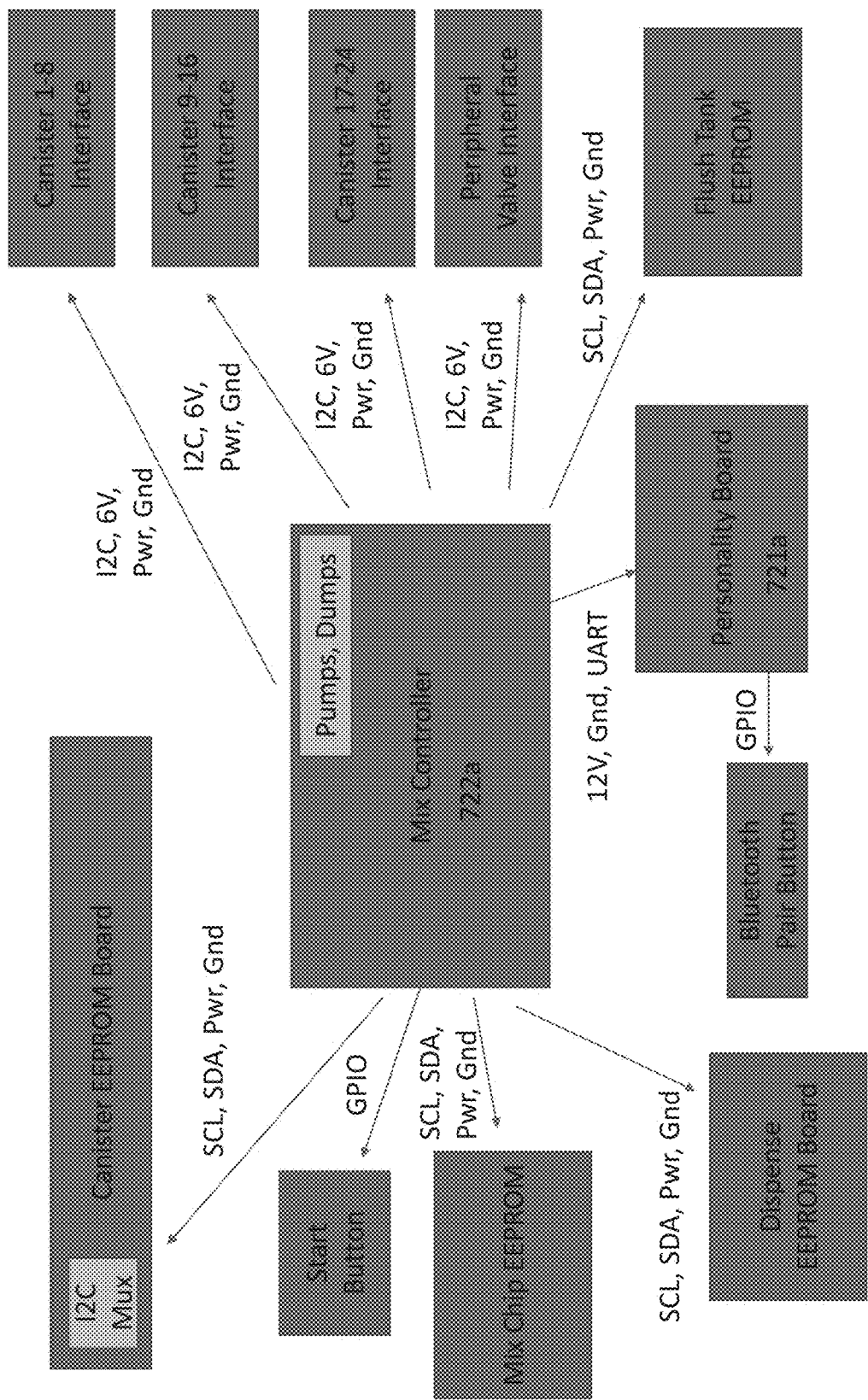
FIG. 7B provides an example electrical architecture diagram for some embodiments of the OBD.

FIG. 7B provides an example electrical architecture diagram for some embodiments, showing major electrical components of some OBD systems and how they communicate with one another. For example, a blend recipe is retrieved to and/or received at the personality board 721*a* (e.g., received from an OBD smart phone app on a smart phone), which relays it to the mix controller 722*a*. The mix controller 722*a* directly energizes the pumps and solenoids responsible for dispensing and mixing the fluids. In some embodiments, the mix controller 722*a* can also directly read information from the EEPROM on each canister to ensure that it is a valid canister and/or to allow for the OBD smart phone app to retrieve information about the contents of that canister to generate the mix instruction.

Figure 7C:
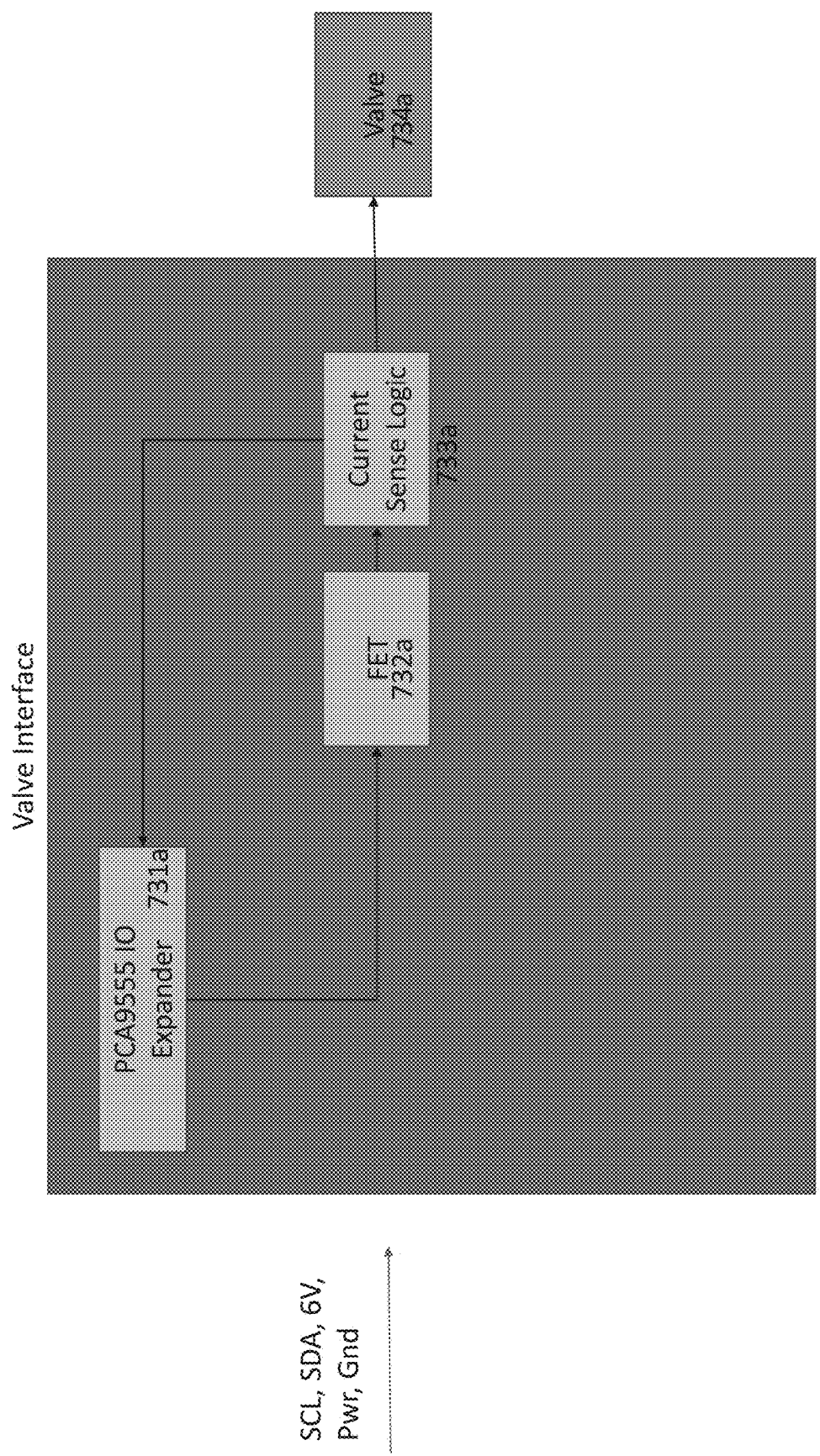
FIG. 7C provides an example basic circuitry diagram according to some embodiments of the OBD.

FIG. 7C provides an example basic circuitry diagram according to some embodiments that can be used to control each of the three-way solenoid and dump valves. In this example, the main processors on the mix controller board uses an IO expander 731*a* to drive a field effect transistor (FET) 732*a*, which applies voltage to the valve 734*a*. A current sense element 733*a* can be used to ensure that current is flowing to the valve. If the current to the valve is different from the expected value, an error can be initiated.

Figure 7D:
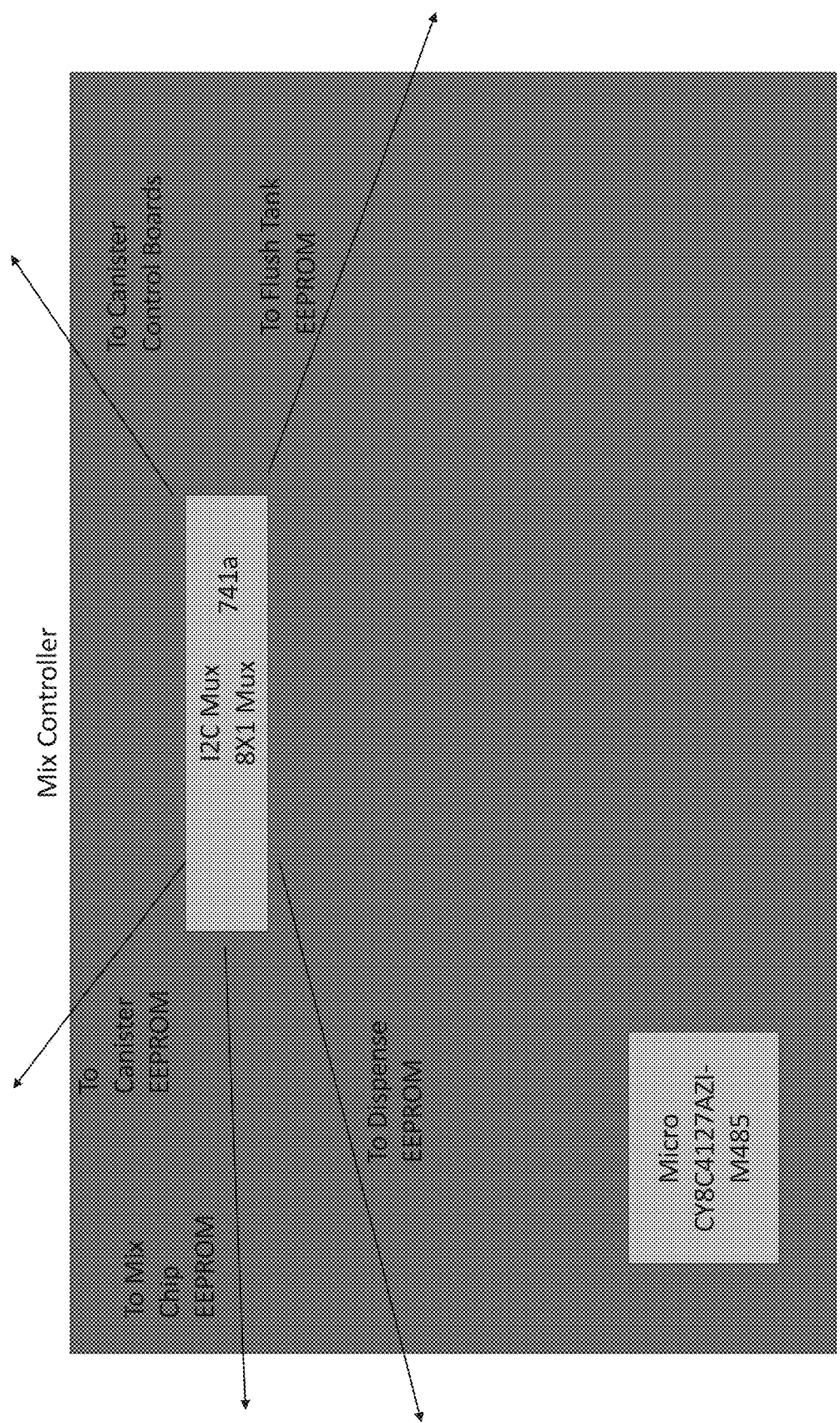
FIG. 7D and FIG. 7E provide additional electronic/circuitry details for some embodiments of the OBD.

FIG. 7D provides shows an example inter-integrated circuit (I2C) 741*a* interface used to communicate with the various peripherals, including the EEPROMs located on the canisters, microfluidic chip, flush tanks, and dispense accessory, according to some embodiments.

Figure 7E:
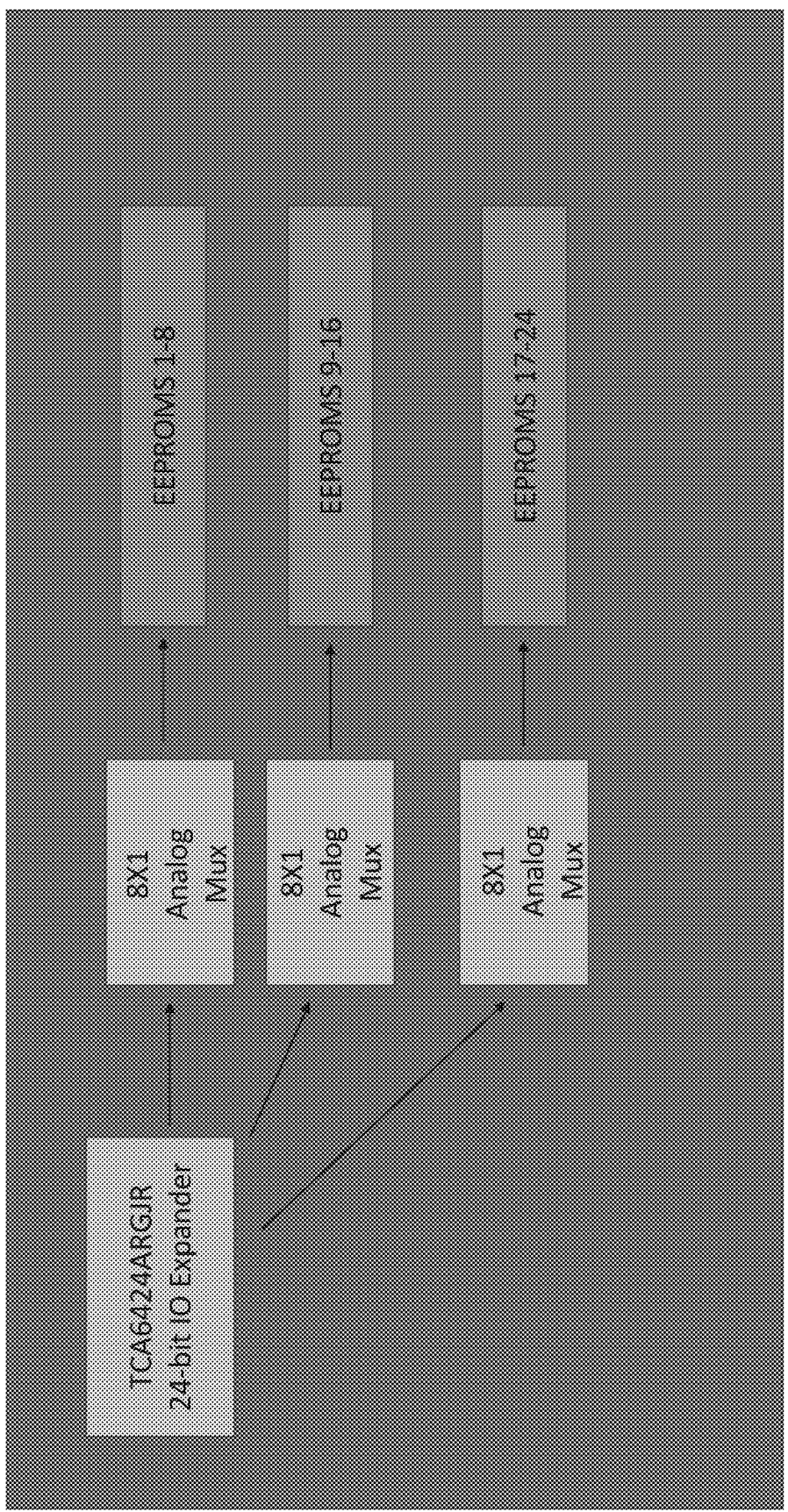

FIG. 7E provides an example use of an IO expander to communicate with three separate 8×1 analog multiplexers, each of which can read and write the EEPROMs of 8 canisters.

Figure 7F:
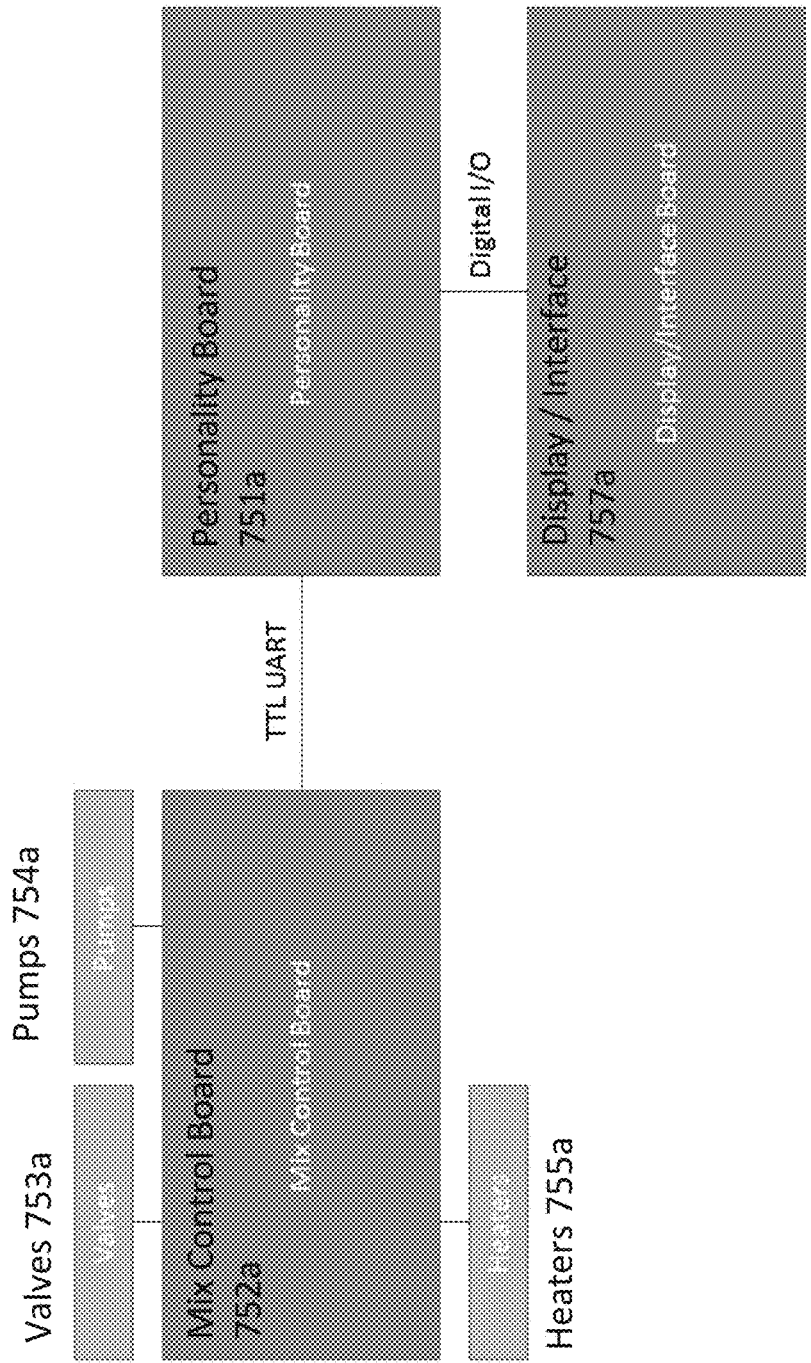
FIG. 7F provides an example electronics architecture for some embodiments of the OBD.

FIG. 7F provides an example electronics architecture showing an abstracted view according to some embodiments of the OBD system. The mixer controller/mix control board 752*a* is responsible for the control of valves 753*a*, pumps 754*a*, and heaters 755*a* and/or heater elements. The mix control board 752*a* communicates with the personality board 751*a* which can drive a display 757*a* or other interface. In some embodiments, the display 757*a* is an array of multi-colored LEDs that can, for example, be located on the personality board 751*a*, a secondary board, an LCD display, a touchscreen, and/or the like.

Below are various pin designations for example programmable system-on-chip (PSoC) processors on the mixing board and the personality board according to some embodiments of the OBD system (e.g., as discussed in FIGS. 7A-7F).

Mix Control Board
PSOC 3-100 pin (CY8C3866AXI-040)
Flash for temporary recipe storage (S25FL116K0XMFI043) (16M, 2X8)
3 PWM outputs for pump control (buffered for 6V pumps)•3 digital outputs for dump control (buffered for 6V valves)
24 digital outputs for fluid control (buffered for 6V valves)
2 digital outputs for air control (buffered for 6V valves)
2 digital outputs for flush control (buffered for 6V valves)
1 digital output for vacuum control (buffered for 6V valve)
1 digital output for dispense control (buffered for 6V valve)
2 digital outputs for mix chamber control (buffered for 6V valves)
2 digital outputs for heater control (buffered for heater voltage)
3 analog inputs for pressure sensors (buffered for +/− output from sensor)
2 analog inputs for temperature sensors
2 GPIO lines for UART
4 GPIO lines for SPI
2 GPIO lines for I2C (canister communications)

TABLE A

| Pin | Signal |
|---|---|
| P2.5 | SPI_MISO |
| P2.6 | SPI_MOSI |
| P2.7 | SPI_CLK |
| P12.4 | SPI_SS |
| P5.6 | UART_RX |
| P5.7 | UART_TX |
| P2.4 | Analog_Pressure_1 |
| P2.3 | Analog_Pressure_2 |
| P2.2 | Analog_Pressure_3 |
| P2.1 | Analog_Temperature_1 |
| P2.0 | Analog_Temperature_2 |
| P12.0 | I2C_SCL |
| P12.1 | I2C_SDA |
| P12.5 | DigOut_Canister1 |
| P6.4 | DigOut_Canister2 |
| P6.5 | DigOut_Canister3 |
| P6.6 | DigOut_Canister4 |
| P6.7 | DigOut_Canister5 |
| P5.0 | DigOut_Canister6 |
| P5.1 | DigOut_Canister7 |
| P5.2 | DigOut_Canister8 |
| P5.3 | DigOut_Canister9 |
| P1.2 | DigOut_Canister10 |
| P1.5 | DigOut_Canister11 |
| P1.6 | DigOut_Canister12 |
| P1.7 | DigOut_Canister13 |
| P12.6 | DigOut_Canister14 |
| P12.7 | DigOut_Canister15 |
| P5.4 | DigOut_Canister16 |
| P5.5 | DigOut_Canister17 |
| P15.0 | DigOut_Canister18 |
| P15.1 | DigOut_Canister19 |
| P3.0 | DigOut_Canister20 |
| P3.1 | DigOut_Canister21 |
| P3.2 | DigOut_Canister22 |
| P3.3 | DigOut_Canister23 |
| P3.4 | DigOut_Canister24 |
| P3.5 | DigOut_AirControl1 |
| P3.6 | DigOut_AirControl2 |
| P3.7 | DigOut_FlushControl1 |
| P15.2 | DigOut_FlushControl2 |
| P15.3 | DigOut_VacuumControl |
| P12.2 | DigOut_DispenseControl |
| P12.3 | DigOut_MixControl1 |
| P4.0 | DigOut_MixControl2 |
| P4.1 | PWM_Pump1 |
| P4.2 | PWM_Pump2 |
| P0.0 | PWM_VacuumPump |
| P0.1 | PWM_Heater1 |
| P0.2 | PWM_Heater2 |

A2D scaled for 0 to 6.144V Bluetooth Personality Board (in some embodiments)
PSOC4 for BLE interface (CY8C4248LQI-BL483)
Flash for recipe storage (S25FL512SAGMFI011) (512M, 64×8)

USB-to-UART for USB interface (FTDI FT230XS-R)
12-output SPI DAC to drive LED driver for interface LED control (AD8804ARZ)
2 GPIO for UART to mix control board
2 GPIO for UART-to-USB interface
5 GPIO for SPI
1 GPIO for interface button

TABLE B

| Pin | Signal |
| --- | --- |
| P1.4 | UART_MIX_Rx |
| P1.5 | UART_MIX_Tx |
| P0.0 | UART_USB_Rx |
| P0.1 | UART_USB_Tx |
| P3.0 | SPI_MISO |
| P3.1 | SPI_MOSI |
| P3.2 | SPI_CLK |
| P3.3 | SPI_SS_FLASH |
| P3.6 | SPI_SS_DAC |
| P3.7 | DigIn_InterfaceButton |
| P3.5 | DigOut_Bluetooth_LED |
| P3.4 | DigOut_LEDDriver_Enable |

In some embodiments, the 2 UARTs and SPI fill the resources of the PSOC4 when running the BLE (BLUETOOTH low energy) stack. In some implementations, no additional internal digital peripherals (PWM, etc) can be used. In some implementations, there are spare GPIO pins for reading status lines, etc. In some implementations, the A2D can be utilized.

According to some embodiments, an OBD mix control board can utilize a specified communications protocol to communicate with a host, e.g., via a USB-based and/or UART-based communication interface. In such embodiments, the host can send the mix control board a command in the packet format. The mix control board can respond with a response packet, e.g., of the same format, to notify if the command was processed successfully or not.

As discussed above, in some embodiments, the OBD includes a personality board providing communications path(s). In some embodiments, the personality board provides, for example, a BLUETOOTH 4.0 interface (BT4) and/or a USB interface. In some embodiments, the BT4 or similar interface is configured to be used by tablet and smart phone OBD applications to communicate with the OBD main device. The USB interface can be configured to facilitate firmware updates, manufacturing tests, service troubleshooting, etc.

In some embodiments, regardless of communication methodology (e.g., BLE, USB, etc.) 20 byte communications packet (such as discussed above in Table C) is used. In some embodiments, the communication and security can be handled via the BLE interface. In some embodiments, for the OBD to respond to BLE or USB commands, a security mechanism or control must be released in order for the OBD to respond to commands. The security mechanism/control prevents unauthorized access to the OBD. In some embodiments, the communications cycle comprises (a) host constructs communications packet it wishes to send to OBD; (b) if release security is required for the command, then host releases security; (c) host writes n-byte communications to a first characteristic; (d) after the BLE write complete response, the host can read the response data from first or second characteristic. The host can also monitor notifications for second characteristic, and read the response from second characteristic when the characteristic is notified. The security mechanism(s) or control(s) are configured to prevent unauthorized access to the OBD. For example, even though BLUETOOTH data packets are encrypted, BT4 communication may still be vulnerable to being spied upon by unauthorized listeners. OBD implements security features so that unauthorized listeners cannot discover the OBD command protocol and command the device to perform unwanted acts. When the security is active, the OBD will not execute commands. As an example, a security mechanism or tool can be implemented in the following manner: the mobile OBD application on the mobile device can ask the OBD for its security key using. The OBD will generate a specified number of random bytes and then use an encryption formula to calculate the proper response from the application. The application receives the random bytes from the OBD and perform the encryption formula. The application will then send the random bytes of the encrypted data to the OBD via a specified characteristic. OBD can check to see if the mobile application's encryption matches the OBD encryption. If the encrypted data matches, security is released and the OBD can respond to commands. However, if invalid encrypted data is received (e.g., received 3 consecutive times), the OBD can be configured to lock down and no longer process release security commands. Such embodiments can prevent or reduce the success of brute force hack attacks on the security mechanism. In some embodiments, the power to the OBD must be cycled to release the lock down.

Figure 8A:
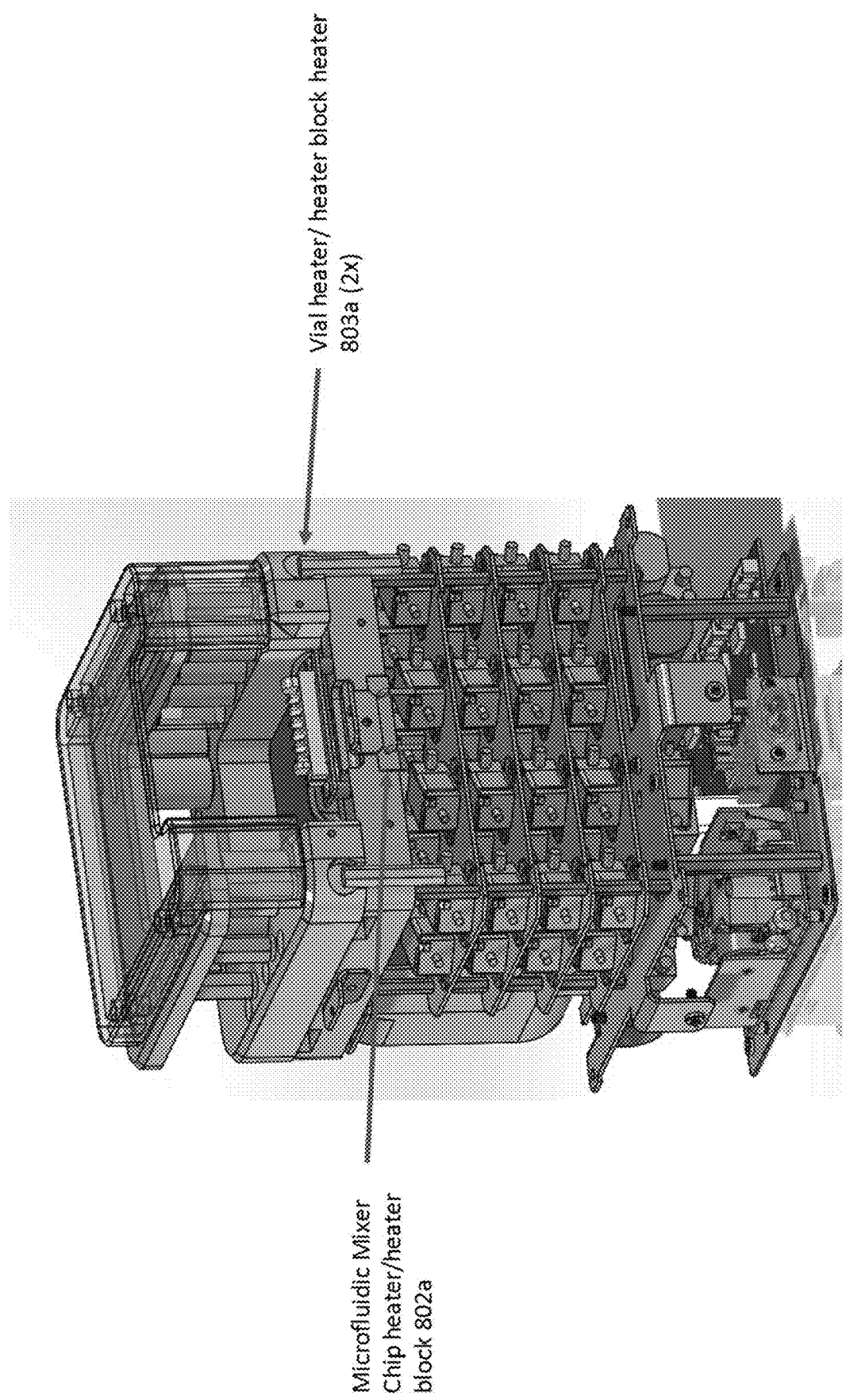
FIG. 8A provides an overview of heating the OBD for some embodiments.

In some embodiments, heating the fluid vials and the microfluidic mixer chip can be necessary to achieve the mixing of the fluids of varying viscosities, and thus important or vital to correct, accurate, and reliable OBD system performance. The heaters/heater elements are configured to control the viscosity of the flow through the OBD system precisely. In some implementations, as illustrated in FIG. 8A, this control of heating and/or providing a specified heating to various parts of the system can be used to normalize the fluid flow, and can include heating the fluids in both the vials/reservoirs and through the mixing operation (i.e., through the flow paths and/or in the microfluidic mixer chip). Such embodiments can use a microfluidic mixer chip heater 802a (and/or heater block, heater element(s), etc.), and one or more vial/reservoir heaters 803a (and/or heater block(s), heater element(s), etc.). Heaters and/or heater blocks can include and/or be formed from a variety of materials (steel, aluminum, ceramic, etc.) and can be powered by a variety of sources (resistance heating, induction heater, radiant heating, radio heating, combustion heating, etc.).

Figure 8B:
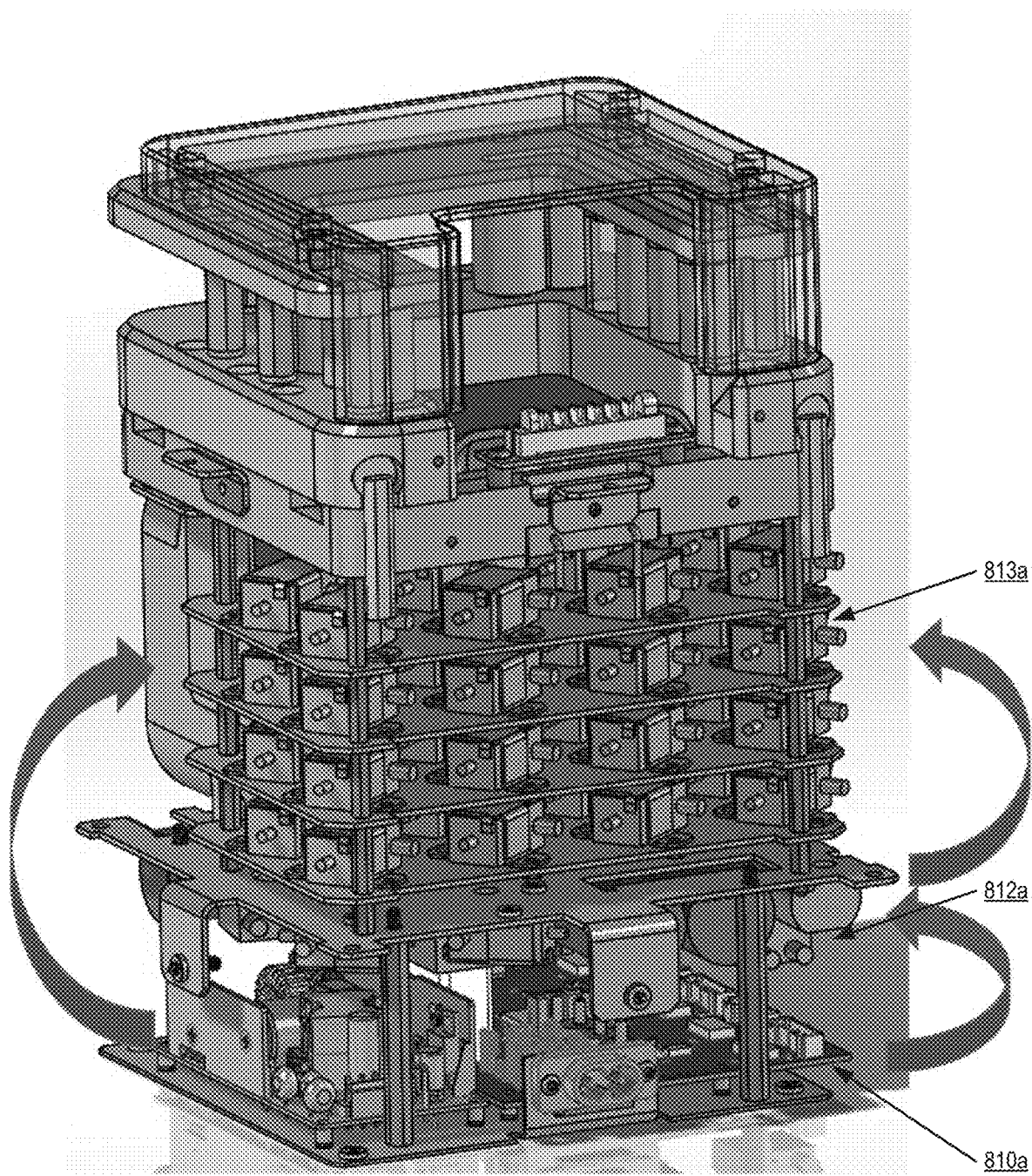
FIG. 8B and FIG. 8C provide an overview of microfluidic control in the OBD, according to some embodiments.
Figure 8C:
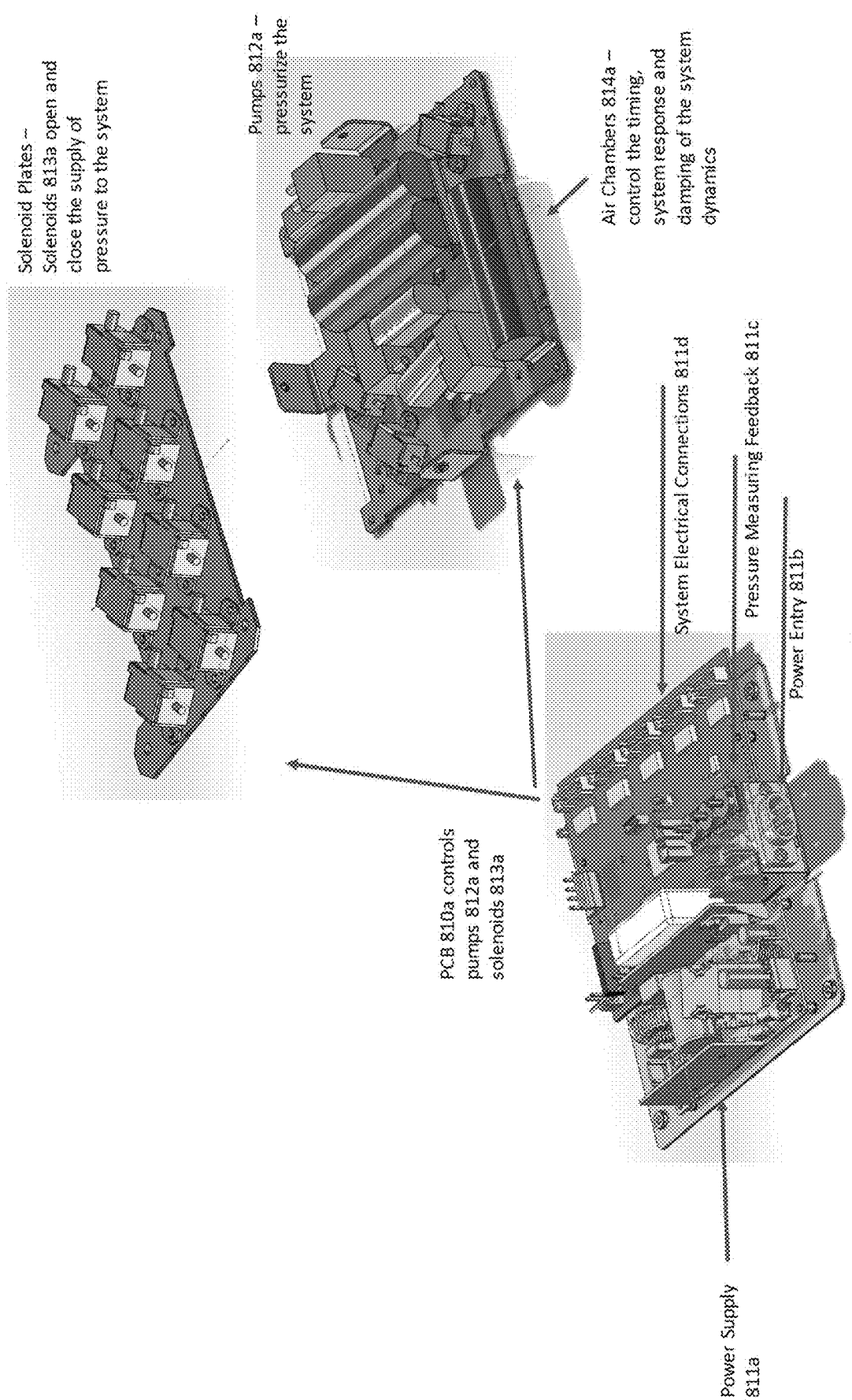

FIG. 8B shows the internal structure for some embodiments of the OBD, including a mixer controller/PCB 810a, pumps 812a, solenoid plates/solenoids 813a. As illustrated in FIG. 8C, the mixer controller/PCB 810a includes and/or is connected to a power supply 811a, a power entry/power port 811b, pressure measuring feedback sensors/input 811c, and/or system electrical connections 811d. The mixer controller/PCB 810a is configured to control pumps 812a and solenoids 813a. The solenoid plates/solenoids 813a open and close the supply of pressure to the system, and the pumps 812a pressurize the system. Air chambers 814a can be utilized by the OBD to control the timing, system response, and/or damping of system dynamics.

FIG. 8D provides an overview of example system user feedback for some embodiments of the OBD where a main controller/mixer controller/PCB 810a communicates to a user feedback component, such as a user feedback PCB 820a, that can communicate with and/or alert a user with a communication component 821a (such as a controllable OBD logo) regarding operational details and/or status. For example, the user feedback PCB 820*a* can control an LED or series of LEDs 822*a* and the OBD logo 821*a* can comprise a series of light pipes connected to LEDs 822*a* on the user feedback PCD 820*a*.

Figure 8F:
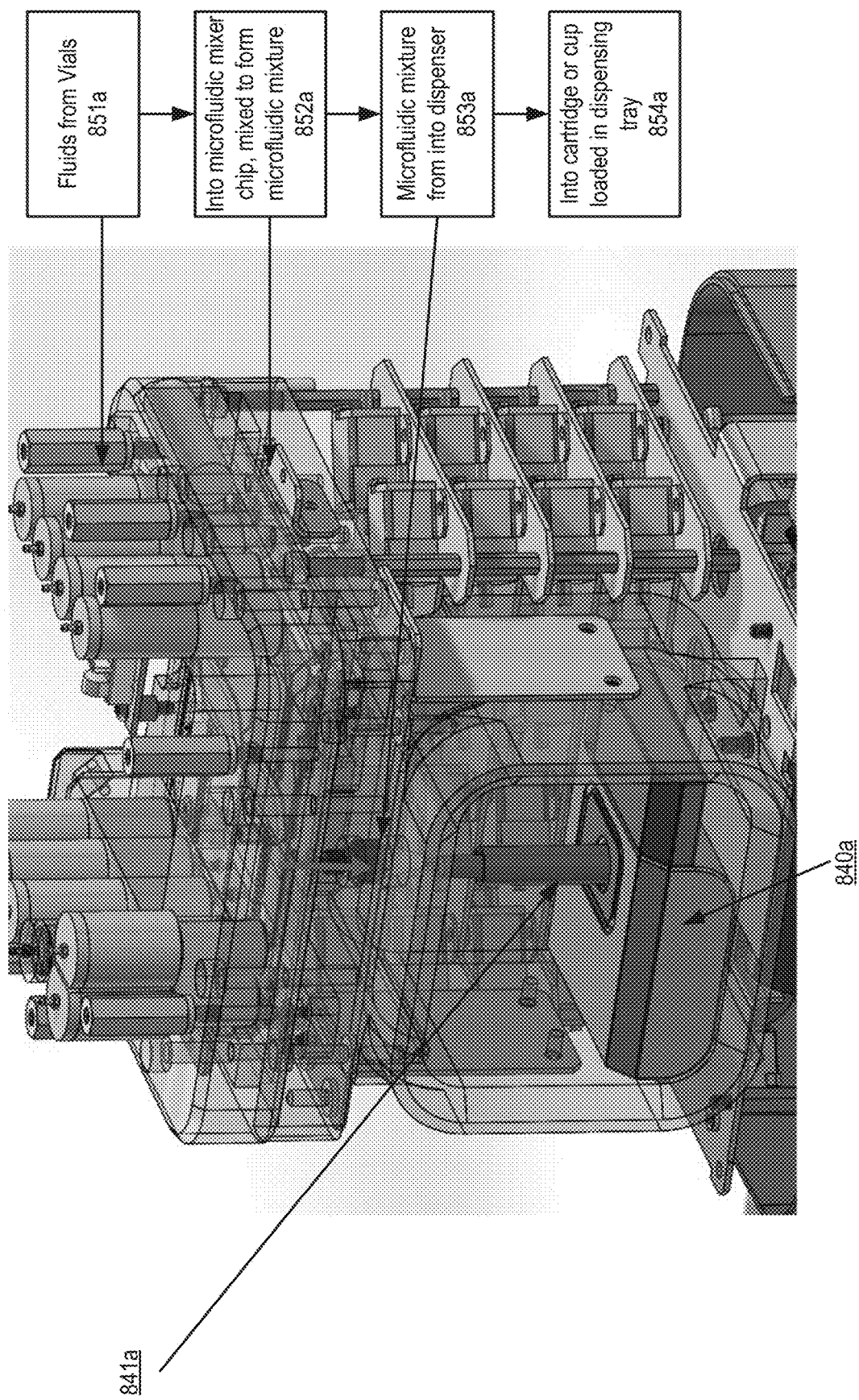

FIG. 8E shows an embodiment where a dispensing tray 840*a* is removed from an OBD system. Such a tray can be used to facilitate secure and efficient loading of vessels/receptacles, as well as make it easier for a user utilize the system (i.e., by not requiring them to manually align a receptacle for the microfluidic mixture). The tray 840*a* can be loaded with a dispensing/receiving cartridge/receptacle 841*a* or cup, and the loaded tray can be inserted, attached, and/or latched back into the OBD system in the dispense cavity. In some embodiments, latch or attachment mechanisms, such as magnets, can be used to secure the tray 840*a* to the OBD prior to dispensing the microfluidic mixture. In some embodiments, the OBD can be configured with releasable attachment mechanisms (electromagnetic latches, actuated latches, etc.). In some embodiments, the OBD can be configured to only accept specified receptacles, such as vape cartridges, OBD vials, etc., to control safety and purity of the dispensed microfluidic mixture. As illustrated in FIG. 8F, fluids from the vials flow 851*a* into the microfluidic mixer chip where they are mixed to form the microfluidic mixture 852*a* which is transferred into the dispenser 853*a* and from the dispenser into a cartridge or cup 854*a* loaded in the tray.

Figure 8G:
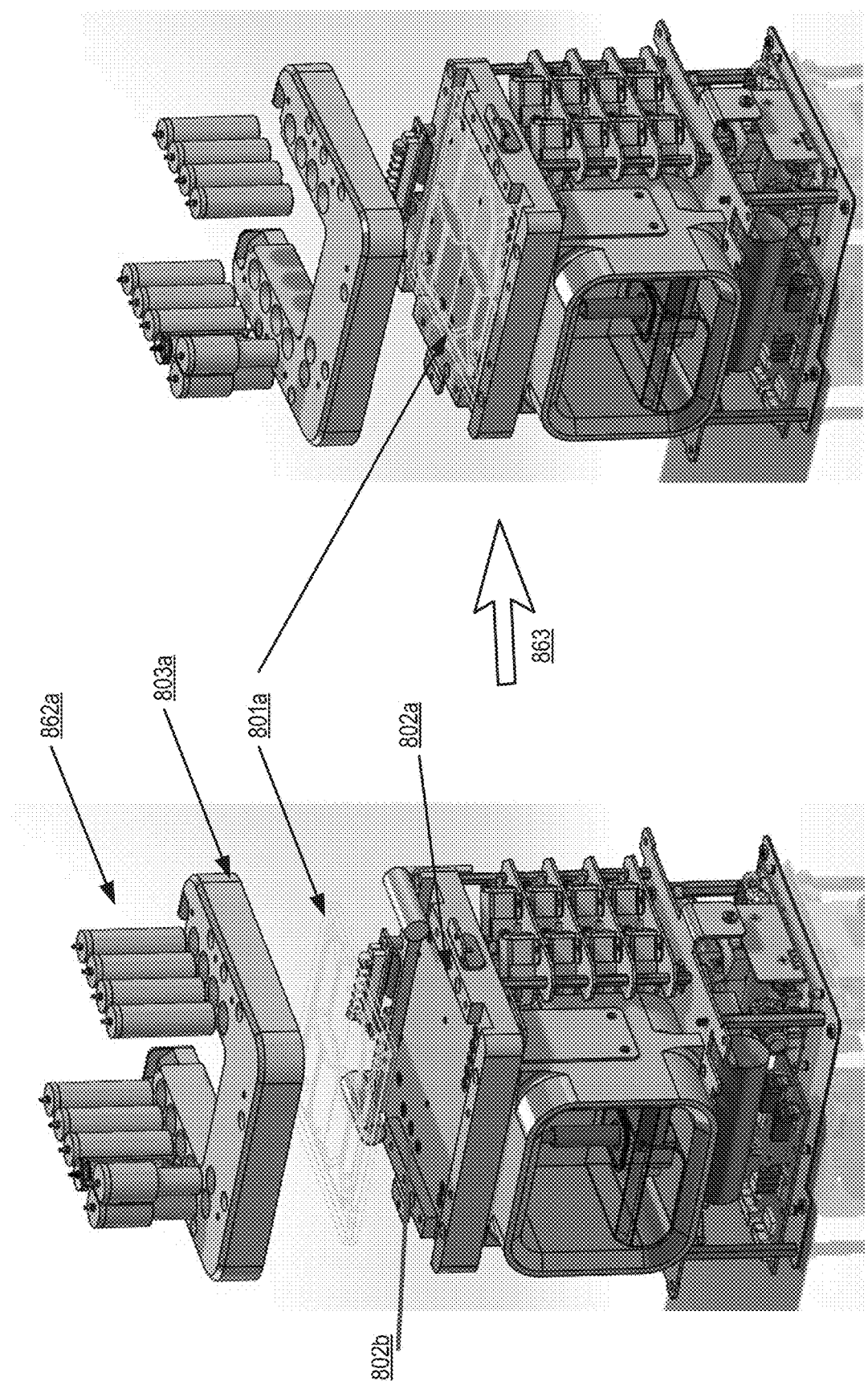
FIG. 8G provides an overview of inserting and/or replacing a microfluidic mixer chip, for some embodiments of the OBD.

FIG. 8G provides an overview of inserting and/or replacing a microfluidic mixer chip, for some embodiments of the OBD. To load or reload a microfluidic mixer chip (for example, for a new use, such as fragrance making, after using the OBD for medical, recreational, or cooking application), the vials 862*a* and vial heater 803*a* are raised up. If there is an existing microfluidic mixer chip, it can be removed from the mixer chip heater block 802*a* and a new microfluidic mixer chip 801*a* placed down 863 on the mixer chip heater block 802*a*. In some embodiments, the mixer chip heater block 802*a* can include connection ports 802*b* that allow system pneumatics to directly couple to the microfluidic mixer chip 801*a*. In some such embodiments, the mixer chip heater block 802*a* both heats the microfluidic mixer chip 801*a* and provides the pneumatic path to the microfluidic mixer chip 801*a* so that valves can be opened and closed, allowing fluids to flow.

FIG. 8H provides an overview of inserting and/or replacing fluid vials for some embodiments of the OBD. To load or reload one or more vials (e.g., if an ingredient has run out or the user wishes to try a new ingredient), any old or empty vials are removed from the vial heater 803*a*, the vial heater is lowered onto and/or secured over the microfluidic mixer chip 801*a*, and new or replacement vials 862*a* are placed into the vial heater 803*a*. Then a cap 865*a* is lowered onto the vials to create a seal, on both the top interface of the vial(s) and with the bottom interface with the microfluidic mixer chip, thereby connecting and sealing the pneumatic system of the OBD. The cap 865*a* can comprise a unitary cap and/or comprise multiple caps, such as a sealing cap and a cable management cap.

Figure 8I:
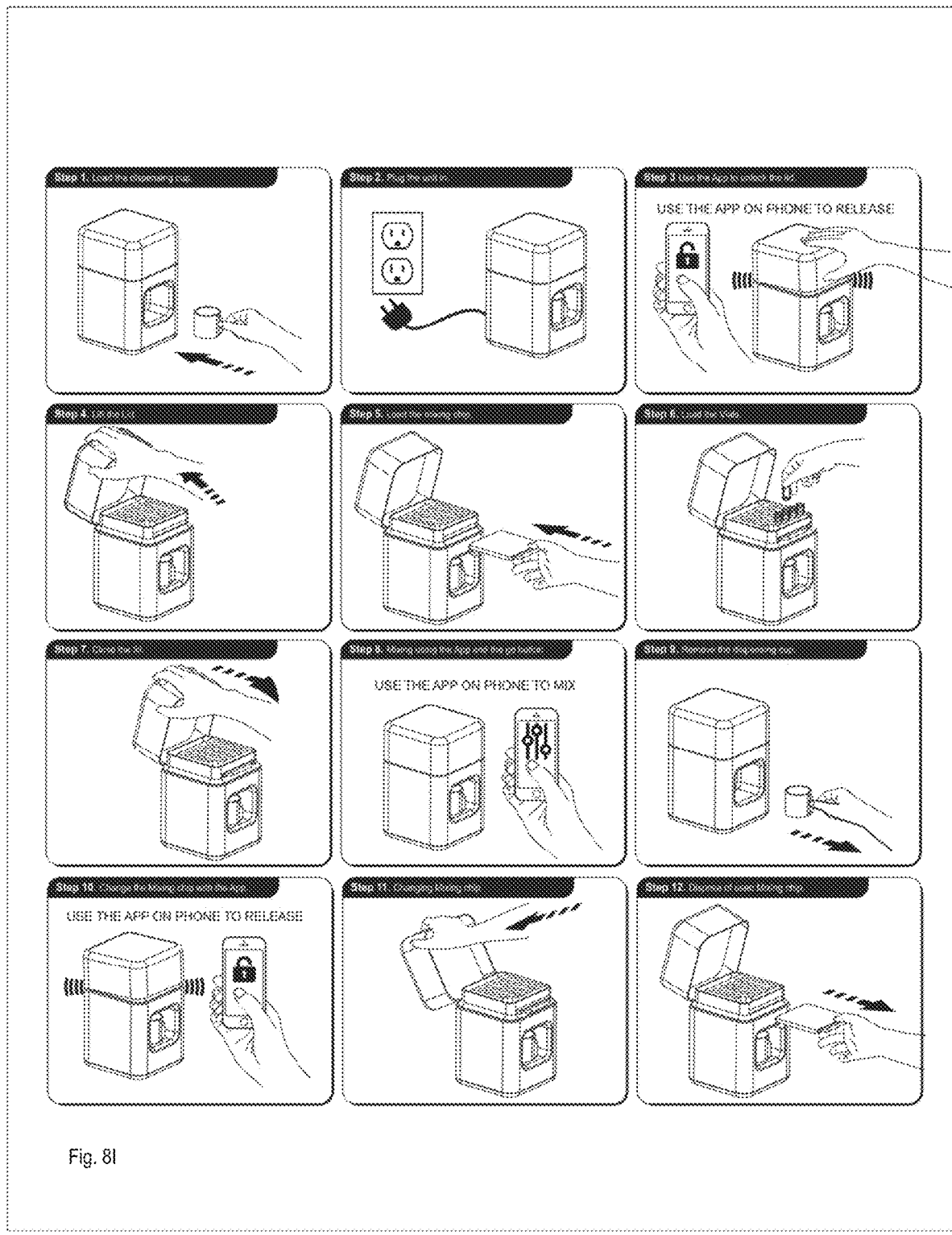
FIG. 8I provides example user guidance illustrations for some embodiments of the OBD.

FIG. 8I provides example user guidance illustrations for some embodiments of the OBD, with illustrations on set up, microfluidic chip replacement, and vial replacement.

Figure 9A:
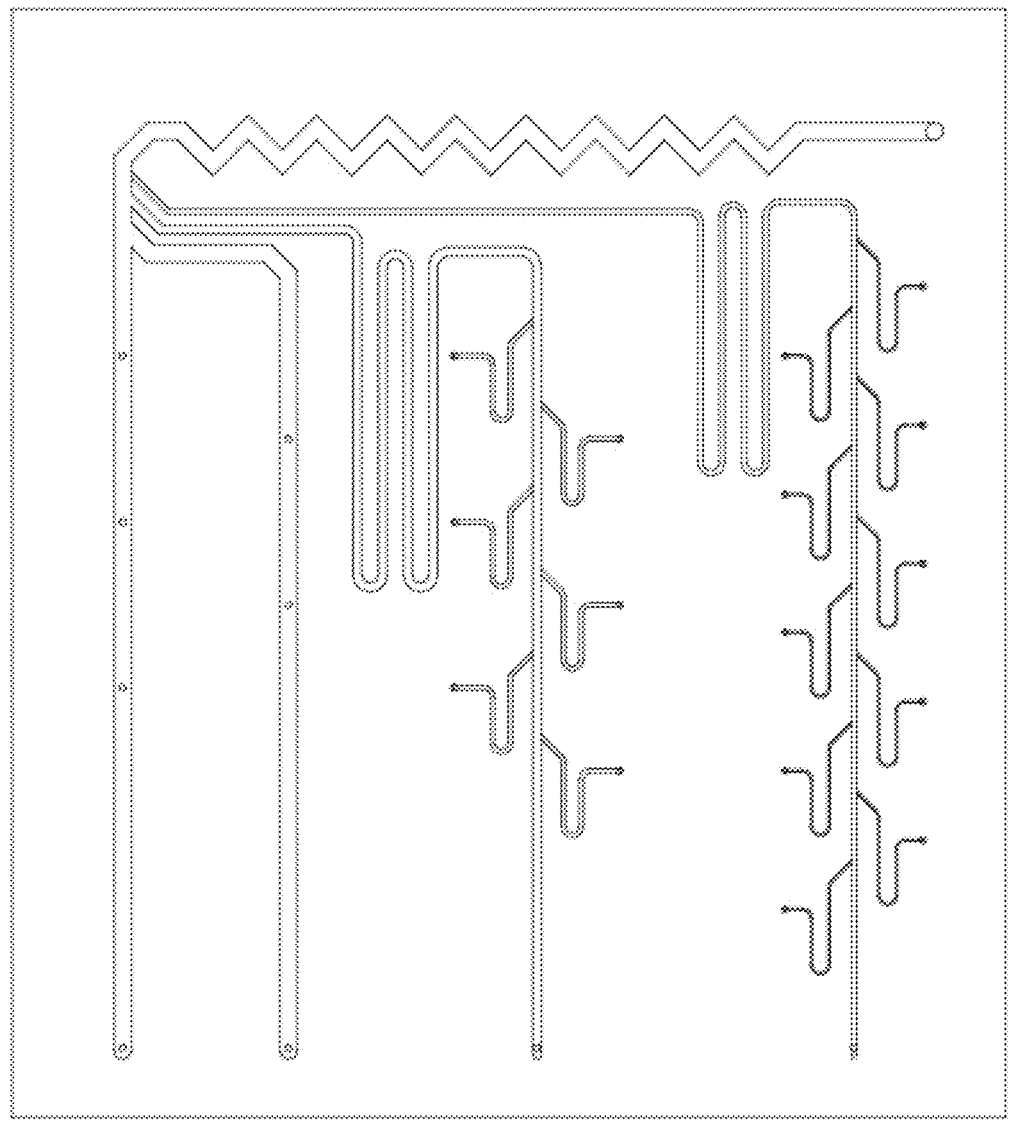
FIGS. 9A, 9B, and 9C illustrate example OBD microfluidic mixer chips for some embodiments according to the disclosure.
Figure 9B:
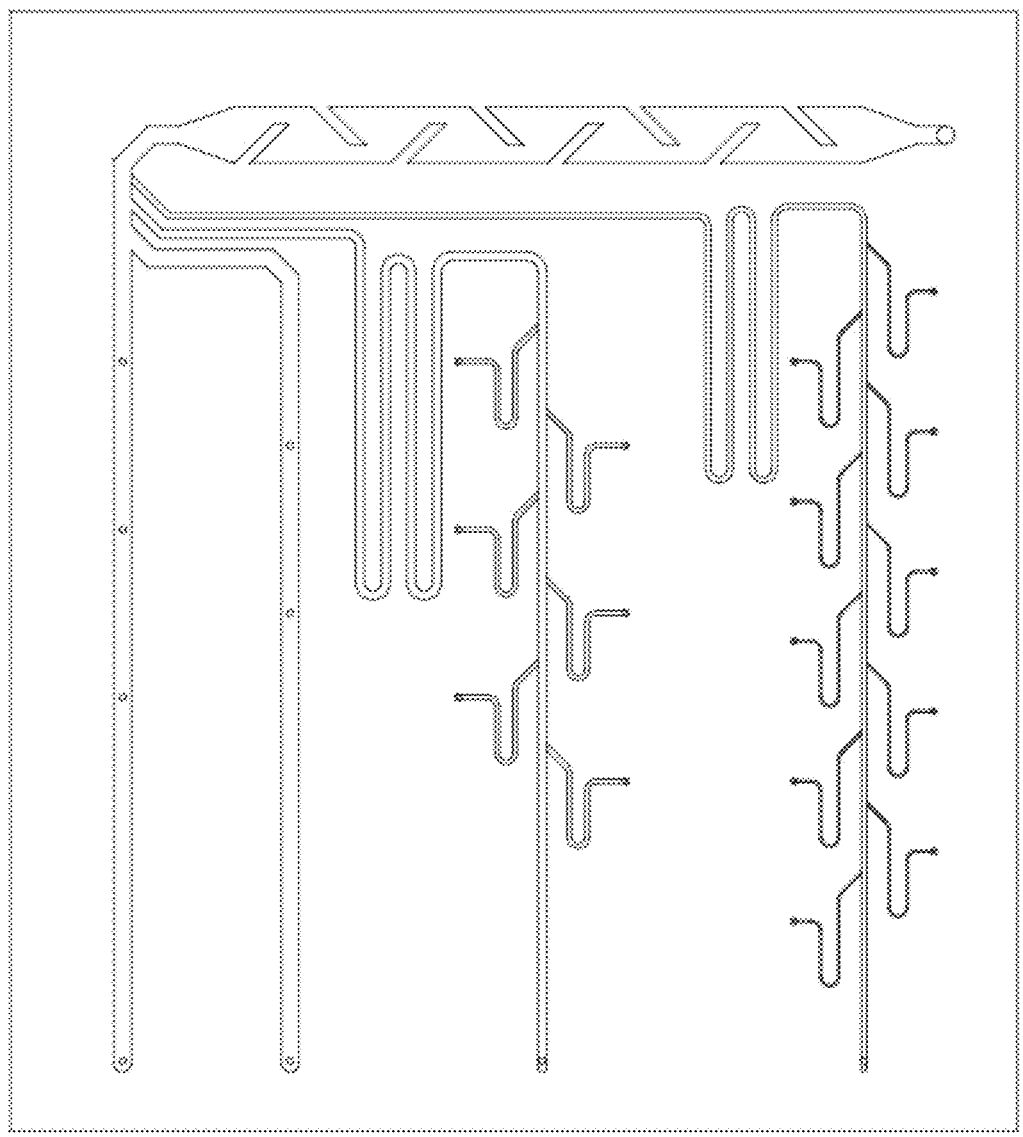
Figure 9C:
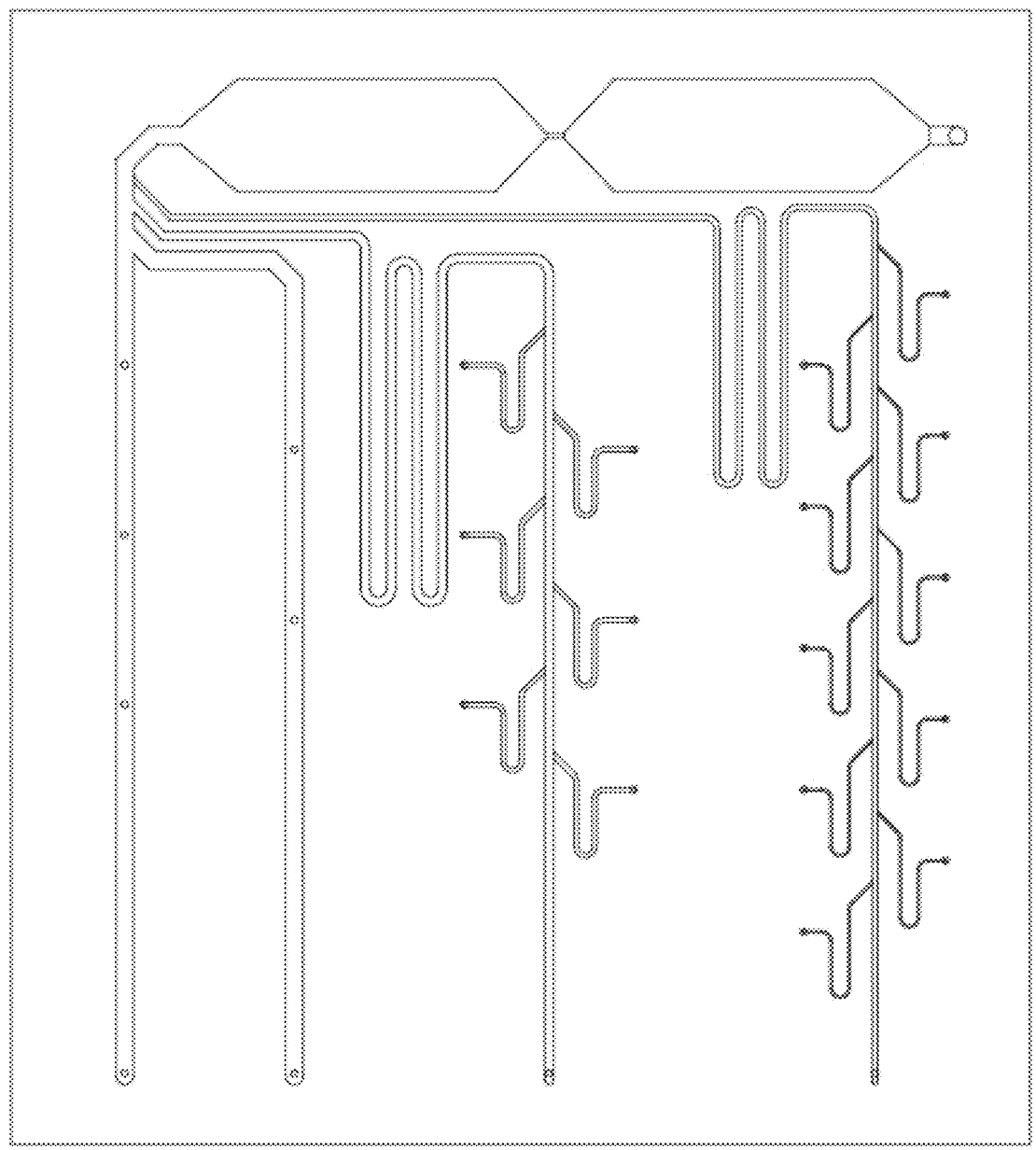

FIG. 9A, FIG. 9B, and FIG. 9C illustrate example OBD microfluidic mixer chips, according to some embodiments Channel parameters are determined by the application and implementation, and can correspond to the relative viscosity of the fluids for the channel(s). For example, for a microfluidic mixer chip configured for use with cannabinoids, the cannabinoid main flow channel can be configured to be 2000 micrometers wide×1000 micrometers deep. For bases and/or flavonoids, the inlet channel can be 500 micrometers wide× 300 micrometers deep and the bases/flavonoids main flow channel 1000 micrometers wide×1000 micrometers deep. For terpenes, the inlet channel can be 250 micrometers wide×100 micrometers deep and the terpene main flow channel 600 micrometers wide×300 micrometers deep. These parameters are examples only, and are not intended to be limiting. However, these examples provide illustrative ratios for channel size/fluid viscosity that can be generalized to some embodiments.

FIG. 10 shows an example microfluidic mixer chip assembly according to some embodiments. As shown, in such embodiments, there are four parts, including a mixer chip top 1001 (additional detail in FIG. 10A), mixer chip VIA 1011 (additional detail in FIG. 10B), mixer chip membrane 1021 (additional detail in FIG. 10C), and mixer chip bottom 1031 (additional detail in FIG. 10D). In some implementations, the four parts are heat-bonded, e.g., using a displacement technique in a class 100,000 clean room. In some implementations, no adhesives are used in bonding/forming the microfluidic mixer chip. In some embodiments, the parts are bonded using methods as disclosed by Ren et al., Whole-Teflon microfluidic chips (PNAS 2011 108 (20) 8162-8166; doi:10.1073/pnas.1100356108), the entirety of which is incorporated by reference for all purposes. In some embodiments, the microfluidic mixer chip can include and/or integrate monolithic pneumatic valves and/or pumps.

Figure 10C:
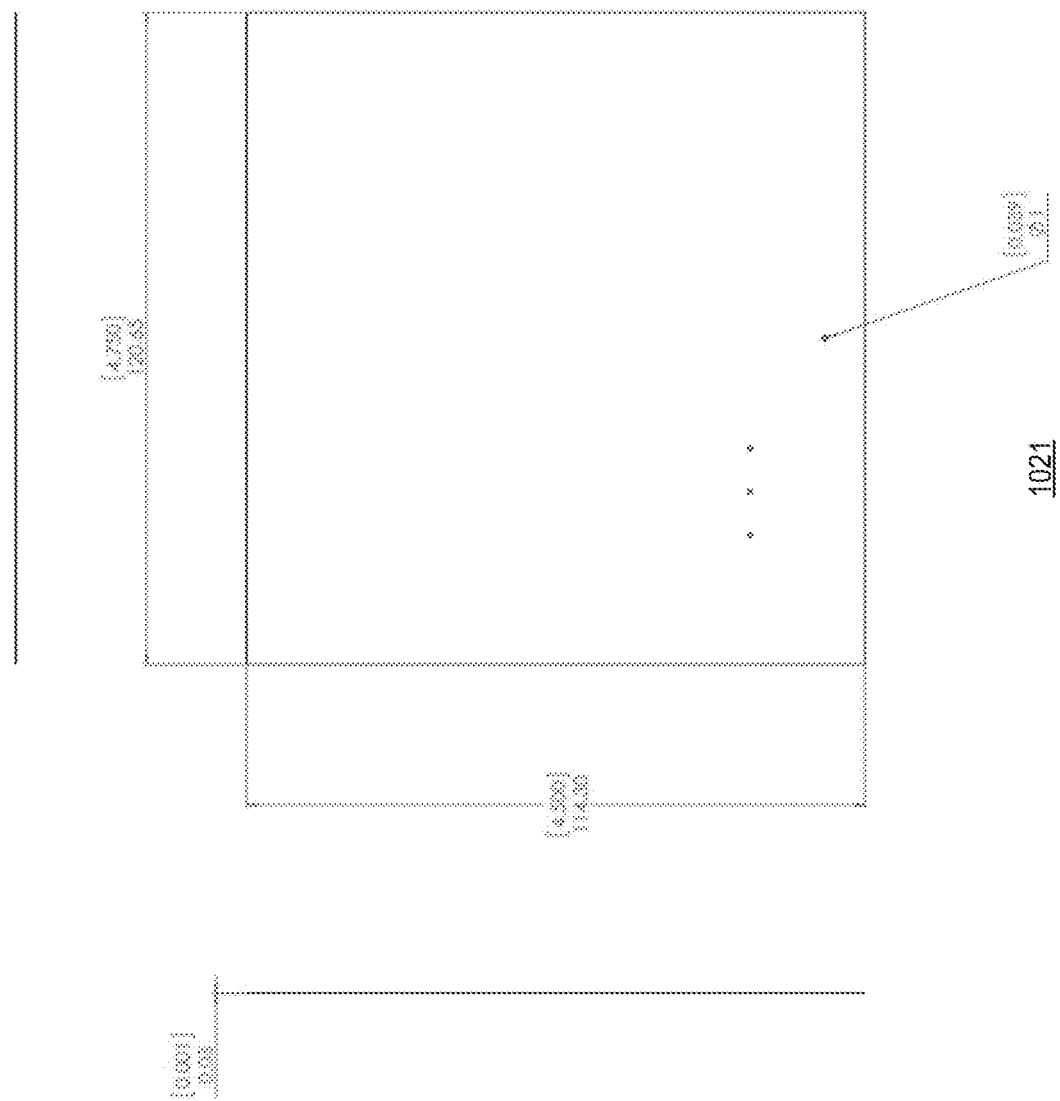
FIG. 10-FIG. 10D illustrate an example microfluidic mixer chip assembly according to some embodiments.
FIG. 10E-FIG. 10G are pictures of a heat-bonded FEP microfluidic mixer chip according to some embodiments of the disclosure.
Figure 10D:
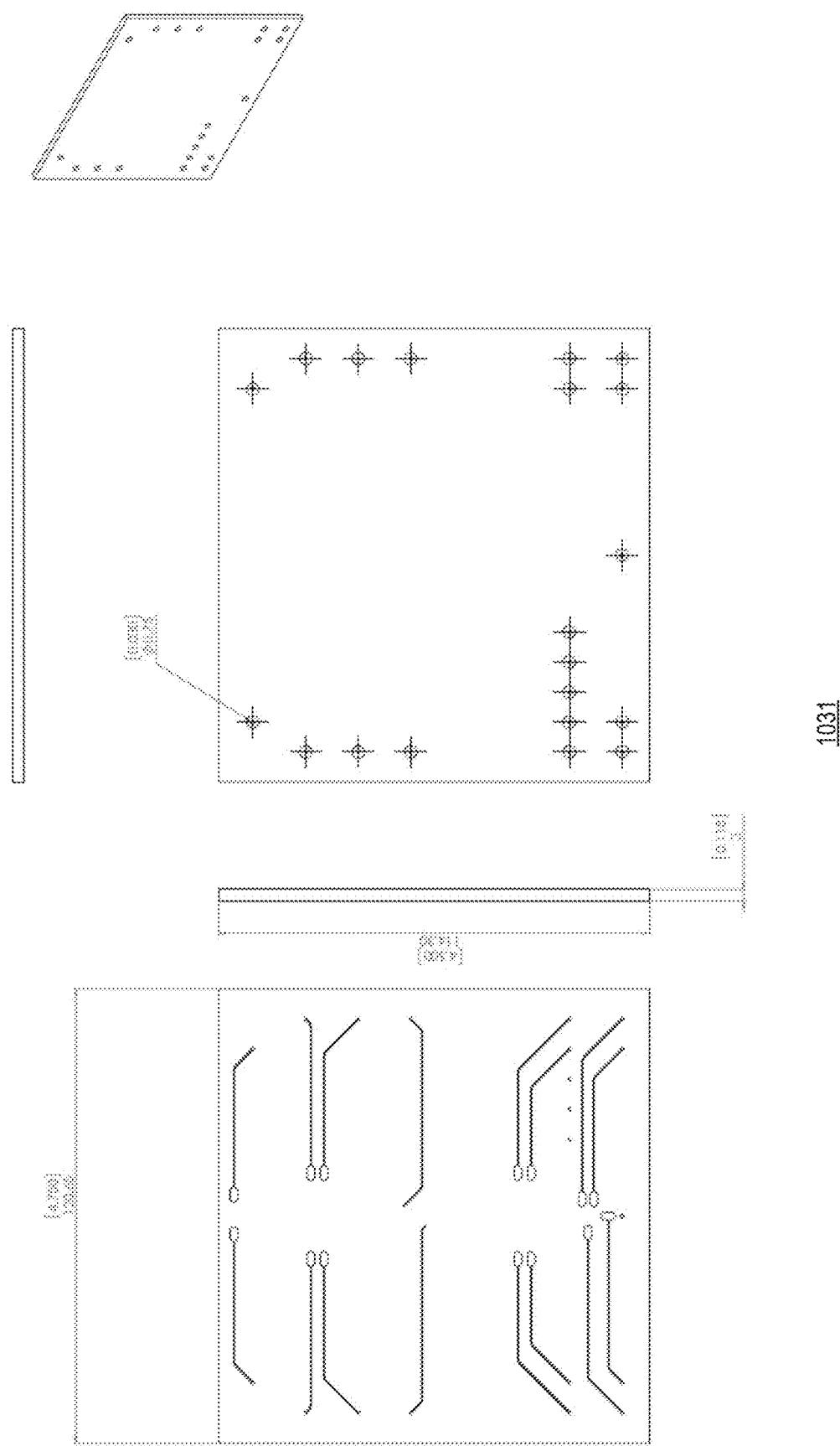
Figure 10E:
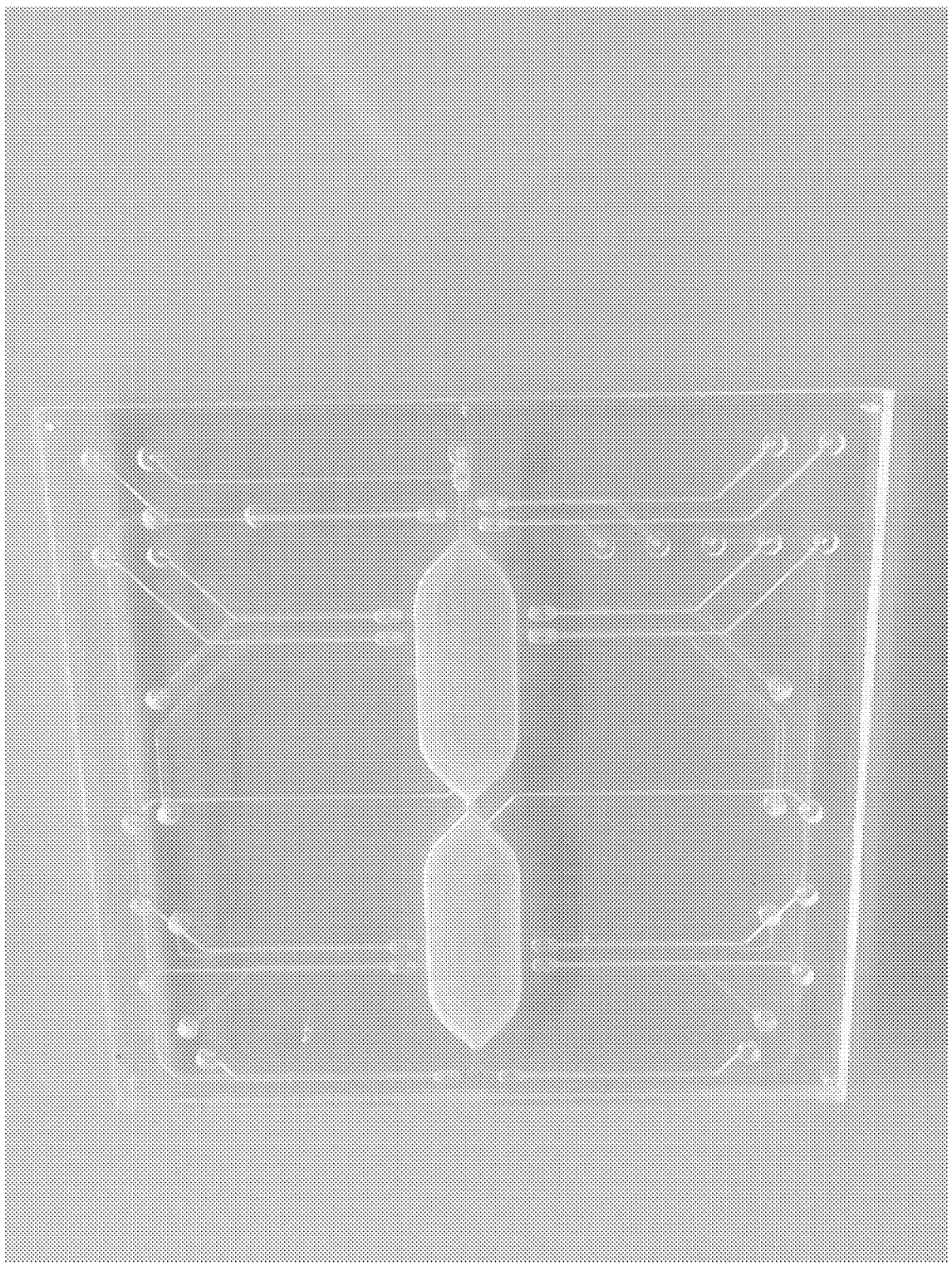
Figure 10F:
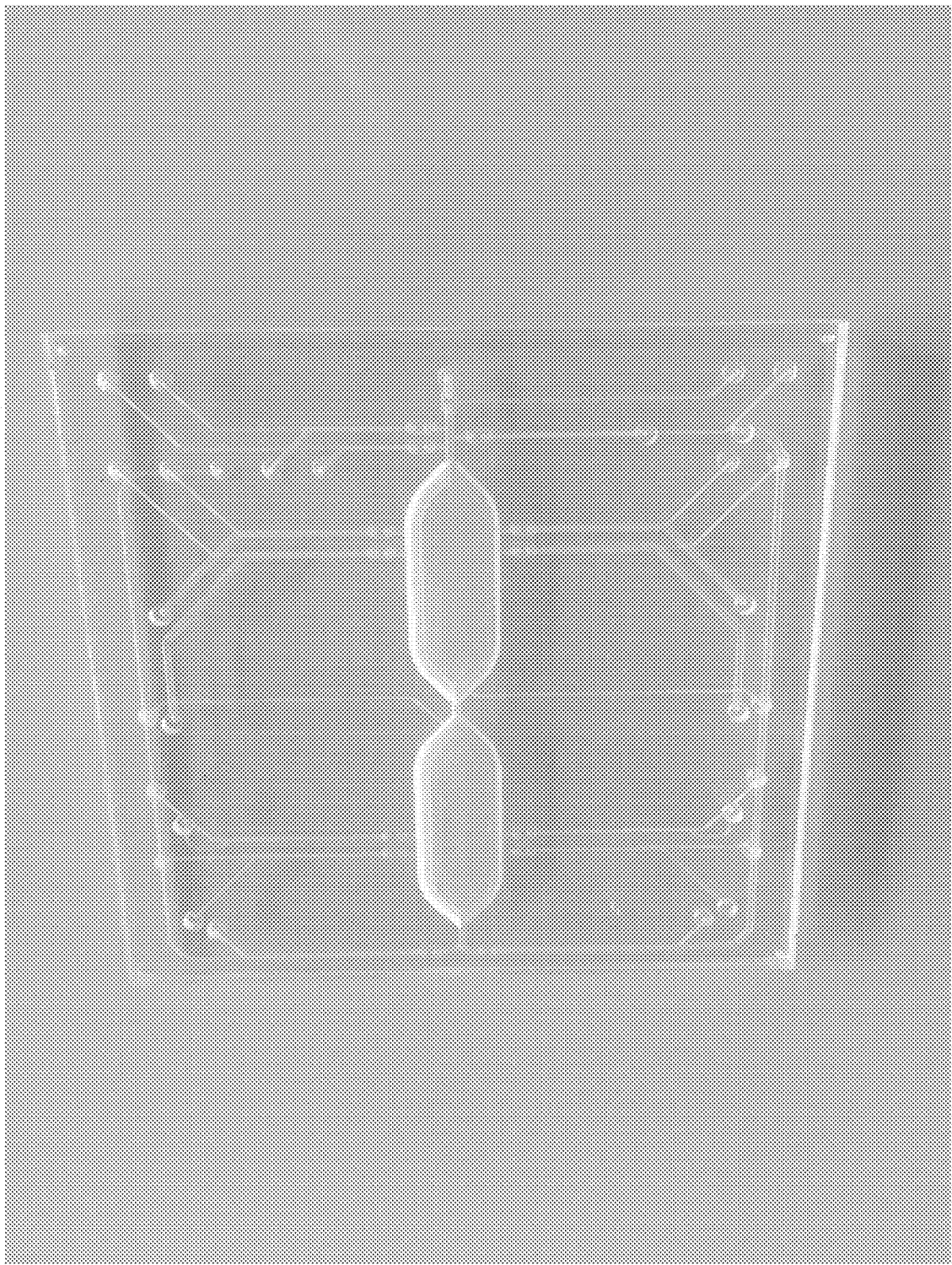
Figure 10G:
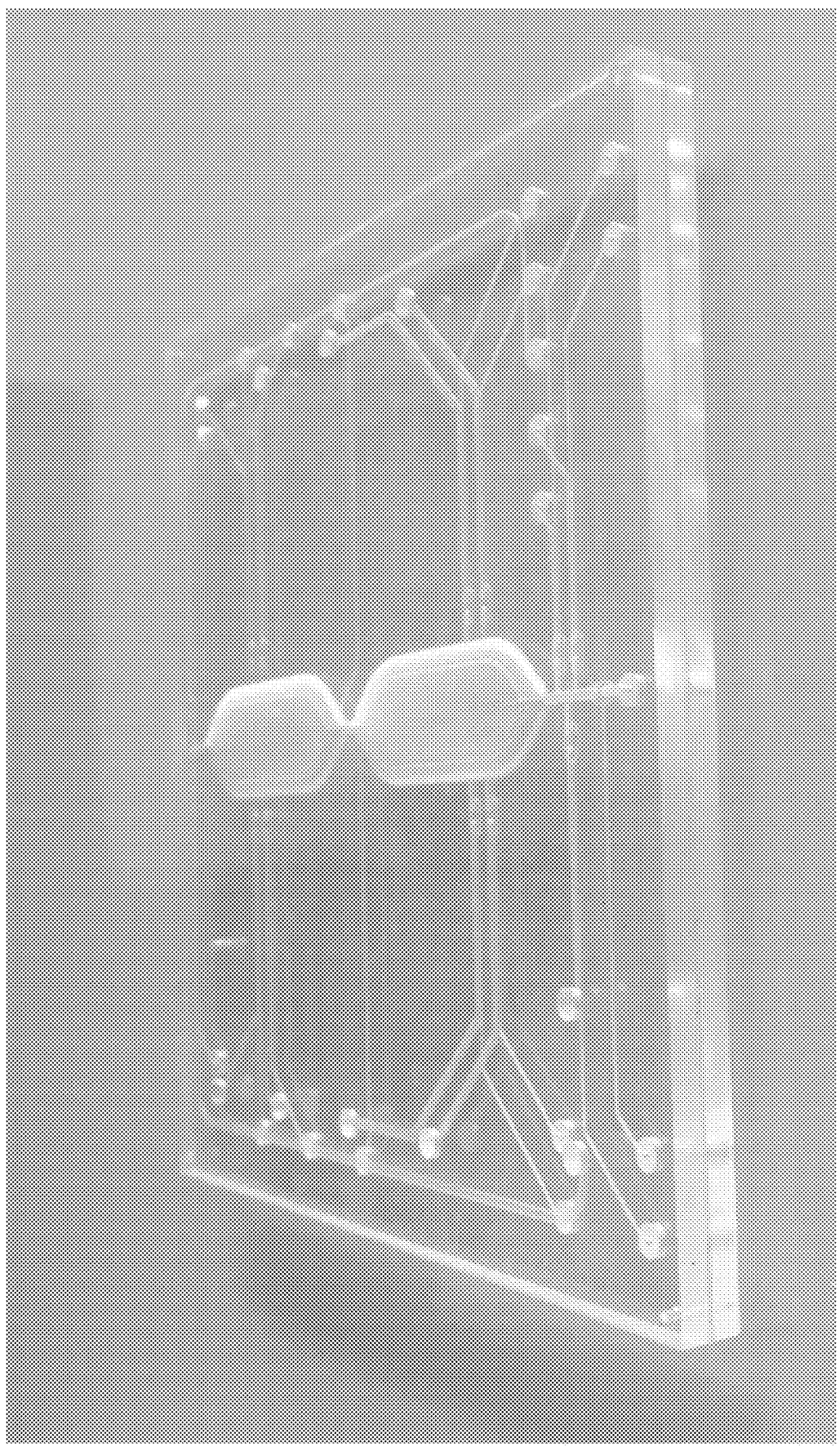

A variety of materials, including polymers, copolymers, resins, silicon, glass, PDMS, polytetrafluoroethylene, perfluoroalkoxy polymer resin, TEFLON etc., can be utilized in making the microfluidic mixer chips, and the microfluidic mixer chip can comprise, consist essentially of, or consist of such a material or mixtures of materials. In some embodiments, some or all of the above parts are made from fluorinated ethylene propylene (FEP), a copolymer of hexafluoropropylene and tetrafluoroethylene. In some embodiments, the microfluidic mixer chip consists of or consists essentially of FEP, and the parts are heat bonded. As disclosed herein, such embodiments are well-suited for cannabinoid-related applications, as they can resist solvent effects from terpenes, and thereby be used multiple times without risk of contamination. In some embodiments, such microfluidic mixer chips are monolithically formed and/or include elements, such as pneumatic valves and/or pumps, which are monolithically formed. FIGS. 10E-10G are pictures of a heat-bonded FEP microfluidic mixer chip according to some such embodiments of the disclosure.

Some embodiments of the OBD are configured to work with a broad range of temperatures so that can work with a variety of liquids, and some embodiments are configured to not exceed a specified temperature threshold, such as 140 F (e.g., a temperature that is safe to the touch), while other embodiments can go higher (e.g., some cannabinoids are stable up to 300 F and can require relatively high temperatures to get appropriate viscosities), and such high-temperature embodiments include safety features and insulation to avoid overheating and to prevent a user from accidentally burning themselves. Some embodiments can also be configured with a minimum temperature, such as 100 F, below which the OBD will not dispense fluids.

Depending on the embodiment, temperatures for fluids within the OBD can range from 100 degrees F. to 300 degrees F., including any integers there between, and including any ranges between integers there between, including from about 100 to 105 degrees F., from about 105 to 110 degrees F., from about 110 to 115 degrees F., from about 115 to 120 degrees F., from about 120 to 125 degrees F., from about 125 to 130 degrees F., from about 130 to 135 degrees F., from about 135 to 140 degrees F., from about 140 to 145 degrees F., from about 145 to 150 degrees F., from about 150 to 155 degrees F., from about 155 to 160 degrees F., from about 160 to 165 degrees F., from about 165 to 170 degrees F., from about 170 to 175 degrees F., from about 175 to 180 degrees F., from about 180 to 185 degrees F., from about 185 to 190 degrees F., from about 190 to 195 degrees F., from about 195 to 200 degrees F., from about 200 to 205 degrees F., from about 205 to 210 degrees F., from about 210 to 215 degrees F., from about 215 to 220 degrees F., from about 220 to 225 degrees F., from about 225 to 230 degrees F., from about 230 to 235 degrees F., from about 235 to 240 degrees F., from about 240 to 245 degrees F., from about 245 to 250 degrees F., from about 250 to 255 degrees F., from about 255 to 260 degrees F., from about 260 to 265 degrees F., from about 265 to 270 degrees F., from about 270 to 275 degrees F., from about 275 to 280 degrees F., from about 280 to 285 degrees F., from about 285 to 290 degrees F., from about 290 to 295 degrees F., from about 295 to 300 degrees F., and/or any subranges there between or combined ranges (e.g., from about 145 to 245 degrees F., etc.).

In some embodiments, temperatures/heating is focused on a tank, pathway/channel, and/or other specified portion or portions of the OBD and/or microfluidic mixer chip. In some embodiments, pressures within the OBD can range from 0 to 100 PSI, depending on the implementation. In some embodiments, pressures from 0 to 100 PSI are used to control the valves, including pressures such as 0.1 to 10 PSI, 10 to 20 PSI, 20 to 30 PSI, 30 to 40 PSI, 40 to 50 PSI, 50 to 60 PSI, 60 to 70 PSI, 70 to 80 PSI, 80 to 90 PSI, 90-100 PSI, and/or any integers there between, or ranges therebetween, including, for example, about 1 PSI, about 2 PSI, about 3 PSI, about 4 PSI, about 5 PSI, about 6 PSI, about 7 PSI, about 8 PSI, about 9 PSI, or about 10 PSI. In some embodiments, pressures from 0 to 100 PSI are used to pressurize the (typically heated) ingredients in the canisters to cause them to flow, including pressures such as 0.1 to 10 PSI, 10 to 20 PSI, 20 to 30 PSI, 30 to 40 PSI, 40 to 50 PSI, 50 to 60 PSI, 60 to 70 PSI, 70 to 80 PSI, 80 to 90 PSI, 90-100 PSI, and/or any integers there between, or ranges therebetween, including, for example, about 0.01 PSI, about 0.05 PSI, about 1 PSI, about 1.5 PSI, about 2 PSI, about 2.5 PSI, about 3 PSI, about 3.5 PSI, about 4 PSI, about 4.5 PSI, about 5 PSI, about 5.5 PSI, about 6 PSI, about 6.5 PSI, about 7 PSI, about 7.5 PSI, about 8 PSI, about 8.5 PSI, about 9 PSI, about 9.5 PSI, or about 10 PSI.

In some embodiments, viscosities for the fluids that the OBD handles/processes can range from 0.1 cP to 5,000 cP, including 1 cP, 100 cP, 500 cP, 1,000 cP, 2,000 cP, 3,000 cP, 4,000 cP, 5,000 cP, and/or any integers there between, or ranges therebetween.

Figure 11A:
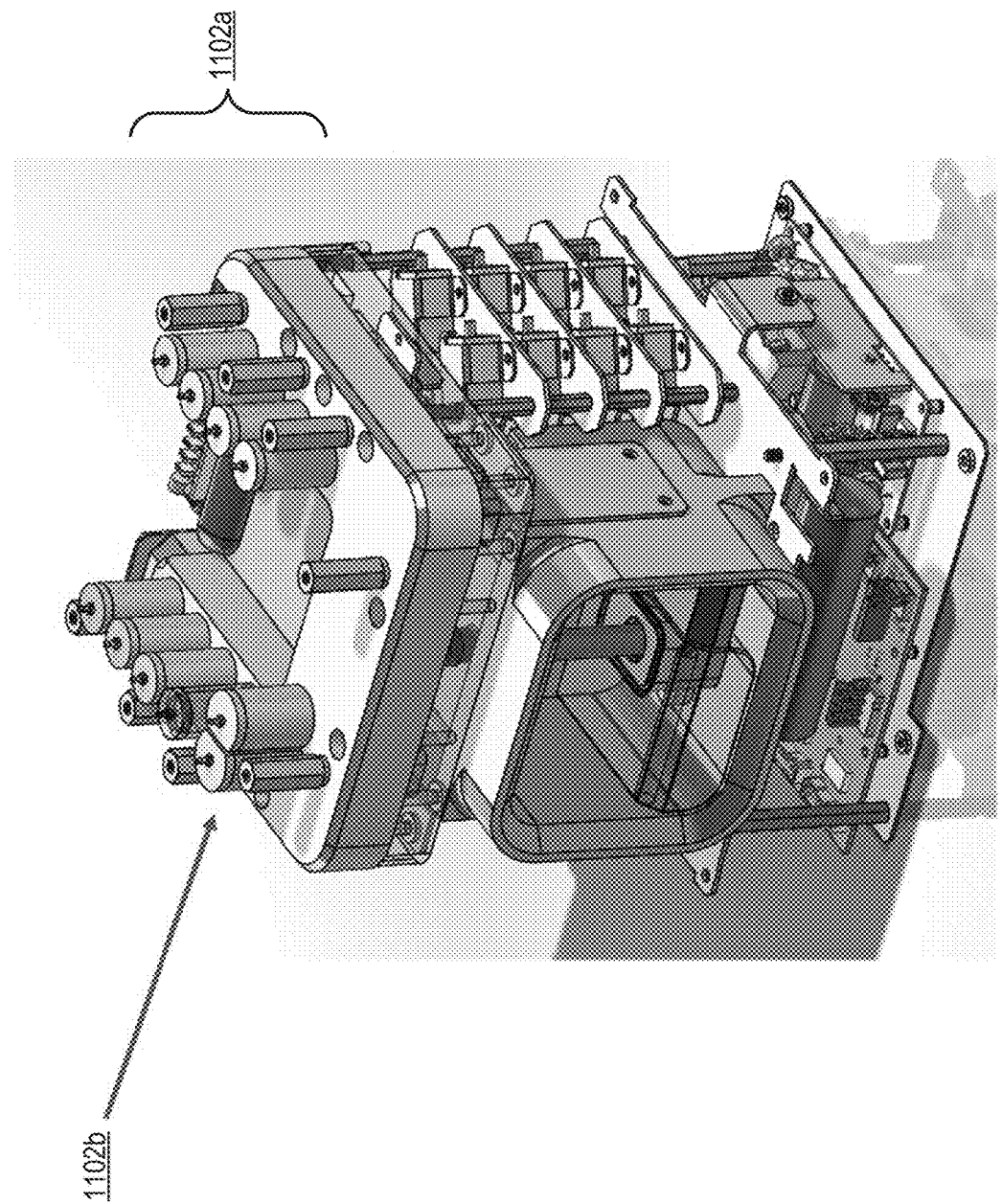
FIG. 11A provides an overview of a OBD system cleaning implementation, according to some embodiments.

In some embodiments, the OBD can include a cleaning cycle. Such a cleaning cycle can prolong the life of the OBD and/or the microfluidic mixer chip. Such cleaning cycles/methods can include heating the microfluidic mixer chip (or portions thereof) to temperatures above its normal dispense temperature to aid in melting residual substances, passing air/gas/liquid and/or solvent through the main flow channels under pressure, and/or applying acoustic energy to the microfluidic mixer chip to aid cleaning. Additionally or alternatively, in some embodiments, the OBD can include lasers or ultra-fast lasers configured to burn away residual organics attached to the channel walls followed by a burst of air or other fluid to clean away the ash. As illustrated in FIG. 11A, in some embodiments, of the plurality of fluid vials 1102a, one or more vials 1102b can include cleaning solutions (e.g., EtOH and/or the like) that can be run through the system to clean/purge the system after each use.

In some embodiments, a microfluidic mixer chip can include piezo pumps built into the microfluidic mixer chip itself.

In some embodiments, a microfluidic mixer chip and/or the OBD processes for compounding and activating ingredients that otherwise are difficult or impossible to dispense to a user (e.g., compounding medicines that have a relatively short shelf life once compounded could otherwise require a patient to visit a compounding pharmacy several times a week).

In some embodiments, a microfluidic mixer chip and/or the OBD is configured to add an emulsifying agent, homogenize ingredients (e.g., with a homogenizer disposed within the microfluidic mixer chip or as a component of or attachment to the OBD), blend powdered ingredients/components (e.g., with a powder blender), add a filtration solution, concentrate and/or purify ingredients, provide thermal cycling, conduct/provide pH testing and/or provide pH balancing (e.g., with acidic/basic solutions in corresponding tanks), and/or provide advanced microfluidic chemical synthesis. The OBD can also include a system for analyzing the blend of ingredients prior to dispensing to ensure accuracy (e.g., by incorporation of a miniaturized molecular sensor within the OBD). The OBD can additionally or alternatively include a system for testing ingredients for purity and/or potency prior to adding/mixing them (e.g., by incorporation of a molecular sensor or sensors at or near the cartridge/tank receiver of the OBD).

In some embodiments, for complex mix and/or dispense cycles, the OBD can be configured to vary pressure within a main air channel over the dispense time, and thus provide more precise control over fluid flow rates and more accuracy for some fluids if the pressure is lowered as they are dispensed.

In some embodiments, the OBD is configured to pressurize the entire microfluidic mixer chip during a dispense cycle, e.g., by including a solenoid valve on the outlet port allowing it to be closed off. Fluid flow can then be controlled by applying pressure to individual fluid cartridges higher than the pressure within the microfluidic mixer chip. The fluid flow is dependent on the pressure differential ($P_{cartridge} - P_{system}$). The compression of air within the system is dictated by ($V2/V_1 = P_{system}/P_{cartridge}$). By increasing the system pressure and keeping the difference between cartridge pressure and system pressure constant, the OBD can provide the same flow rate with less air compression, reducing dispense error contributed by the compressibility of air within the system.

Figure 12A:
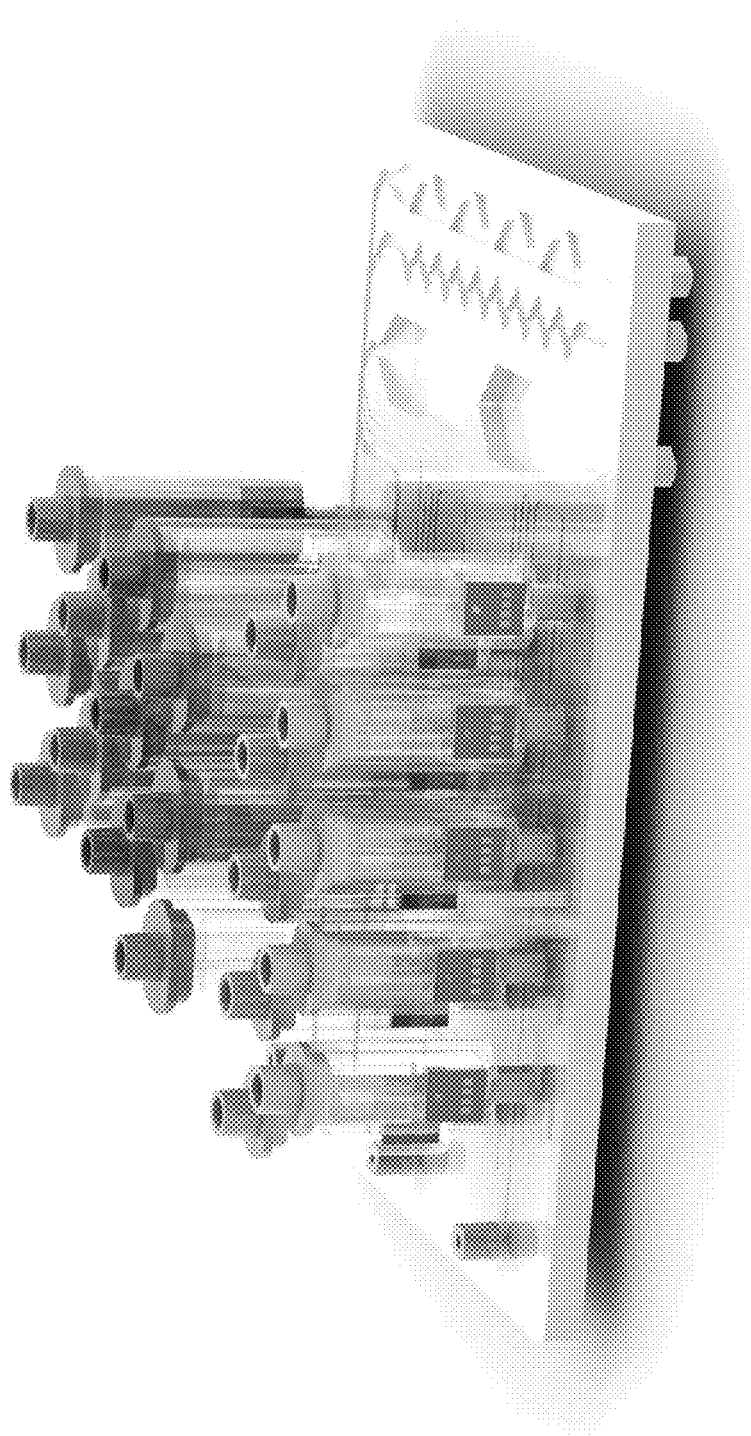
FIG. 12A shows a OBD microfluidic mixer chip with a plurality of fluid tanks/cartridges disposed thereon for some embodiments according to the disclosure.
Figure 12C:
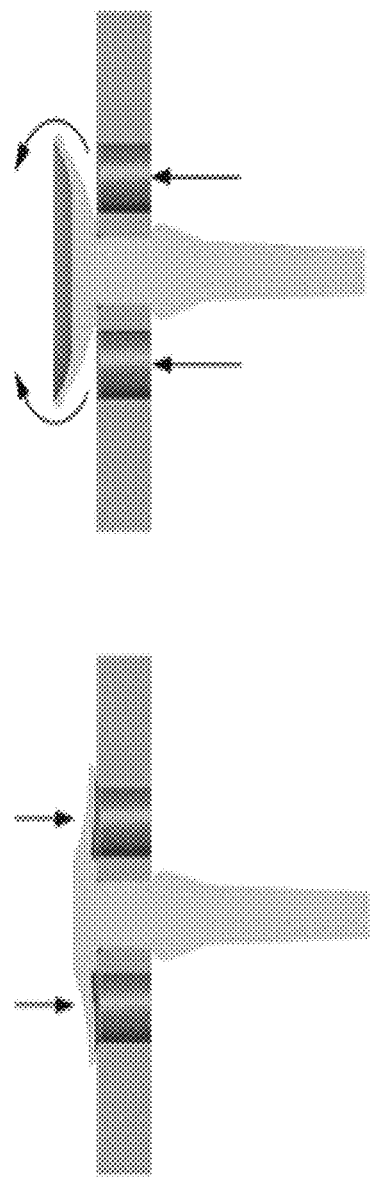
Figure 13A:
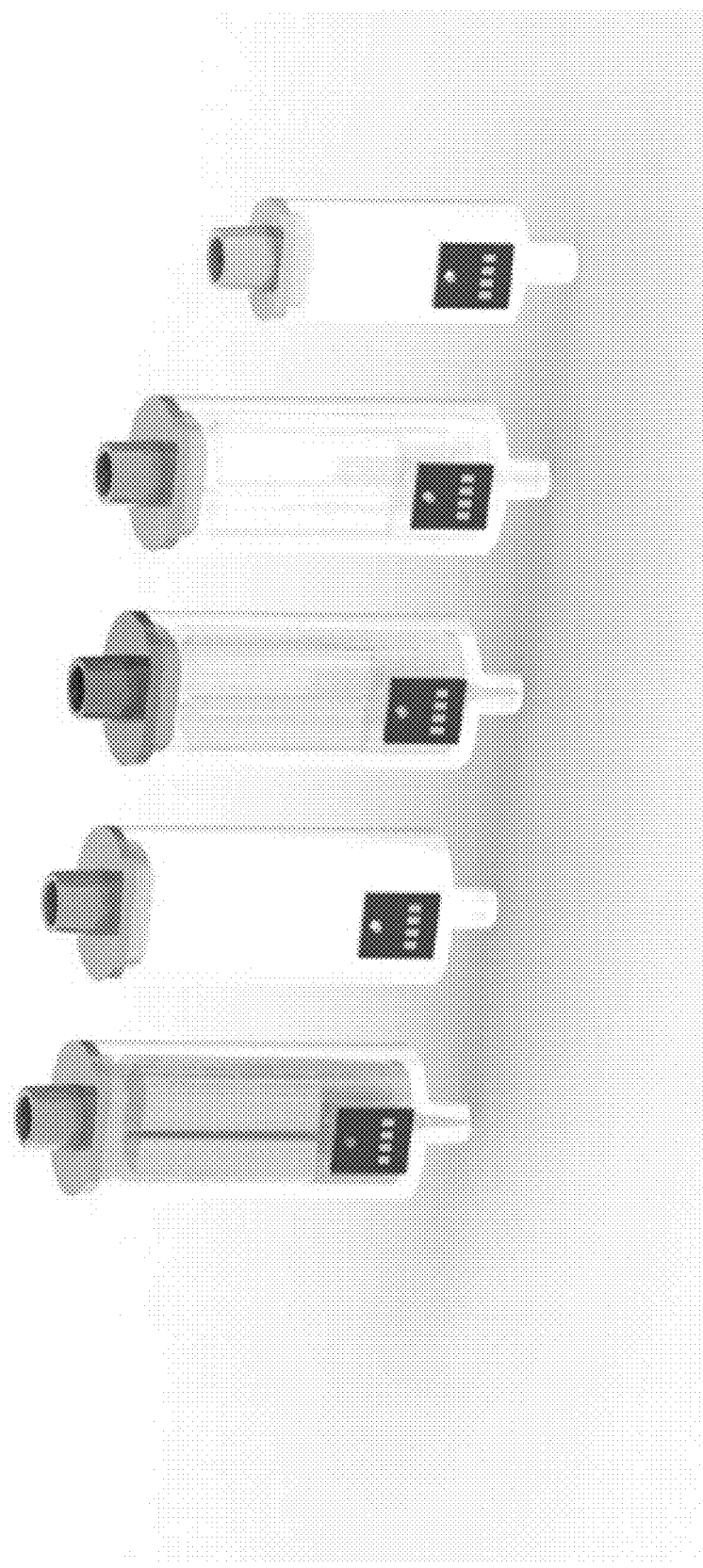
FIGS. 13A to 13F show examples of OBD fluid tanks for some embodiments according to the disclosure.
Figure 13B:
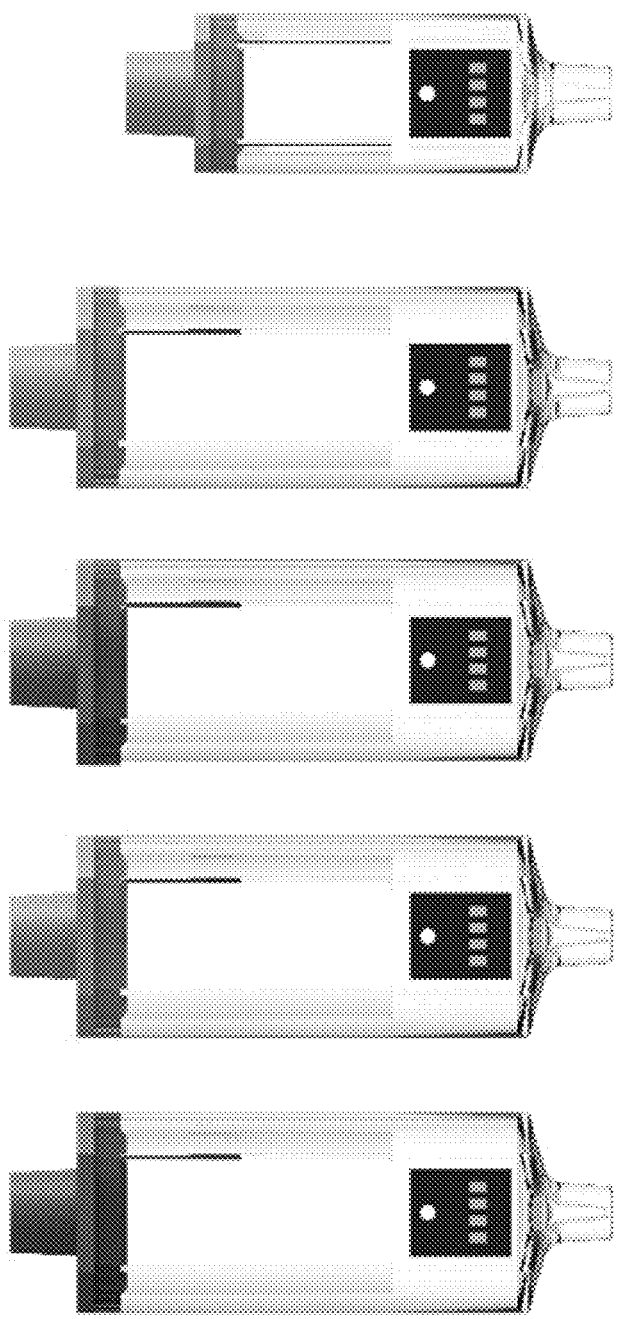
Figure 13C:
Figure 13D:
Figure 13E:
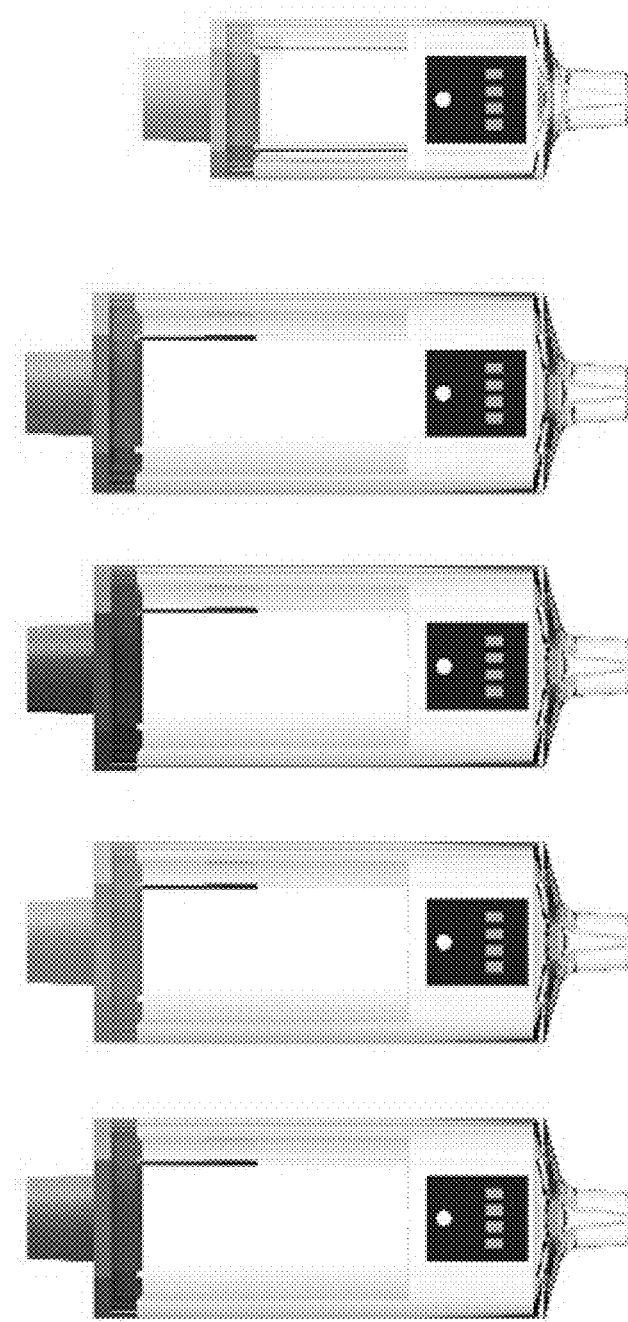
Figure 13F:
Figure 14A:
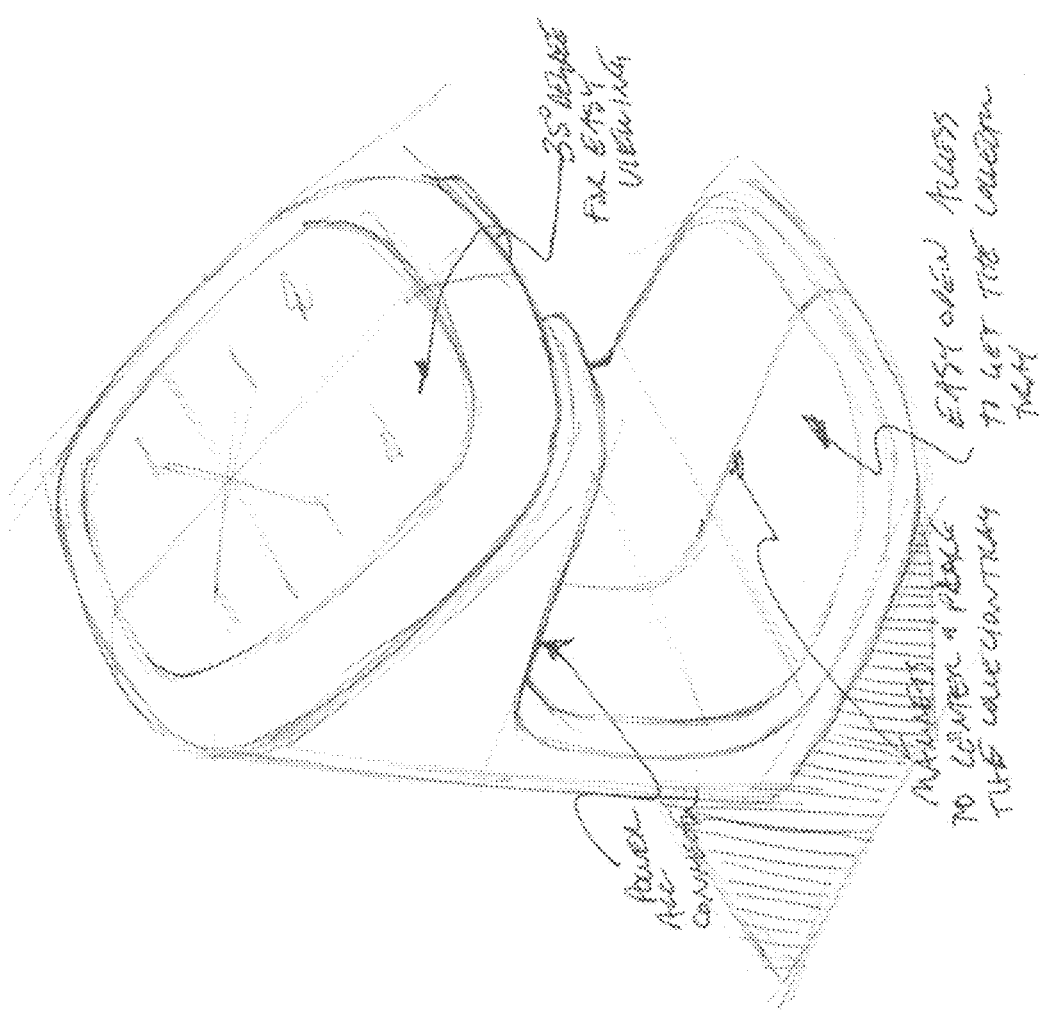
Figure 14B:
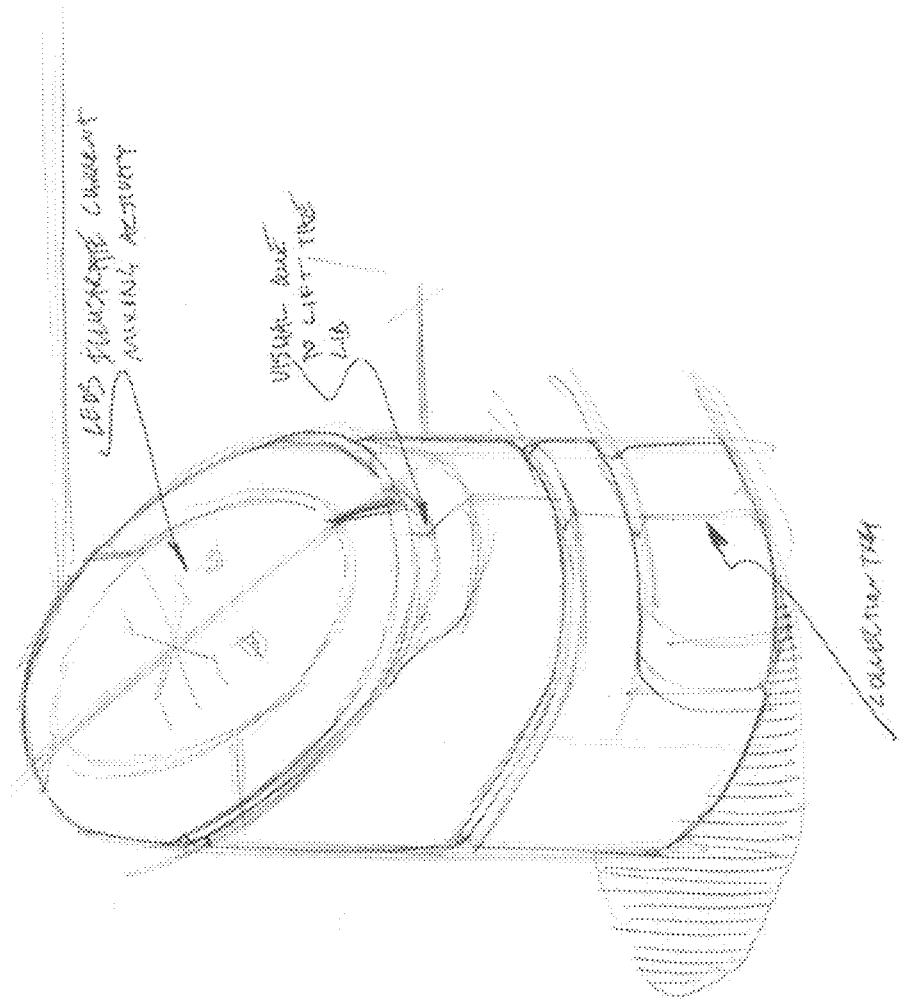
Figure 14C:
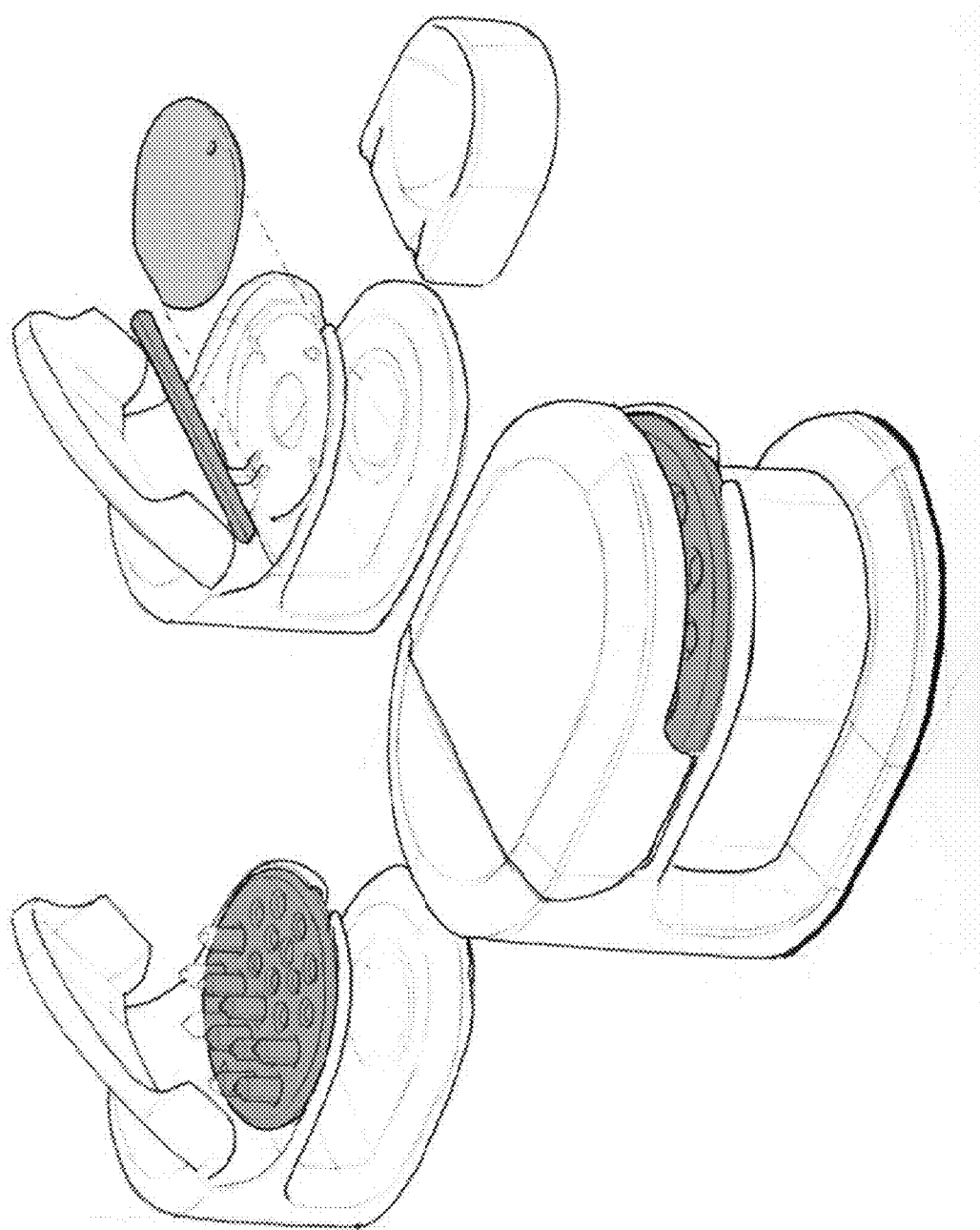
Figure 14D:
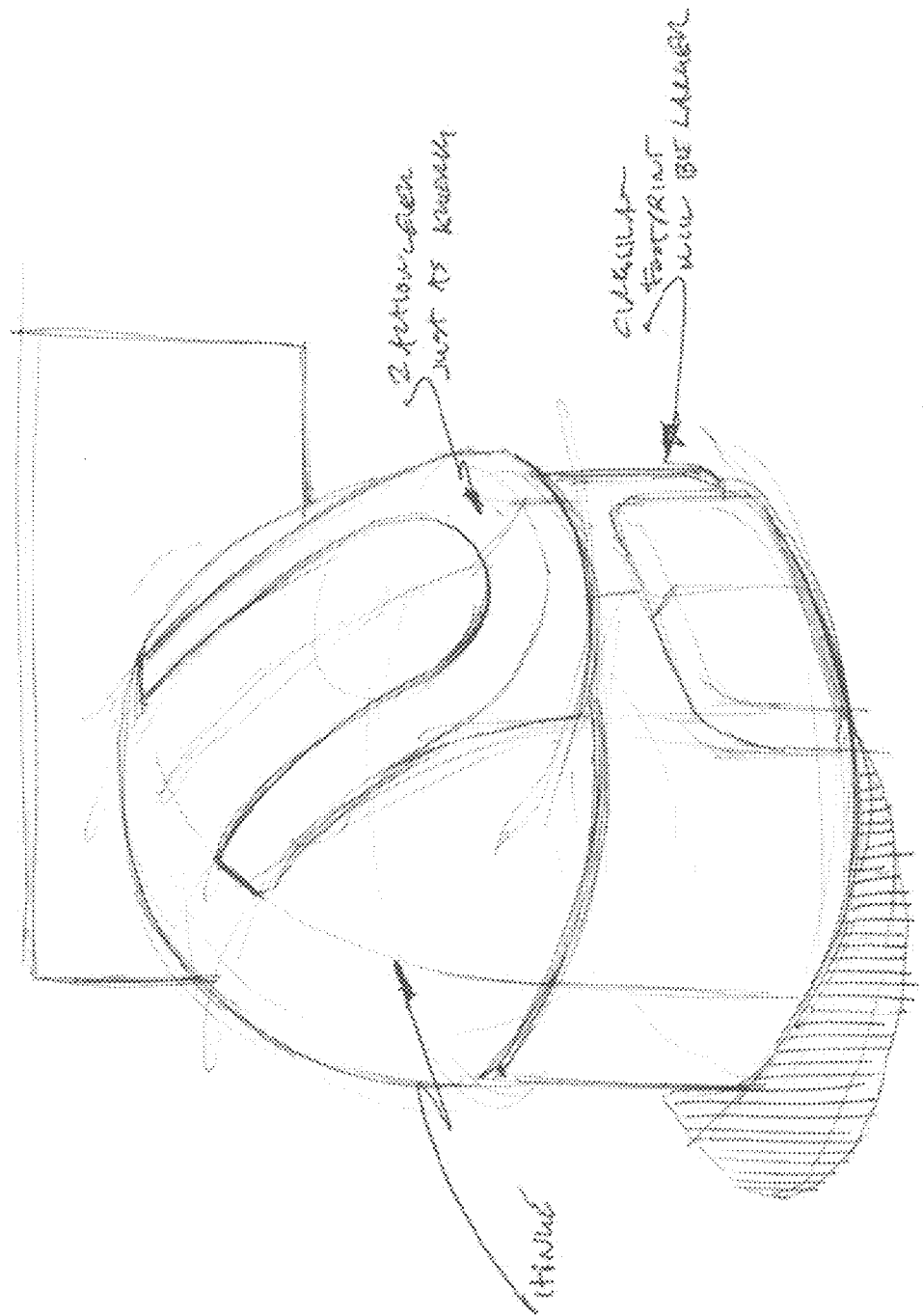
Figure 14E:
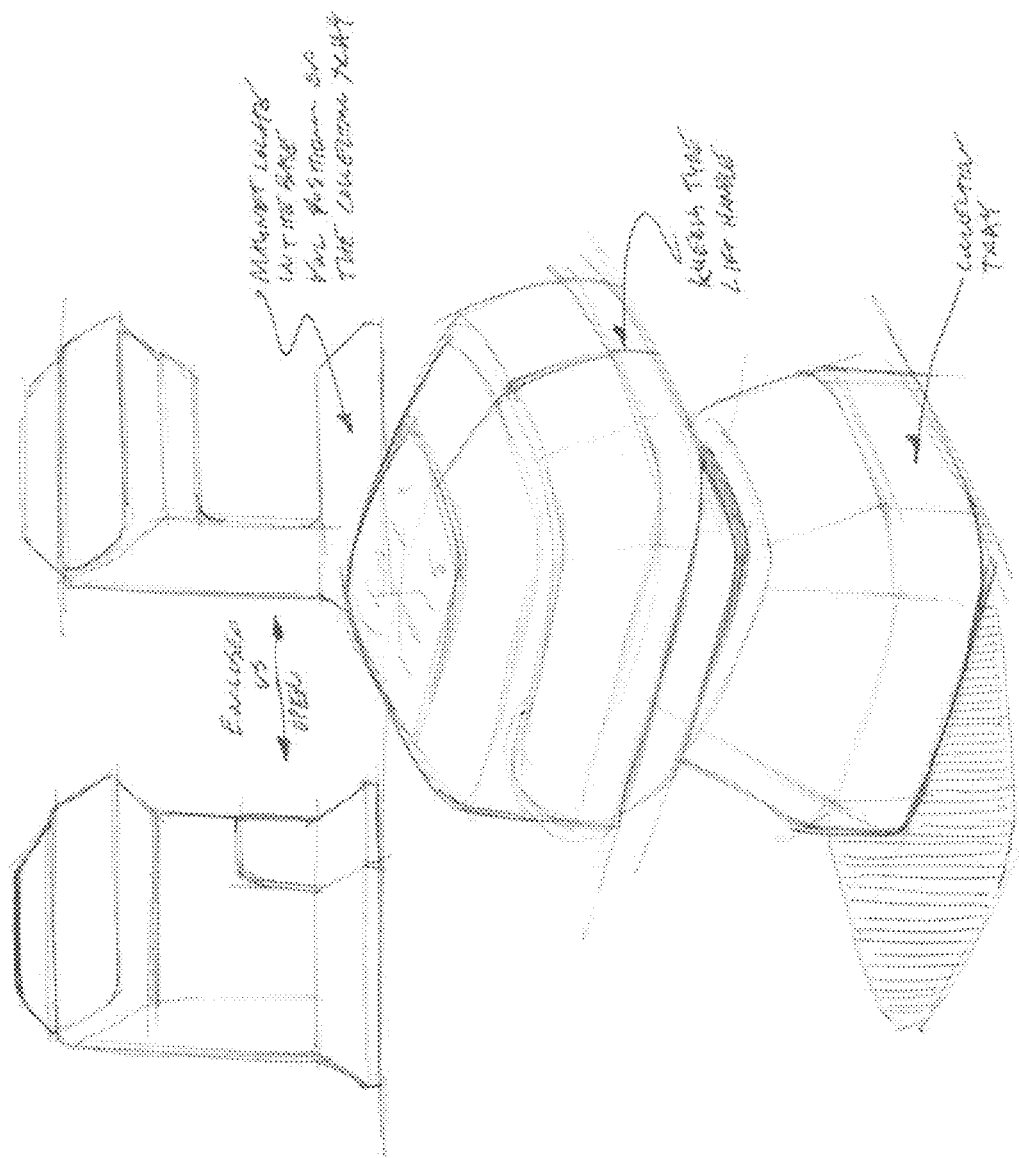
Figure 14F:
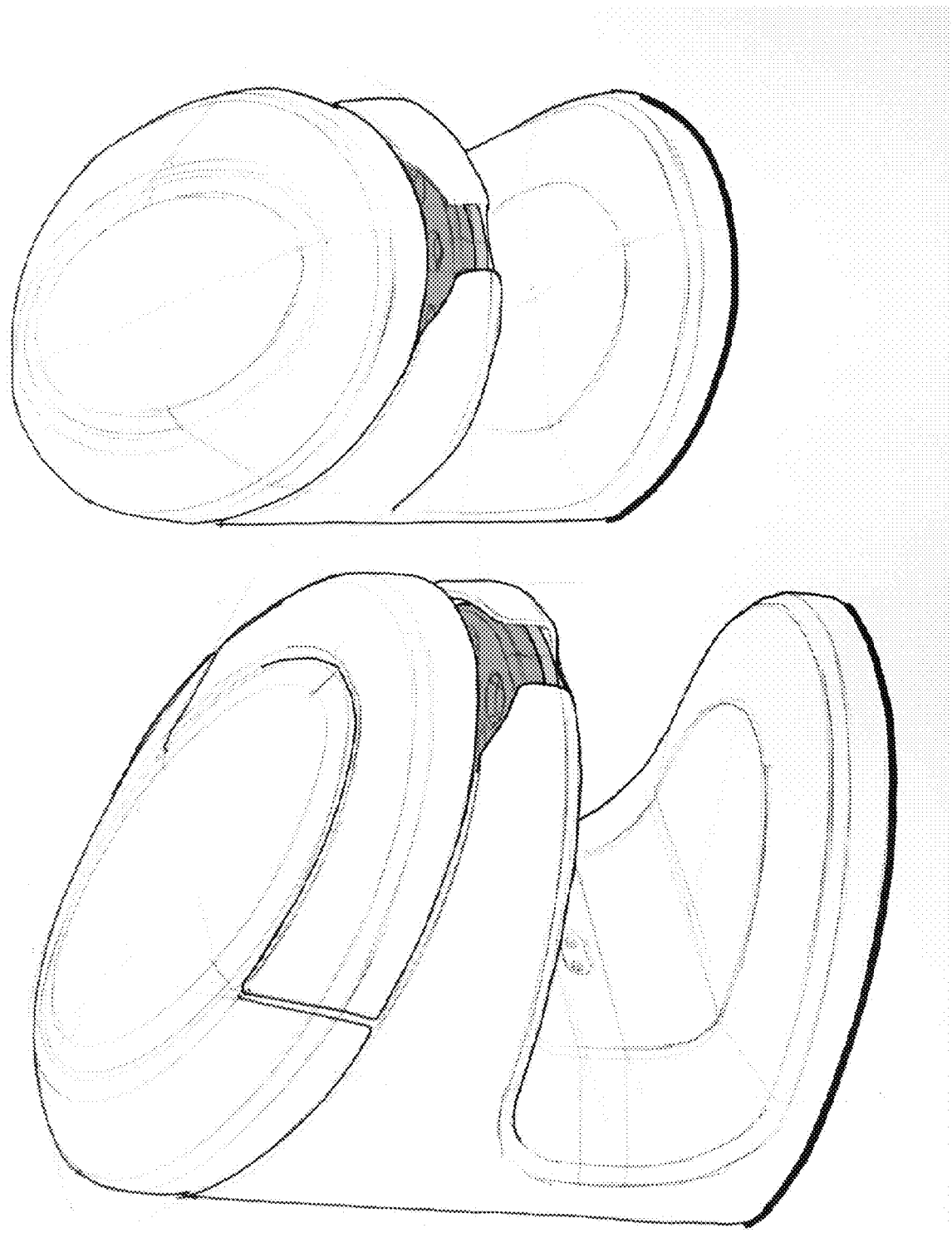
Figure 14G:
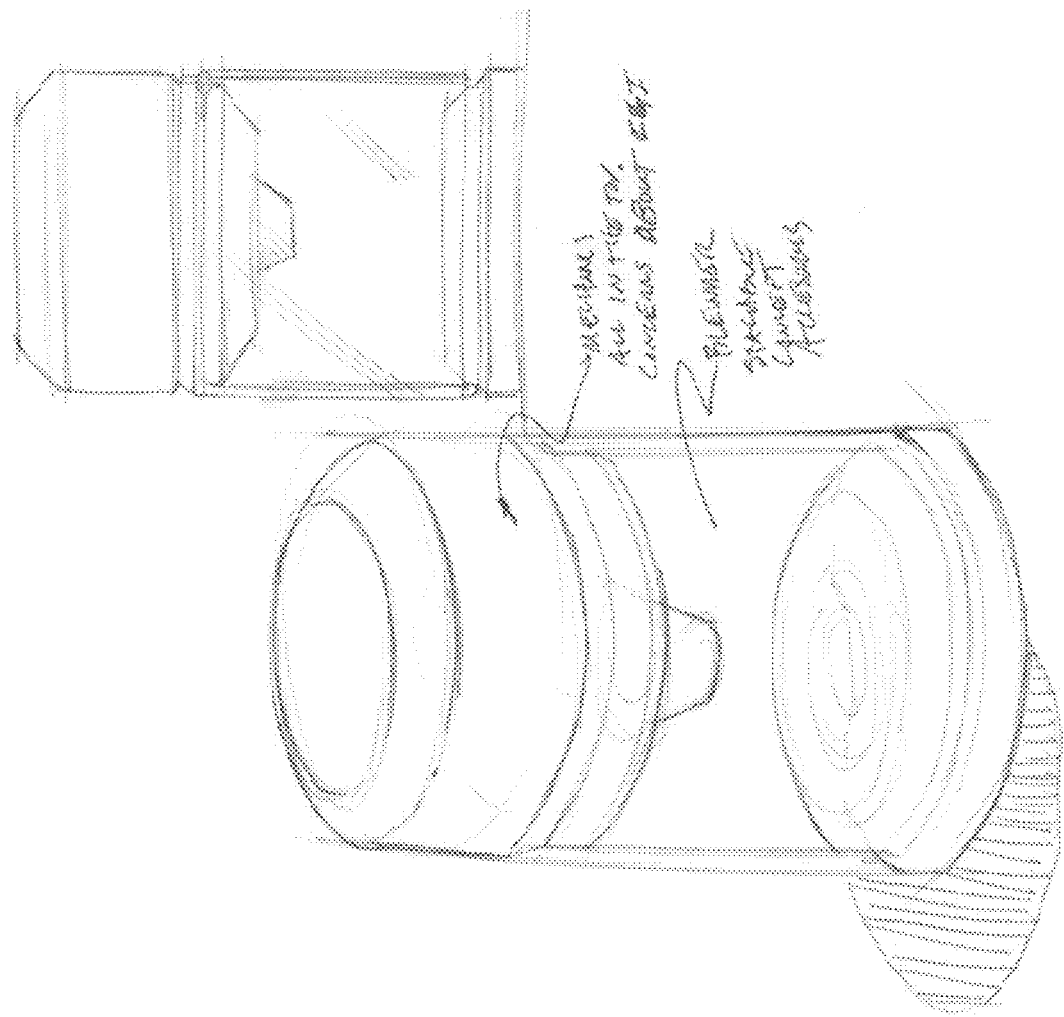
Figure 14H:
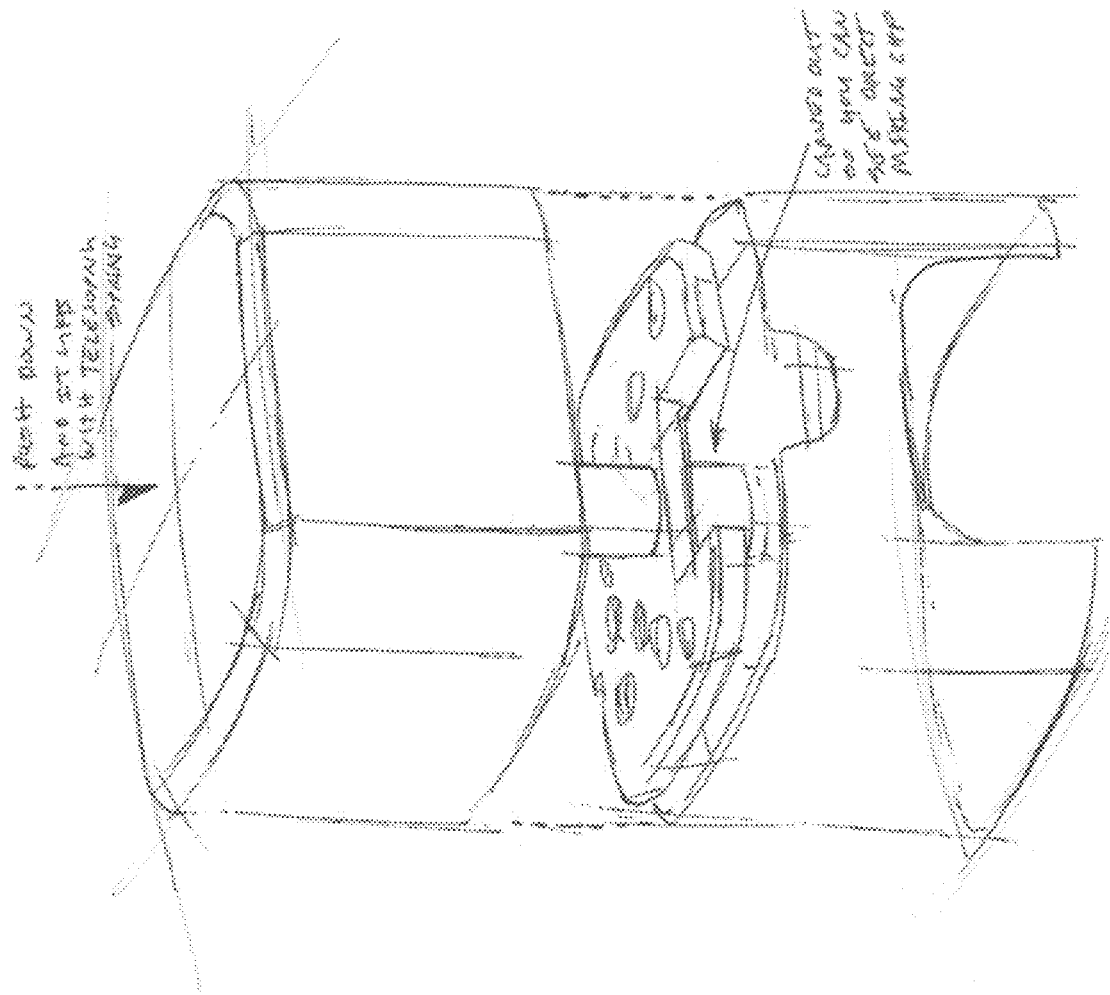
Figure 141:
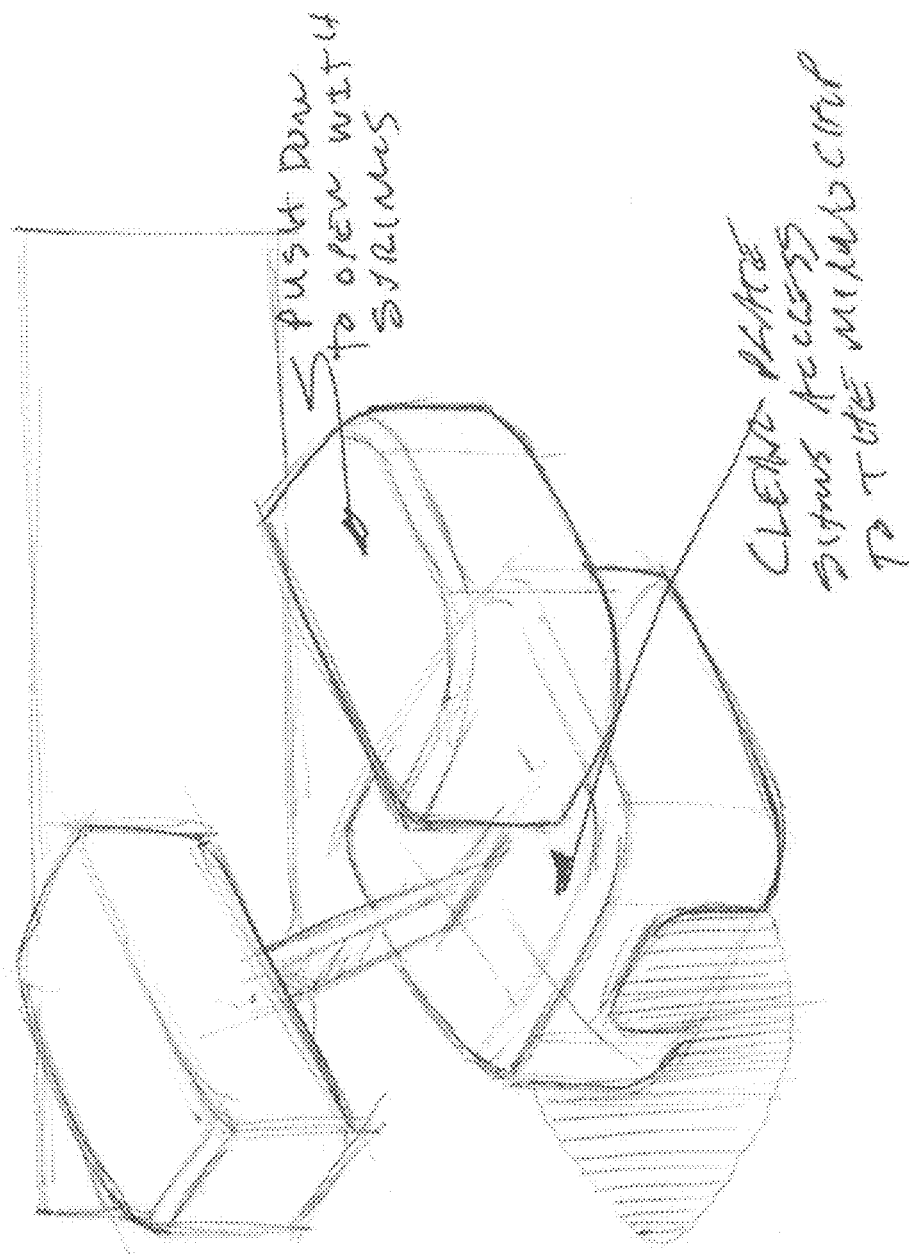
Figure 14J:
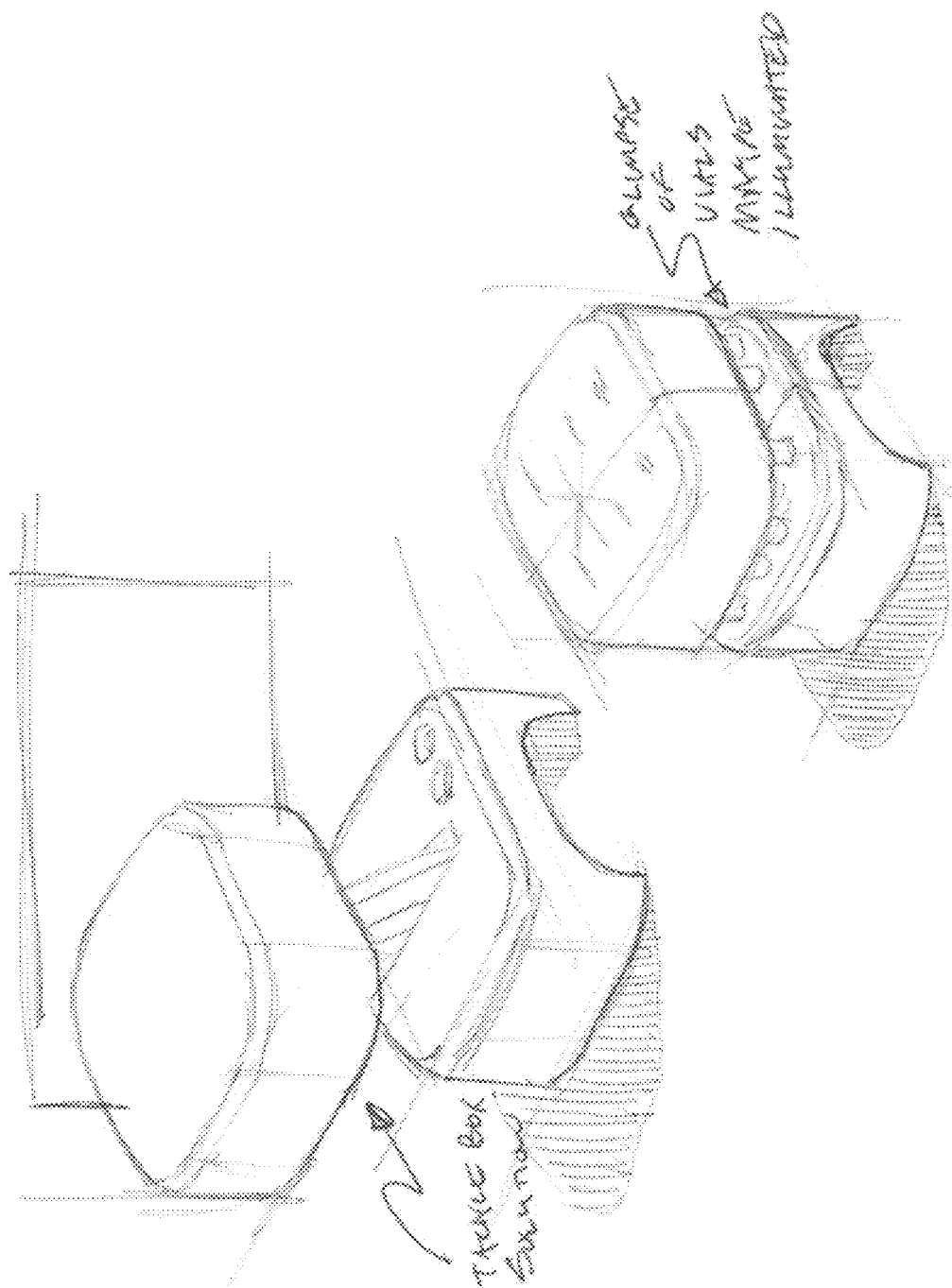
Figure 14K:
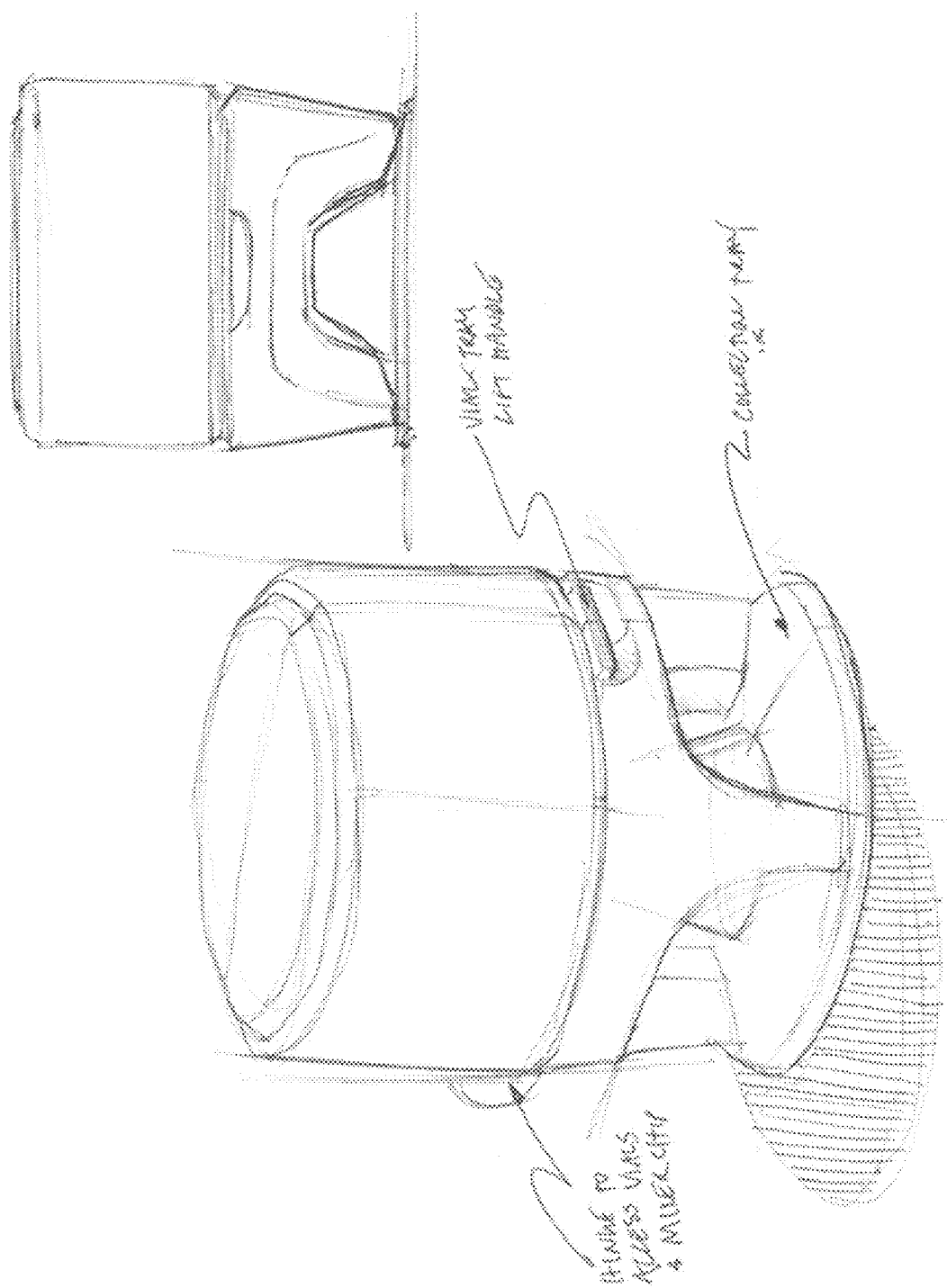
Figure 15:
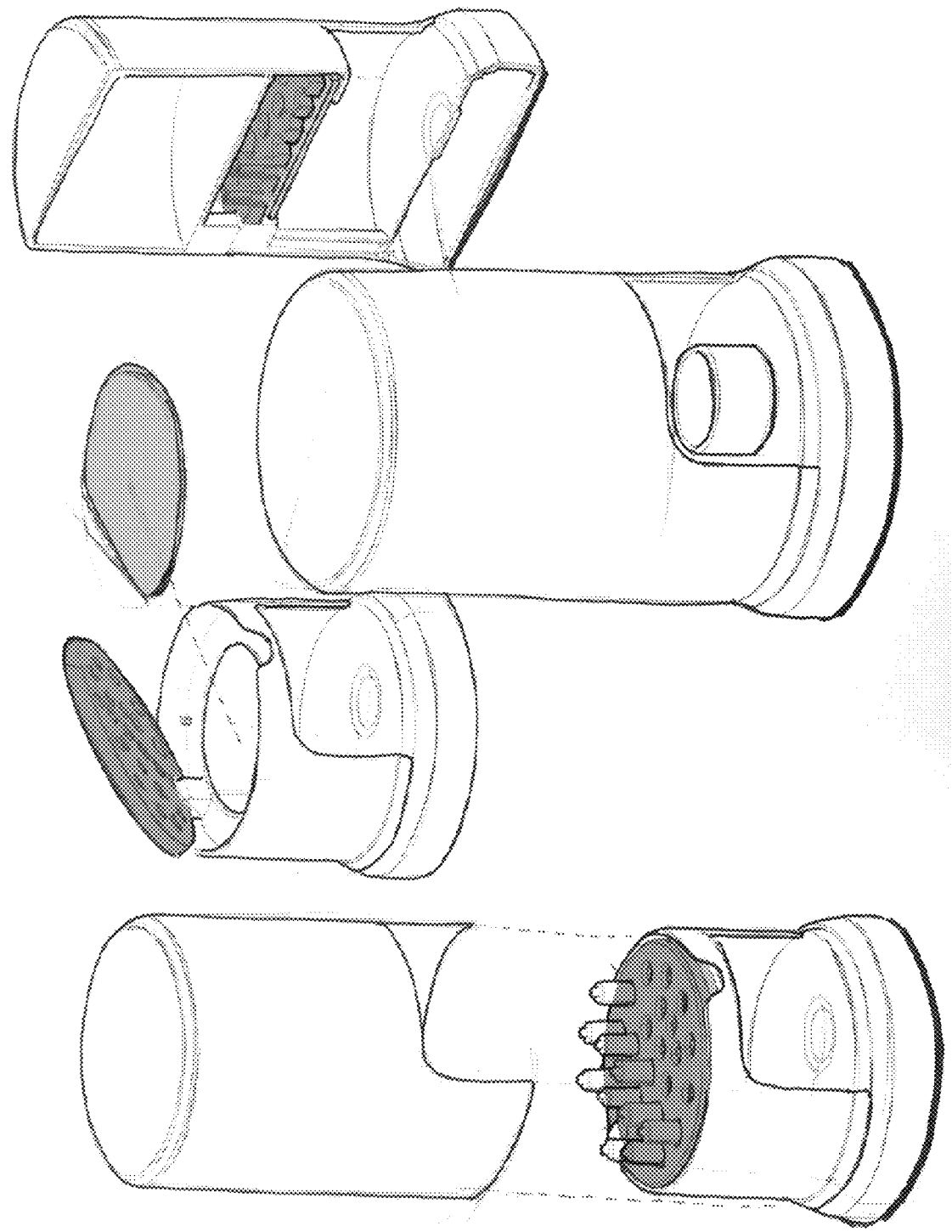
Figure 16A:
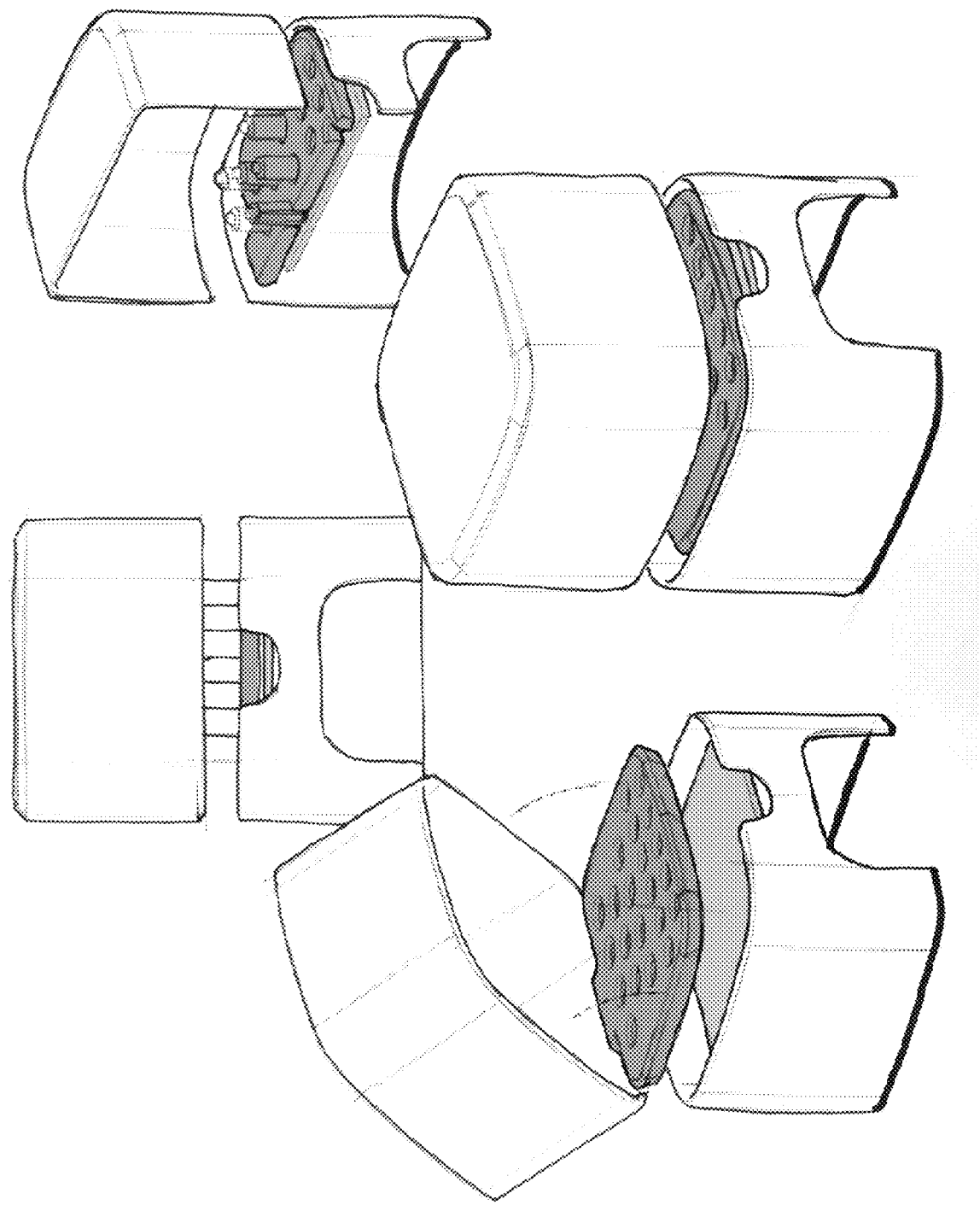
Figure 16B:
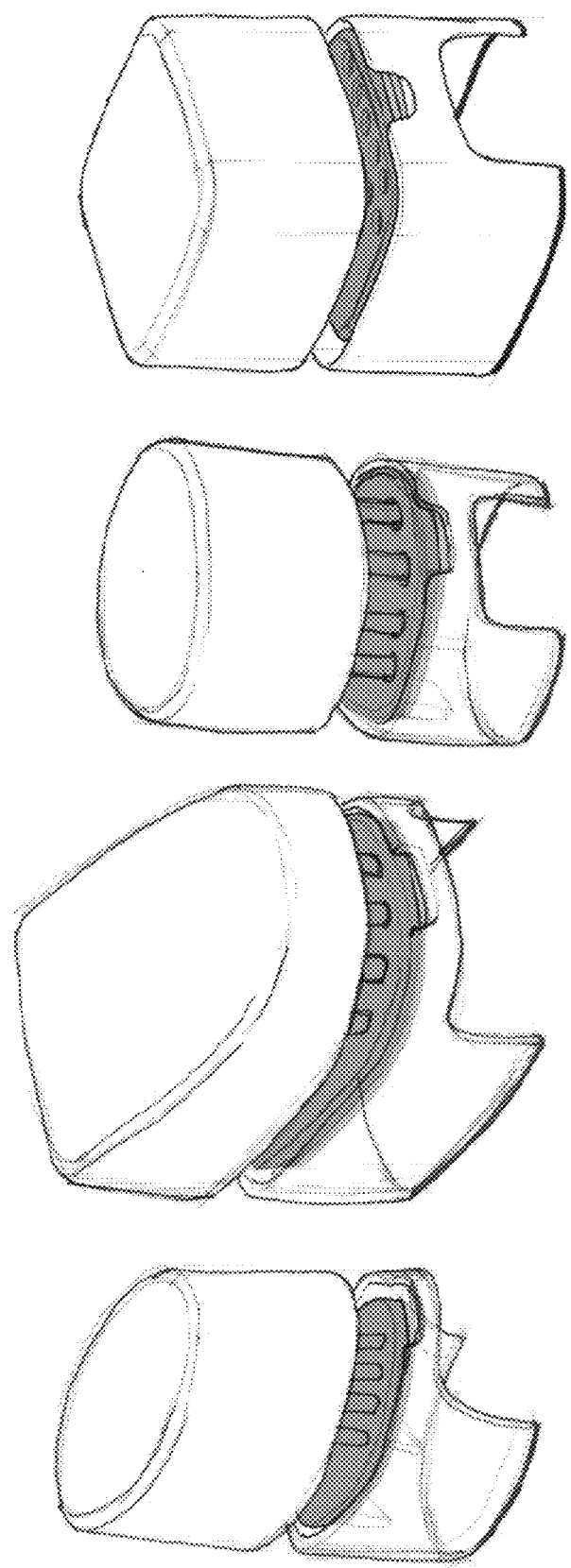
Figure 16C:
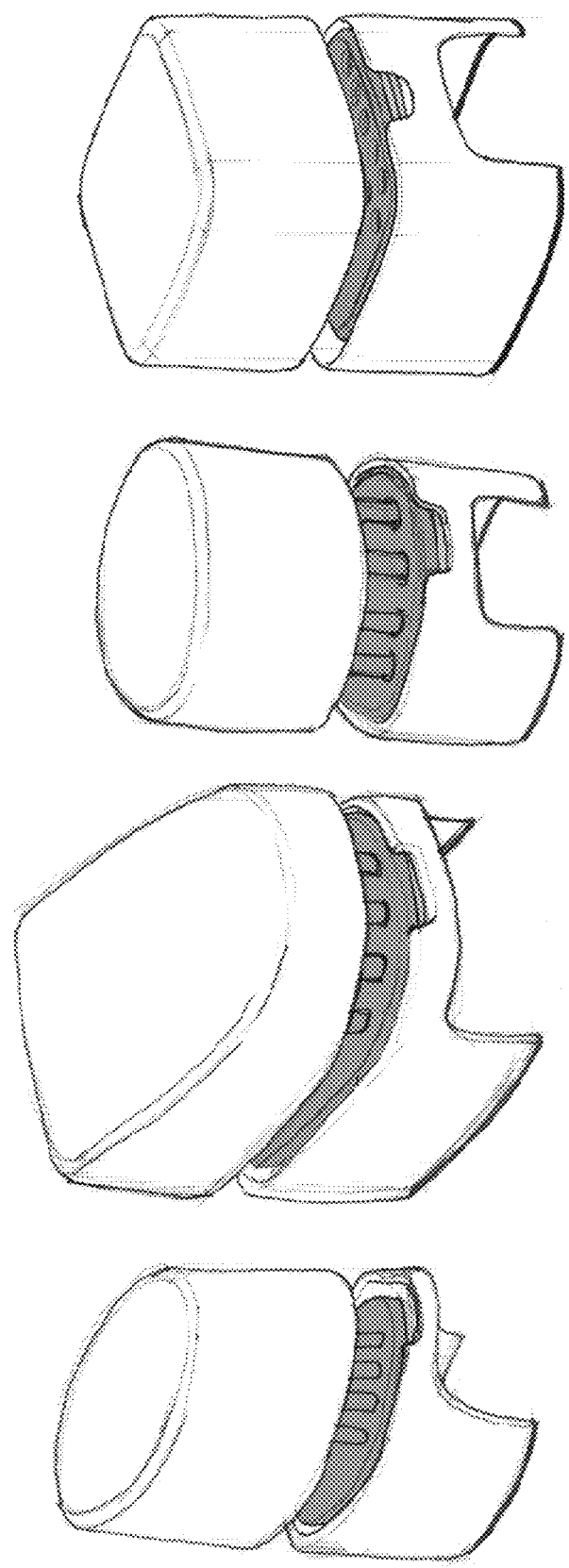
Figure 17A:
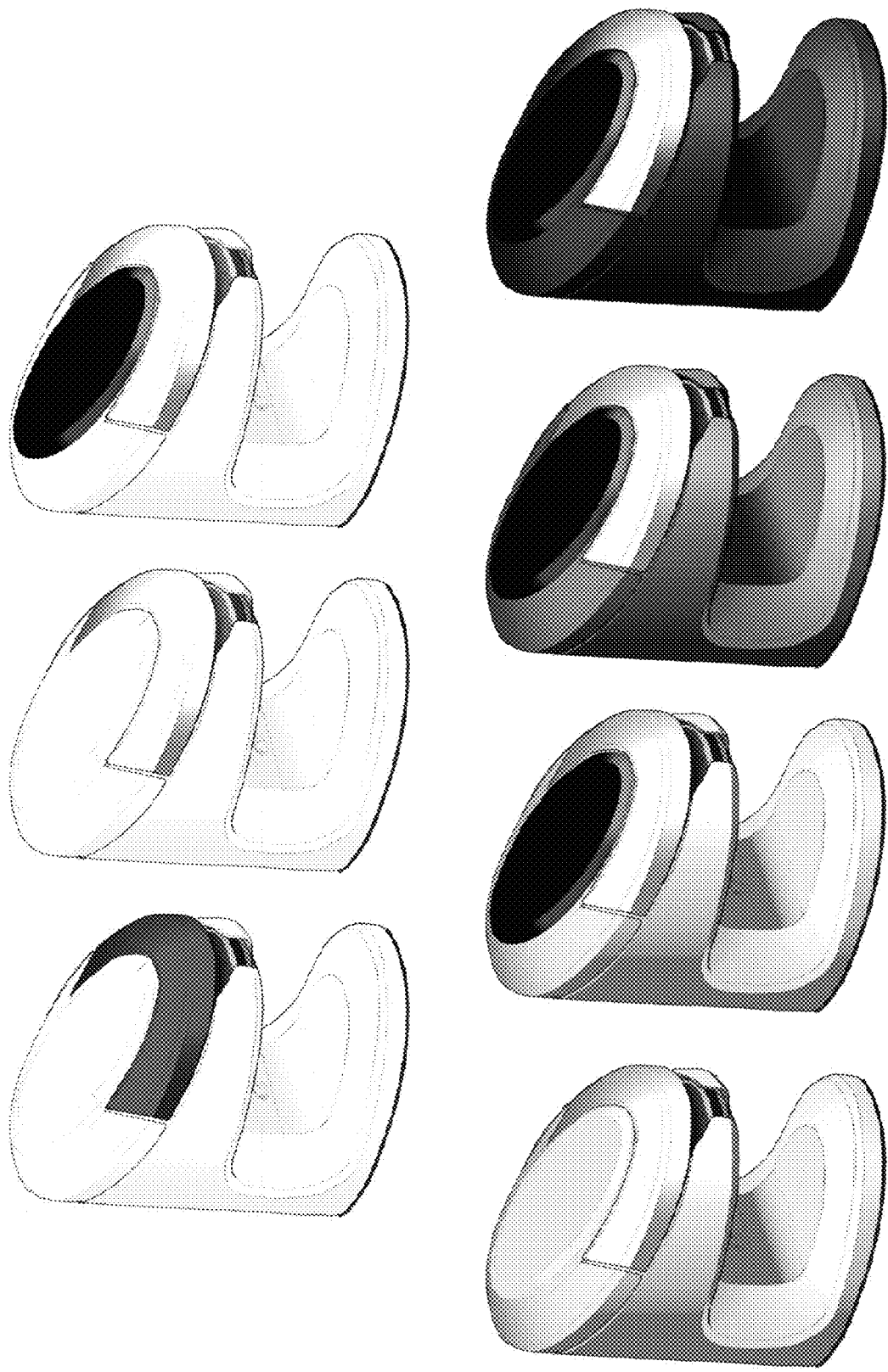
Figure 17B:
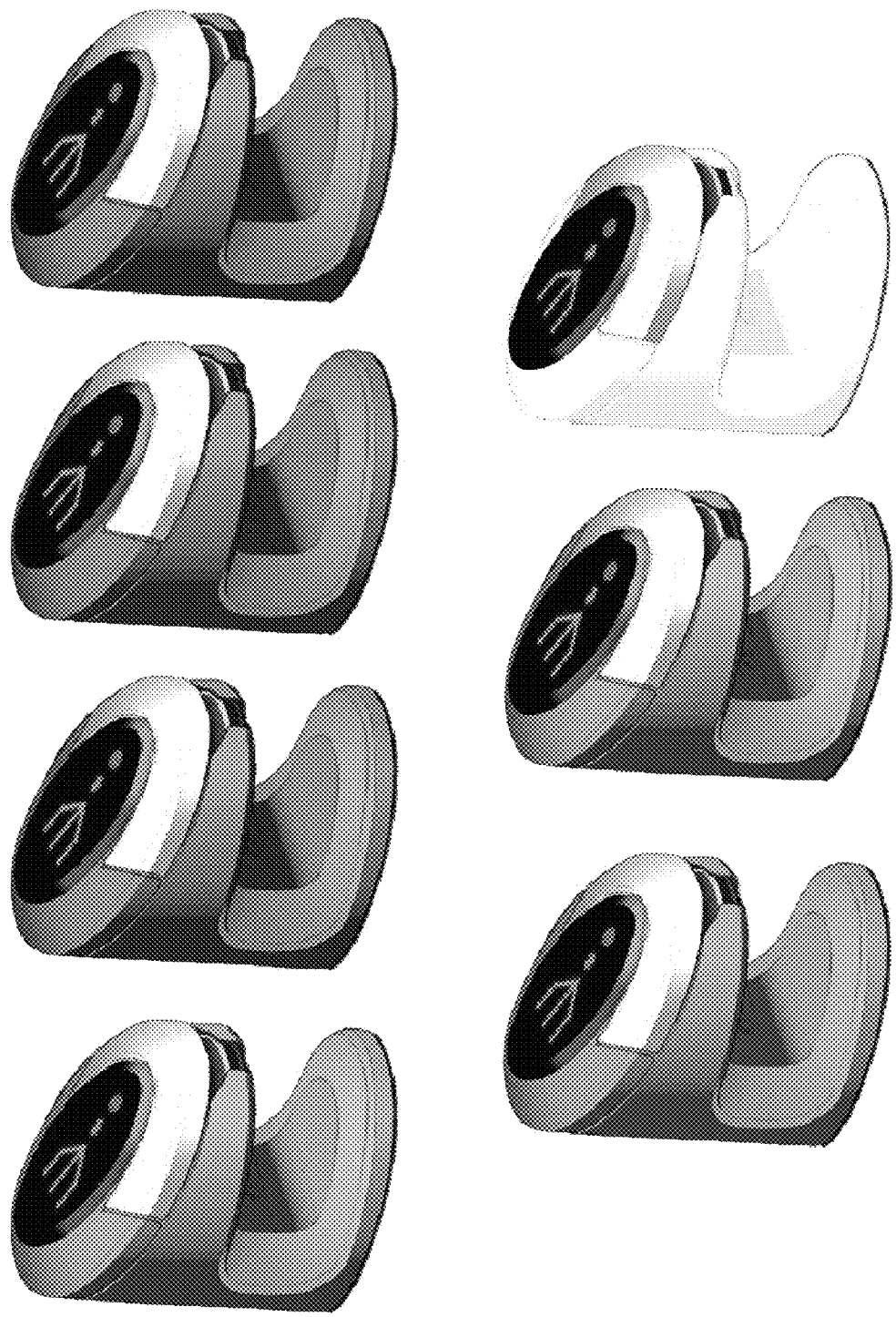
Figure 18C:
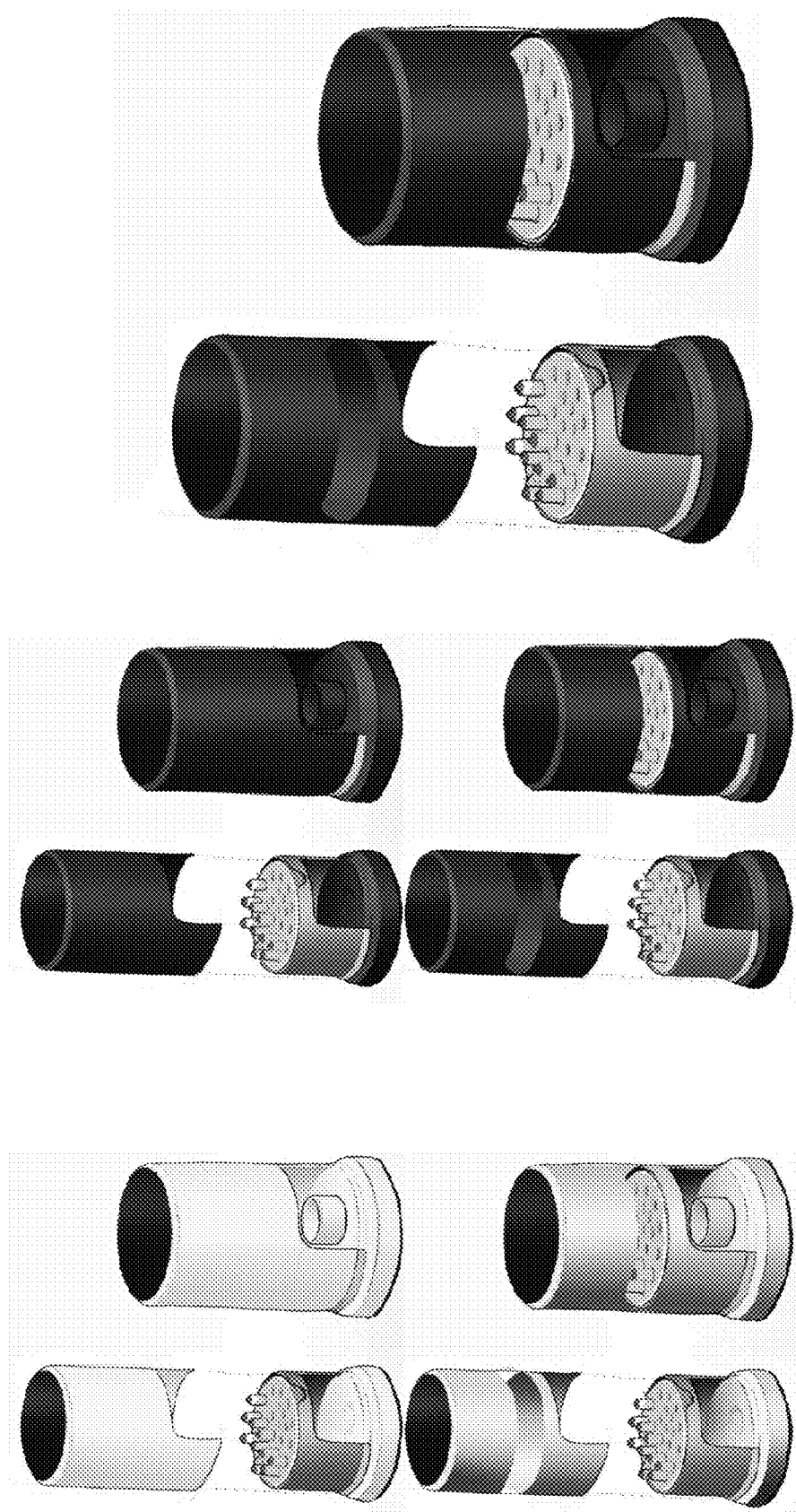
Figure 19B:
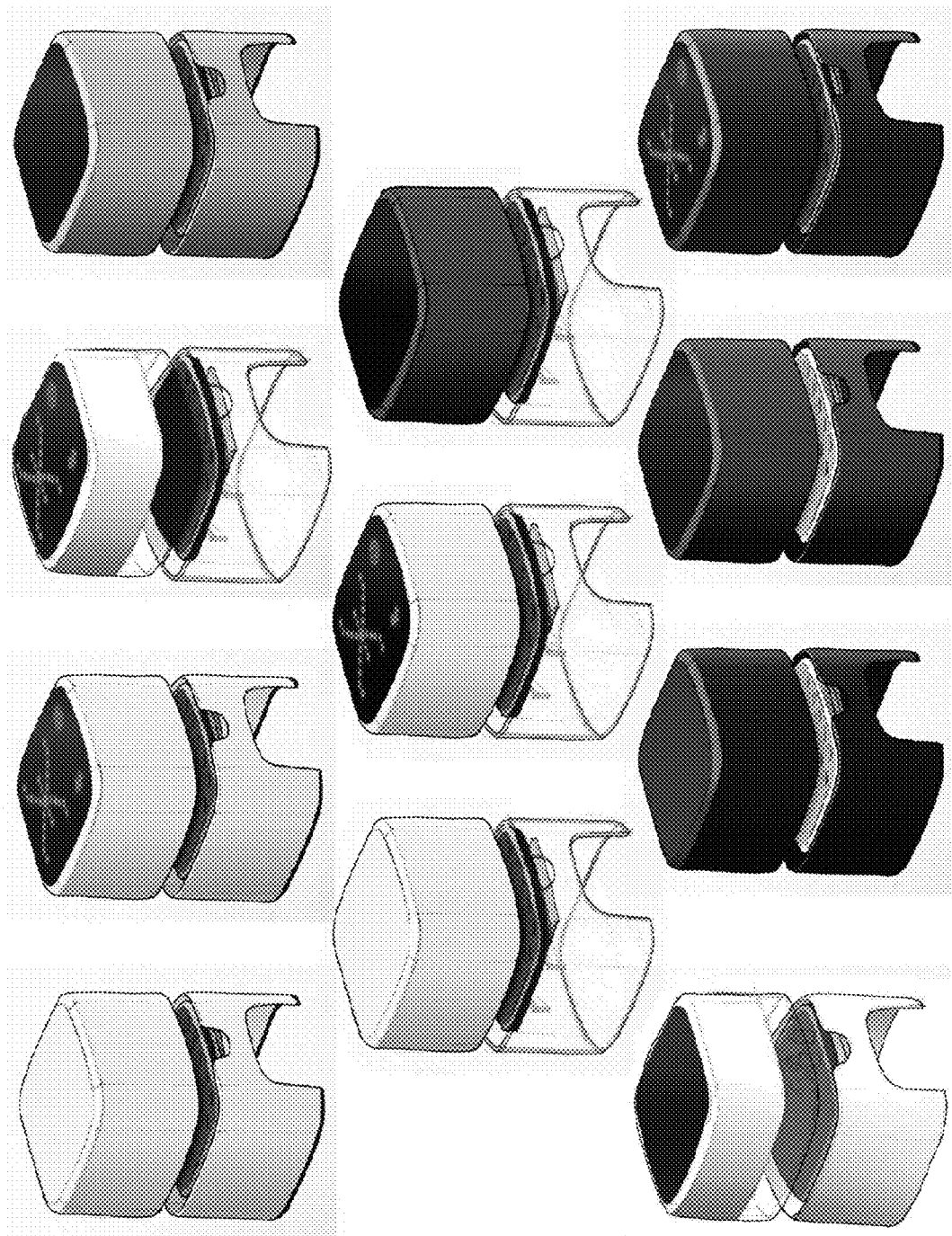

FIG. 12A shows an example OBD microfluidic mixer chip with a plurality of fluid tanks/cartridges disposed thereon. Some embodiments of the OBD microfluidic mixer chip include one or more valves near the interface between the fluid cartridge/fluid tank and the microfluidic mixer chip to prevent or reduce unwanted pressurization and compression of the air volume within the cartridge. Some embodiments utilize a check valve, such as a duckbill valve (e.g., FIG. 12B) or an umbrella valve (e.g., FIG. 12C) to the tip of the cartridge where fluid is dispensed. Additionally or alternatively, a check valve can be included at the inlet port on a microfluidic mixer chip. In some such embodiments, such a valve can also seal a port on the chip if a fluid cartridge/tank is not installed. In some embodiments, the microfluidic mixer chip includes a flexible layer, configured such that pressure-activated valves near the inlet ports can be defined or formed thereon/therein. Although discussed in terms of mixing of fluids occurring in a microfluidic mixer chip, it is to be understood that some embodiment of the OBD, the microfluidic mixer chip (mixer chip, or chip) can instead accurately meter and dispense microfluidic amounts of the fluids and the mixing be conducted outside the chip, such as in the a collection vessel (e.g., a vial, vape cartridge, bowl, etc).

FIG. 13A-FIG. 13F show examples of OBD fluid tanks, including an identifier component (e.g., microchip, RFID, QR/bar code, etc.) disposed on a flat surface thereof, and including coloring/color coding.

FIG. 14A-FIG. 19B show examples of OBD designs and configurations, according to some embodiments. Such designs can be configured with locks/lock mechanisms, for example, to prevent access by unauthorized individuals (e.g., child access locks on the cartridge(s) and dispensing port), prevent access during mixing and/or heating, restrict access to certain components (e.g., semi-permanent components may require special keys or authorization to service/replace to assure the OBD is safe to operate and sterile), etc. Some embodiments can include transparent and/or semi-transparent portions (which can additionally be backlit, in some embodiments) that allow viewing of the internal components and/or provide visibility to the progression of the mixing.

Figure 20:
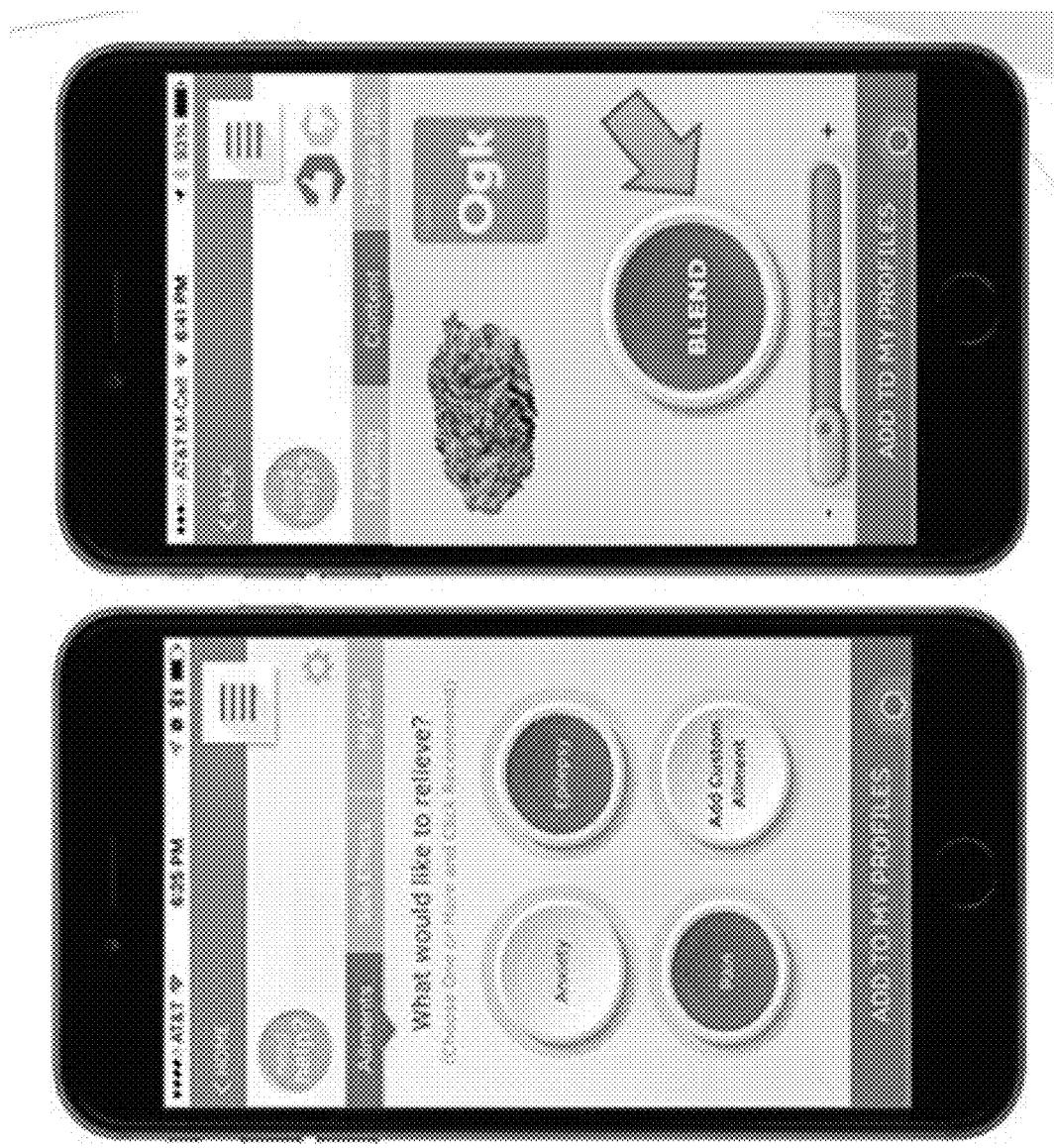
FIG. 20 provides an example OBD mobile device application user interface for some embodiments according to the disclosure.

FIG. 20 provides an example OBD mobile device application user interface, according to some embodiments.

Figure 21:
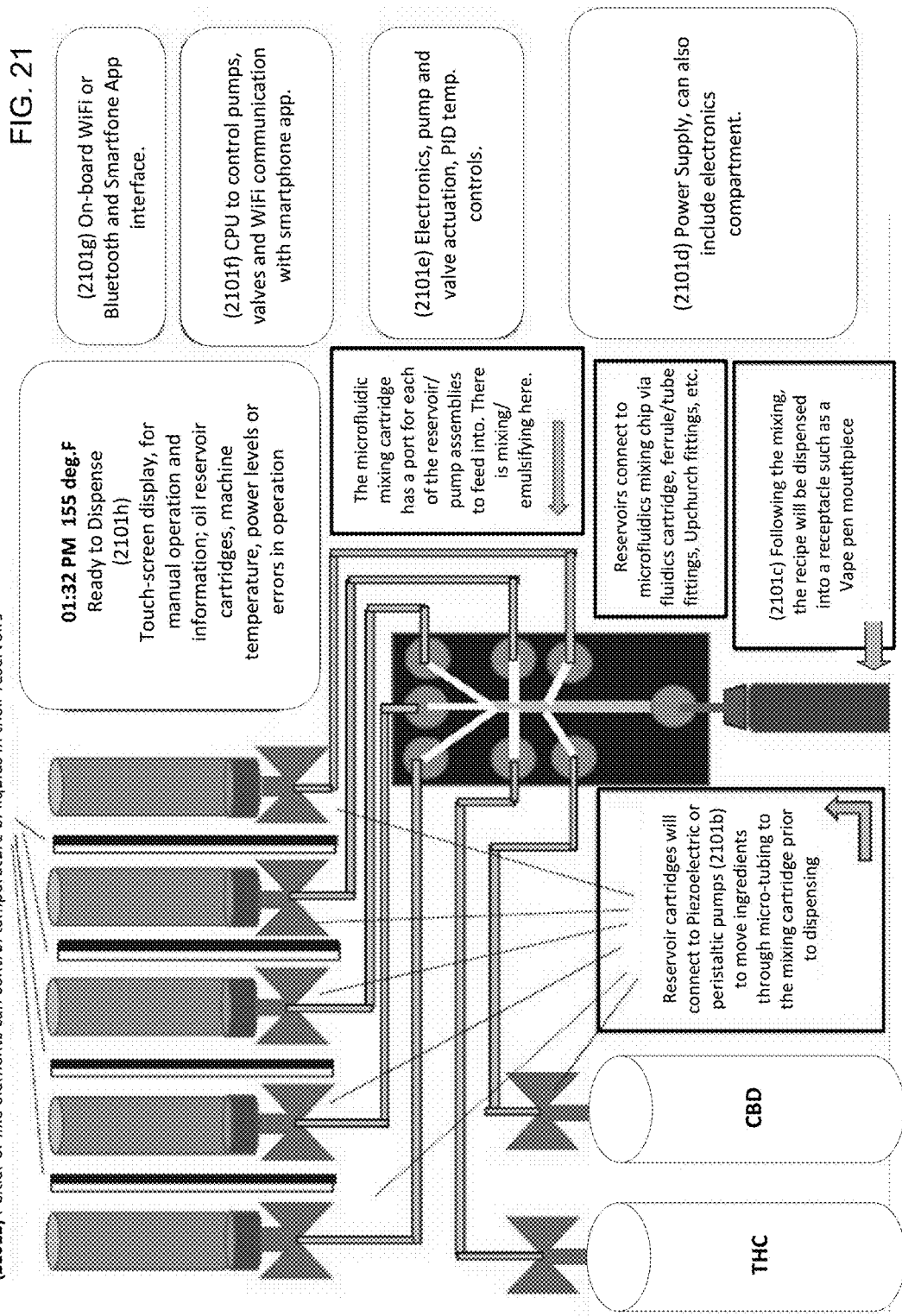
Figure 24A:
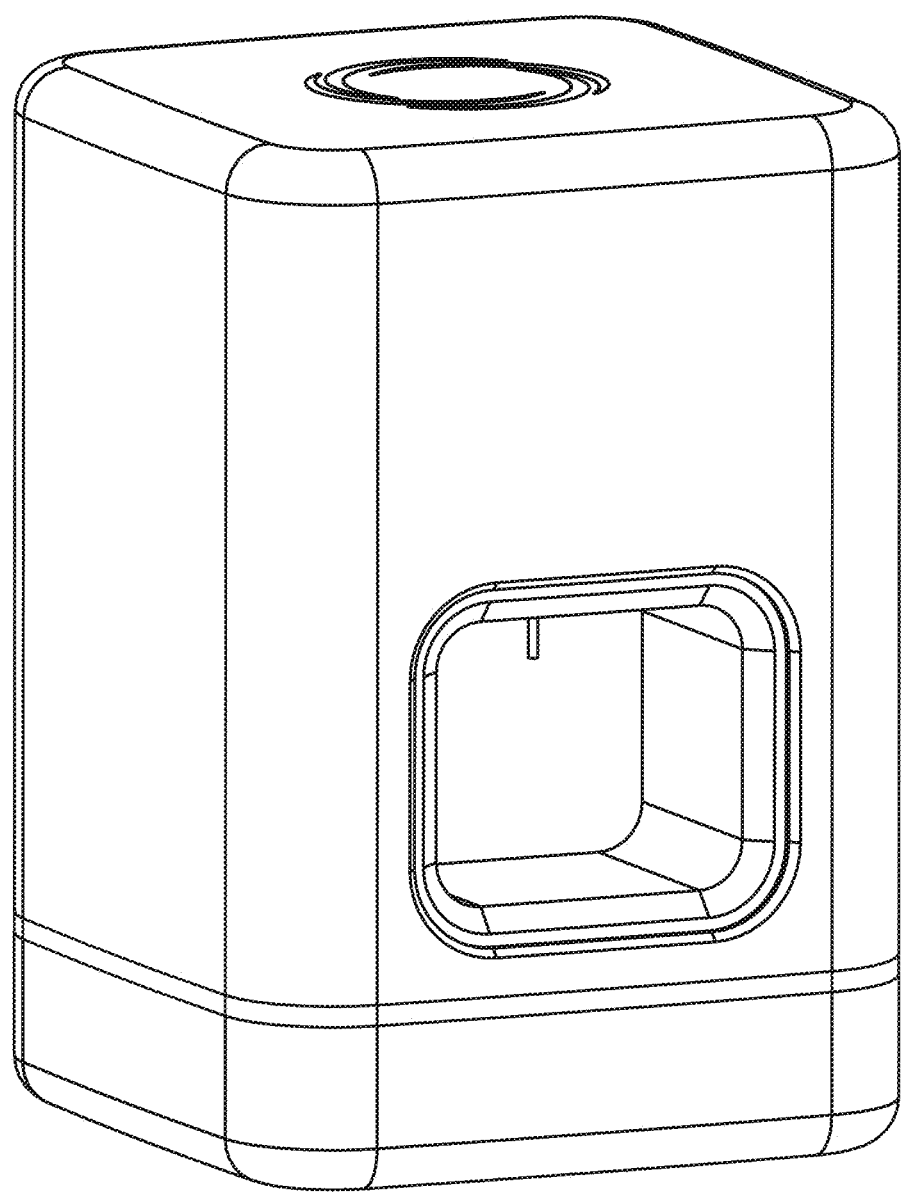
FIGS. 24A to 26E provide details for example OBDs according to some embodiments of the disclosure.
Figure 24B:
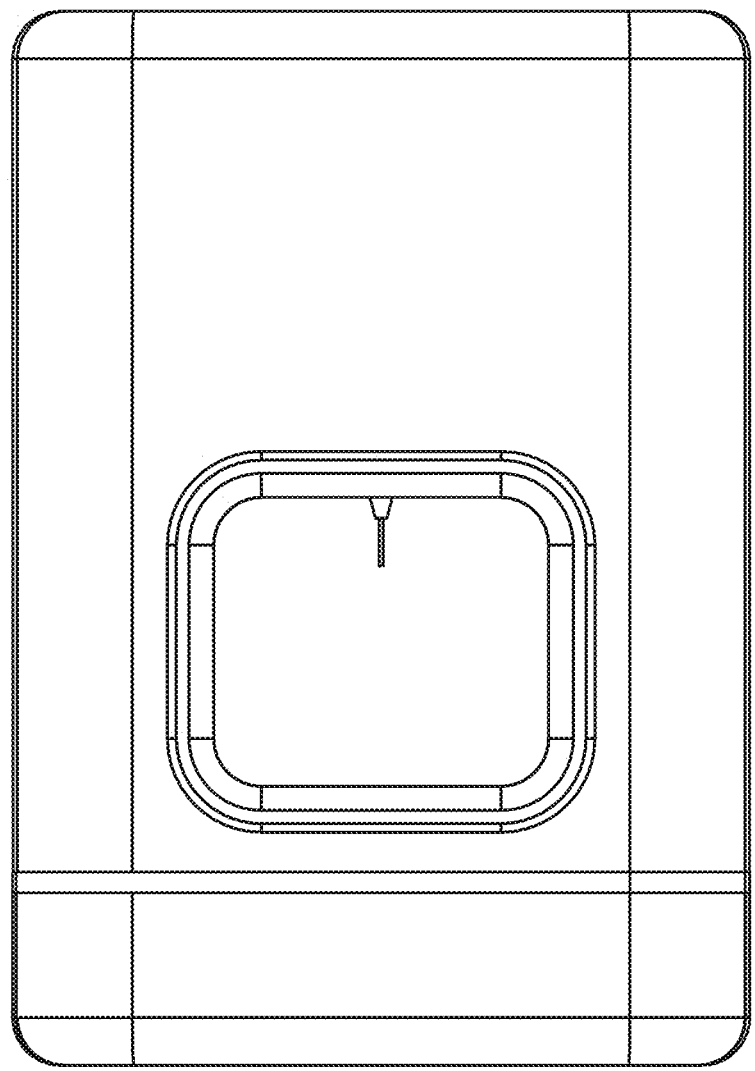
Figure 24C:
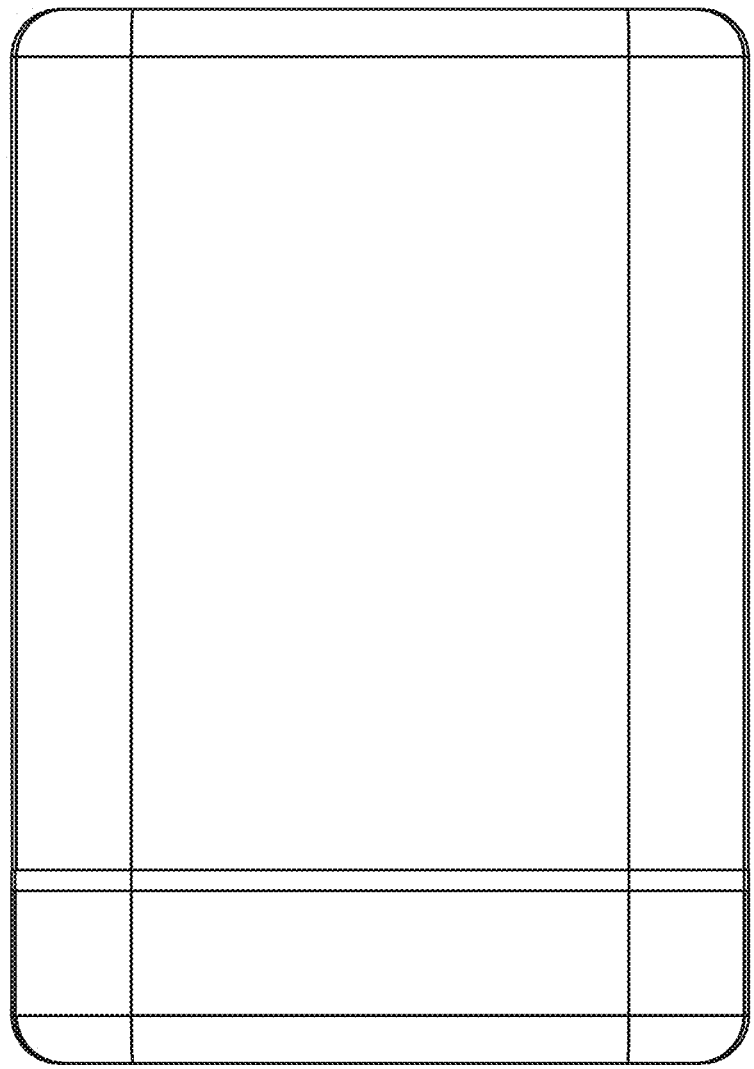
Figure 24D:
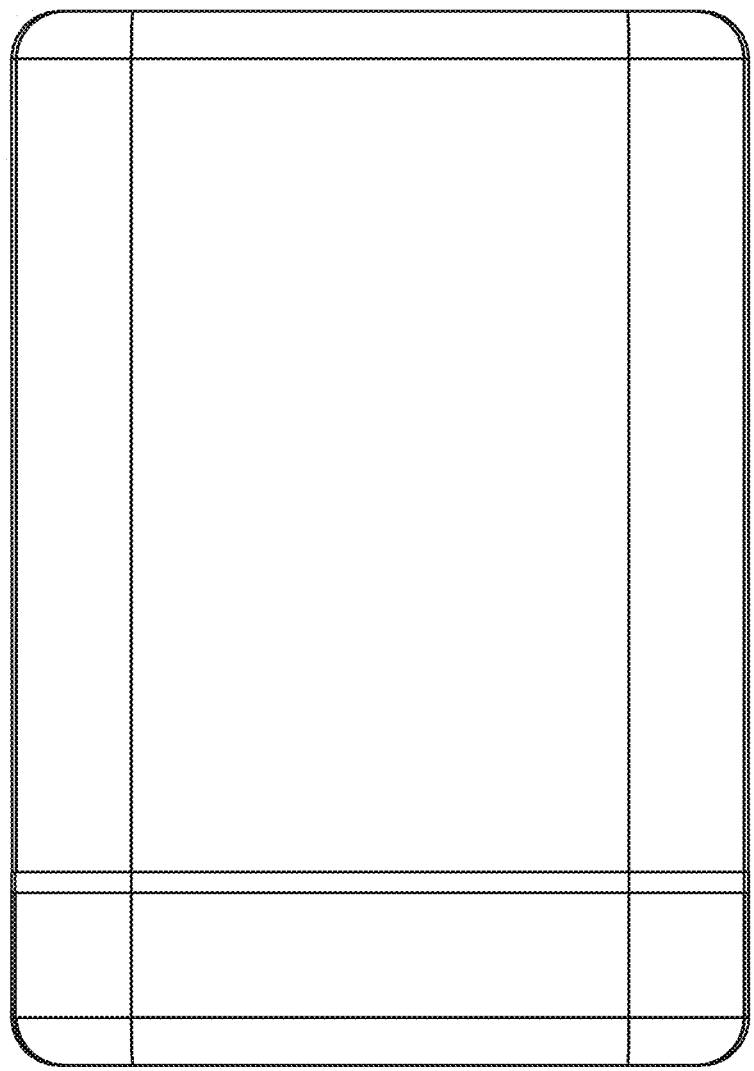
Figure 24E:
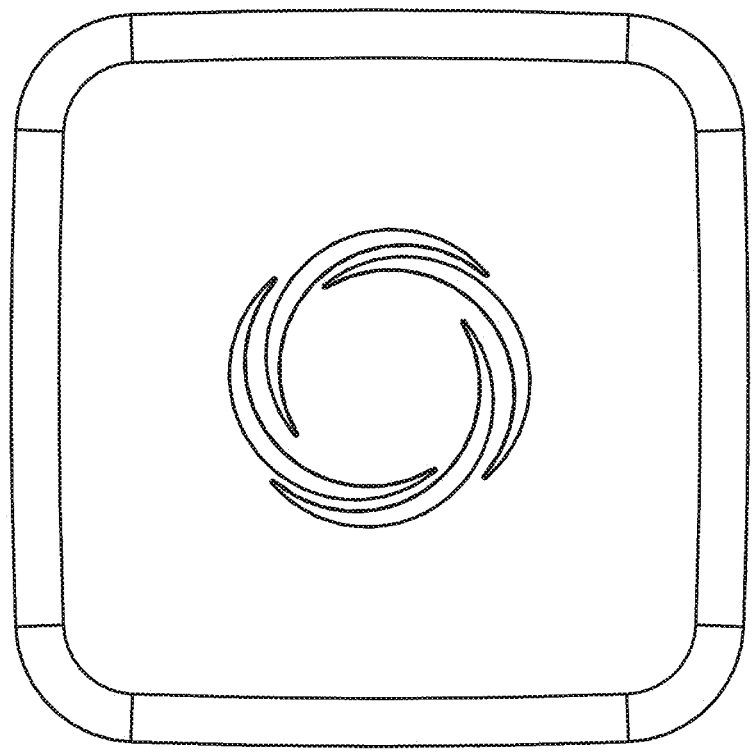
Figure 25A:
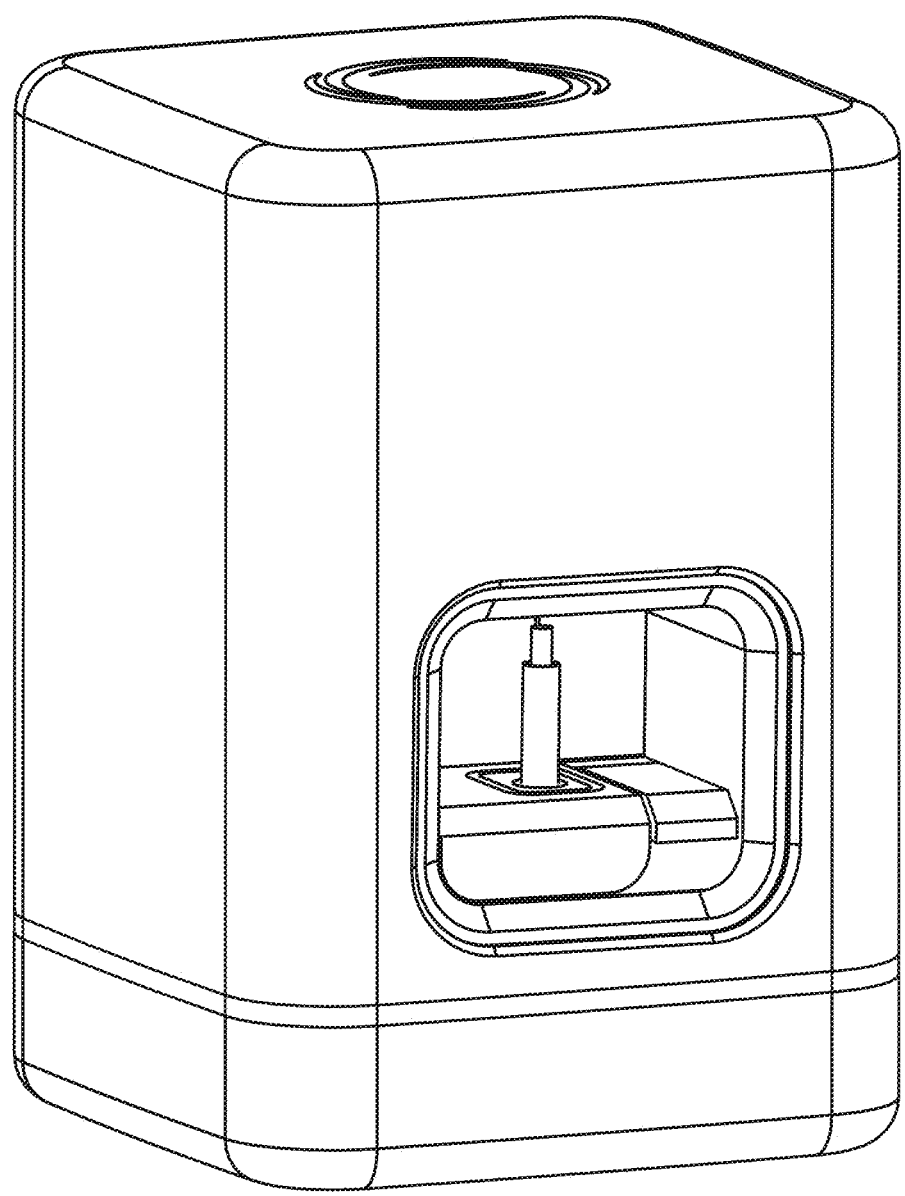
Figure 25B:
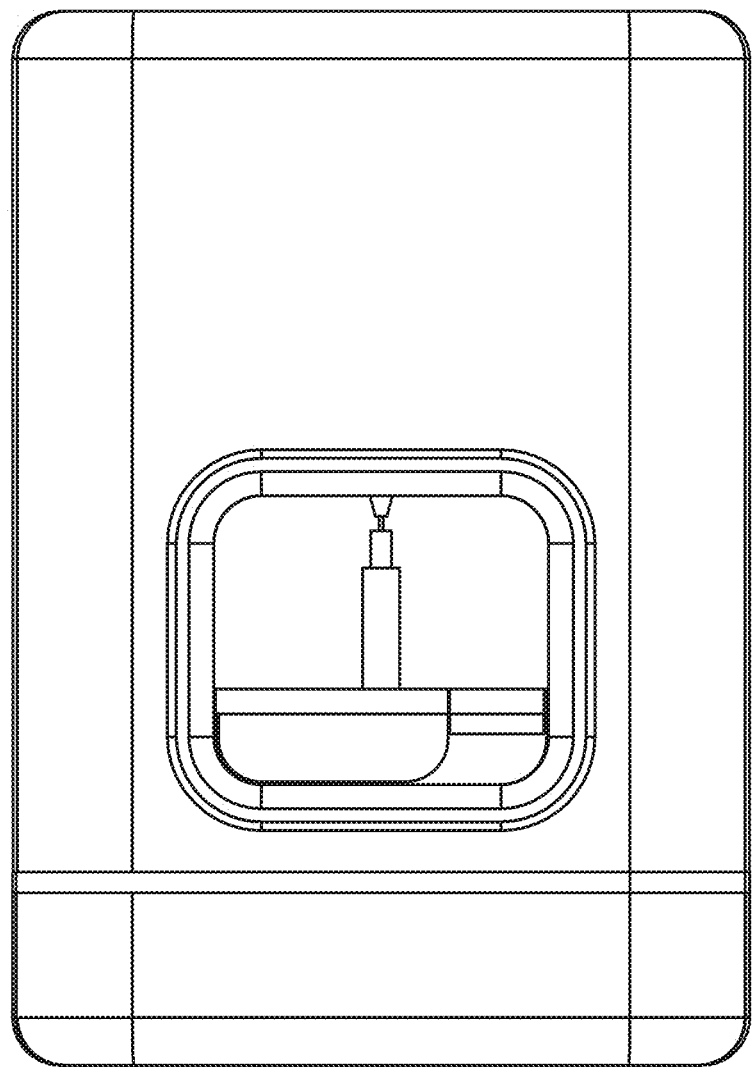
Figure 25C:
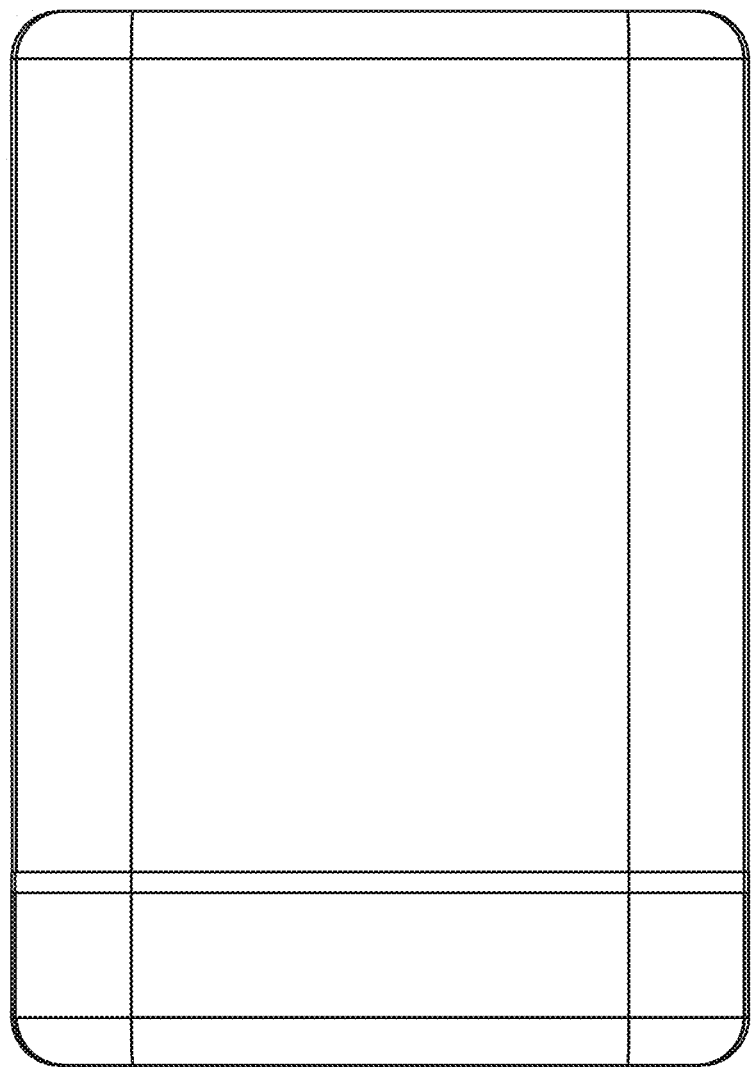
Figure 25D:
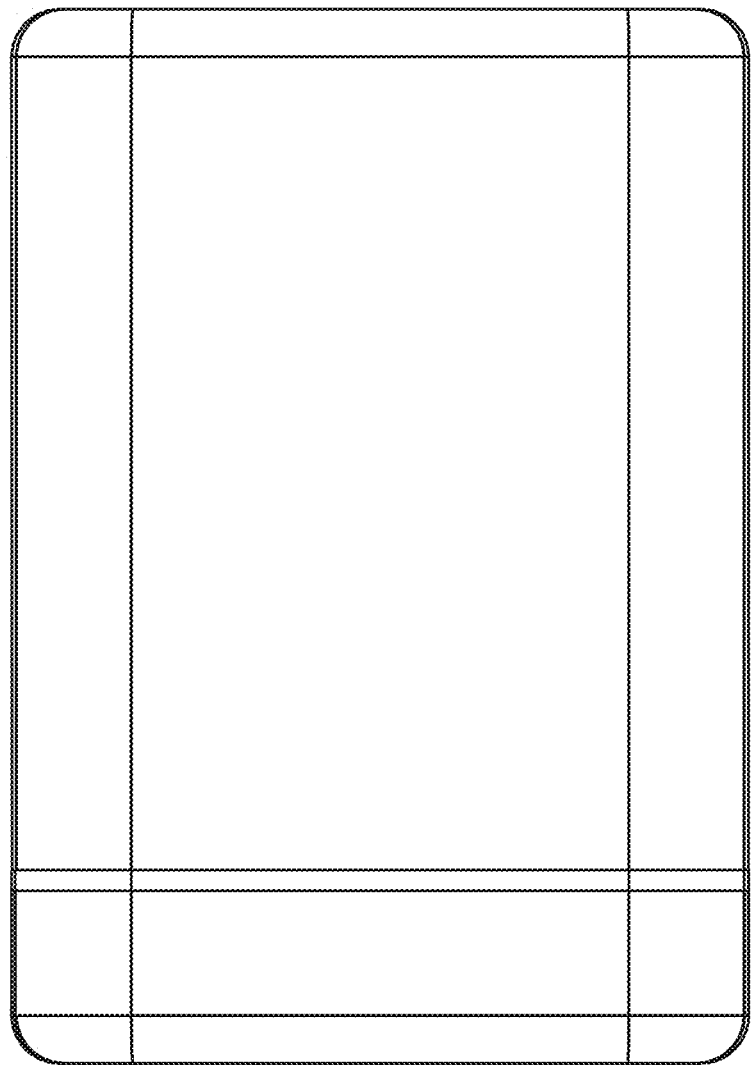
Figure 25E:
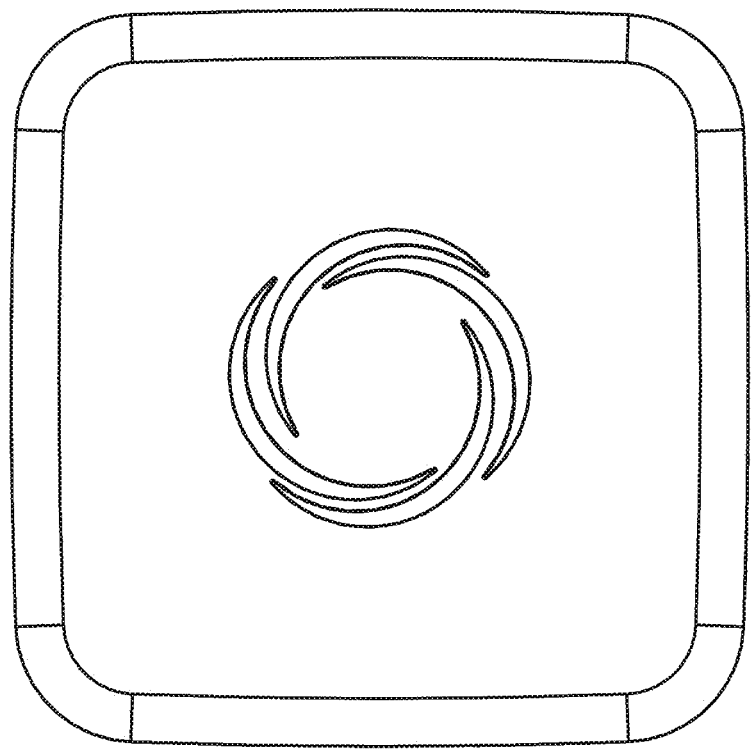
Figure 26A:
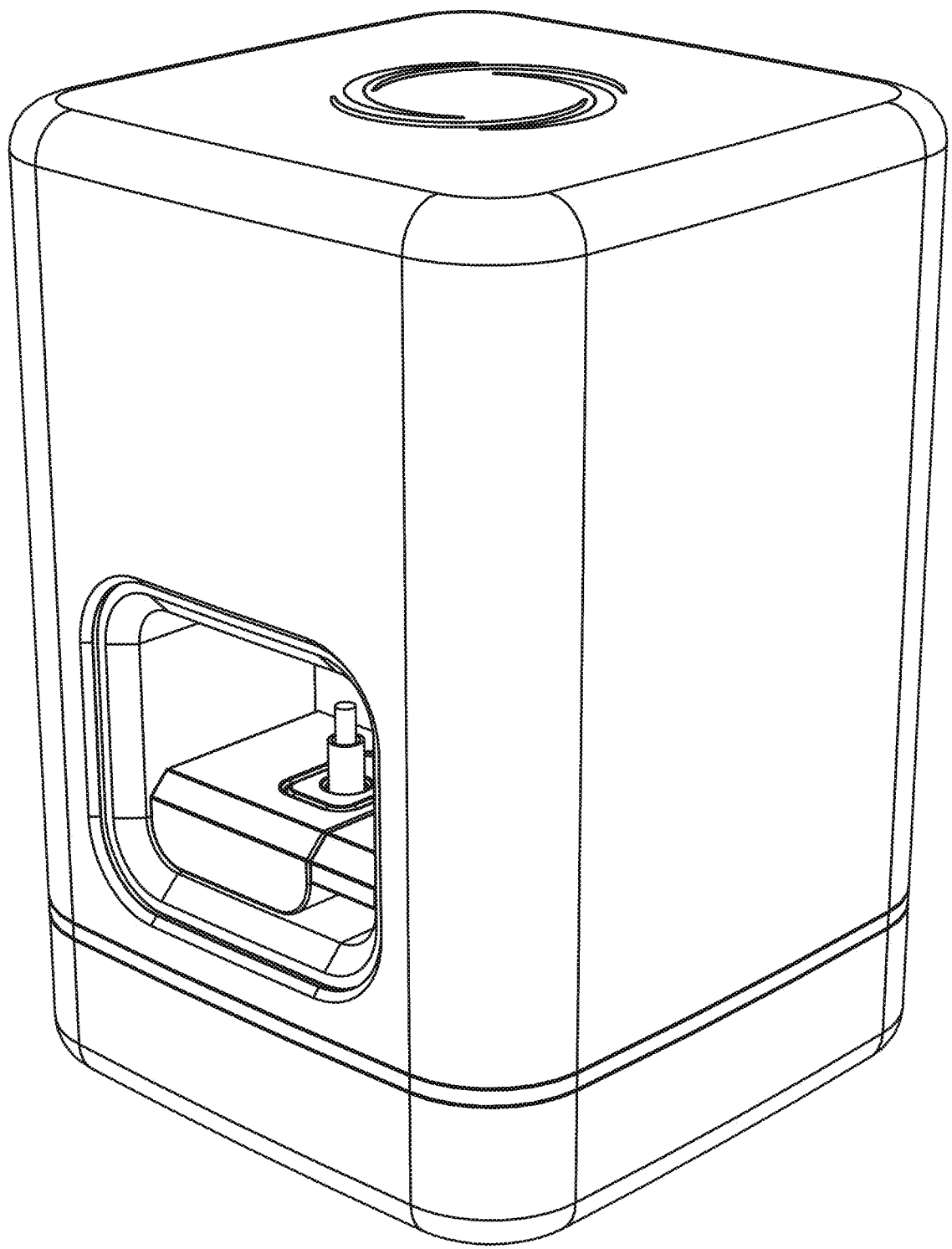
Figure 26B:
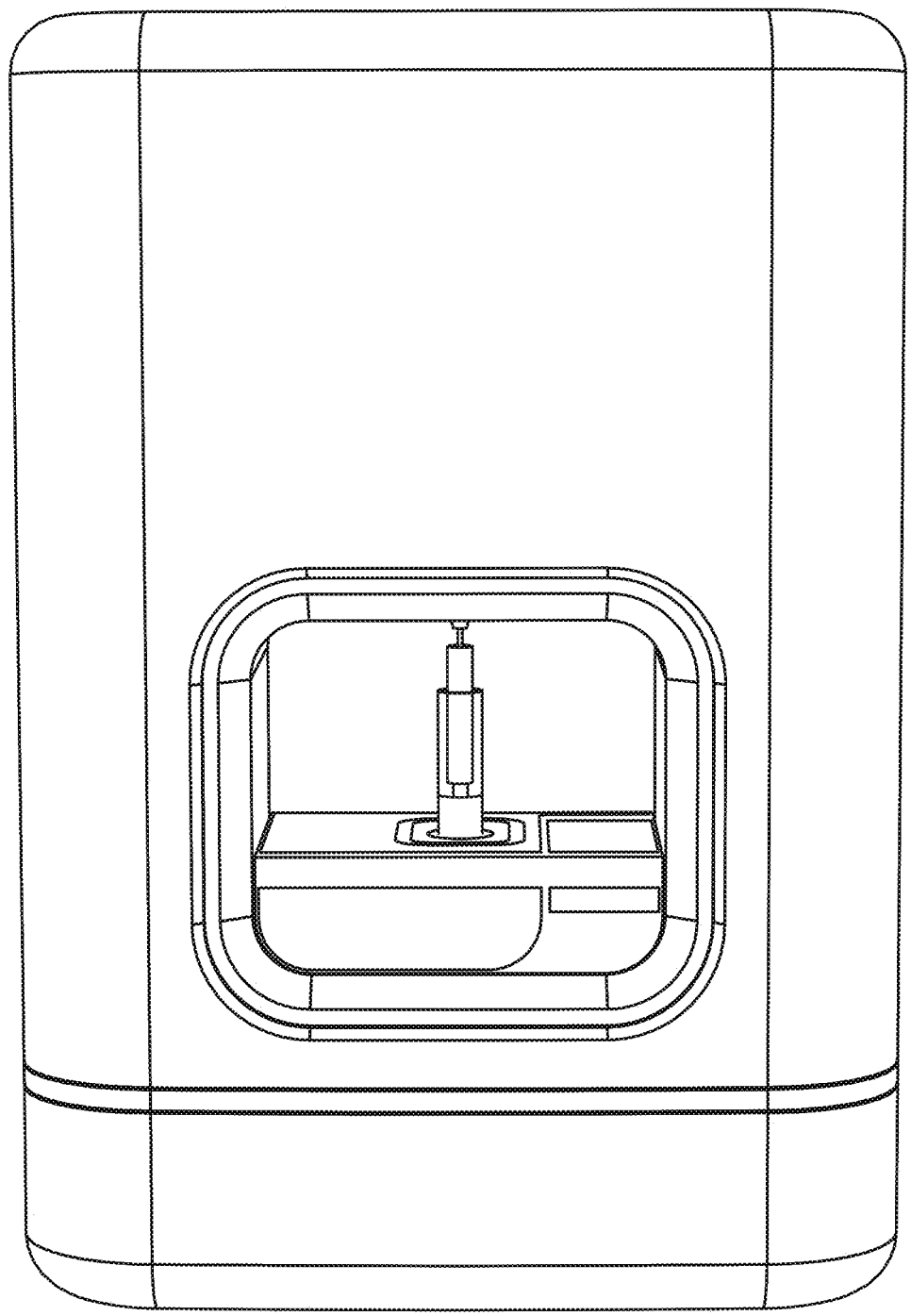
Figure 26C:
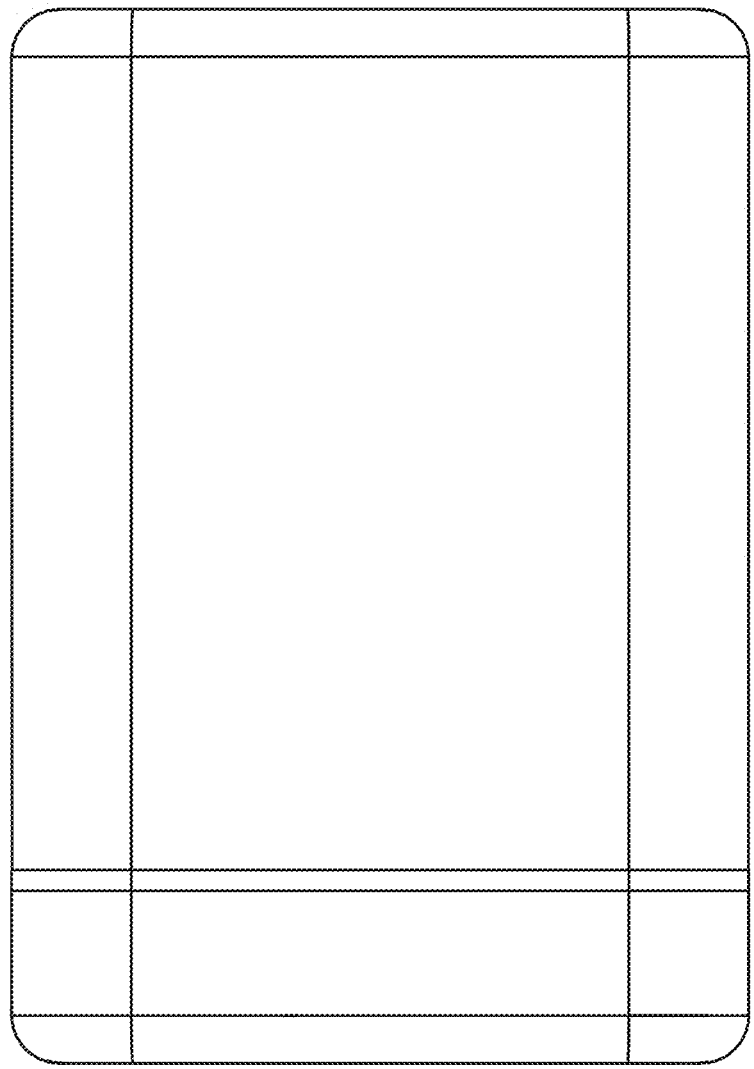
Figure 26D:
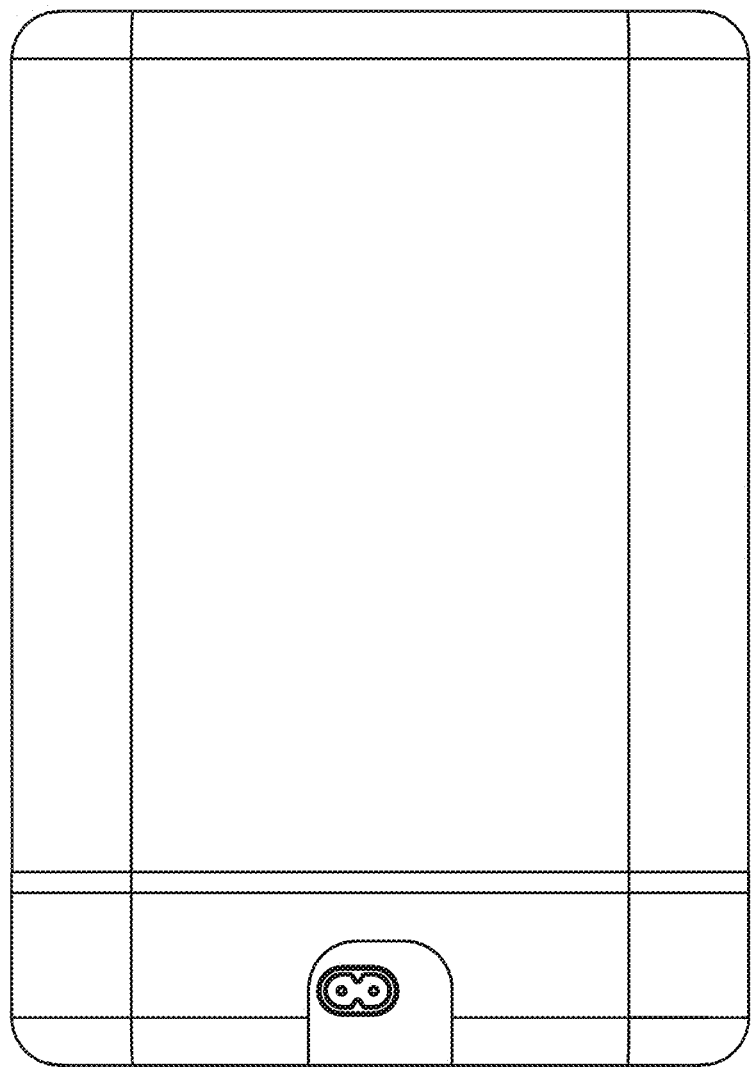
Figure 26E:
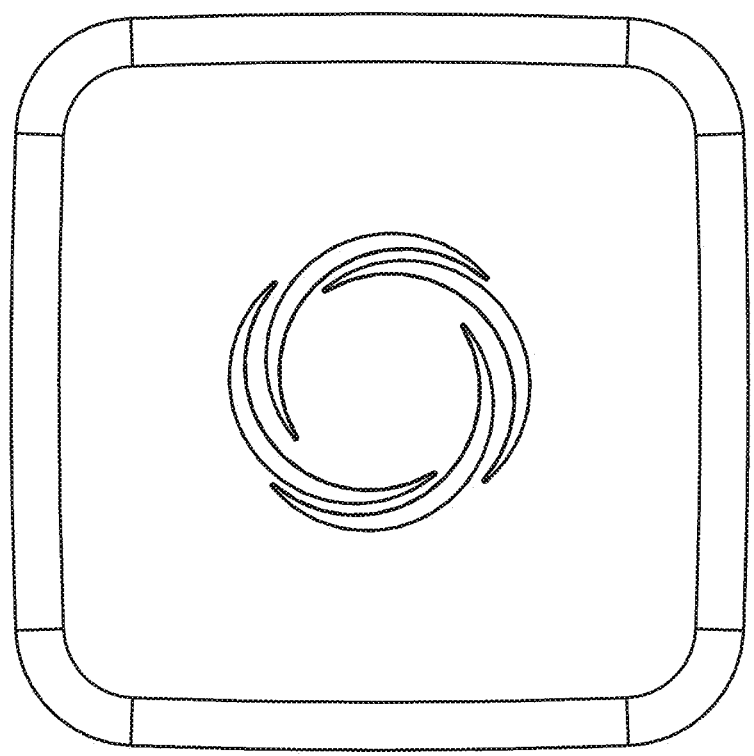

For cannabis industry applications, the OBD can be configured to a variety of different components and oils, such as the 25 different oils shown in FIG. 21. Such components/oils can include THC, CBD, CBG and 20 of the primary terpenes found in the majority of cannabis strains. One or more further ports can be made available for the user to introduce flavoring(s) to their mixtures. These different fluids can be stored either on/in the machine in various quantities (e.g., from 0.250 ml to 3 ml, from 0.1 ml to 100 ml, etc.), and/or in a storage case on or adjacent to the OBD.

Some of components (e.g., terpenes and cannabinoids) are fairly viscous and are temperature controlled (e.g., up to 150 degrees F.) by the OBD in order to facilitate good fluid flow during pumping, mixing and dispensing. In some embodiments, temperature control is achieved through the use of Peltier elements and PID controllers (e.g., 2101a). Various pumps (e.g., 2101b) may be utilized, including by way of non-limiting example, stepper-syringe type, peristaltic, or piezoelectric pumps, and one or more pumps may be utilized or selected to be most effective in working with fluids of varying viscosities. For example, certain pumps may be utilized for some flow paths associated with fluids having a particular viscosity (and/or volume), while other pumps are used for flow paths of fluids with other viscosities (and/or volume).

In some embodiments, fluids are blended in various quantities, depending on which is being used. Some of the fluids can regularly constitute a higher percentage of the final (e.g., 0.1 mL-3 mL) product and can therefore be pumped in relatively larger volumes (e.g., 250 □L to 800 □L). Others will be used in much smaller quantities and only require to be pumped in relatively smaller volumes (e.g., approx. >1 □L-100 □L). As such, the types of pumps and/or fluid cartridge dispensing port size required to move the various fluids can vary accordingly.

In some embodiments of the OBD, a user selects a recipe from a smartphone App, HTML 5 website, and/or the like, modifies the recipe if desired and orders the device to produce it using an OBD interface. The device can mix the cannabinoid oils (such as THC, CBD and CBG); Terpenes; Flavors (synthetic and natural); and bases (e.g., VG, PG) in order to create custom vapes and blended oils with a variety of flavors, aromas, medicinal and psychotropic effects.

In some embodiments, the different components, oils and terpenes are pumped into a common chamber or tube and are mixed to create a homogenous product.

The fluids can be mixed in a variety of ways, including using turbulent flow, ultra-sonic vibration, pumping air through the mixture, using a mixing cartridge, and/or the like. In some embodiments, a removable and replaceable microfluidic mixer chip, such as detailed herein, can be utilized.

The fluids are then dispensed into a receptacle in specified quantities (e.g., from a 0.1 mL or less Micro-vape to 3.0 mL or more). In some embodiments of the OBD, the receptacle can be interchangeable with most on-market vaping batteries and tips so the user can easily disconnect the receptacle and begin vaping.

Fluid types that can be used in some embodiments of the OBD include, by way of non-limiting example: Oils, Cannabinoids, Nicotine, Terpenes, Terpinoids, Flavonoids, Cannaflavins, Esters, botanical extracts, endocannabinoid agonists, aromatics, and/or the like. The list of Cannabinoid oils, Cannabinoids, Terpenes (including primary terpenes found in Cannabis), Terpinoids, Flavonoids and Cannaflavins that the OBD can utilize is large, and a non-limiting example list is provided as Table 2.

TABLE 2

Example Cannabinoids:

| | Complete name |
|---|---|
| D9-THC Class | |
| D9-THC | D9-Tetrahydrocannabinol |
| D9-THCA-A | D9-Tetrahydrocannabinolic acid A |
| D9-THCA-B | D9-Tetrahydrocannabinolic acid B |
| D9-THCV | D9-Tetrahydrocannabivarin |
| D9-THCVA | D9-Tetrahydrocannabivarinic acid |
| D9-THC-C4 | D9-Tetrahydrocanabinol acid C4 |
| D9-THCA-C4 | D9-Tetrahydrocanabinolic acid C4 |
| D9-THCO | D9-tetrahydrocannabiorcol |
| D9-THCOA | D9-tetrahydrocannabiorcolic acid |
| b-Fenchyl-D9-THCA | b-fenchyl-D9-tetrahydrocannabinolate |
| a-Fenchyl-D9-THCA | a-fenchyl-D9-tetrahydrocannabinolate |
| epi-Bornyl-D9-THCA | epi-bornyl-D9-tetrahydrocannabinolate |
| Bornyl-D9-THCA | bornyl-D9-tetrahydrocannabinolate |
| a-Terpenyl-D9-THCA | a-terpenyl-D9-tetrahydrocannabinolate |
| 4-Terpenyl-D9-THCA | 4-terpenyl-D9-tetrahydrocannabinolate |
| a-Cadinyl-D9-THCA | a-cadinyl-D9-tetrahydrocannabinolate |
| g-Eudesmyl-D9-THCA | g-eudesmyl-D9-tetrahydrocannabinolate |
| Cannabisol | Cannabisol |
| cis-D9-THC | (−)-D9-cis(6aS,10aR)-tetrahydrocannabinol |
| D8-THC Class | |
| D8-THC | D8-Tetrahydrocannabinol |
| D8-THCA | D8-Tetrahydrocannabinolic acid |
| CBG Class | |
| CBG-C5 | Cannabigerol |
| CBGA | Cannabigerolic acid |
| CBGM | Cannabigerol monomethyl ether |
| CBGAM | Cannabigerolic acid monomethyl ether |
| CBGV | Cannabigerovarin |
| CBGVA | Cannabigerovarinic acid |
| (Z)-CBG-C5 | Cannabinerolic acid |
| g-Eudesmyl-CBGA | y-Eudesmyl cannabigerolate |
| a-Cadinyl-CBGA | a-Cadinyl cannabigerolate |
| 5-Ac-4-OH-CBG | 5-acetyl-4-hydroxycannabigerol |
| 6,7-trans-CBGA | (±)-6,7-trans-epoxycannabigerolic acid |
| 6,7-cis-CBGA | (±)-6,7-cis-expoxycannabigerolic acid |

TABLE 2-continued

Example Cannabinoids:

| | Complete name |
|---|---|
| 6,7-cis-CBG | (±)-6,7-cis-epoxycannabigerol |
| 6,7-trans-CBG | (±)-6,7-trans-expoxycannabigerol |
| 2,3-Di-OH-CBG | carmagerol |
| C15-CBG | sesquicannabigerol |
| CBC Class | |
| CBC-C5 | Cannabichromene |
| CBCA-C5 | Cannabichromenic acid |
| CBCV-C3 | Cannabichromevarin |
| CBCVA | Cannabichromevarinic acid |
| 4-Ac-CBC | (±)-4-acetoxycannabichromene |
| 3″-OH-D4″-CBC | (±)-3″-hydroxy-D4″-cannabichromene |
| 7-OH-CBC | (−)-7-hydroxycannabichromane |
| CBD Class | |
| CBD | Cannabidiol |
| CBDA | Cannabidiolic acid |
| CBDV | Cannabinodivarin |
| CBDVA | Cannabinodivarinic acid |
| CBDM | Canabidiol monomethyl ether |
| CBD-C1 | Cannabidiorcol |
| CBD-C4 | Cannabidiol-C4 |
| Cyclo5-CBD | Cannabimovone |
| CBND Class | |
| CBND-C5 | Cannabinodiol |
| CBND-C3 | Cannabinodivarin |
| CBE Class | |
| CBE-C5 | Cannabielsoin |
| CBEA-C5 A | Cannabielsoinic acid A |
| CBEA-C5 B | Cannabielsoinic acid B |
| CBE-C3 | Cannabielsoin |
| CBEA-C3 B | Cannabielsoinic acid B |
| CBL Class | |
| CBL | Cannabicyclol |
| CBLA | Cannabicyclolic acid |
| CBL-C3 | Cannabicyclovarin |
| CBN Class | |
| CBN | Cannabinol |
| CBNA | Cannabinolic acid A |
| CBN-C3 | Cannabivarin |
| CBN-C1 | Cannabiorcol |
| CBNM | Cannabinol methyl ether |
| CBN-C4 | Cannabinol-C4 |
| CBN-C2 | Cannabinol-C2 |
| 4-Terpenyl-CBNA | 4-Terpenyl Cannabinolate |
| 8-OH-CBN | 8-Hydroxycannabinol |
| 8-OH-CBNA | 8-Hydroxycannabinolic acid |
| CBT Class | |
| (−)-trans-CBT-C5 | (−)-trans-Cannabitriol |
| (+)-trans-CBT-C5 | (+)-trans-Cannabitriol |
| (±)-cis-CBT-C5 | (±)-cis-Cannabitriol |
| (±)-trans-CBT-C3 | (±)-trans-Cannabitriol-C3 |
| (−)-trans-CBT-OEt-C5 | (−)-trans-10-Ethoxycannabitriol |
| (−)-trans-CBT-OEt-C3 | (−)-trans-10-Ethoxycannabitriol-C3 |
| CBT-C3 homologue | Cannabitriol-C3 (unkown stereochemistry) |
| 8-OH-CBT-C5 | 8-Hydroxycannabitriol |
| CBDA-C5 9-O-CBT-C5 ester | Cannabidiolic acid tetrahydrocannabitriol ester |
| Miscellaneous | |
| DCBF-C5 | Dehydrocannabifuran |
| CBF-C5 | Cannabifuran |
| OH-Iso-HHCV-C3 | 8-Hydroxy-isohexahydrocannabivarin |
| CBCN-C5 | Cannabichromanone-C5 |
| CBCN-C3 | Cannabichromanone-C3 |
| CBCT-C5 | Cannabicitran |
| OTHC | 10-Oxo-D6a(10a)-tetrahydrocannabinol |
| CBR | Cannabiripsol |
| CBTT | Cannabitetrol |
| cis-D7-iso-THCV | (±)-D7-cis-isotetrahydrocannabivarin-C3 |
| trans-D7-iso-THCV | (−)-D7-trans-(1R,3R,6R)-isotetrahydrocannabivarin-C3 |
| trans-D7-iso-THC | (−)-D7-trans-(1R,3R,6R)-isotetrahydrocannabinol-C5 |
| CBCN-A | Cannabichromanone-A |
| CBCN-B | Cannabichromanone-B |
| CBCN-C | Cannabichromanone-C |
| CBCN-D | Cannabichromanone-D |
| CBCON-C5 | (−)-7R-cannabicoumarone |
| CBCONA-C5 | (−)-7R-cannabicoumaronic acid |
| Cannabioxepane | Cannabioxepane |
| 4-acetoxy-2-geranyl-5-hydroxy-3-n-pentylphenol | |
| 2-geranyl-5-hydroxy-3-n-pentyl-1,4-benzoquinone | |
| 5-acetoxy-6-geranyl-3-n-pentylphenol-1,4-benzoquinone | |

Example Terpenes

α Pinene
Linalool
Myrcene
Limonene
Ocimene
Terpinolene
Terpineol
Valencene
β Caryophyllene
α Humulene
Phellandrene
Carene
Terpinene
Fenchol
Borneol
Bisabolol
Phytol
Camphene
Sabinene
Camphor
Isoborneol
Menthol
Cedrene
Nerolidol
Guaiol
Isopulegol
Geranyl Acetate
Cymene
Eucalyptol
Pulegone

Example Flavonoids, Cannaflavins cannflavine A
cannflavine B
cannflavine C
vitexin
isovitexin
apigenin
kaempferol
quercetin
luteolin
orientin

Example Essential Oils

- cardmom
- balsam fir
- basil
- bergamot
- black pepper
- angelica
- blue cypress
- carrot seed
- cedarwood
- celery seed
- cinnamon
- cinnamon bark
- cistus
- citronella
- clary sage
- clove
- copaiba
- coriander
- cypress
- dill
- dorado azul
- elemi
- eucaluptus
- fennel
- frankincense
- geranium
- chamomile
- ginger
- goldenrod
- grapefruit
- helichrysum
- hinoki
- hong kuai
- hyssop
- spruce
- lemon
- juniper agar oil
- oodh
- ajwain
- angelica root
- anise
- asafoetida
- balsam of Peru
- Basil
- Bay oil
- Bergamot
- Buchu
- birch Camphor
- Cannabis flower
- Calamodin
- Calamansi
- Caraway Cardamom seed
- Calamus
- Cinnamon
- Cistus
- Citron
- Clary Sage
- Coconut
- Clove
- Coffee
- Coriander
- Costmary
- Costus root
- Cranberry seed
- Cubeb
- Cumin
- Black seed
- Cypress oil
- Cypriol
- Curry leaf
- Davana
- Dill
- Elecampane
- Elemi
- Eucalyptus
- Fennel seed
- Fenugreek
- Fir
- Frankincense
- Galangal
- Galbanum
- Geranium
- Geranol
- Ginger
- Grapefruit
- Henna
- Helichrysum
- Hickory nut
- Horseradish
- Hyssop
- Idaho-grown Tansy
- Jasmine
- Juniper berry
- Laurus nobilis
- Lavender
- Ledum
- Lemon
- Lemongrass
- Lime
- Litsea cubeba
- Linaloe
- Mandarin
- Marjoram
- Melaleuca See Tea tree
- Melissa
- Mentha arvensis
- Moringa
- Mountain Savory
- Mugwort
- Mustard
- Myrrh
- Myrtle
- Neem
- Neem Tree
- Neroli
- Nutmeg
- Orange
- Oregano
- Orris
- Palo Santo
- Parsley
- Patchouli
- Perilla
- Peppermint
- Petitgrain
- Pine
- Ravensara
- Red Cedar
- Roman Chamomile
- Rose
- Rosehip
- Rosemary
- Rosewood
- Sage
- Star anise
- Sandalwood
- Sassafras
- Savory
- Schisandra
- Spearmint
- Spikenard
- Spruce
- Tangerine
- Tarragon
- Tea
- Thyme
- Tsuga
- Turmeric
- Valerian
- Warionia
- Vetiver
- Western red cedar
- Wintergreen
- Yarrow
- Ylang-ylang
- Zedoary In embodiments of the OBD, fluids are moved in very small amounts (e.g., 1 □l or less) at various flow-rates using a system of pumps, e.g., peristaltic and piezoelectric pumps and/or a combination of larger pumps and micro-fluidic valves (e.g., 2101b). The fluids are mixed and homogenized, in either a user-replaceable or permanent mixing manifold, prior to being dispensed into a receptacle (e.g. 2101c).

In some embodiments, the OBD can be automatically calibrated based on the THC and CBD content of the source tanks. In some embodiments, power supply (e.g., 2101d), electronics boards (e.g., 2101e), CPU (e.g., 2101f) and WiFi/Bluetooth radios (e.g., 2101g) are all on board. An example touch screen display for manual operation and monitoring OBD functions is shown 2101h. The OBD can connect via an OBD on-demand ordering app or website (e.g., Oblend.com) via Bluetooth, WiFi, etc. In some embodiments, the OBD, e.g., via a micro-chip or bar-code embedded in each cartridge, can issue a notification when low on ingredients and can be set to reorder (e.g., from Oblend.com) automatically.

An OBD or associated vendor can be accessible via web or smart-phone app for the users of the OBD to post and find favorite recipes; recipes with medical applications; recipes with veterinary applications; social sharing, articles/blogs and other information about cannabis, terpenes and more.

In some embodiment, a user will be adding ingredient(s) that are sourced by the user, and the OBD can recalibrate automatically and/or be recalibrated to allow for variant concentrations and/or viscosities of fluid.

In some embodiments, the OBD is configured such that different oils and components will not touch a common chamber of the machine except for the final mixing and dispensing phase. The OBD can use disposable cartridges and/or a cleaning protocol to prevent cross-contamination of oils and other components.

As illustrated in FIG. 22, fluids can be provided to the user in pre-filled smart cartridges. The device can identify the cartridge via (e.g., via QR/bar-code, microchip, etc.) and determine: Contents, Handling requirements, Amount of fluid used/remaining in the cartridge, etc. Color coding of cartridges can be used to assist the user with cartridge replacement, and assist in identifying: fluids that may be considered extreme or unpleasant in excessive quantities; fluids that are typically combined in order to create common flavors or smells; fluids that have different flow rates and viscosities; etc. In some embodiments, fluids can be added to a smart cartridge by Third Parties and sold to the user. The Third party registers the fluid type, handling requirements, etc. with the OBD and/or associated entity. Upon approval, the Third Party could be provided with authentication/authorization information (for example, the Third Party could receive information to print out, create, update a label, QR/bar-code, microchip, etc., and attach it to or otherwise associate it with the smart cartridge. In such embodiments, the device will be configured to not accept cartridges that have not been tagged/registered/authorized with the proper security/authentication/safety information/codes.

In some embodiments, for fluids that have different flow rates and/or viscosities, the cartridges and/or internal components are designed to deliver equivalent flow rates for various materials to most effectively blend and dispense a wide range of ingredient oils within a specified time period (e.g., within one minute of being ordered). To achieve this, the OBD utilizes different internal diameter openings on tubing, fittings, materials, and/or heatings. Embodiments of the OBD incorporate methods for metering fluids within a microfluidic chip.

The OBD includes a machine that can store, mix to specific ratios and dispense automatically, a variety of liquids utilizing an App control. The following are example general specifications, according to some embodiments.

The Fluid Types utilized by the OBD can cover a wide range of pH and viscosity, and OBD components can accordingly handle a wide range of fluid pH, from acidic to basic. In some embodiments, components can be lipophobic, e.g., borosilicate tubing, polypropylene, etc. Fluid types include: Oils (Cannabinoids and Endocannabinoid agonists); Volatile aromatics (Terpenes and Esters); PG: Propylene Glycol; VG: vegetable Glycerin; Small amounts of water and/or alcohol (e.g., EtOH).

In some embodiments, the OBD can be configured to maintain temperatures (e.g., internal device temperatures) within a range that keeps oils liquid (e.g., around 150 F) and/or be configured to rapidly heat the temp of some or all surfaces that contact oils, such as cartridge/tubing, to any appropriate specified temp (e.g., in a range from room temperature to 150 F), such that the oils are fluid and can move and mix.

Example Amounts in cartridge: 0.5 ml-3 ml

Example Fluids moved for mixing in amounts from: 1 □L-1 mL

The cartridge size can be as small as 5 mm×5 cm cylinder or smaller, up to 1 cm×15 cm or larger, according to some embodiments.

The OBD can be configured to take up little counter space, and example device dimensions and no larger than a coffee maker/Soda Stream/toaster. In some embodiments, the OBD may be configured for wall or under-cabinet mounting, or otherwise configured to conserve space.

In some embodiments, the programming and micro-electronics of the OBD are configured as follows: a microcontroller based circuit to control the device; take fluid from up to 24 containers and mix them, to a specified amount (e.g., user selected) into a single receptacle, and may be mixed in a specified order (e.g., per user or per recipe), mix as many or as few as specified, and in an amount specified, from any container, from, e.g., 1 □L to 1 ml (e.g., 1 □L from container A; 5 □L from container B; and 300 □L from container C). The OBD can adjust the temperature of any of the 24 containers, and/or the internal temp of the device, to one or more specified temperatures (e.g., from room temperature to 150 F), in order to ensure easy mixing and fluid flow.

The OBD can identify the fluid type and handling requirements for any of the containers, such as via QR/barcode and/or micro-chip.

The OBD can also track the amount of fluid dispensed from each container and associate to the chip or bar code so that if container is removed and later reinserted the device knows how much fluid is left. The OBD can also utilize sensor to check amounts via pressure and/or optical measurement.

The OBD can utilize networking, such as WiFi/Bluetooth radio/etc., for communication between a smartphone/app, a webservice, and the Micro-controller/CPU. The OBD can connect to a wife/Bluetooth network, be able to be controlled by a smartphone app, send status updates to the phone, and self-order new cartridges, e.g., through an online store, when necessary.

The OBD can be configured such that the microcontroller based circuit (discussed above) can be controlled from a smartphone, tablet, laptop, computer, or other compute device, communicatively connected via wired (e.g., USB) or wireless (e.g., BLUETOOTH) connection, either directly and/or over a network (e.g., Internet), though some embodiments are secured such that they cannot be remotely compromised or hacked. In some embodiments, the smartphone or other device can have complete control of the functions described, via a micro-controller based circuit or circuits. The OBD can communicate status with a smartphone, fluid types and amounts in machine, etc. In some embodiments, particularly for advanced/intensive processing, the OBD can utilize a connected device (e.g., a mobile device running an OBD software application) for processing of certain information and/or making processor-intensive determinations.

In some embodiments, the OBD is configured for exacting microfluidics and fluid handling. Implementations of embodiments that include viscous cannabinoid oils have been configured such that error tolerances are +/−10%, +/−9%, +/−8%, +/−7%, +/−6%, +/−5%, and in some configurations, error tolerance can be reduced to +/−4%, +/−3%, +/−2%, and even +/−1% when the configurations of the system are tightly regulated.

Some embodiments include a fluid container or "cartridge" system for the OBD. Fluids in container are heated and/or pumped out to be mixed into a homogeneous solution. Generally, small size is advantageous, and sizes can range, for example, from 5 mm×5 cm cylinder to a 1 cm×15 cm cylinder. Some sizes can hold up to 3 ml of fluid. Some implementations can control temperature up to 150 F. Some can be Tillable using a machine similar to a standard mass production vape tank filling machine. Cartridges can contain a number of different fluid types as discussed herein. Cartridges provide a system for moving a wide range of volumes and viscosities, e.g., from 1 □l to 1 ml, into the mixing cartridge. Cartridges can be configured to handle a wide range of fluid types and pH without leaching or leaking. Cartridges can connect to OBD using secure fittings, such as Luer fittings. Cartridges and/or fittings can be formed from lipophobic and/or hydrophobic material, polypropylene, etc., and/or may have appropriate coatings or be otherwise configured for general fluid use or for use with specific fluids based on the properties of those fluids. Cartridges can be configured to be inexpensive and mass producible. A cartridge can be configured to be easy for a novice user to handle, store, identify, and insert into the device. Cartridges can be configured to be secure such that they cannot easily be opened unintentionally or accidently, or spilled or tampered with. Cartridges can be color coded and matched to color on device. The device can identify a cartridge upon insertion via (bar-code or microchip or other) and reads: Contents, Handling requirements, Amount of fluid used (so that it can be removed and inserted again later). The cartridge may also include a quality control, anti-counterfeit, and/or anti-tamper element, such as a vacuum seal portion, serial number, validation code, etc.

In some embodiments of the OBD, adding and removing a cartridge can be similar to inserting an ink cartridge, so the user can easily add or remove a cartridge/container from the device. The cartridge can be under pressure and can be securely sealed using secure fittings, such as a LUER-LOK fitting (e.g., with flowrate of 100-150 uL/min if hydraulic).

The OBD is configured to handle hundreds of insertion and removal events without leaking or blocking up, and in some implementations, can be re-sealable if components are removed. The cartridge can be configured for handling by a novice user, so that it is easy to handle, store, identify, and insert into the device, and can include labeling and color coding on cartridge.

In some embodiments, there may be a Self-Priming event trigger where Fluid from cartridge is primed into place upon insertion and ready for precision handling of fluids. The configuration of the OBD and/or cartridges can be such that there is no or minimal gap of fluid between the cartridge and the entry point to the mixing manifold. The OBD can also be configured for self-cleaning and clearing of tubing and connection to mixing manifold.

In some embodiments, to support fluid handling and movement, the OBD provides a system for moving fluid out of the cartridges, into a metering cartridge then a mixing cartridge or manifold and out into a receptacle. Fluid Pumping can be via: pneumatic or hydraulic, multi-pump or single pump.

Parts of the OBD that contact the oils or other components can be configured accordingly (e.g., lipophobic). In order to provide temperature(s) to facilitate handling of the oils and other components (e.g., due to the viscous nature of oils, heating can be required to maintain accurate and effective flow), a system of Peltier elements or the like, heat sinks, cooling fans, etc., can be utilized. The contact parts can also be configured to handle acid and/or base pH fluids.

The OBD provides precision-controlled fluid movement of 1 □L or less to 1 mL or more from any of the 24 cartridges to a blending manifold. While many of the volumes to be pumped can be small, for the larger 200-800 uL, which may be more viscous, hydraulic action and tubing can be used. Example pumps include multiple small Piezoelectric Pumps, such as Bartels Micropumps mp6-PPSU, single larger Cavro XP Syringe Pump Or Exigo pump. The OBD can utilize micro valves, controlled by a microcontroller (as discussed above) to direct the flow of oils through the machine (e.g., Tagasako Solenoid Diaphragm pumps using PTFE (Teflon)).

The OBD provides a system for blending and emulsifying the fluids. A blending manifold into which the fluids can flow and be mixed, in any specified order, can be configured to emulsify the fluids (e.g., via ultrasonic, microfluidic, air), and maintain a stable temperature of mixture across a range of specified temps, e.g., from room to 150F or more. The time to reach a specified mix temperature can depend on the embodiment and application, and can include times to reach temperature of 5 seconds, 10 seconds, 20 seconds, 30 seconds, 45 seconds, 60 seconds, 120 seconds, 180 second, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, and/or any integers there between, or ranges there between.

A temperature controlled fluidics cartridge can be used to channel multiple oils/components for a recipe and blend into a single, stable homogenous mixture. An example fluidic mixing cartridge can include a mixing chamber with a plurality (e.g., 24) of fluid inputs from the instrument, and may be expandable (e.g., up to 256 fluid inputs). In some embodiments, cartridges can be reused and/or recycled. In some embodiments, the cartridge can assemble to the instrument by the user. In some embodiments, a mixture from the cartridge mixing chamber can be transferred to a collection tube and receptacle. In some embodiments, each fluid is added from the bottom of the cartridge mixing chamber to create mixing. Additional mixing may be provided by air dispensed through the mixing chamber and/or ultrasonics.

The OBD also provides methods for dispensing the fluid mixture into a user placed receptacle. In some embodiments, the dispensing nozzle sits over a filling port for a Tillable receptacle. In some implementations, users can place a variety of receptacles ranging in size up to 50 mm×100 mm under the nozzle, while in other embodiment, the OBD can be configured to work with specified receptacles and thereby provide additional security and quality control.

The OBD provides for mechanical blending and/or emulsifying/homogenizing of the oils and/or other components prior to dispensing.

In some embodiments, forcing oils and/or other components through a single small fluidics port may cause turbulence enough to complete this process. In some embodiments, emulsification may be accomplished with ultrasonic mixing/agitation and/or air (or other gas, such as nitrogen, and/or a mixture of pharmaceutical/food grade gases).

The OBD can also provide a system for cleaning the machine. For example, in some embodiments, a user-replaceable mixer chip/manifold can be flushed out or replaced. Potentially highly sticky, viscous materials can be used, some of which have the consistency of honey or coconut oil at lower temperatures. Some embodiments may be configured to use food and/or pharmaceutical grade cleaners (e.g., H2O/EtOH) that will risk contamination of the device. Some embodiments may be configured to avoid use of on-board cleaning fluids by minimizing the amount of time/locations that the oils are touching the same surfaces or in the same chamber or conduit within the machine. As discussed above, materials and/or coatings may be configured for ease of cleaning and maintenance of accuracy (e.g., tubing and cartridge surfaces could be lipophobic).

In some embodiments, the OBD is supported by an online resource of recipes and more (e.g., Oblend.com). Users can discover, share and build recipes for use in the OBD. The online resource can also suggest recipes to the user based on data aggregated from their history, social network, demographics, and the ingredients currently in the device. Ingredient adjustments can be provided, listed, and/or suggested, including adding ingredients, removing ingredients, and/or new ingredients. Users can also order fluid cartridges and replacement parts for the OBD. In some embodiments, recipes may be proprietary, and the OBD can be configured accordingly.

Users can instruct the OBD to dispense OBD-blends on demand, and such blends can be developed to encourage Micro-Vaping. Micro-vaping is defined as a 100 □l or less vape tank created by the user for consumption/use either immediately or within a few hours. A micro-vape of 100 □l will provide approximately 30 puffs vs a standard 300 puff 1 mL vape cartridge. This micro-vaping will enable the user to build a cannabis vape experience on demand tailored for a specific mood or environment. Much like a single cup of coffee, a single micro-vape can be for short-term use.

There is currently no device that can be used by the home user, or local retail store, to blend fluids such as cannabinoid oils, esters, terpenes, and more, in micro-fluidic ratios (e.g., 1 microliter), to create a custom mixture that fits their personal desires or life-style. Doing so manually is extremely difficult and requires specialized knowledge, hard to find materials and basic chemistry equipment such as micropipettes.

For example; in the cannabis industry oils for vaping or oral ingestion are produced in large batches often from a single strain of plant. The flavor, smell and psychotropic effects are derived from the mixture of THC, CBD, CBG and the terpenes that occur in that plant naturally. One batch of oil from the "same" strain however, may vary slightly than a different batch from that "same" strain due to a variety of factors; growing conditions, protocols variations during oil processing, freshness of flower being processed, etc.

In some embodiments, the OBD can be utilized to approximate specific flavor and effects, for example, in cannabis applications, using pure and organic, extracted THC, CBD, CBG, other cannabinoids and terpenes that can be sourced to customers, in established ratios or "recipes" that can be reproduced.

At the broadest scope, some embodiments of the OBD allows a user to create or choose a recipe for and then produce a precisely blended mixture of fluids on-demand. Individual fluids may be mixed in amounts as small as 1 □l or less and over 3 ml. This allows the user to have an amount that may last an hour, a day, week or month depending on their desires. The OBD can mix and homogenize the fluids in any predefined order prior to dispensing, and the order may be configured to provide a desired flavor, aroma, and/or effect. Fluids may be mixed for consumption, vaping, massage, skin care, aromatic vaporization, etc.

Although discussed in terms of vaping herein, the OBD can be used in a variety of industries and applications ranging from: use in massage therapy for instant custom therapeutic oils, recreational and medicinal cannabis and nicotine vaping; cannabis oils for oral consumption; cooking oils production; at home aroma therapy; and use in pharmacies for filling prescriptions, hospitals and research facilities (e.g., for research and/or clinical trials) bars, gyms, health food stores, and for adding blends fot beverages, at-home or on-mobile smell-o-vision, creating scents in public areas such as hotels, movie theaters, bars, restaurants, be built into a vehicle for on-demand aromatic scents, and/or the like.

While some examples shown herein hold 24 fluid types, additional version and/or embodiments of the OBD, such as those aimed at pharmacies, hospitals, and/or research facilities, may hold and manage several hundred different fluids in a variety of reservoirs. A more simplistic model may only provide, for example, 10 ports.

Currently, there is also no online resource for building and sharing recipes that can be blended by an OBD.

The OBD can be configured to quickly provide blends to users, such that there is little wait time. In some embodiments, the OBD can be configured to heat up in anticipation of a blend (i.e., start heating at 4 pm because a user typically requests a blend around 10 to 15 minutes later). The fast blend time is another advantage of some embodiments and includes blend times, from user request on OBD app to dispensing in ranges from about 10 seconds to about 40 minutes, including about 10 seconds, 20 seconds, 30 seconds, 45 seconds, 60 seconds, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 30 minutes, 40 minutes, and/or any integers there between, or ranges there between.

Another novel aspect of the OBD is that users can use a simplified interface to increase or decrease the active ingredients, such as the cannabinoid and terpene ratios found in cannabis vapes, in the final mixture. This gives the end user unprecedented controls over the cannabis experience they will be able to tailor create.

Example: a user that wants help sleeping may choose a recipe from an OBD site (e.g., Oblend.com) that is high in the terpene Linalool and the cannabinoid CBD, or for a more awake experience a user may choose a different THC oil with extra Pinene and/or Limonene.

The OBD is a vital tool for home-use, retail and pharmaceutical, clinical trials and research (e.g., as performed by hospitals, universities, physicians, and research scientists, etc.), compounding pharmacies, physicians (e.g., prescribing medicines (including cannabis/cannabinoid medicines) and/or vitamins), homeopathic, and massage industries.

Through research it has been determined that different mixtures of terpenes and different cannabinoids create an unlimited variety of effects for each individual user, and this is the first home use device to allow the user to create such mixtures and effects which include medical and recreational uses.

In some embodiments, the OBD and fluids to be used in it, other than regulated ones like THC, can be sourced centrally and sold to the customer in pre-filled cartridges and mixing kits. These include: sourced and packaged terpenes to be used in the OBD; sourced/packaged pre-mixed concentrated flavors and esters; cannabinoids, other than THC, i.e., CBD, CBG, also to be used in the OBD; custom, proprietary, "open" cartridges for user that want to add their own ingredients to the OBD; etc.

OBD accessories can include: Gelatin or other pill filler; ultrasonic oil diffuser, custom vaping receptacles, tips, batteries, etc., as well as one or more "Micro-vapes" and corresponding cartridges.

In some embodiments, the OBD (and/or OBD app and/or server) can be configured to capture usage information, including frequency of use, application type, user demographics, medical disorder user searching or trying to treat, recipe/ingredients selected, adjustment/customization of ingredients, frequency, form of use (e.g., vape, tincture, skin application, etc.). Such data can also, in some embodiments, be used to identify "clusters" of succesful ingredients/ formulations used by individuals with various demographics to treat for various medical disorders. For example, the OBD can capture usage information such as (1) the amount (either relative or actual) of ingredients used (e.g., amount of terpenes, CBDs, THCs, etc.); (2) the frequency of use/ intake; (3) recipes used and/or how users customize/modify recipes/protocols; (4) form(s) of use/ingestion (e.g., edible, vape, tincture, etc.); and/or (5) qualitative or quantitative user feedback or input (e.g., user liked/disliked particular blend, particular blend made user feel relaxed or awake, user made blend to address back pain). Captured information from users can be processed and analyzed for a variety of applications, for example, used to reorder frequently used ingredients, used to provide blending suggestions to other users (including other user that have been identified as similar to a particular user based on demographics, usage information, etc.), provide user usage information to a medical professional that is overseeing a particular user (e.g., a doctor that prescribed that a user take a given blend or amount of a specific active ingredient), and monitoring/ treatment of certain medical indications and ailments such as Parkinson's, Pain, Seizures, Epilepsy, Alzheimer's, Depression, ADHD, Anxiety, Cancer etc., and/or emotional effects. In addition, this data can be used to determine successful formulations for treating medical disorders in order to conduct clinical trials and ultimately file patents on successful drug formulations. In some embodiments, certain aspects or components of the OBD can be configured to be regulated/controlled by an administrator, such as a doctor. In some such applications, specific blends or ingredients are monitored or controlled in accordance with inputs/limits provided by the administrator (or required by regulations, reimbursement rules, etc.). In some embodiments, the OBD provides automatic ordering, billing, shipping, and/or invoicing for tank/cartridge replacements, such as when they become low or when user orders. In some embodiments, replacements are provided with a recycle/return capability, such as a return shipping label, to facilitate a user sending empty tanks/cartridges for recycling or disposal. Although discussed for human medical applications, the OBD can also be configured for veterinary applications, plant/agriculture health and protection (including formulating pest deterrents), etc.

In some implementations, a user's smartphone or other portable compute device (e.g., running an OBD application) can link to or with a nearby OBD system/device (e.g., via BLUETOOTH, RFID, near-field communication (NFC), and/or the like) and generate a validation/authentication request, for example containing a security certificate and/or credentials (e.g., username and password) to authenticate a user's identity, age, prescription, etc., along with user preference information (e.g., preferred blends/mixtures, use type (vaping, aromatherapy, etc.), and/or user location information (e.g., using portable compute device GPS coordinates and/or the like). In some embodiments, validation/authentication can be used to unlock the device (e.g., for refilling, maintenance, etc.) and/or to use the device for dispensing a mixture/blend. In some instances, the GPS coordinates can be used to secure the device against improper use. For example, if the device is taken outside a specified geographic region where one or more of the liquids or other components are not permitted, some or all functionality of the OBD may be disabled or locked down to prevent improper or illegal dispensing. The OBD can be configured to be locked down for a specified time, and/or until the proper GPS location is subsequently received and/or an authorized user has removed the lock down.

For example, a user's smartphone or other portable compute device (e.g., running an OBD application) can provide a blend options request in the form of a (Secure) Hypertext Transfer Protocol ("HTTP(S)") POST message including data formatted according to the eXtensible Markup Language ("XML"). An example blend options request, in the form of an example HTTP(S) POST message including XML-formatted data, is provided below:

```
POST /blendreguest.php HTTP/1.1
Host: www.oblend.com/blend_options
Content-Type: Application/XML
<?XML version = "1.0" encoding = "UTF-8"?>
<blend_options_reguest>
    <request_ID>20030414</request_ID>
    <timestamp>yyyy-mm-dd hh:mmE-:ss</timestamp>
    <user_ID>TomAHiro@homemail4.ut</user_ID>
    <credentials>
      <password>321Secret</password>
      <access_key>F0RT7777</access_key>
    <GPS_coord>Latitude_Longitude_Elevation</GPS_coord>
  <preference_details>
    <blend_ID>150</blend_ID>
    <Active_ID>CBD</Active_ID>
    <fill_amount>0.8mL</fill_amount>
...
  </preference_details>
  <user_details>
    <user_IP>192.168.xx.xxx</user_IP>
    <user_type>smartphone</user_type>
    <user_model>iPhone 6</user_model>
    <OS>iOS 9</OS>
    <OBDapp_installed_flag>true</OBDapp_installed_flag>
...
  </user_details>
</blend_options_request>
```

In some embodiments, a blend is transmitted to the OBD not using XML, and instead, a recipe is translated from (Ingredient, Amount), e.g., on an OBD app on a smartphone, into binary commands that are transmitted to the OBD for running the recipe on the OBD. Table 3 below provides an example recipe file comprising binary data that the OBD implements as valve timings to run/implement a particular mix routine/blend.

TABLE 3

| | | | | | | | | |
|---|---|---|---|---|---|---|---|---|
| 0 | 0 | 0 | 0 | 0 | 0 | 140 | 0 | 9 |
| 0 | 0 | 0 | 224 | 0 | 40 | 140 | 0 | 9 |
| 64 | 0 | 0 | 0 | 0 | 40 | 140 | 0 | 200 |
| 0 | 0 | 0 | 0 | 0 | 40 | 140 | 0 | 8 |
| 0 | 0 | 0 | 64 | 0 | 40 | 140 | 0 | 9 |
| 0 | 0 | 0 | 192 | 0 | 40 | 140 | 0 | 0 |
| 0 | 0 | 0 | 128 | 0 | 40 | 140 | 0 | 8 |
| 0 | 0 | 0 | 192 | 0 | 40 | 140 | 0 | 0 |
| 0 | 0 | 0 | 64 | 0 | 40 | 140 | 0 | 8 |
| 0 | 0 | 0 | 192 | 0 | 40 | 140 | 0 | 0 |
| 0 | 0 | 0 | 128 | 0 | 40 | 140 | 0 | 8 |
| 0 | 0 | 0 | 192 | 0 | 40 | 140 | 0 | 0 |
| 0 | 0 | 0 | 64 | 0 | 40 | 140 | 0 | 8 |
| 0 | 0 | 0 | 192 | 0 | 40 | 140 | 0 | 0 |
| 0 | 0 | 0 | 128 | 0 | 40 | 140 | 0 | 8 |
| 0 | 0 | 0 | 192 | 0 | 40 | 140 | 0 | 0 |
| 0 | 0 | 0 | 64 | 0 | 40 | 140 | 0 | 8 |
| 0 | 0 | 0 | 192 | 0 | 40 | 140 | 0 | 0 |
| 0 | 0 | 0 | 128 | 0 | 40 | 140 | 0 | 8 |
| 0 | 0 | 0 | 192 | 0 | 40 | 140 | 0 | 0 |
| 0 | 0 | 0 | 64 | 0 | 40 | 140 | 0 | 8 |
| 0 | 0 | 0 | 192 | 0 | 40 | 140 | 0 | 0 |
| 0 | 0 | 0 | 128 | 0 | 40 | 140 | 0 | 8 |
| 0 | 0 | 0 | 192 | 0 | 40 | 140 | 0 | 0 |
| 0 | 0 | 0 | 64 | 0 | 40 | 140 | 0 | 8 |
| 0 | 0 | 0 | 192 | 0 | 40 | 140 | 0 | 0 |
| 0 | 0 | 0 | 128 | 0 | 40 | 140 | 0 | 8 |
| 0 | 0 | 0 | 192 | 0 | 40 | 140 | 0 | 0 |
| 0 | 0 | 0 | 64 | 0 | 40 | 140 | 0 | 8 |
| 0 | 0 | 0 | 192 | 0 | 40 | 140 | 0 | 0 |
| 0 | 0 | 0 | 128 | 0 | 40 | 140 | 0 | 8 |
| 0 | 0 | 0 | 192 | 0 | 40 | 140 | 0 | 0 |
| 0 | 0 | 0 | 64 | 0 | 40 | 140 | 0 | 8 |
| 0 | 0 | 0 | 192 | 0 | 40 | 140 | 0 | 0 |
| 0 | 0 | 0 | 128 | 0 | 40 | 140 | 0 | 8 |
| 0 | 0 | 0 | 224 | 0 | 40 | 140 | 0 | 0 |
| 0 | 0 | 0 | 96 | 0 | 40 | 140 | 0 | 18 |
| 0 | 0 | 0 | 224 | 0 | 40 | 140 | 0 | 19 |
| 0 | 0 | 0 | 225 | 0 | 40 | 140 | 0 | 0 |
| 0 | 0 | 0 | 33 | 0 | 40 | 140 | 0 | 28 |
| 0 | 0 | 0 | 97 | 0 | 40 | 140 | 0 | 49 |
| 0 | 0 | 0 | 225 | 0 | 40 | 140 | 0 | 49 |
| 0 | 0 | 0 | 161 | 0 | 40 | 140 | 0 | 0 |
| 0 | 0 | 0 | 33 | 0 | 40 | 140 | 0 | 18 |
| 0 | 0 | 0 | 97 | 0 | 40 | 140 | 0 | 19 |
| 0 | 0 | 0 | 225 | 0 | 40 | 140 | 0 | 0 |
| 0 | 0 | 0 | 161 | 0 | 40 | 140 | 0 | 18 |
| 0 | 0 | 0 | 225 | 0 | 40 | 140 | 0 | 0 |
| 0 | 0 | 0 | 97 | 0 | 40 | 140 | 0 | 18 |
| 0 | 0 | 0 | 225 | 0 | 40 | 140 | 0 | 20 |
| 0 | 0 | 0 | 33 | 0 | 40 | 140 | 0 | 19 |
| 0 | 0 | 0 | 32 | 0 | 40 | 140 | 0 | 9 |
| 0 | 0 | 0 | 0 | 0 | 40 | 140 | 0 | 49 |
| 0 | 0 | 0 | 0 | 0 | 0 | 140 | 0 | 19 |
| 100 | | | | | | | | |

In other embodiments, the blend options request may be generated as a result of a user manually requesting, e.g., via an interface on the OBD, information pertaining blending and dispensing options provided by the OBD. The OBD and/or OBD app can, in some embodiments, send a user preferences request to an OBD server. In some implementations, the OBD server can receive a (Secure) Hypertext Transfer Protocol ("HTTP(S)") POST message including data formatted according to the eXtensible Markup Language ("XML"). An example user preferences request, in the form of a HTTP(S) POST message including XML-formatted data, is provided below:

```
POST /sample_user_preference_query.php HTTP/1.1
Host: www.oblend.com/obd_dispense
Content-Type: Application/XML
<?XML version = "1.0" encoding = "UTF-8"?>
<sample_query_request>
    <request_ID>20061003</request_ID>
    <timestamp>yyyy-mm-dd hh:mmE-:ss</timestamp>
    <user_ID>SethAHiro@homemail4.nj</user_ID>
    <credentials>
        <password>Secure123</password>
        <access_key>Fort1992</access_key>
    <GPS_coord>Latitude_Longitude_Elevation</GPS_coord>
    <sample_user_preference_query name="user_profile">
     <query num=1>
       Select Type.Number, Blend.NumberFormulation.Pref from
   User_Profiles where UserAccountNum=SethAHiroNum
     ...
     </query>
     <query>
     ...
     </query>
    </sample_user_preference_query>
</sample_query_request>
```

The OBD server can perform the requested query (e.g., via user account preference query) on a user account database to determine user preference information (e.g., preferred blend(s)/formulation(s), preferred use(s), use device type(s) owned/used, preferred filling amount(s), etc.). The OBD server can, in turn and as a result of the query, return a user preferences response to the OBD.

The OBD and/or OBD app can compile information obtained from one or both of the user mobile compute device and a OBD user account database (e.g., via an OBD server) in order to provide blending/mixing interface options, including one or more of the following: user authentication verification, location(s) of OBD(s), blend liquids/ingredient levels available within the OBD(s), reorder information, payment information, etc., and may display the available blend liquids to the user, e.g., via the user mobile compute device and/or via a user interface on the OBD. In some embodiments, the OBD is not configured with substantial processing capability and is instead configured to receive and execute recipes and other instructions from an OBD app and/or OBD server, which can improve the overall functionality of the OBD as it will not require upgrades or updates that could otherwise be expensive or difficult, and instead rely on changes or updates to the OBD app or OBD server.

In some embodiments, the OBD can be configured to provide blends based on a user profile. For example, a user can provide a saliva sample (e.g., to the OBD server or a third party in communication with the OBD server) and that sample used to determine a vitamin, mineral, or other deficiency, and the OBD can receive and provide a blend that addresses the determined deficiency. User profiles can be based on chromosomal analysis, genome analysis, chemical analysis, etc., and such profiles can be utilized to provide a blend that is tailored to the user. In some applications, an administrator/doctor can provide a "prescription" for patient to the OBD (i.e., over a secure network and via a authenticated and verified communication) and that prescription determines some or all of the mixing and dispensing provided by the OBD. In some embodiments, the OBD is configured to receive ingredients that are prescription ingredients, and can include a validation mechanism or process. For example, the OBD can include one or more ports that require physical and/or logical (i.e., computer-based) compatability to assure that the ingredient is from the proper source and/or verify to an administrator or regulator that the ingredient has been attached/supplied to the OBD and is being dispensed properly. In some embodiments, the OBD can be configured to utilize profiles, such as those discussed in U.S. Pat. App. Pub. No. 2016/0300289 (the entirety of which is herein expressly incorporated by reference for all purposes), to provide a blend or blends for a user.

The OBD can be configured for a variety of applications and for a variety of industries, including but not limited to the cannabis industry, medicine/hospital/pharmacy, aroma industry, mixology, personal products, vitamins, etc. For example, the OBD can provide blends for tinctures (including medicinal tinctures), butters and oils (including for cooking/baking), balms/creams/lotions/etc., edibles/ingestibles (confections, drinks, pills, capsules, etc.), sprays, lubricants, shampoos/conditioners, perfumes/colognes, bath soaps, bubble bath materials, massage oil, body lotion, sunscreen, e-cigarette vape blends that include nicotine, cooking oils with botanical oils and/or spices/spice oils to create "taste"-infused and/or healthy cooking oils, as drink mixers/additives, etc. The OBD can be configured to form or facilitate the formation of such products (e.g., the microblend can be added to a base that is warmed to a specified temperature, such as by an attachment to the OBD that has a macro mixer and heating element. The particular amounts that can be processed and received by the OBD are variable and can be configured for use in such applications (i.e., accept ingredient tanks that are relatively larger than those generally discussed above and provide mixtures in amounts that are larger than those discussed above). In some embodiments, the OBD is configured to be connected/used with one or more other OBD to provide increased functionality (e.g., a plurality of OBDs can be configured to work together and/or be controlled together, such as by one mobile device/ mobile device application instance). Similarly, the size of the OBD can be smaller than is discussed above, such as a "traveler" version that utilizes a smaller set of liquids/ ingredients (e.g., only uses 6 or fewer liquids).

As illustrated by FIG. 23A-FIG. 23F, in some embodiments, there are three pieces within the microfluidic chip/ card assembly: a first rigid piece in which the fluid channels reside, a thin sheet (e.g., comprised of a plastic or elastomer) that can be used to form or define the monolithic membrane valves, and a second rigid piece in which the air channels reside. Each of the rigid pieces can be bonded to the membrane to seal off the channels. Bonding methods can include adhesives, thermal bonding, ultrasonic bonding, and/or the like.

The fluid manifold distributes oils/reagents from each of the cartridges/tanks into a central mixing chamber. The fluid paths can be sized to provide a known flow resistance so that a relationship can be determined/defined between the pressure within a/the cartridge and the flow rate of the fluid into the mixing chamber. Each fluid path can also include a pneumatically-controlled membrane valve, which allows the control electronics to turn the flow of each fluid on and off independently. In some embodiments, also included in the fluid manifold are two lines, one at each end of the mixing chamber, configured to provide for the introduction of a cleaning solution into the mixing chamber. There can be two additional lines that allow for air flow to the mixing chamber so that it can be pressurized or subjected to a vacuum.

The pneumatic manifold can include an inlet port for each of the valves. As an inlet port is pressurized, the flexible membrane within its corresponding valve is forced onto the fluid manifold, preventing fluid from flowing through the valve. As a vacuum is pulled on an inlet port, the differential pressure within the valve pulls the membrane away from the fluid manifold, allowing fluid to flow through the valve.

FIGS. 24A to 26E provide details for example OBDs according to some embodiments of the disclosure.

FIGS. 27A to 27E provide details for an example OBD with a cover removed according to some embodiments of the disclosure.

Figure 27A:
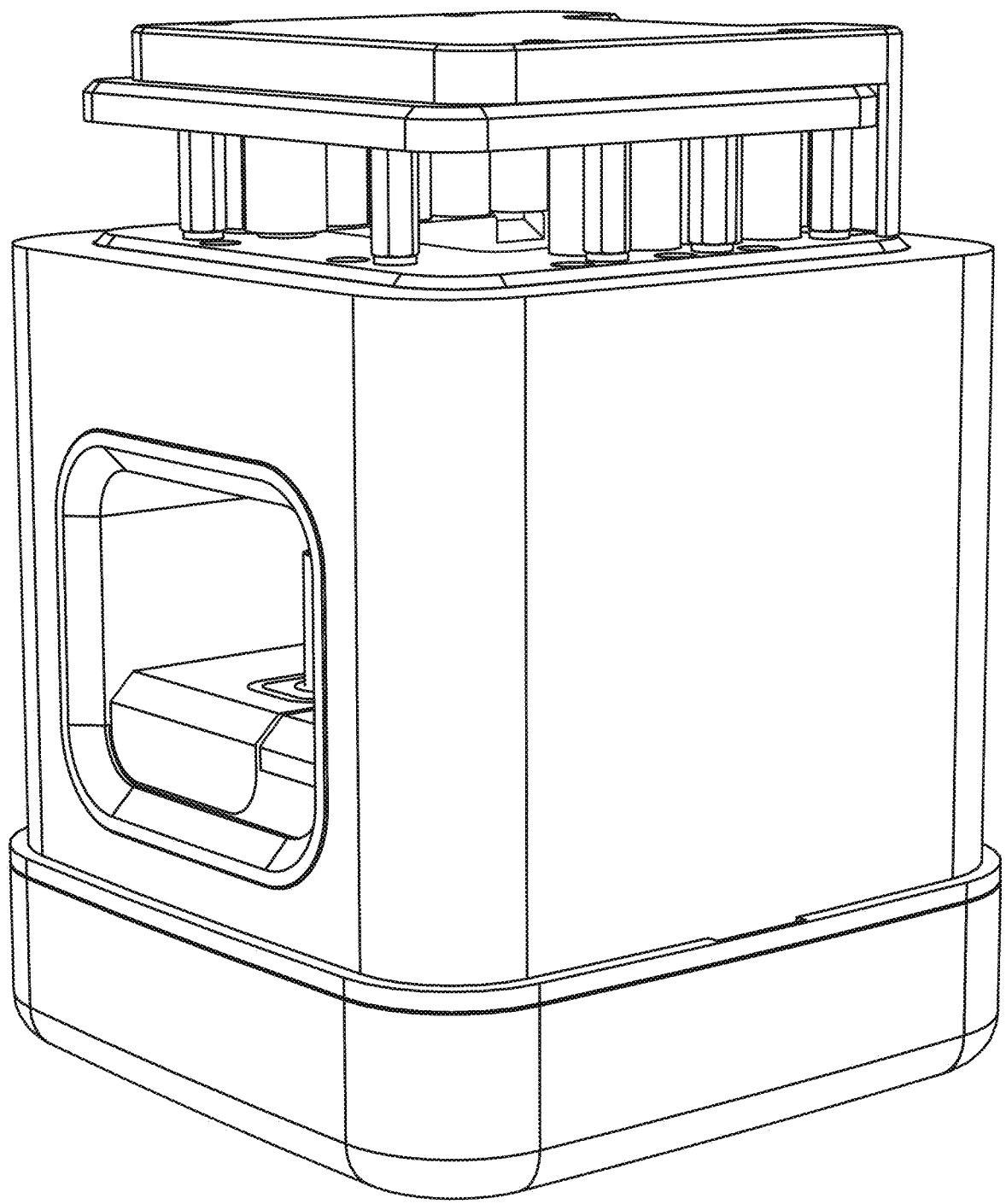
FIGS. 27A to 27E provide details for an example OBD with a cover removed according to some embodiments of the disclosure.
Figure 27B:
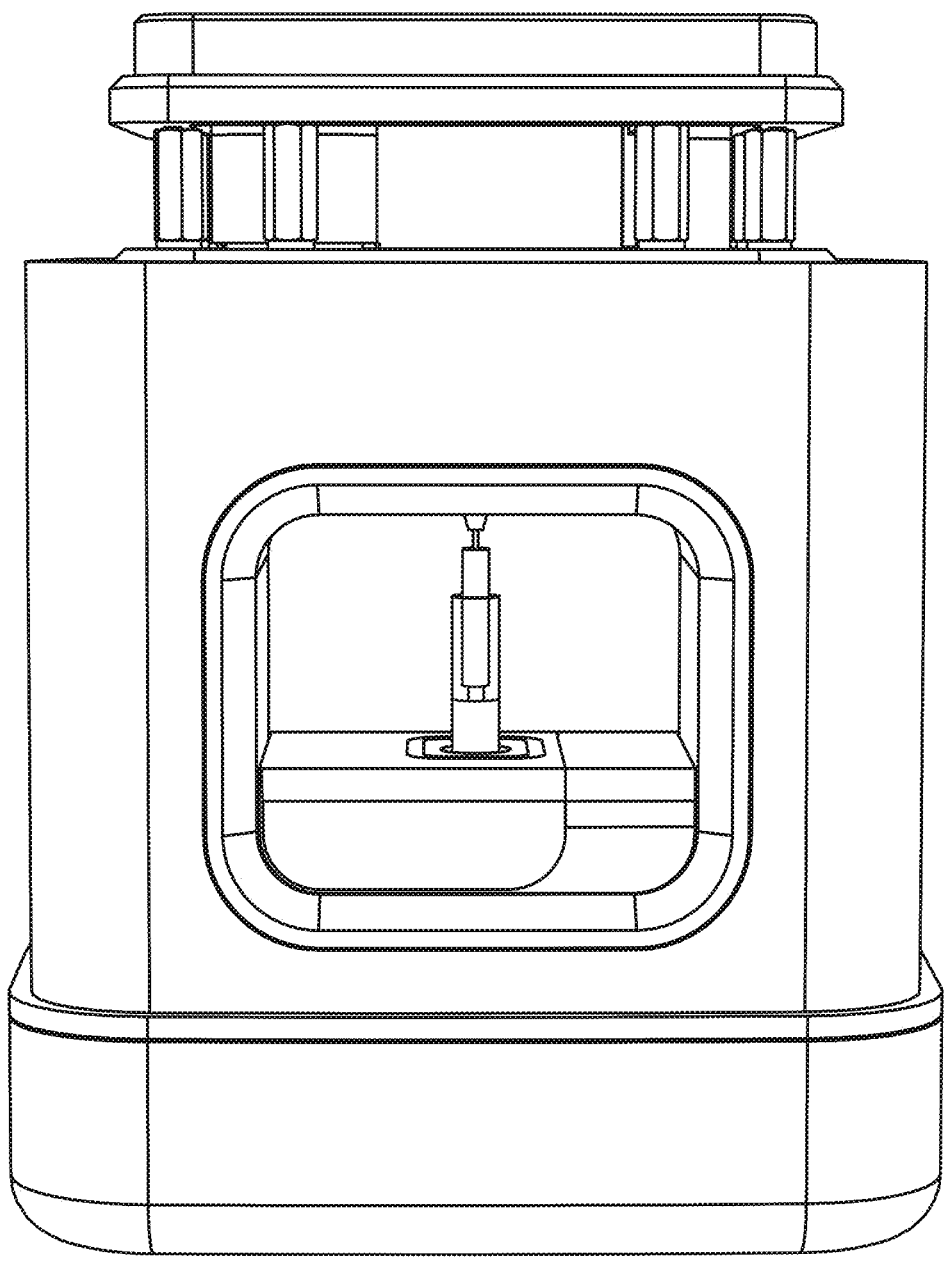
Figure 27C:
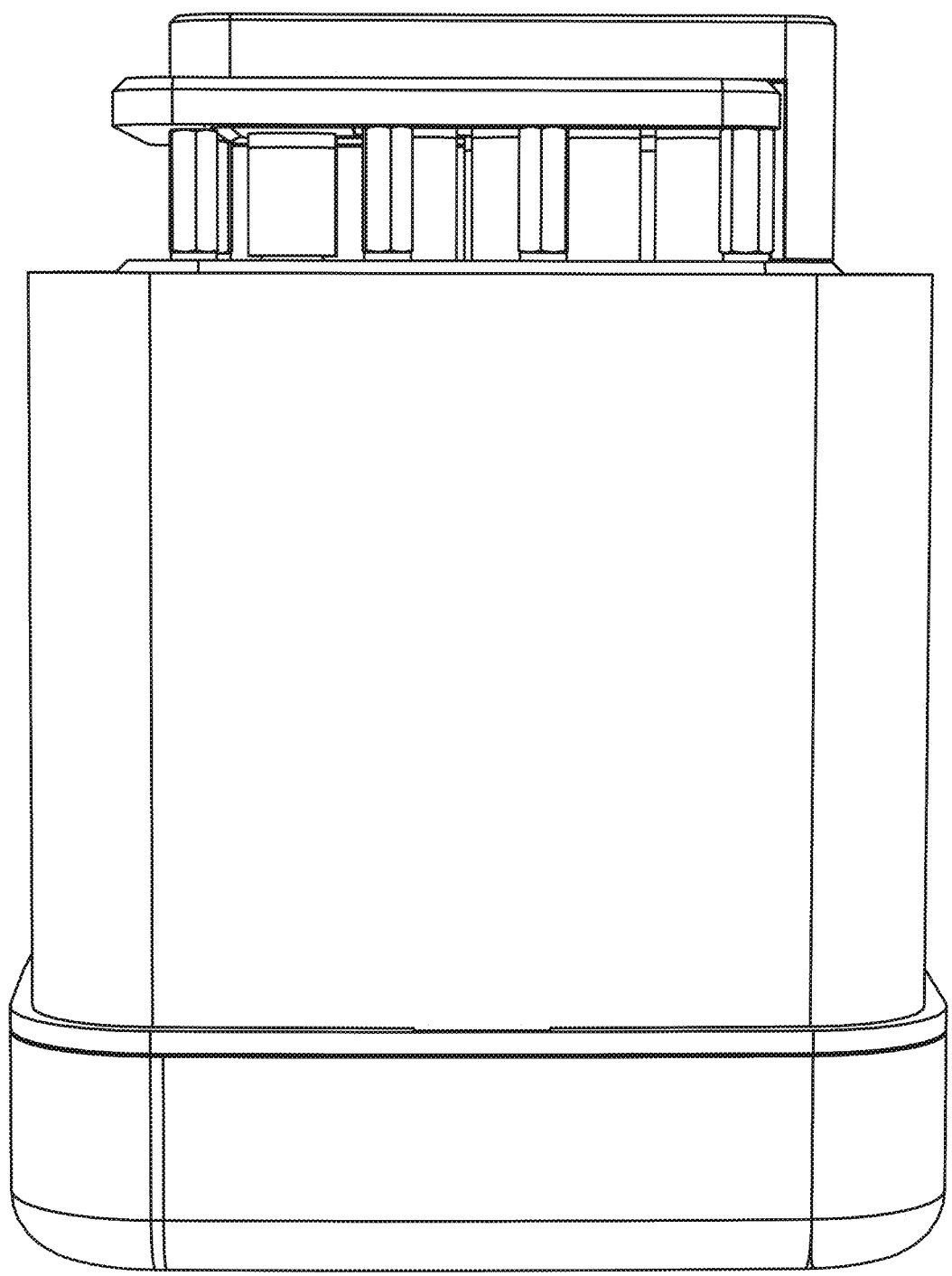
Figure 27D:
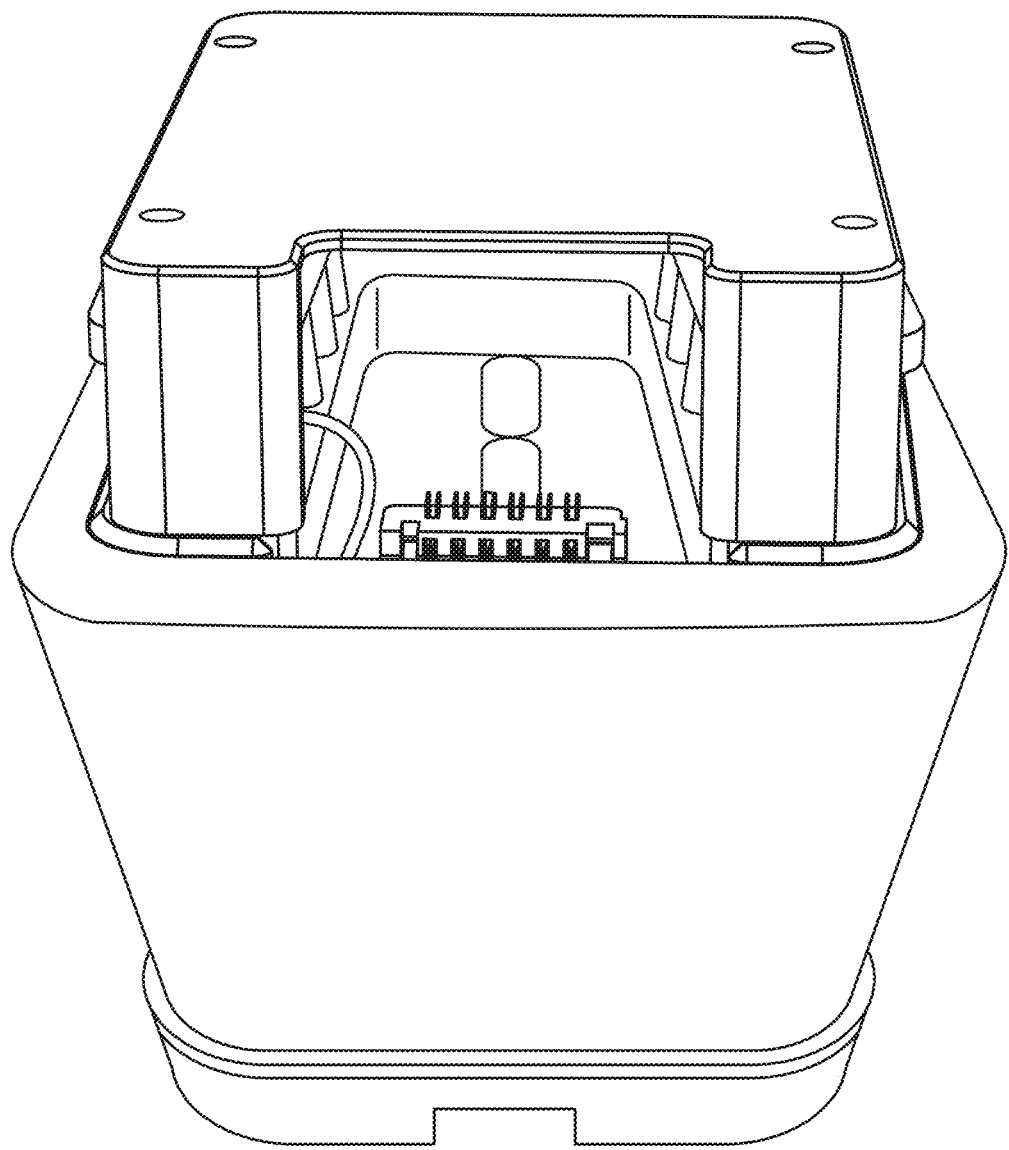
Figure 27E:
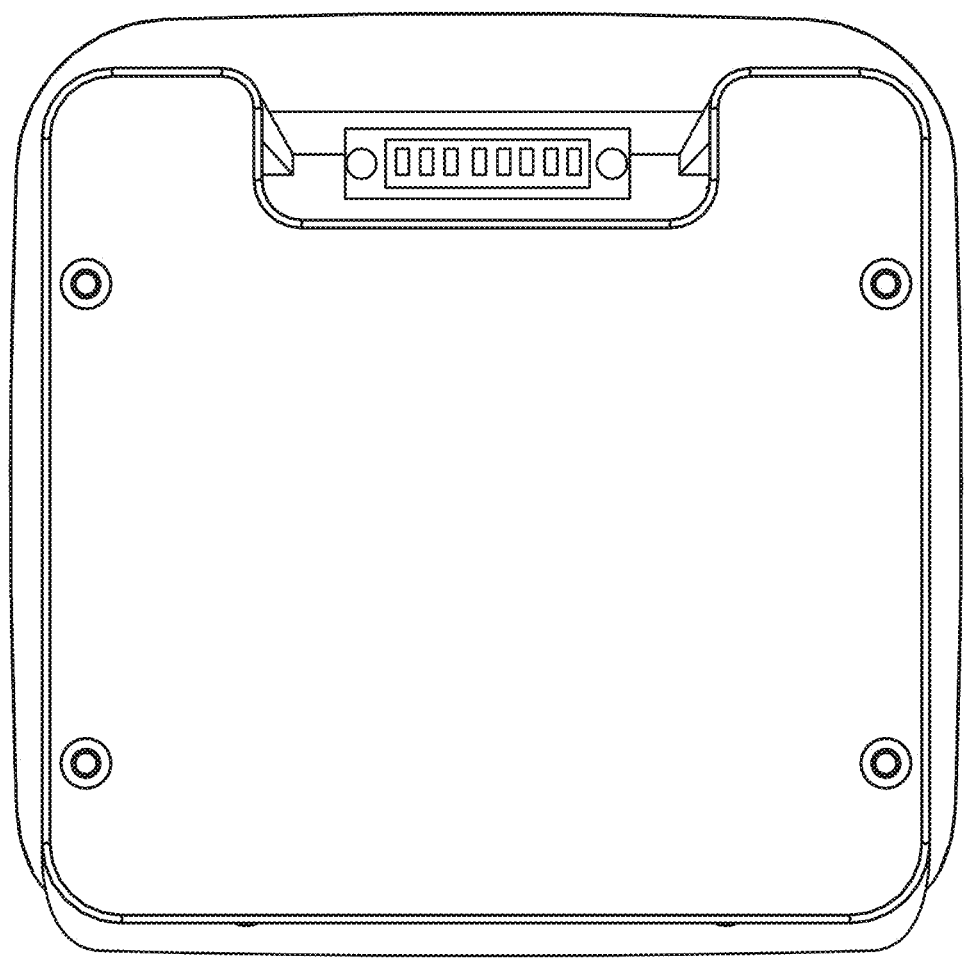
Figure 27F:
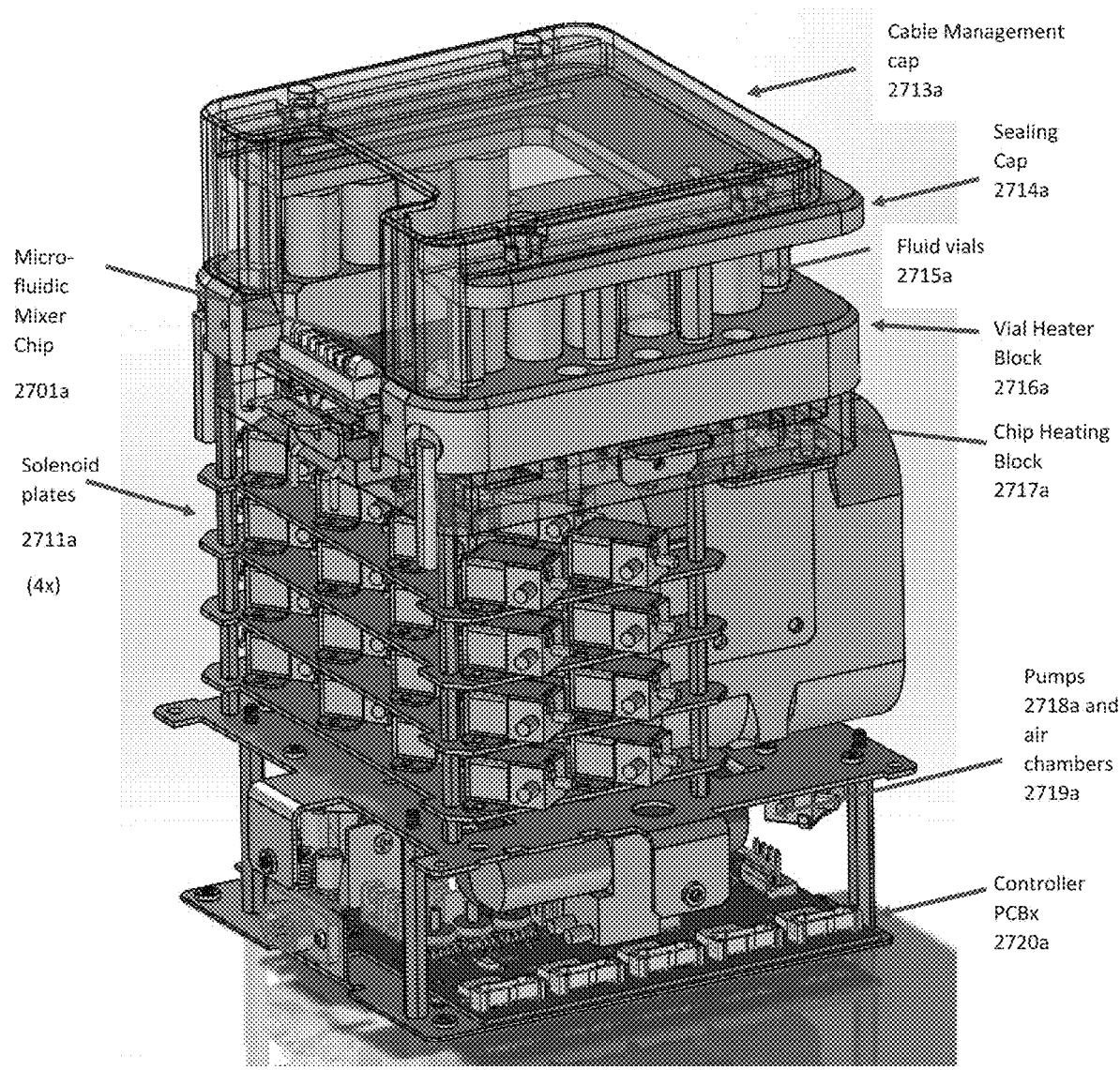
FIG. 27F provides details for an example OBD with cover removed with components labeled.
Figure 27G:
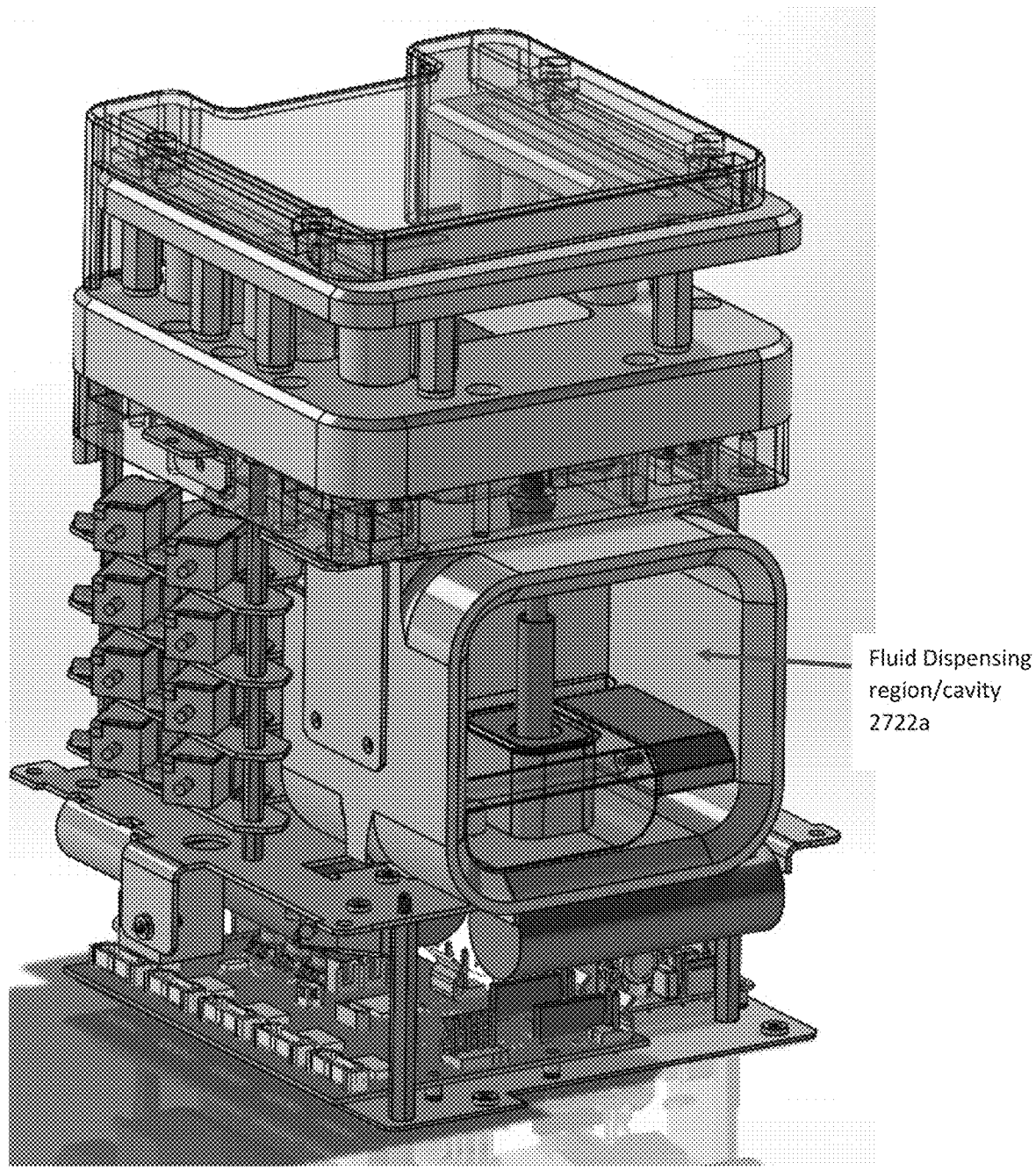
FIG. 27G shows a view of an example OBD showing the fluid dispensing region/cavity.
Figure 27H:
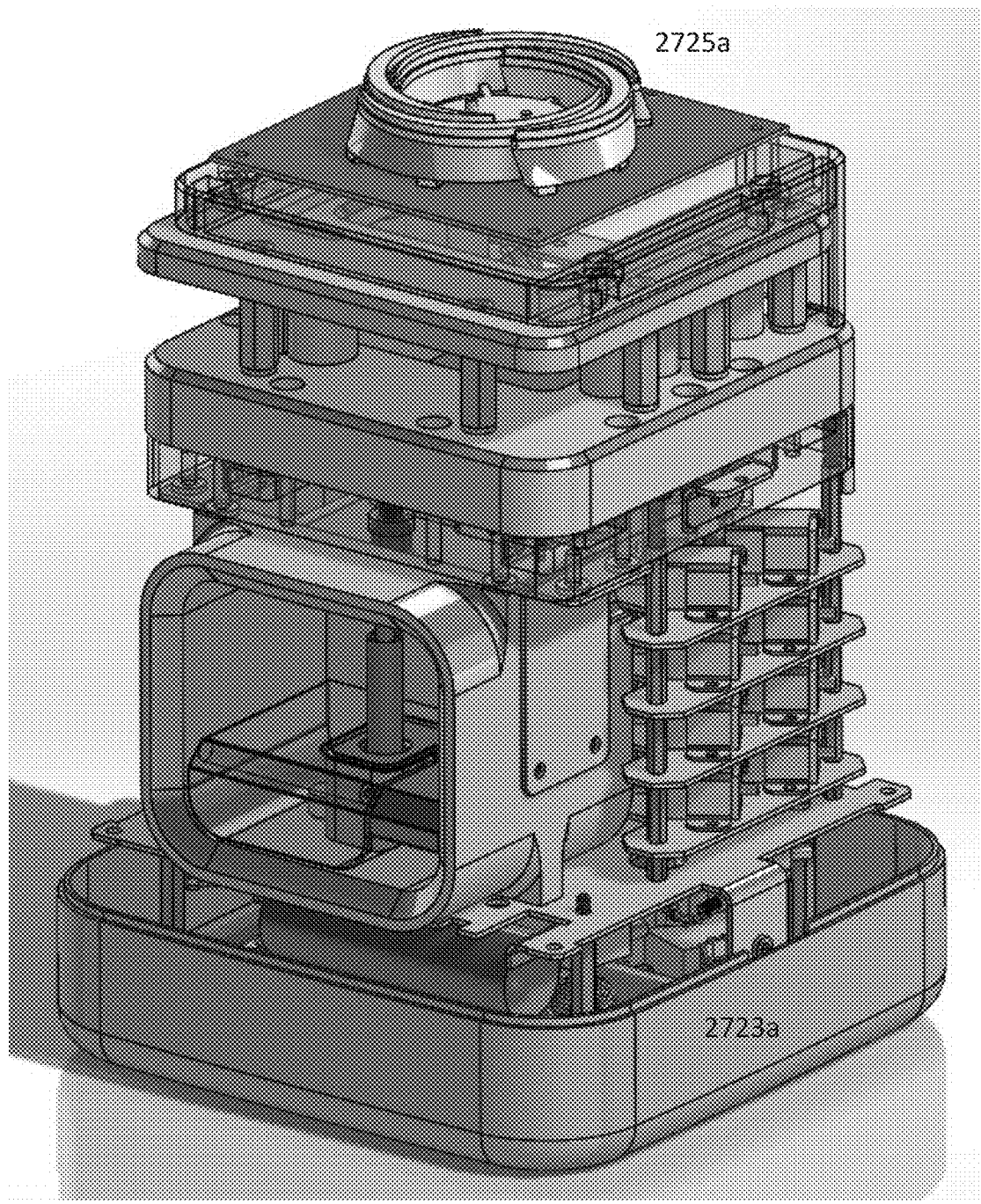
FIG. 27H shows an embodiment of the OBD in a base housing component with an activity indicator.
Figure 271:
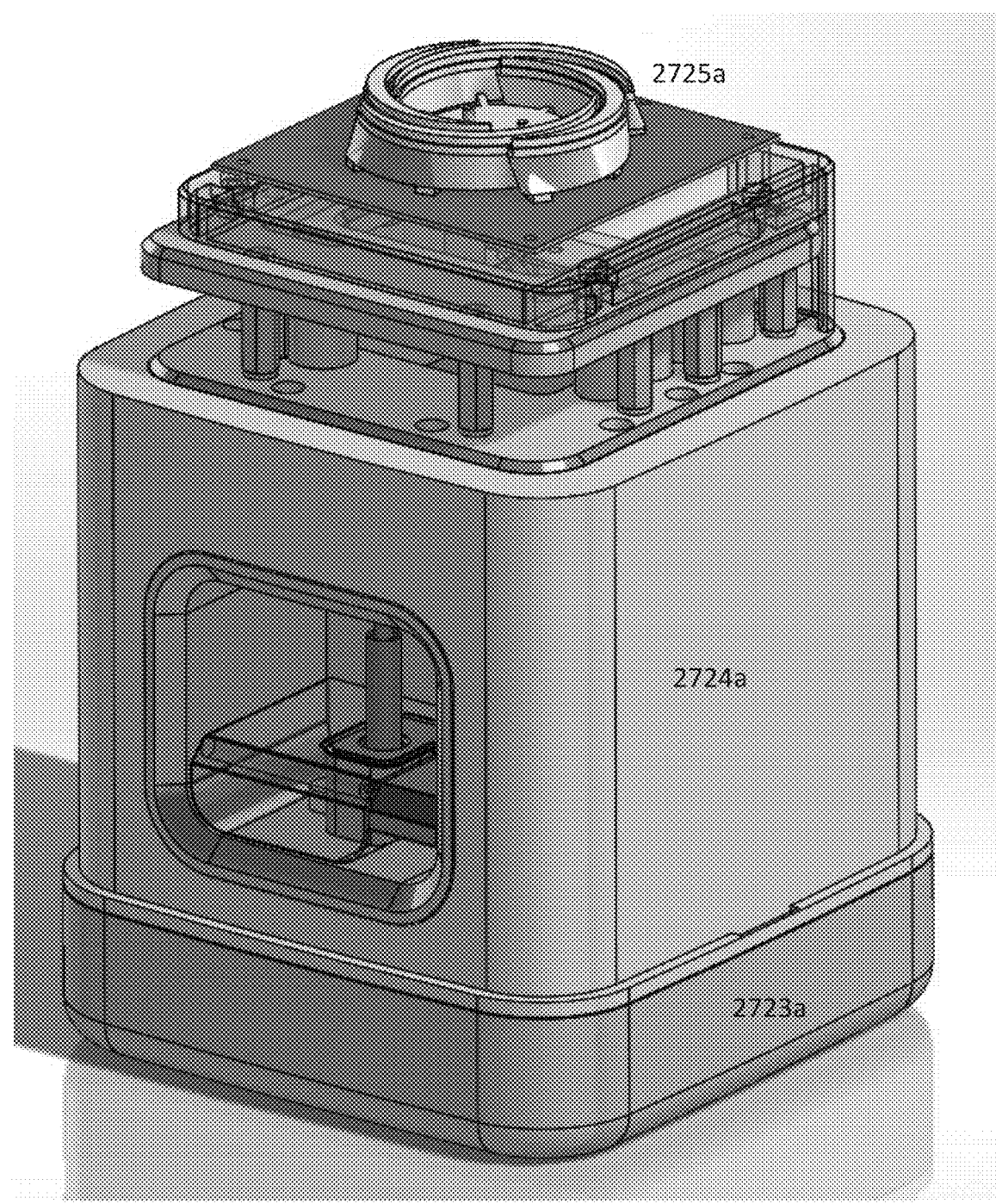
Figure 28A:
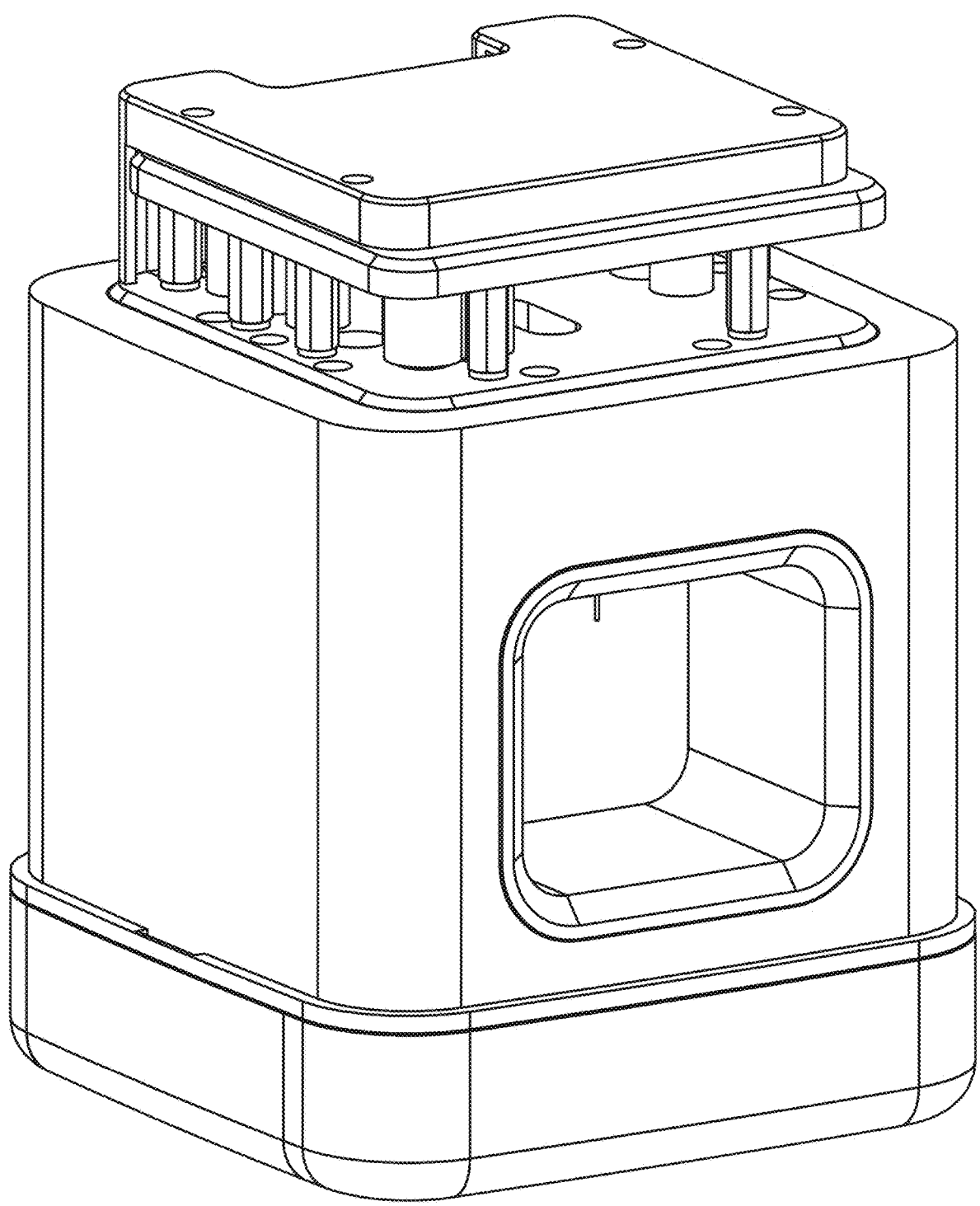
FIGS. 28A to 28H provide internal details of some example OBDs according to some embodiments of the disclosure.
Figure 28B:
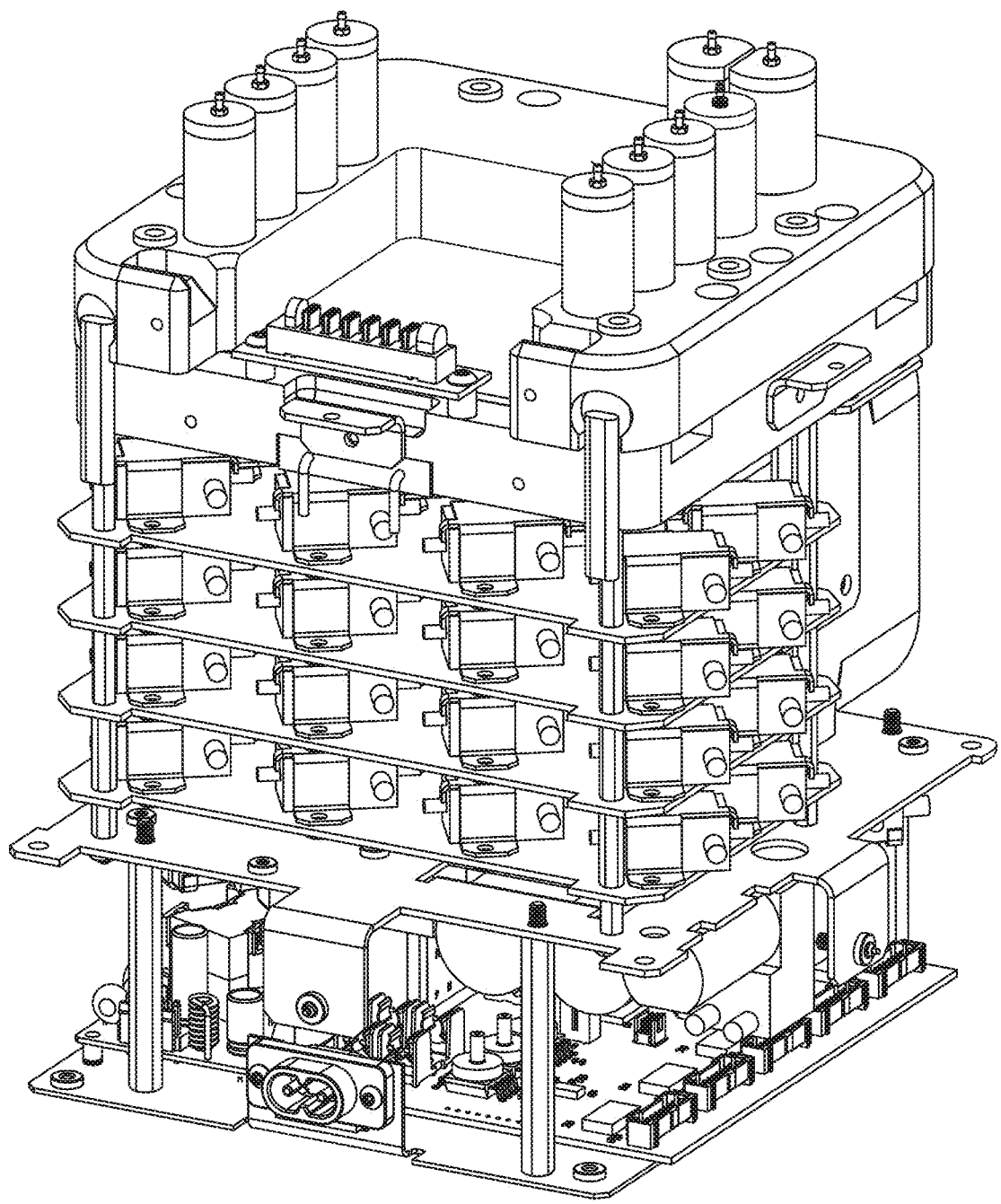
Figure 28C:
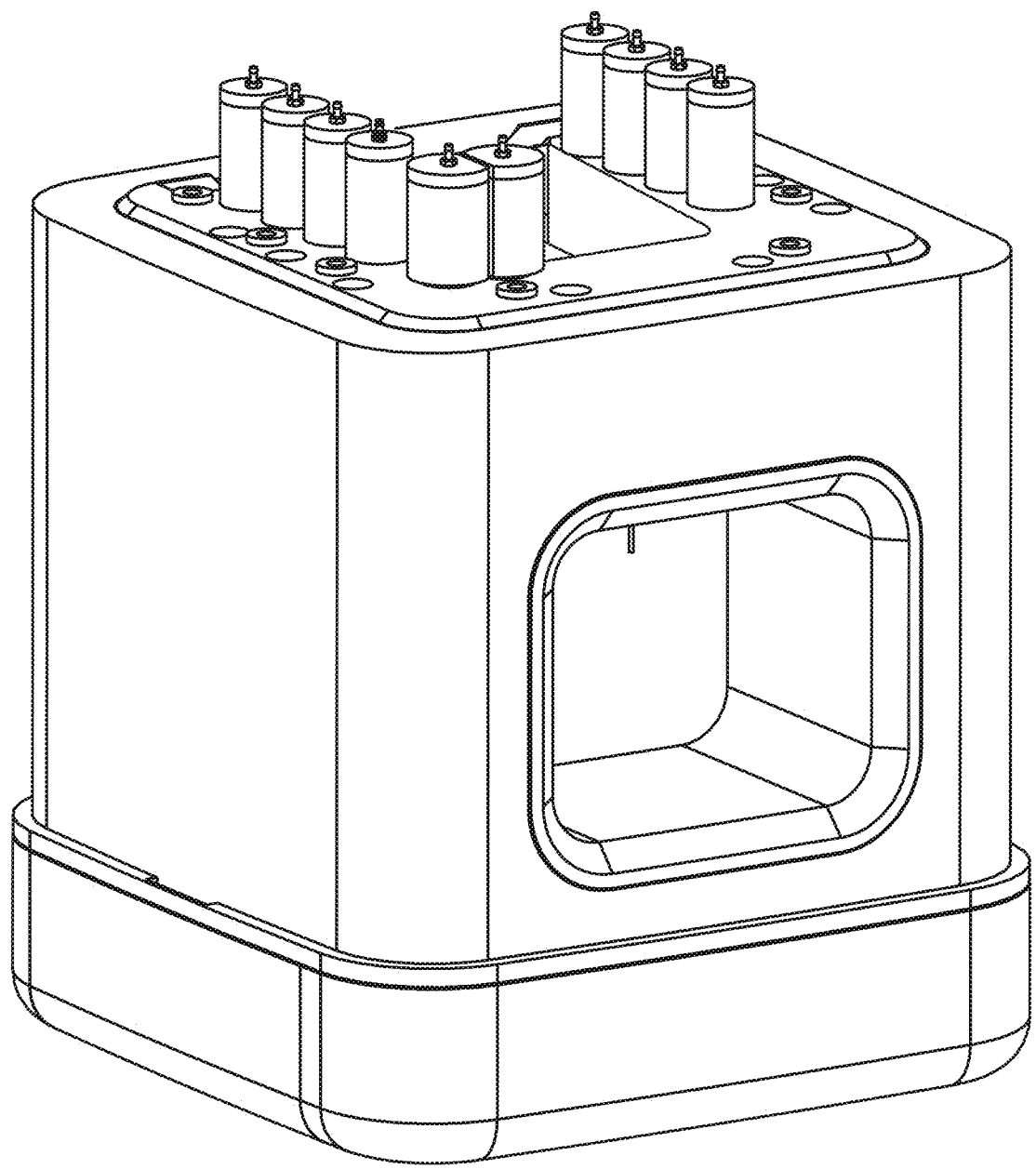
Figure 28D:
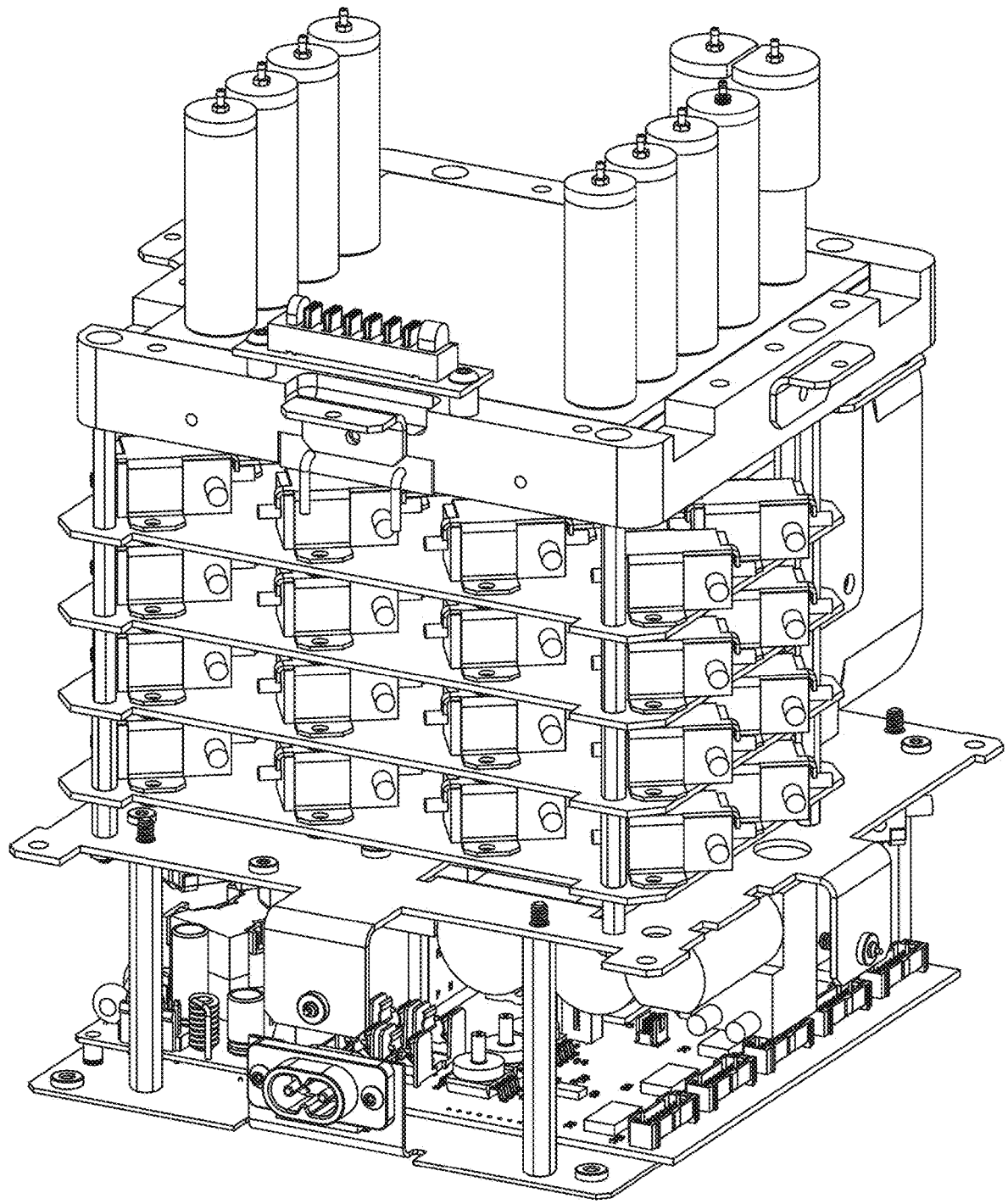
Figure 28E:
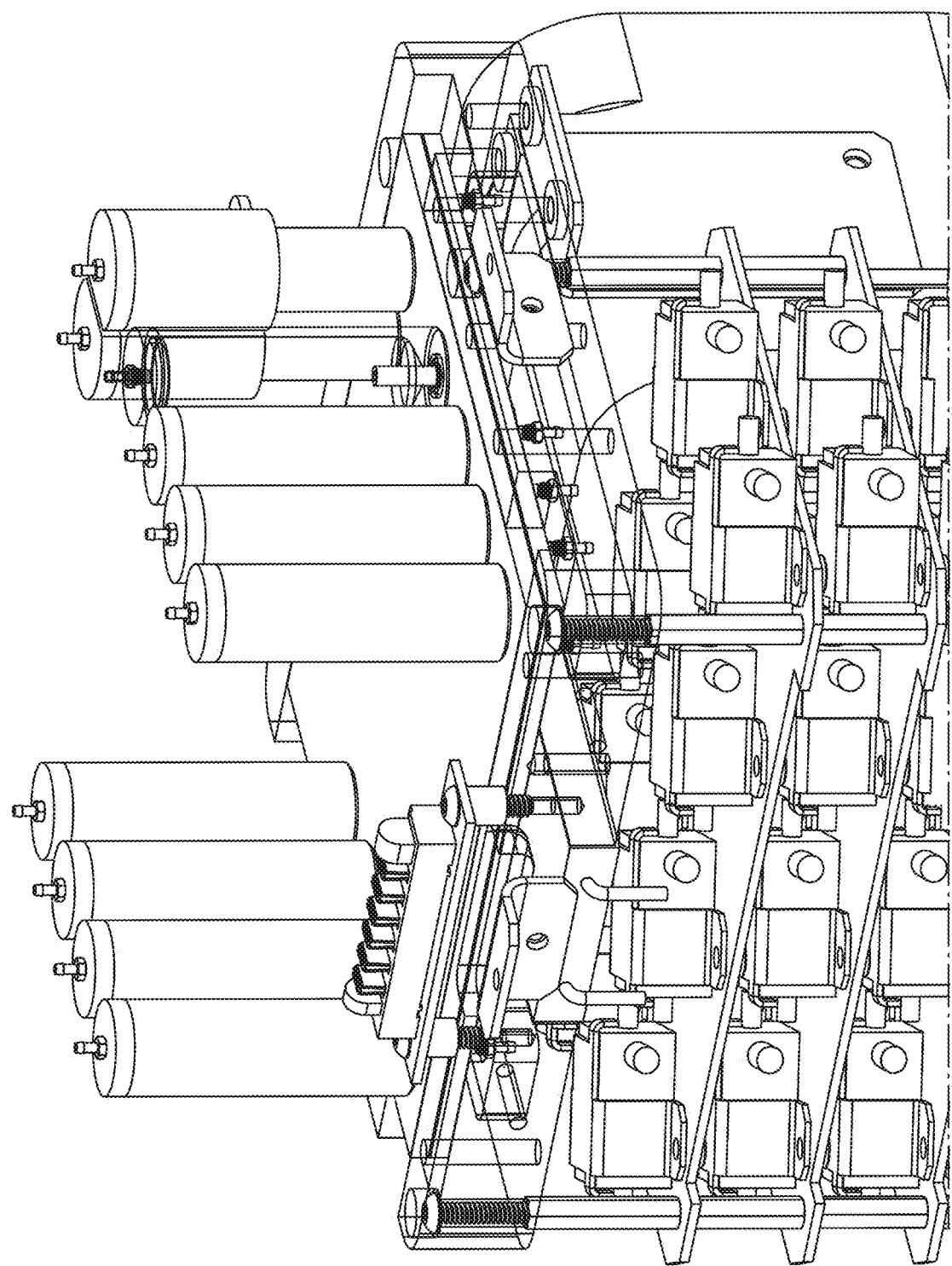
Figure 28F:
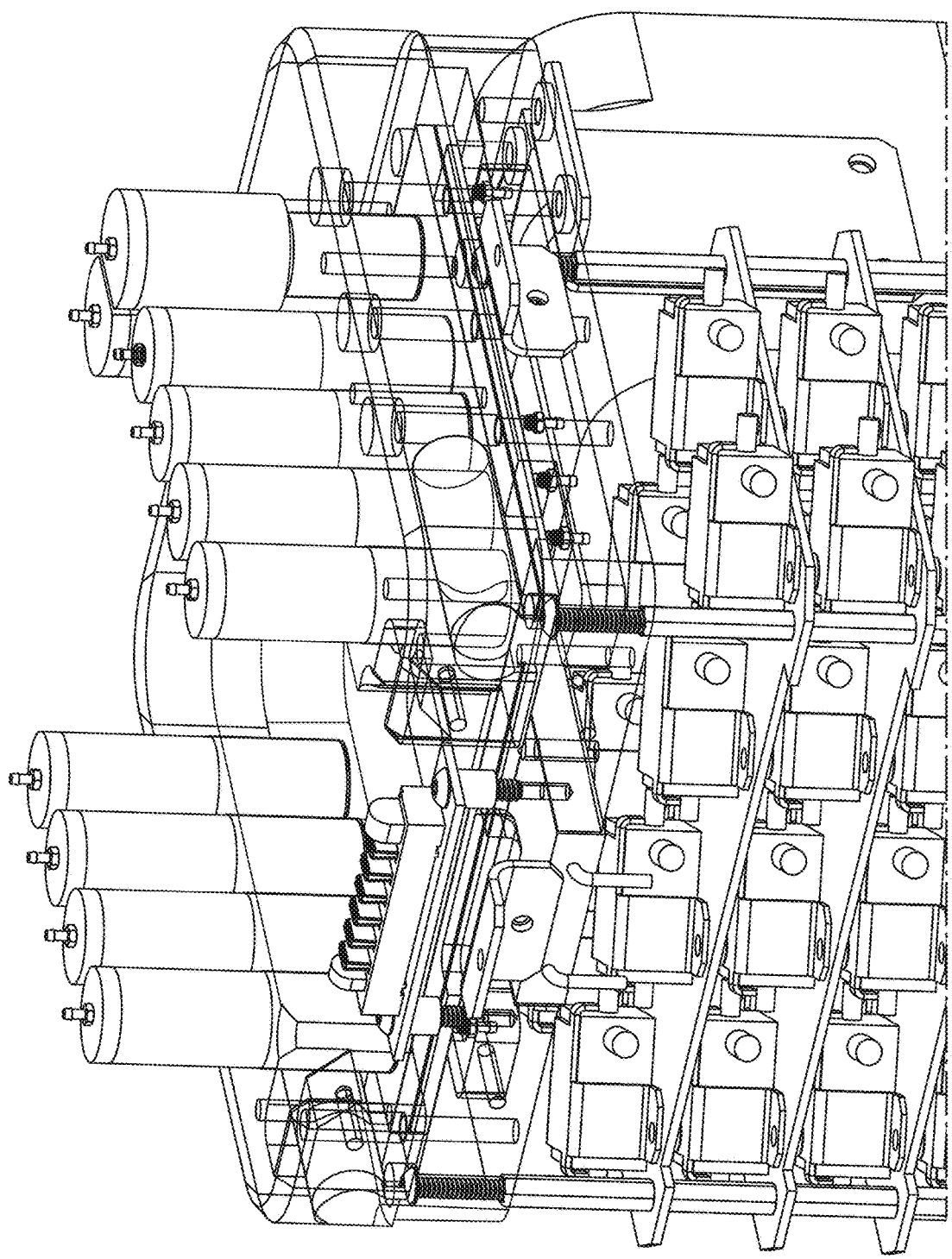
Figure 28G:
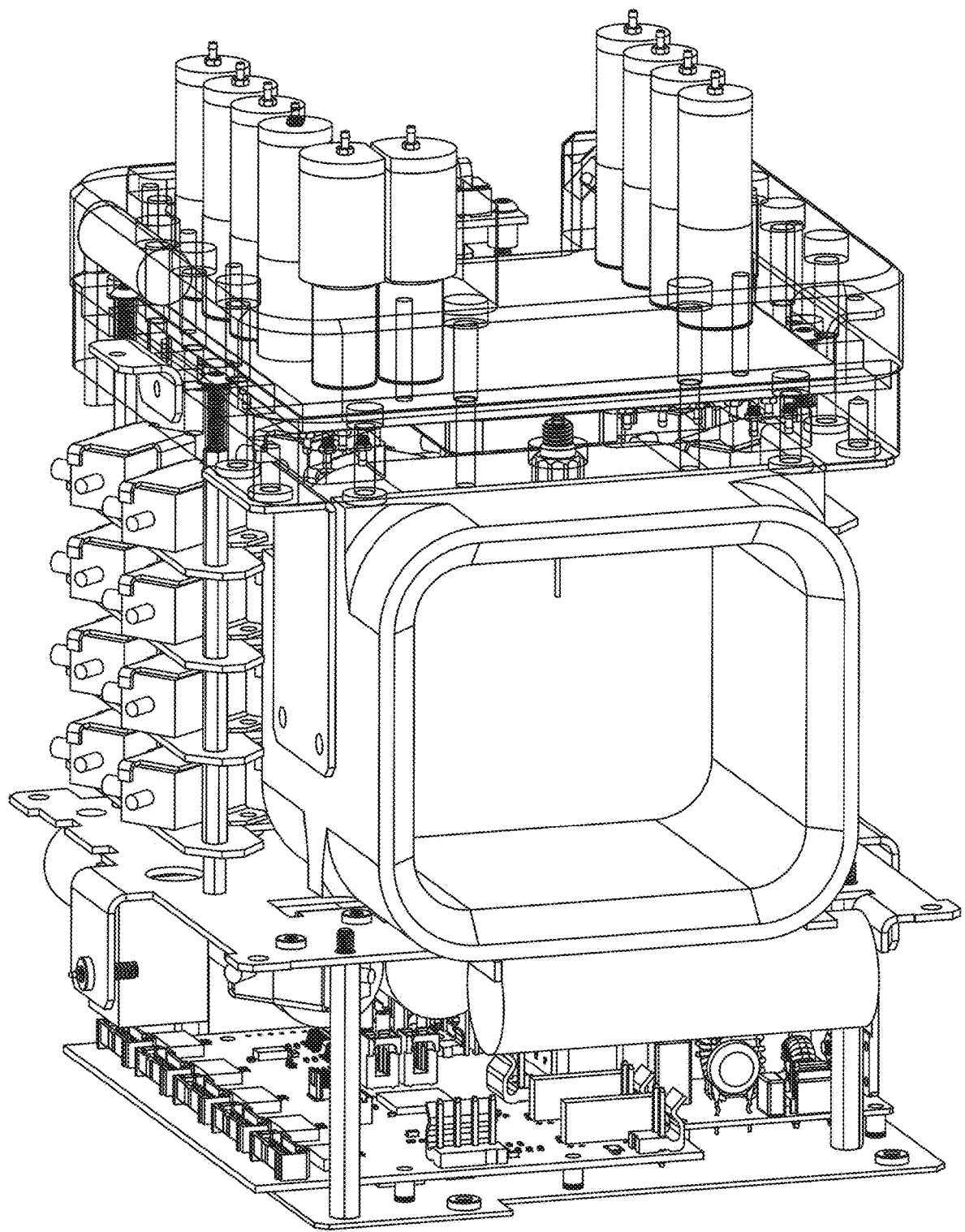
Figure 28H:
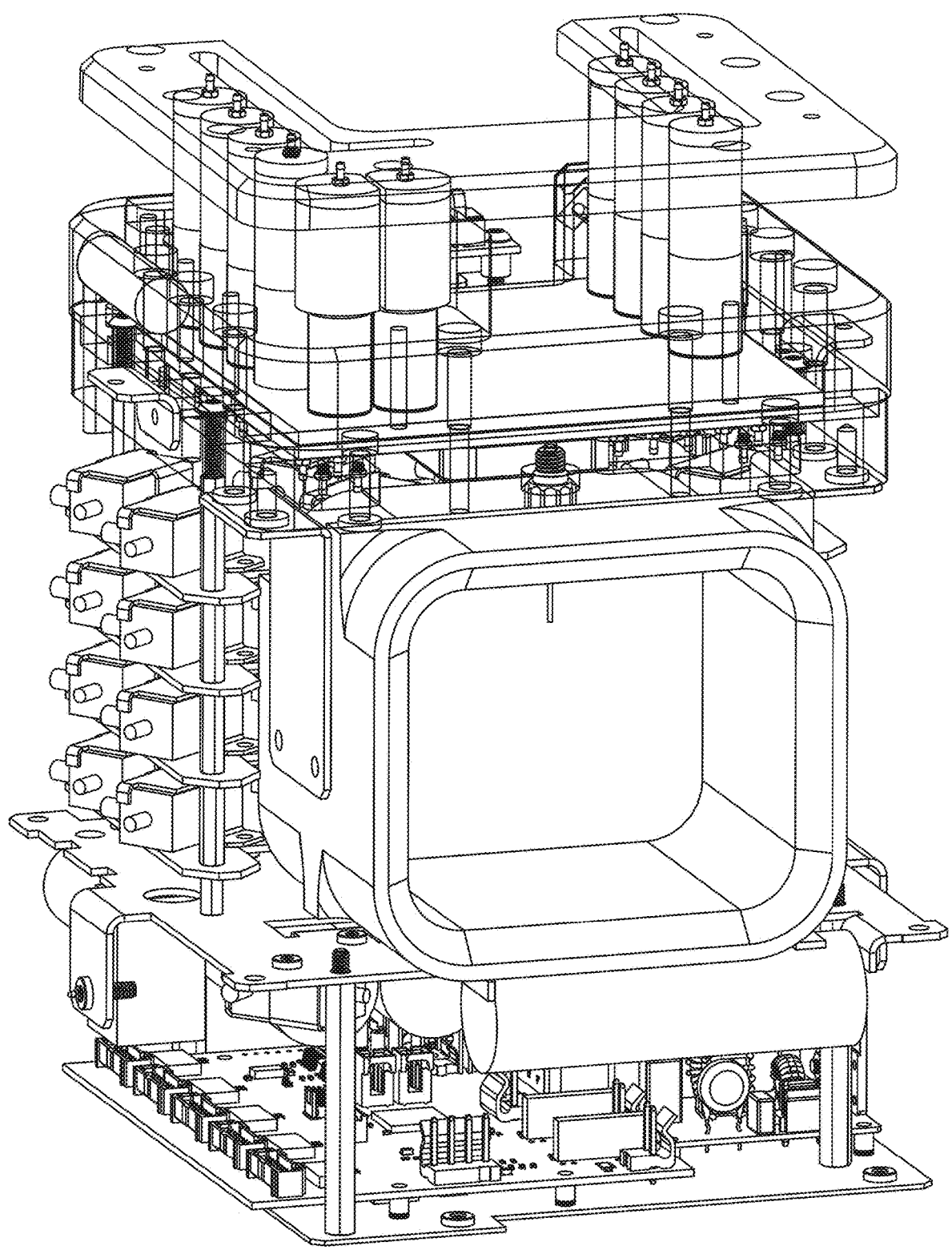

FIG. 27F provides details for an example OBD with cover removed and components including a microfluidic mixer chip 2701a, solenoid plates 2711a, cable management cap 2713a, sealing cap 2714a, fluid vials/cartridges 2715a, a vial heater/heater block 2716a, a microfluidic mixer chip heater/ heating block 2717a, pumps 2718a and air chambers 2719a, and a controller 2720a labeled. FIG. 27G shows another view of the OBD showing the fluid dispensing region/cavity 2722a. FIG. 27H shows an embodiment of the OBD in a base housing component 2723a with an activity indicator 2725a affixed or placed on top, and FIG. 27I shows an embodiment of the OBD in a base housing 2723a and middle housing 2724a that are configured to protect the internal components of the OBD, and also including an activity indicator 2725a affixed or placed on the top of the OBD internal components. In some embodiments, the activity indicator will provide a visual display when the OBD is active (e.g., blending), starting up/warming up, shutting down/turning off, etc.

FIGS. 28A to 28H provide internal details of some example OBDs according to some embodiments of the disclosure, with the same or similar internal components and structure to those shown in FIGS. 27F-27I.

Figure 29:
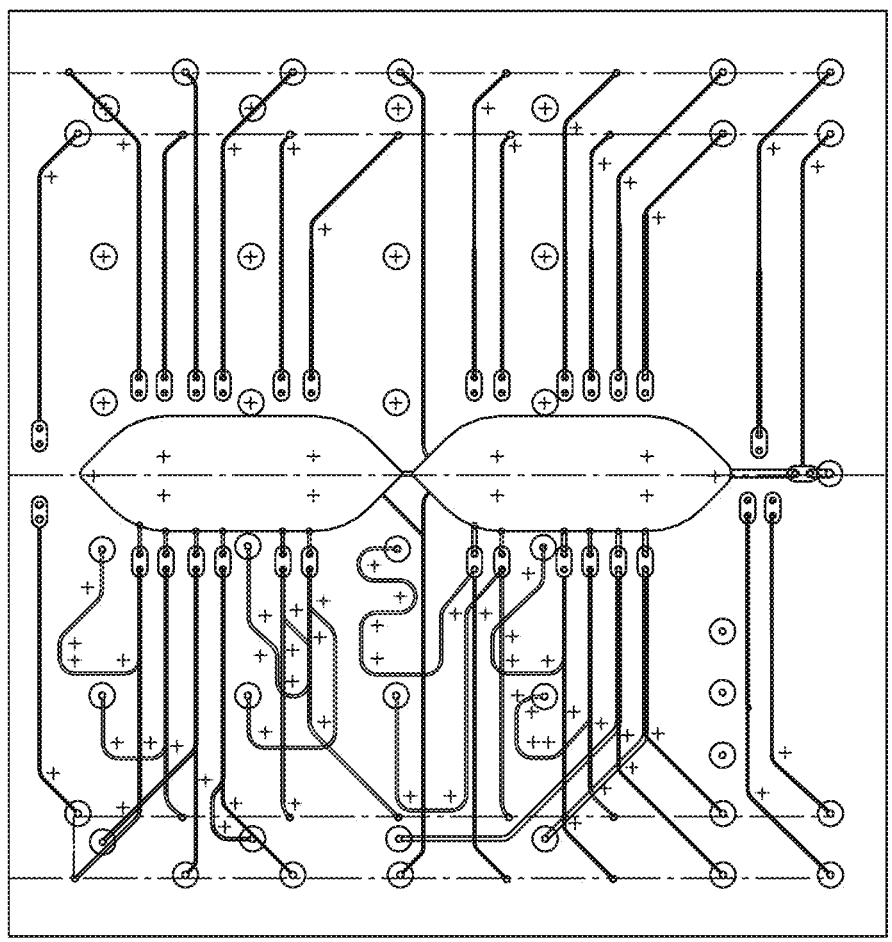
FIG. 29 provides a view of an example OBD microfluidic mixer chip according to some embodiments of the disclosure.

FIG. 29 provides a view of another example OBD microfluidic mixer chip according to some embodiments of the disclosure.

Figure 30A:
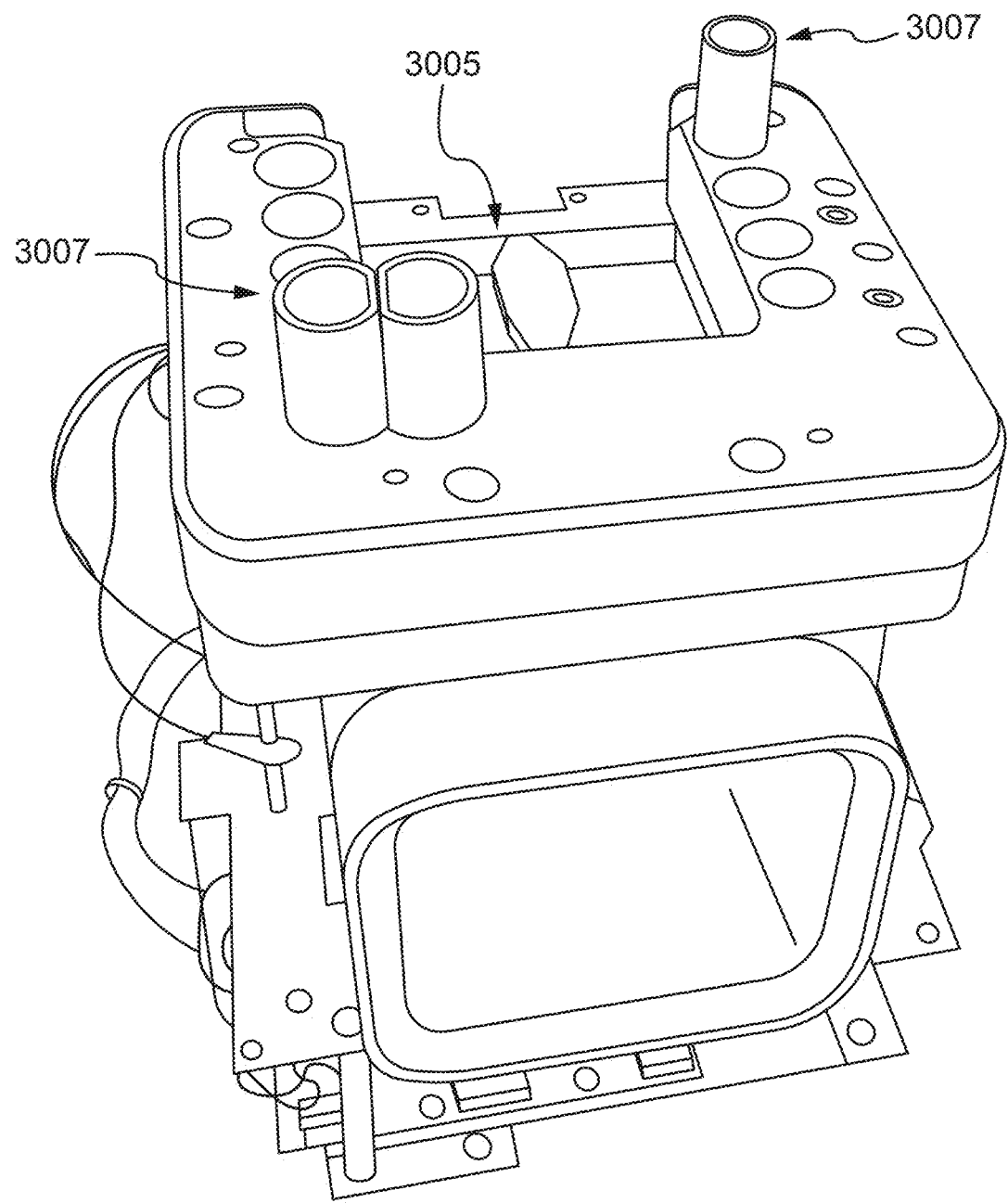
FIGS. 30A-30C shows an example OBD with the cover removed, and including removable reservoirs and an OBD microfluidic mixer chip.
Figure 30B:
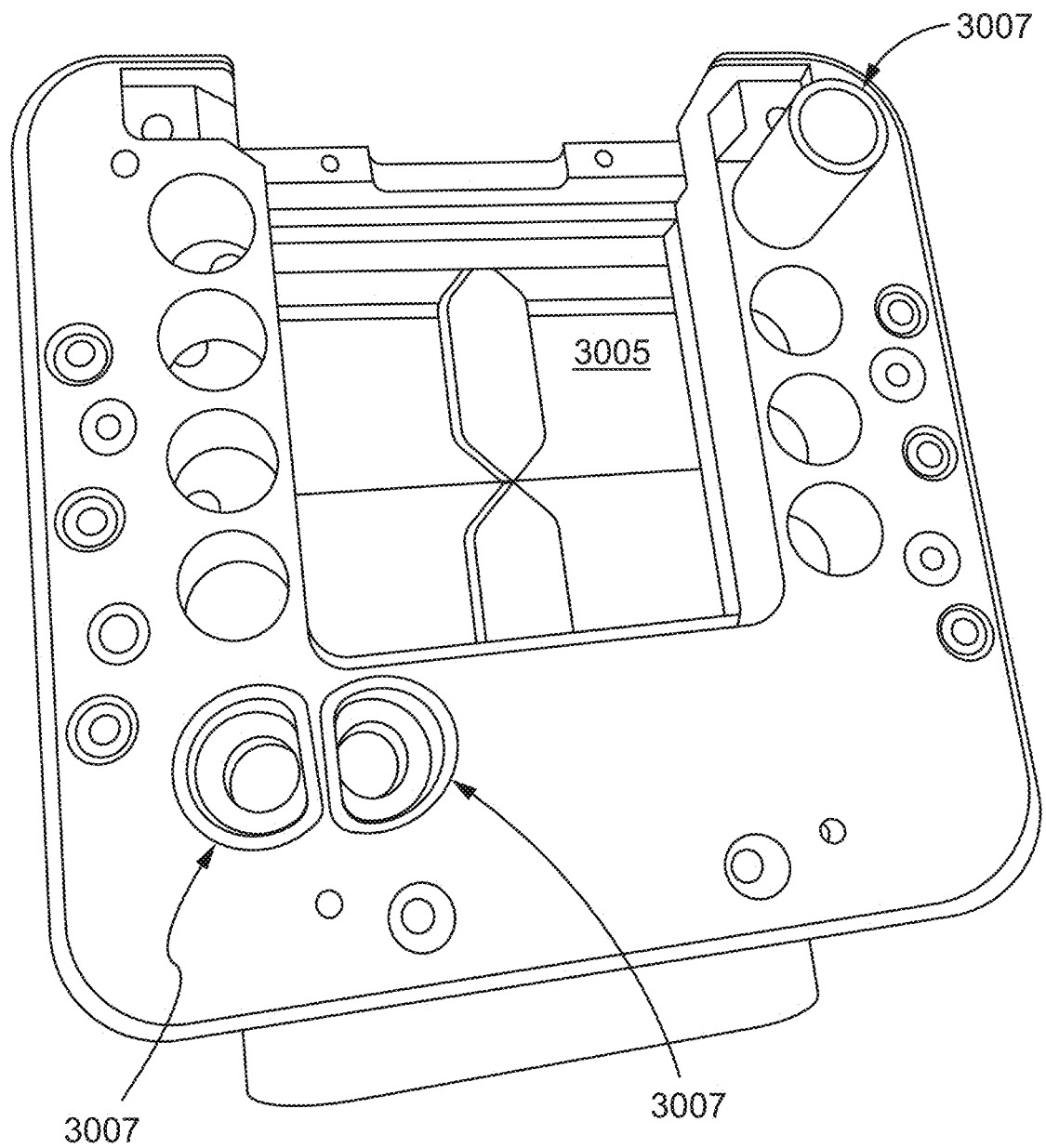
Figure 30C:
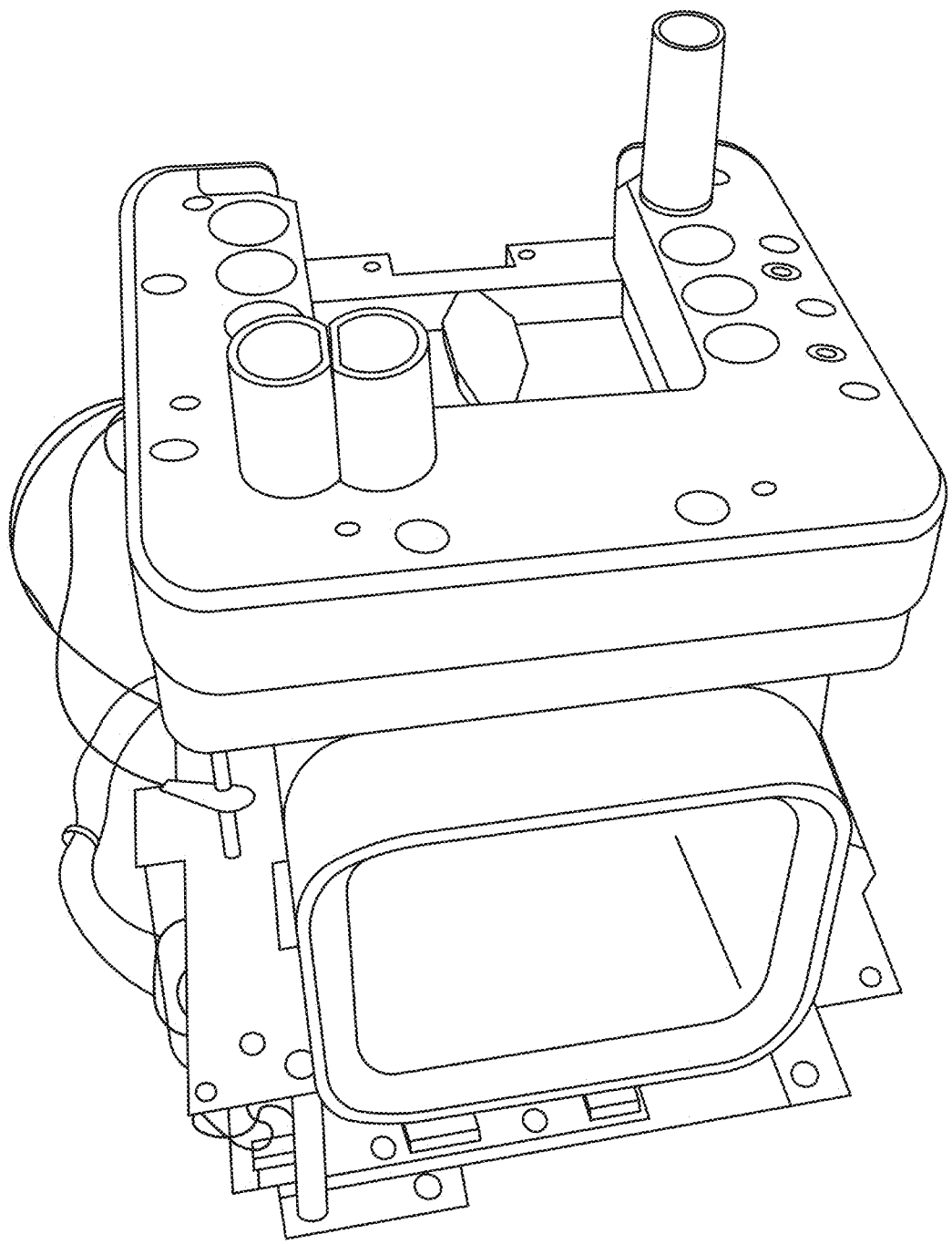
Figure 30J:
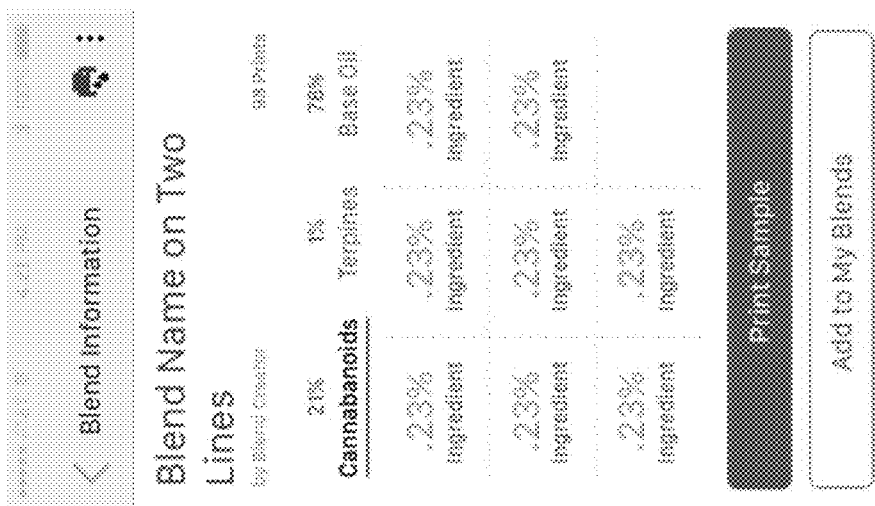
FIG. 30D illustrates an example edit/create blend recipe flow for an OBD interface according to some embodiments.
FIG. 30E illustrates an example recipe/recipe collection overview for an OBD interface according to some embodiments.
FIG. 30F illustrates an example user profile and history overview for an OBD interface according to some embodiments.
FIG. 30G provides an example OBD mobile application architecture according to some embodiments.
FIG. 30H to FIG. 30V provide example user interfaces for an OBD mobile application according to some embodiments.
FIG. 30W provides examples of blends/recipes that the OBD produces.
Figure 30I:
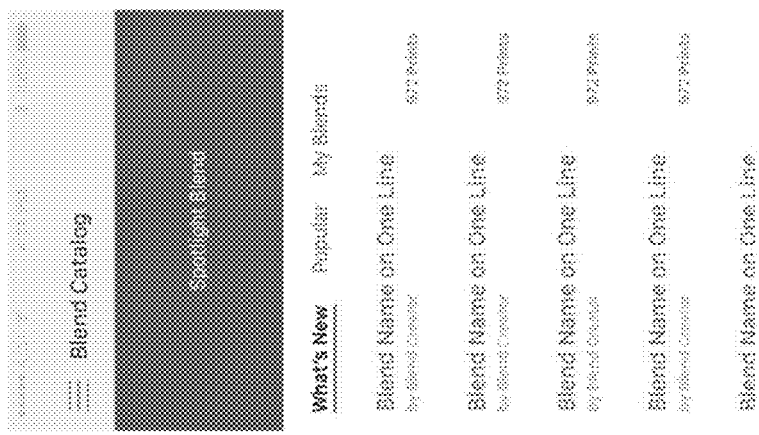

FIGS. 30A-30C shows an example OBD with the cover removed, having removable reservoirs 3007 and an OBD microfluidic mixer chip 3005.

Figure 30H:
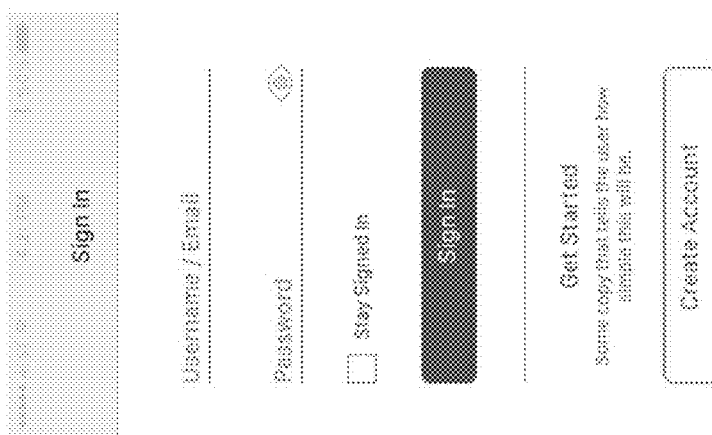
Figure 30S:
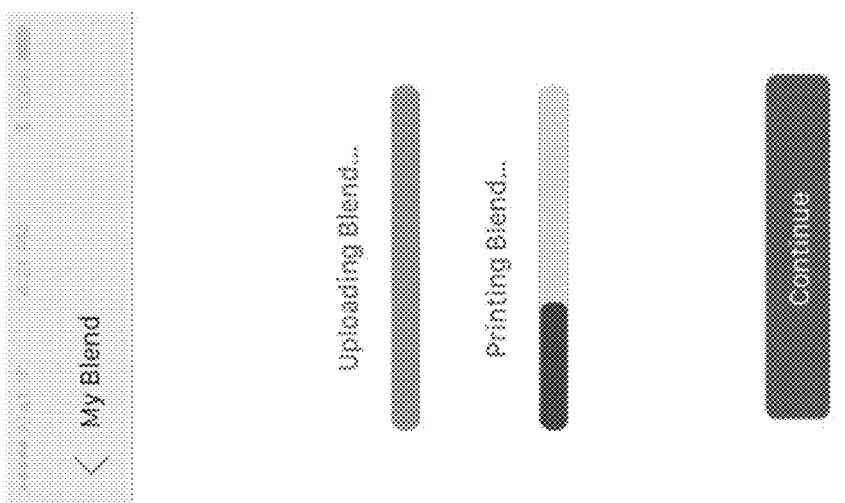
Figure 30R:
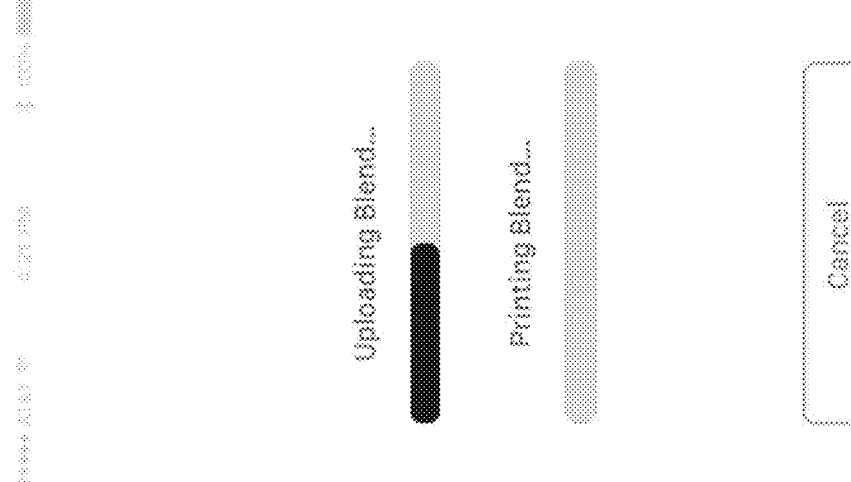
Figure 30Q:
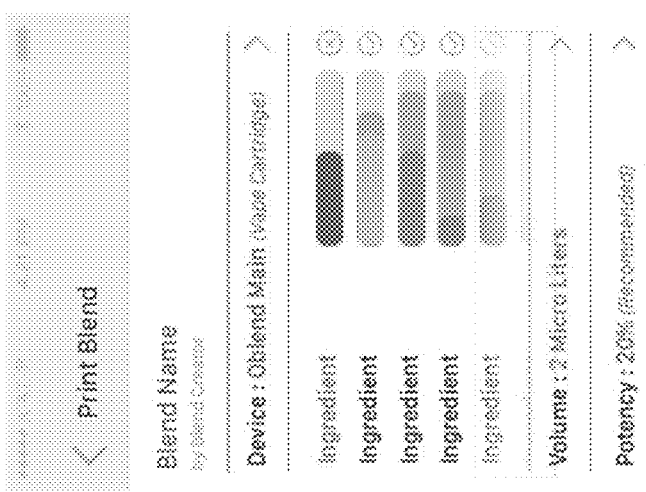
Figure 30V:
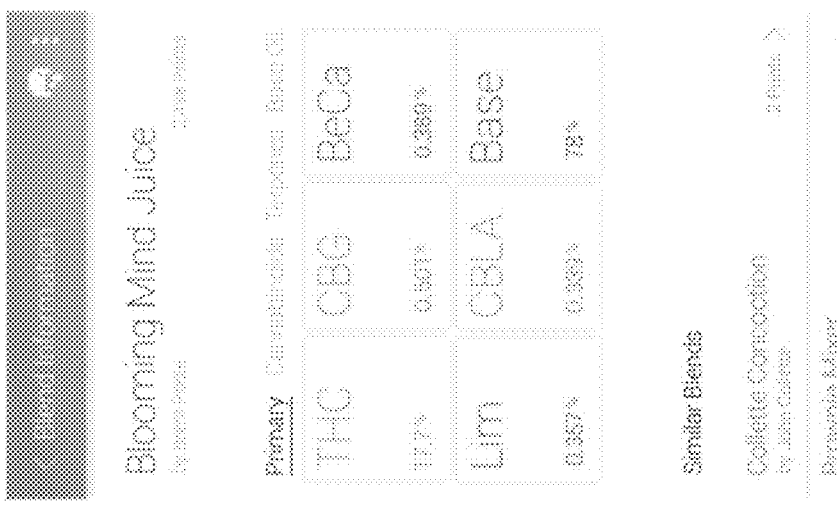
Figure 30U:
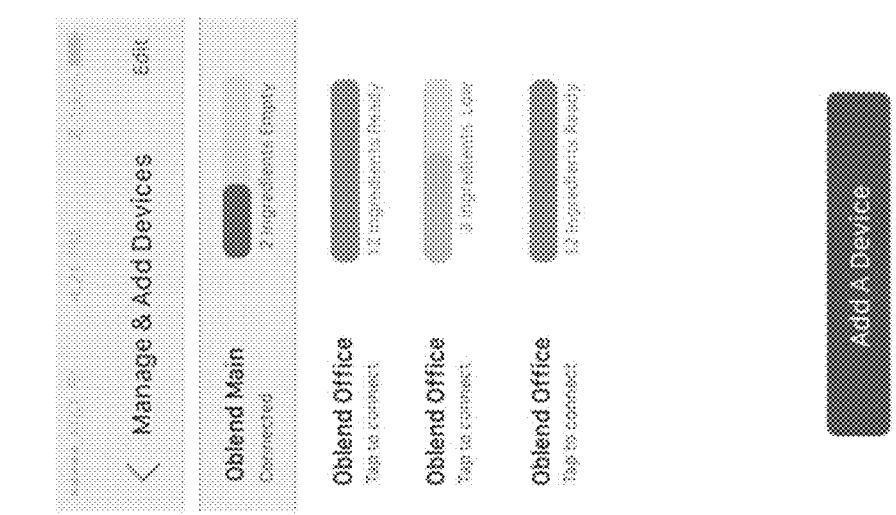
Figure 30T:
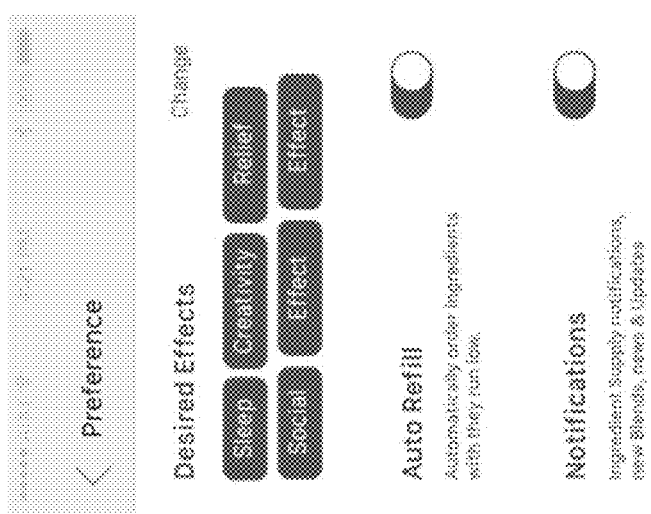

FIG. 30D illustrates an example edit/create blend recipe flow for an OBD interface according to some embodiments, FIG. 30E illustrates an example recipe/recipe collection overview for an OBD interface according to some embodiments, and FIG. 30F illustrates an example user profile and history overview for an OBD interface according to some embodiments; such embodiments may be provided on a web app, device app, and/or mobile application (e.g., executed on a smart phone or tablet). FIG. 30G provides an example OBD mobile application architecture, according to some embodiments. FIGS. 30H-30V provide example user interfaces for an OBD mobile application according to some embodiments where an OBD is configured for communication with a mobile device, the mobile device OBD application configured to allow a user to sign-in, validate, and verify, their identity and/or qualifying trait (e.g., age to access a substance or substances that have prohibitions against use by minors, such that the OBD can assure compliance with applicable regulations and/or laws). FIG. 30W provides examples of blends/recipes that the OBD produces, according to some implementations.

Figure 31:
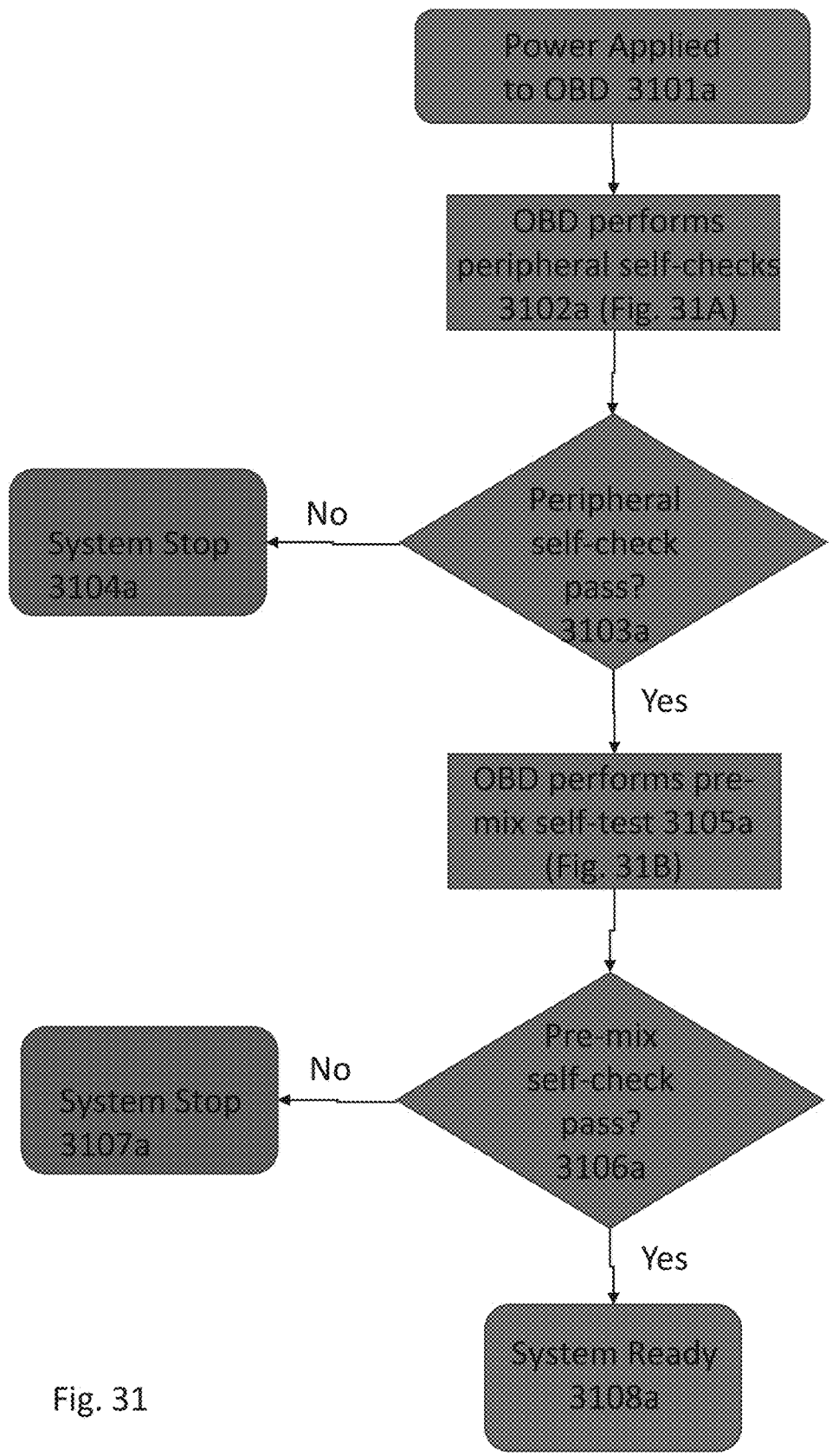
FIG. 31 provides a flow chart illustrating an example OBD start sequence, according to some embodiments.

FIG. 31 provides a flow chart illustrating an example OBD start sequence, according to some embodiments. Here, when power is applied to the OBD 3101a (e.g., turned on), the OBD performs a peripheral self-check 3102a (see also FIG. 31A for additional detail), and if 3103a not passed, the system stops 3104a, but if 3103a passed, OBD performs a pre-mix self-test 3105a (see also FIG. 31B for additional detail), and if 3106a not passed, the system stops 3107a, but if 3106a passed, the system is determined to be ready 3108a.

Figure 31A:
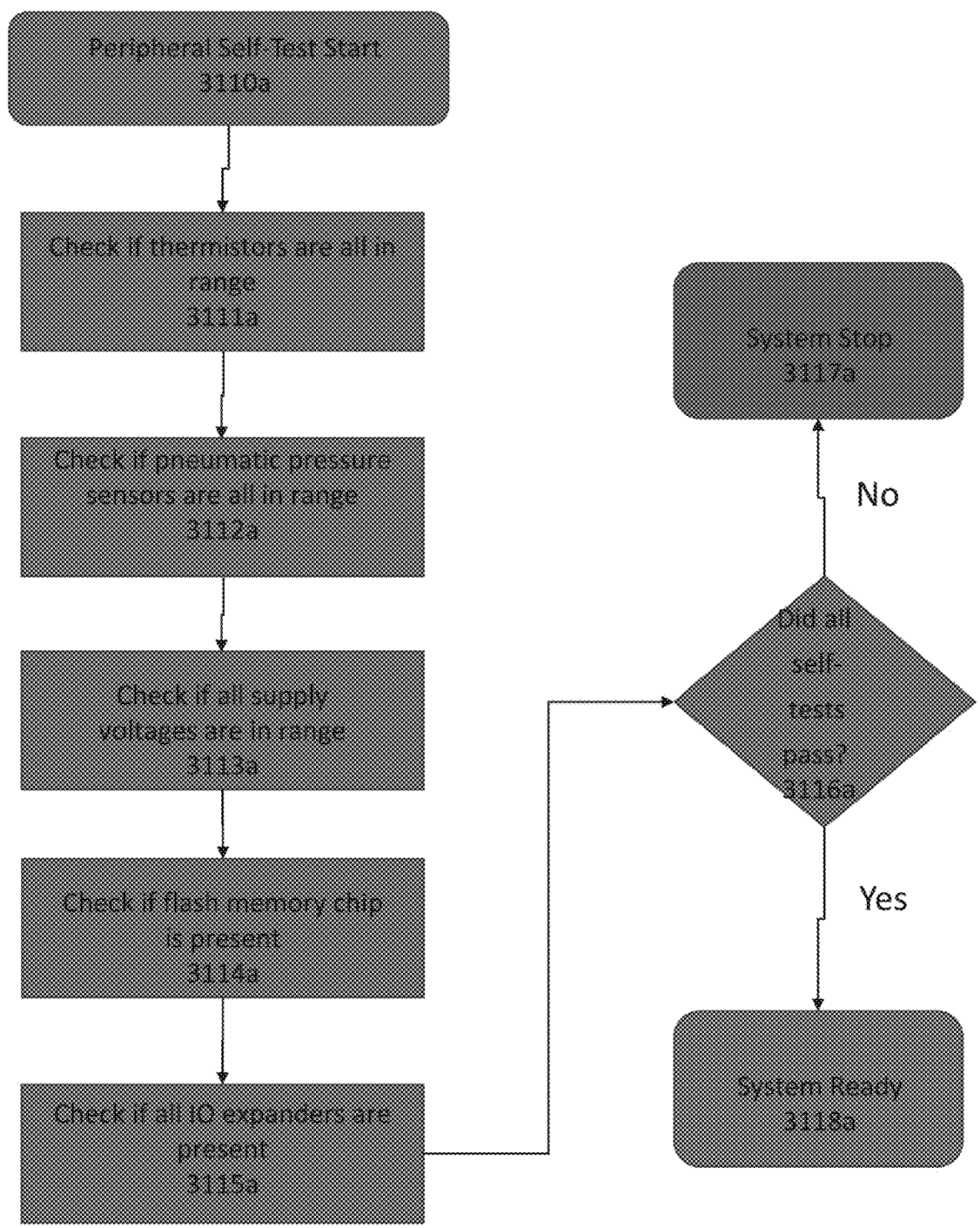
FIG. 31A illustrates an example OBD peripheral self-test flow, according to some embodiments.

FIG. 31A provides a flow chart illustrating an example OBD peripheral self-test, according to some embodiments. At start 3110a, thermistors 3111a, pressure sensors 3112a, and supply voltages 3113a are checked to determine if they are in range, and the presence of a flash memory chip or the like 3114a and IO expanders 3115a are determined. If 3116a not all self-tests are passed, the system is stopped 3117a (and an alert or other noticed issued and/or recorded), while if 3116a all self-tests are passed, the system is determined to be read, at least for peripherals.

Figure 31B:
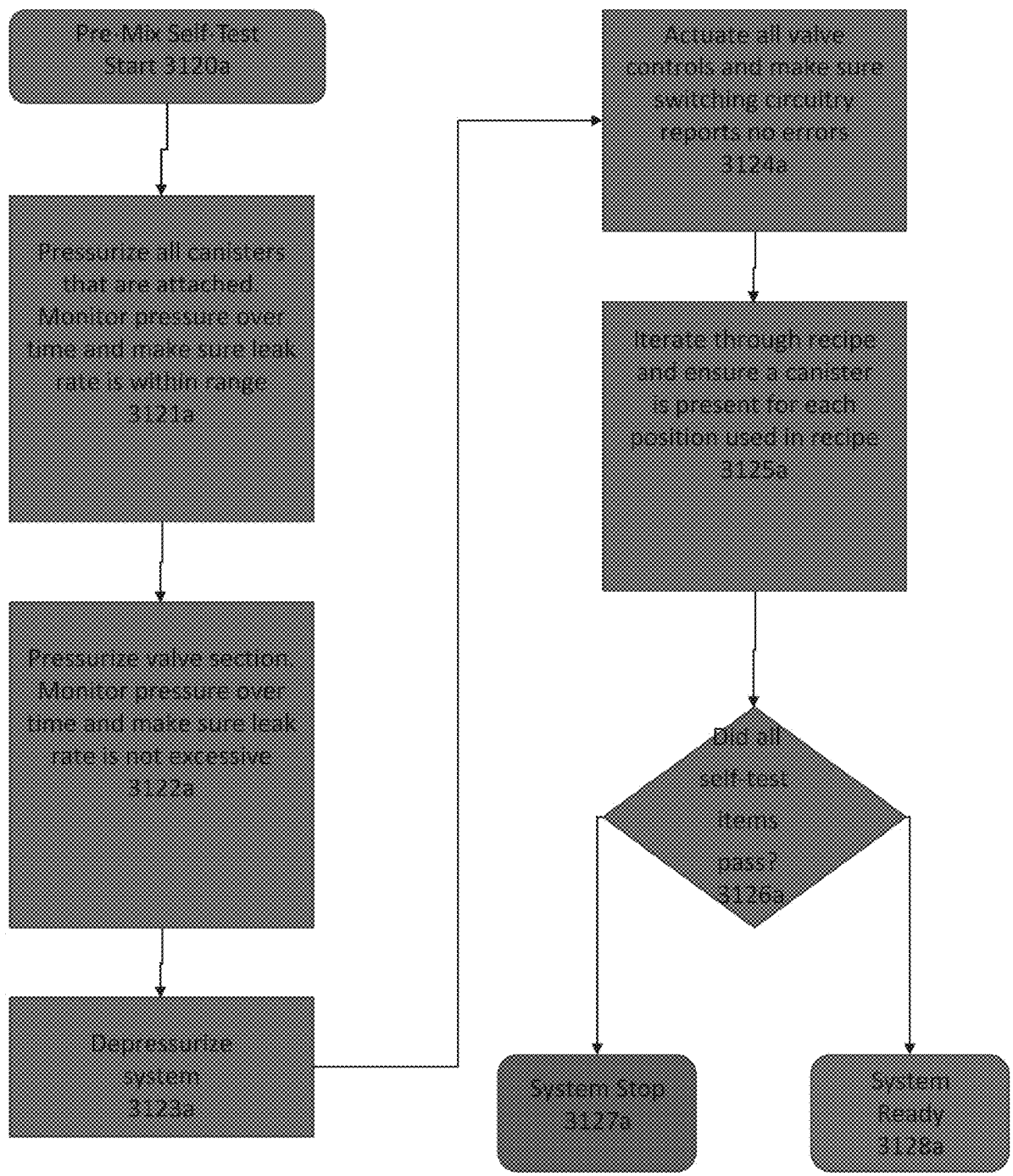
FIG. 31B illustrates an example OBD pre-mix self-test flow, according to some embodiments.

FIG. 31B provides a flow chart illustrating an example OBD pre-mix self-test, according to some embodiments. The test starts 3120a and attached canisters/vials are pressurized 3121a, valve sections are pressurized 3122a, and leak rate determined for each over time. The system is then depressurized 3123a, all valve controls are actuated to make sure switching circuitry reports no errors 3124a, and the recipe is iterated through to ensure a canister is present for each position used in the recipe 3125a. The system is either stopped 3127a or deemed ready 3128a depending on whether all pre-mix self-test items were passed 3126a.

Figure 31C:
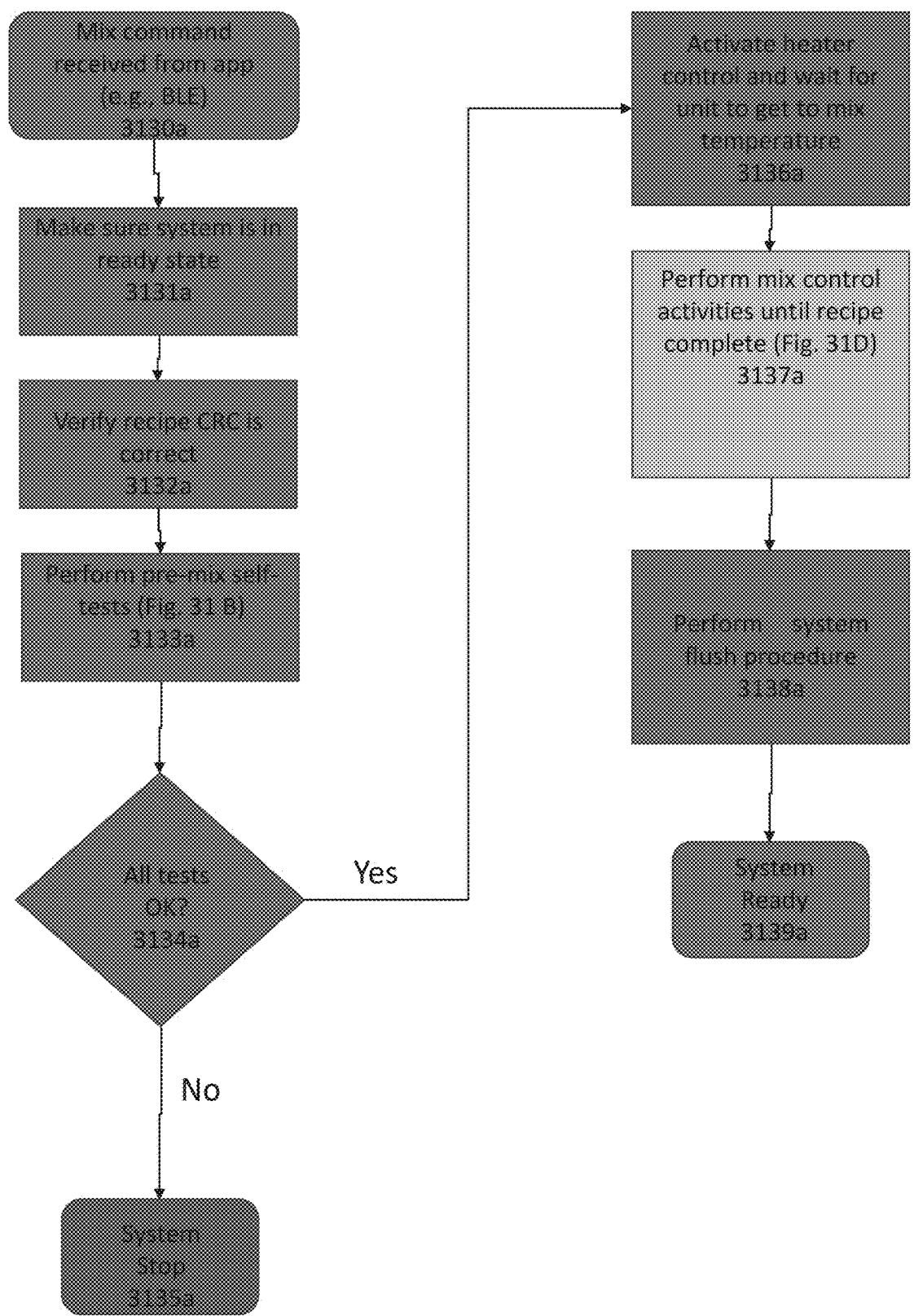
FIG. 31C illustrates example OBD mix state processes, according to some embodiments.

FIG. 31C provides a flow chart illustrating example OBD mix state processes, according to some embodiments. As shown, a mix command is received 3130a (e.g., from an app on a mobile device), and system is confirmed to be ready 3131a, recipe verified 3132a, pre-mix self-test is performed (as discussed above with respect to FIG. 31B), and if all test ok 3134a, the heater control is activated and unit gets to mix temperature 3136a, after which mix control activities are performed until completed 3137a (see FIG. 31D for additional detail), after which system flush procedure is performed 3138a, and the system is ready again 3139a.

Figure 31D:
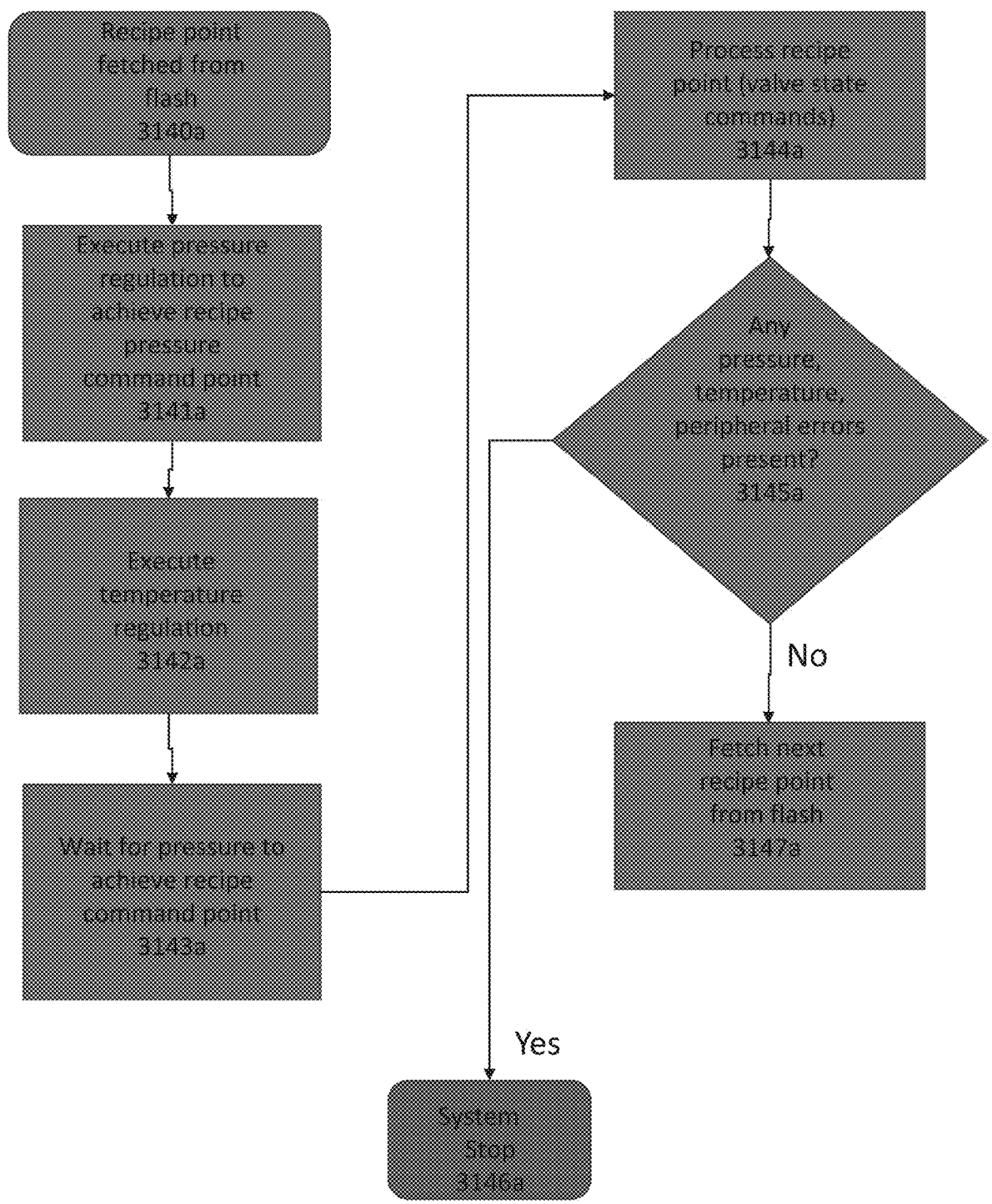
FIG. 31D illustrates an example OBD mix state control flow, according to some embodiments.

FIG. 31D provides a flow chart illustrating example OBD mix state control, according to some embodiments. The recipe point fetched from flash 3140a, pressure regulation is executed to achieve recipe pressure command point 3141a, temperature regulation is executed 3142a, and once the recipe command point pressure is achieved 3142a, process recipe point (e.g., valve state commands) 3144a, and as long as there are no errors present 3145a, the next recipe point is fetched from flash 3147a.

Figure 31E:
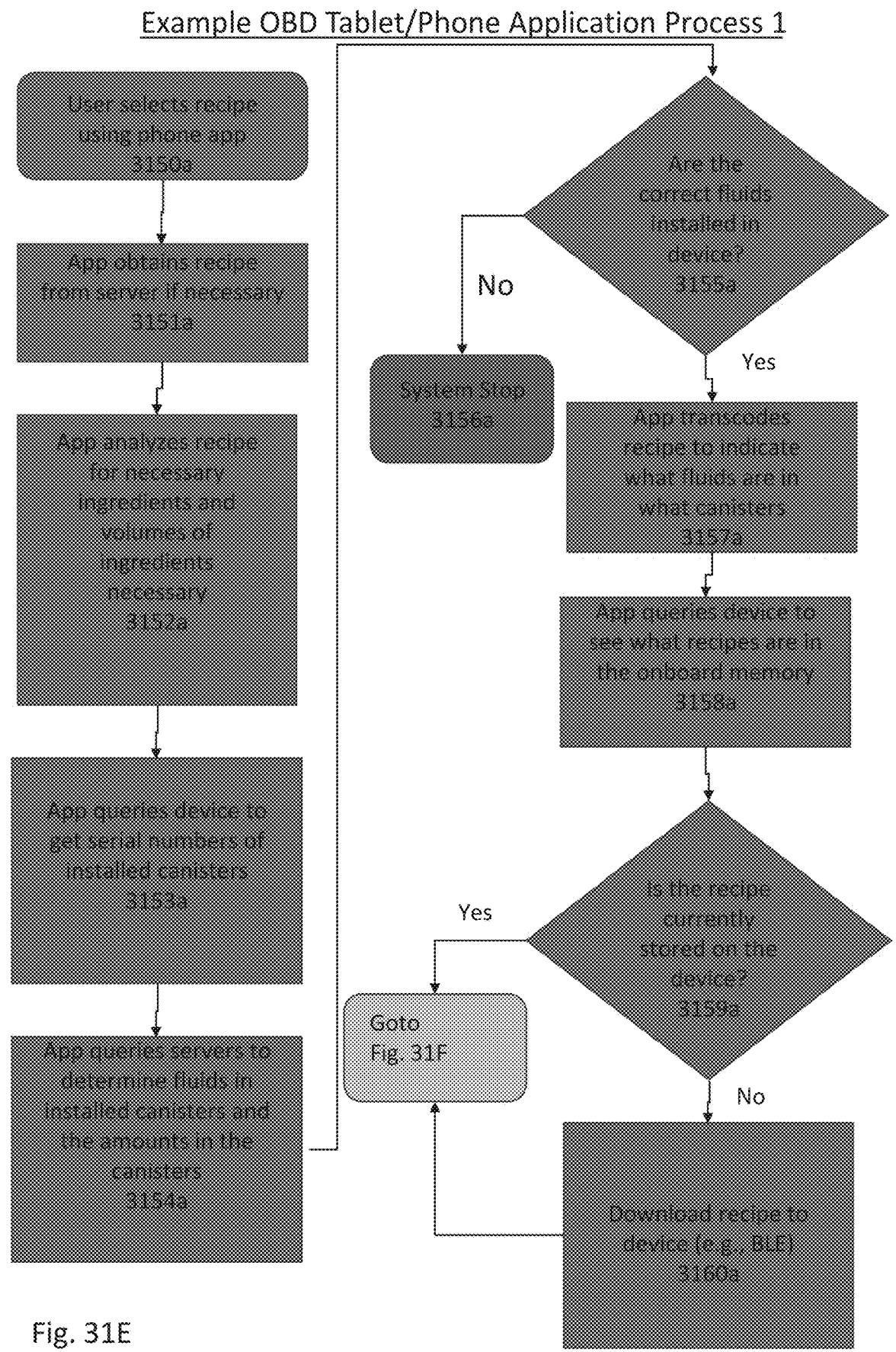
FIG. 31E and FIG. 31F provide a flow chart illustrating example OBD tablet/smart phone application processes, according to some embodiments.
Figure 31F:
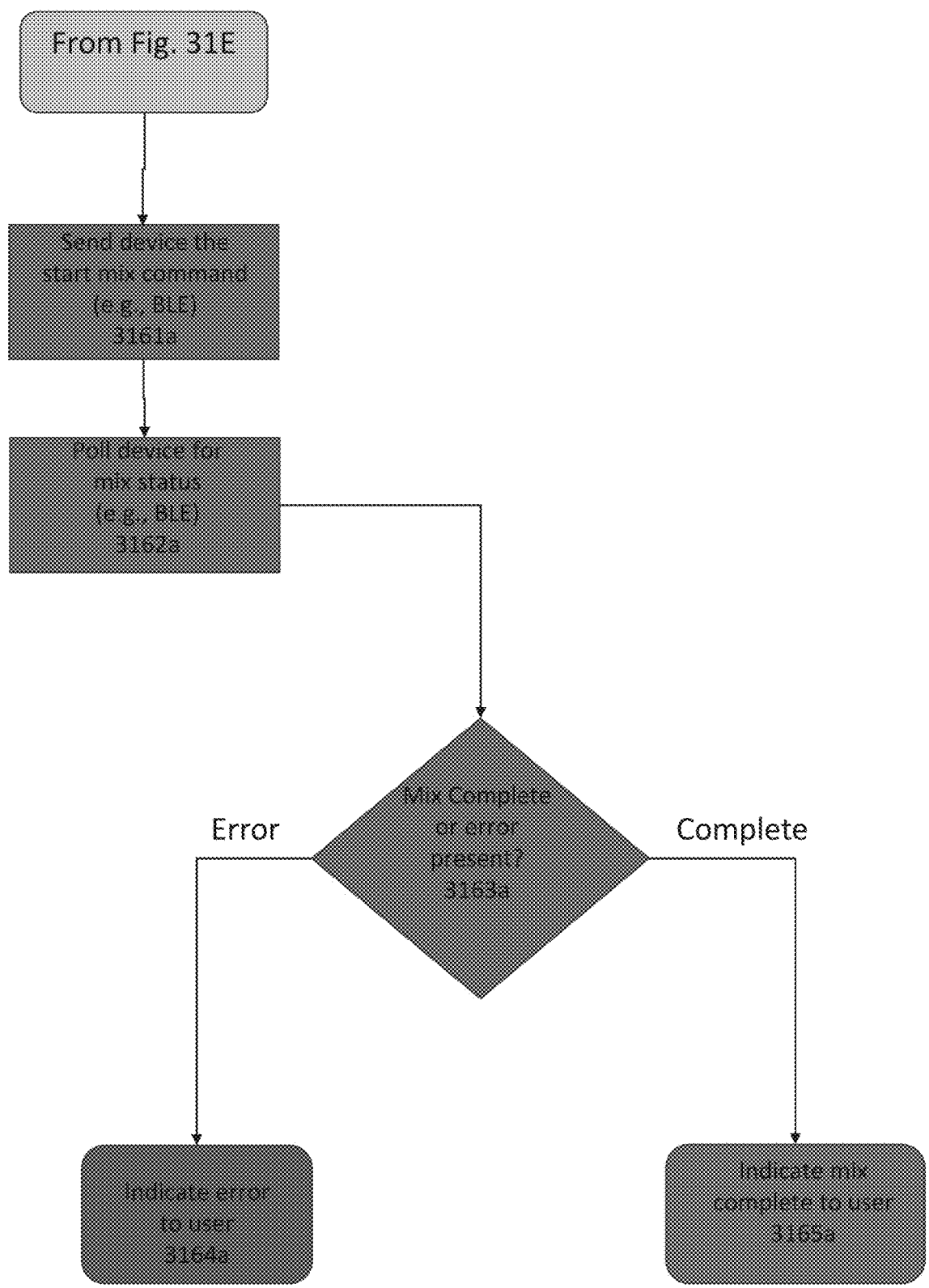

FIG. 31E and FIG. 31F provide a flow chart illustrating example OBD tablet/smart phone application processes, according to some embodiments. As shown, a user can select a blend recipe using an app on their smart phone or tablet 3150a, and if necessary, the app obtains the recipe from the server 3151a, analyzes the recipe for necessary ingredients and volumes/amounts 3152a, queries the OBD to get serial numbers or other identifiers of installed canisters 3153a, and can issue queries to determine fluid amounts of the installed canisters 3154a. In some embodiments, the OBD is configured to track volume levels of individual canisters to assure proper amounts. Additionally, security can be implemented around canisters such that the amount is tracked universally, including authorized refills, and thereby track unauthorized refills or counterfeits and thereby promote consumer/user safety and security (e.g., in such embodiments, only authorized canisters could be utilized in the OBD). If the correct fluids are available/installed 3155a, the mobile app transcodes recipe to indicate which fluids are in which canisters 3157a, and queries OBD to determine which recipes are in onboard memory 3158a. If the recipe is not currently on the OBD 3159a, the app downloads the recipe to the OBD 3160a (e.g., via BLUETOOTH low energy or the like). Then the app sends the OBD a start-mix command 3161a, and polls the OBD for mix status 3162a, and when complete 3163a, notifies the user 3165a. By having a mobile OBD app performing a number of the calculations and analysis for blending, the OBD system can enhance security, reduce OBD processing time, and better address errors or complications (e.g., if a particular ingredient is low or not available/present at the OBD, the mobile app can suggest alternative mixtures, reorder the ingredient, etc.).

As discussed herein, the OBD can be configured to formulate a variety of blends and/or compositions. For example, the OBD can be configured to blend compositions comprising, consisting of, and/or consisting essentially of at least one first purified cannabinoid and at least one of a second purified cannabinoid, a purified terpene, a purified flavonoid, and/or a purified mineral. In some embodiments, the OBD is configured to blend one or more of 7,8-dihydroionone, Acetanisole, Acetic Acid, Acetyl Cedrene, Anethole, Anisole, Benzaldehyde, Bergamotene (α-cis-Bergamotene) (α-trans-Bergamotene), Bisabolol (β-Bisabolol), Borneol, Butanoic/Butyric Acid, Cadinene (α-Cadinene) (γ-Cadinene), Cafestol, Caffeic acid, Camphene, Camphor, Capsaicin, Carene (Δ-3-Carene), Carotene, Carvacrol, Carvone, Dextro-Carvone, Laevo-Carvone, Caryophyllene (β-Caryophyllene), Caryophyllene oxide, Castoreum Absolute, Cedrene (α-Cedrene) (β-Cedrene), Cedrene Epoxide (α-Cedrene Epoxide), Cedrol, Cembrene, Chlorogenic Acid, Cinnamaldehyde (α-amyl-Cinnamaldehyde) (α-hexyl-Cinnamaldehyde), Cinnamic Acid, Cinnamyl Alcohol, Citronellal, Citronellol, Cryptone, Curcumene (α-Curcumene) (γ-Curcumene), Decanal, Dehydrovomifoliol, Diallyl Disulfide, Dihydroactinidiolide, Dimethyl Disulfide, Eicosane/Icosane, Elemene (β-Elemene), Estragole, Ethyl acetate, Ethyl Cinnamate, Ethyl maltol, Eucalyptol/1,8-Cineole, Eudesmol (α-Eudesmol) (μ-Eudesmol) (γ-Eudesmol), Eugenol, Euphol, Farnesene, Farnesol, Fenchol (β-Fenchol), Fenchone, Geraniol, Geranyl acetate, Germacrenes, Germacrene B, Guaia-1(10), 11-diene, Guaiacol, Guaiene (α-Guaiene), Gurjunene (a-Gurjunene), Herniarin, Hexanaldehyde, Hexanoic Acid, Humulene (α-Humulene) (β-Humulene), Ionol (3-oxo-α-ionol) (β-Ionol), Ionone (α-Ionone) (β-Ionone), Ipsdienol, Isoamyl acetate, Isoamyl Alcohol, Isoamyl Formate, Isoborneol, Isomyrcenol, Isopulegol, Isovaleric Acid, Isoprene, Kahweol, Lavandulol, Limonene, β-Linolenic Acid, Linalool, Longifolene, α-Longipinene, Lycopene, Menthol, Methyl butyrate, 3-Mercapto-2-Methylpentanal, Mercaptan/Thiols, β-Mercaptoethanol, Mercaptoacetic Acid, Allyl Mercaptan, Benzyl Mercaptan, Butyl Mercaptan, Ethyl Mercaptan, Methyl Mercaptan, Furfuryl Mercaptan, Ethylene Mercaptan, Propyl Mercaptan, Thenyl Mercaptan, Methyl Salicylate, Methylbutenol, Methyl-2-Methylvalerate, Methyl Thiobutyrate, Myrcene (β-Myrcene), γ-Muurolene, Nepetalactone, Nerol, Nerolidol, Neryl acetate, Nonanaldehyde, Nonanoic Acid, Ocimene, Octanal, Octanoic Acid, P-cymene, Pentyl butyrate, Phellandrene, Phenylacetaldehyde, Phenylethanethiol, Phenylacetic Acid, Phytol, Pinene, β-Pinene, Propanethiol, Pristimerin, Pulegone, Retinol, Rutin, Sabinene, Sabinene Hydrate, cis-Sabinene Hydrate, trans-Sabinene Hydrate, Safranal, α-Selinene, α-Sinensal, β-Sinensal, β-Sitosterol, Squalene, Taxadiene, Terpin hydrate, Terpineol, Terpine-4-ol, α-Terpinene, γ-Terpinene, Terpinolene, Thiophenol, Thujone, Thymol, α-Tocopherol, Tonka Undecanone, Undecanal, Valeraldehyde/Pentanal, Verdoxan, α-Ylangene, Umbelliferone, and/or Vanillin.

In some embodiments, the OBD is configured to blend one or more of Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-C4 (CBD-C4), Cannabidivarinic Acid (CBDVA), Cannabidivarin (CBDV), Cannabidiorcol (CBD-C1), Tetrahydrocannabinolic acid A (THCA-A), Tetrahydrocannabinolic acid B (THCA-B), Tetrahydrocannabinol (THC), Tetrahydrocannabinolic acid C4 (THCA-C4), Tetrahydrocannbinol C4 (THC-C4), Tetrahydrocannabivarinic acid (THCVA), Tetrahydrocannabivarin (THCV), Tetrahydrocannabiorcolic acid (THCA-C1), Tetrahydrocannabiorcol (THC-C1), Delta-7-cis-iso-tetrahydrocannabivarin, Δ8-tetrahydrocannabinolic acid (Δ8-THCA), Δ8-tetrahydrocannabinol (Δ8-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabinolic acid (CBNA), Cannabinol (CBN), Cannabinol methylether (CBNM), Cannabinol-C4 (CBN-C4), Cannabivarin (CBV), Cannabino-C2 (CBN-C2), Cannabiorcol (CBN-C1), Cannabinodiol (CBND), Cannabinodivarin (CBDV), Cannabitriol (CBT), 10-Ethoxy-9-hydroxy-Δ6a-tetrahydrocannabinol, 8,9-Dihydroxy-Δ6a(10a)-tetrahydrocannabinol (8,9-Di-OH-CBT-C5), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-Δ6a(10a)-tetrahydrocannabinol (OTHC), Δ9-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Isocanabinoids, and/or Epigallocatechin gallate.

In some embodiments, the OBD is configured to blend one or more of Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-C4 (CBD-C4), Cannabidivarinic Acid (CBDVA), Cannabidivarin (CBDV), Cannabidiorcol (CBD-C1), Tetrahydrocannabinolic acid A (THCA-A), Tetrahydrocannabinolic acid B (THCA-B), Tetrahydrocannabinol (THC), Tetrahydrocannabinolic acid C4 (THCA-C4), Tetrahydrocannbinol C4 (THC-C4), Tetrahydrocannabivarinic acid (THCVA), Tetrahydrocannabivarin (THCV), Tetrahydrocannabiorcolic acid (THCA-C1), Tetrahydrocannabiorcol (THC-C1), Delta-7-cis-iso-tetrahydrocannabivarin, Δ8-tetrahydrocannabinolic acid (Δ8-THCA), Δ8-tetrahydrocannabinol (Δ8-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabinolic acid (CBNA), Cannabinol (CBN), Cannabinol methylether (CBNM), Cannabinol-C4 (CBN-C4), Cannabivarin (CBV), Cannabino-C2 (CBN-C2), Cannabiorcol (CBN-C1), Cannabinodiol (CBND), Cannabinodivarin (CBDV), Cannabitriol (CBT), 10-Ethoxy-9-hydroxy-Δ6a-tetrahydrocannabinol, 8,9-Dihydroxy-Δ6a(10a)-tetrahydrocannabinol (8,9-Di-OH-CBT-C5), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-Δ6a(10a)-tetrahydrocannabinol (OTHC), Δ9-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Isocanabinoids, Epigallocatechin gallate, Dodeca-2E,4E,8Z,10Z-tetraenoic acid isobutylamide, or Dodeca-2E,4E-dienoic acid isobutylamide; and a second purified cannabinoid chosen from Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-C4 (CBD-C4), Cannabidivarinic Acid (CBDVA), Cannabidivarin (CBDV), Cannabidiorcol (CBD-C1), Tetrahydrocannabinolic acid A (THCA-A), Tetrahydrocannabinolic acid B (THCA-B), Tetrahydrocannabinol (THC), Tetrahydrocannabinolic acid C4 (THCA-C4), Tetrahydrocannbinol C4 (THC-C4), Tetrahydrocannabivarinic acid (THCVA), Tetrahydrocannabivarin (THCV), Tetrahydrocannabiorcolic acid (THCA-C1), Tetrahydrocannabiorcol (THC-C1), Delta-7-cis-iso-tetrahydrocannabivarin, Δ8-tetrahydrocannabinolic acid (Δ8-THCA), Δ8-tetrahydrocannabinol (Δ8-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabinolic acid (CBNA), Cannabinol (CBN), Cannabinol methylether (CBNM), Cannabinol-C4 (CBN-C4), Cannabivarin (CBV), Cannabino-C2 (CBN-C2), Cannabiorcol (CBN-C1), Cannabinodiol (CBND), Cannabinodivarin (CBDV), Cannabitriol (CBT), 10-Ethoxy-9-hydroxy-Δ6a-tetrahydrocannabinol, 8,9-Dihydroxy-Δ6a(10a)-tetrahydrocannabinol (8,9-Di-OH-CBT-C5), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-Δ6a(10a)-tetrahydrocannabinol (OTHC), Δ9-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Isocanabinoids, Epigallocatechin gallate, Dodeca-2E,4E,8Z, 10Z-tetraenoic acid isobutylamide, and/or Dodeca-2E,4E-dienoic acid isobutylamide.

In some embodiments, the OBD is configured to blend one or more of phenolic acids, stilbenoids, dihydroflavonols, anthocyanins, anthocyanidins, polyphenols, tannins, flavones, flavan-3-ols, Flavan-4-ol, Flavan-3,4-diol flavonols, stilbenoids, phytochemicals, antioxidants, homoisoflavonoids, phenylpropanoids, Phloroglucinols coumarins, Phenolic acids, Naphthodianthrones, Steroid glycosides, bioflavonoids, isoflavonoids, and neoflavonoids. In some embodiments, the OBD is configured to blend one or more of Adenosine, Adhyperforin, amentoflavone, Anandamide, Apigenin, Cannaflavin B, Catechin (C), Catechin 3-gallate (Cg), Chlorogenic acid, cichoric acid, caftaric acid, Daidzein, Delphinidin, Eleutherosides, Epicatechin 3-gallate (ECg), Epicatechins, Epicatechin, epigallocatechin, myricetin, Oxalic acid, Pelargonidin, Tannin, Theaflavin-3-gallate, Theanine, Theobromine, Theophylline, Tryptophan, Tyramine, Xanthine, Caffeine, Cannaflavin A, Cannaflavin B, Catechin (C), Catechin 3-gallate (Cg), Epicatechin 3-gallate (ECg), Epicatechins (Epicatechin (EC)), epigallocatechin, Epigallocatechin (EGC), Epigallocatechin 3-gallate (EGCg), Gallocatechin (GC), Gallocatechin 3-gallate (GCg)), Gamma amino butyric acid, Genistein, Ginkgo biloba, Ginsenosides, Quercetin, Quercitrin, and/or Rutin. In some embodiments, the OBD can be configured to blend a variety of compounds, such as those discussed in U.S. Pat. App. Pub. No. 2016/0250270, the entirety of which is herein expressly incorporated by reference for all purposes. In some embodiments, the OBD is configured to blend one or more of Caffeine, Cannaflavin A, Cannaflavin B, Catechin (C), Catechin 3-gallate (Cg), Epicatechin 3-gallate (ECg), Epicatechins (Epicatechin (EC)), epigallocatechin, Epigallocatechin (EGC), Epigallocatechin 3-gallate (EGCg), Gallocatechin (GC), Gallocatechin 3-gallate (GCg)), Gamma amino butyric acid, Genistein, Ginkgo biloba, Ginsenosides, Quercetin, Quercitrin, and/or Rutin.

All combinations of the foregoing concepts and additional concepts discussed in greater detail below (provided such concepts are not mutually inconsistent) are contemplated as being part of the inventive subject matter disclosed herein. The terminology explicitly employed herein that also may appear in any disclosure incorporated by reference should be accorded a meaning most consistent with the particular concepts disclosed herein.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

In order to address various issues and advance the art, the entirety of this application (including the Cover Page, Title, Headings, Background, Summary, Brief Description of the Drawings, Detailed Description, Claims, Abstract, Figures, Appendices, and otherwise) shows, by way of illustration, various embodiments in which the claimed innovations may be practiced. The advantages and features of the application are of a representative sample of embodiments only, and are not exhaustive and/or exclusive. They are presented to assist in understanding and teach the claimed principles.

It should be understood that they are not representative of all claimed innovations. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

Various inventive concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently claimed. Applicant reserves all rights in those unclaimed innovations including the right to claim such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the claims or limitations on equivalents to the claims. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A processor-implemented method, comprising:
  receiving, at an at least one processor of a microfluidic mixer device, an instruction to initiate a blend event at the microfluidic mixer device at least in part in response to user input information from a blend software application;
  initiating the blend event at the microfluidic mixer device in response to receiving the instruction, the microfluidic mixer device including:
    a microfluidic mixer device housing;
    a plurality of microfluidic pumps disposed within the microfluidic mixer device housing;
    a plurality of valves disposed within the microfluidic mixer device housing;
    a dispenser at least partially extending through the microfluidic mixer device housing;
    a removable microfluidic mixer chip disposed within the microfluidic mixer device housing and configured with a plurality of fluid channels, the microfluidic mixer chip configured to receive and meter microfluidic amounts of each of at least a first fluid, a second fluid, and an at least one third fluid, each fluid having a viscosity different from a viscosity of each of the other fluids; and
    a mix controller disposed within the microfluidic mixer device housing and configured to electronically communicate with the blend software application;
  controlling the microfluidic mixer device to make a microfluidic blend via at least one of the microfluidic pumps and at least one of the valves, and in response to the received instruction, the microfluidic mixer device including a plurality of fluid pathways defined therein and contained within the microfluidic mixer device housing, the fluid pathways including a first fluid pathway providing fluid communication from a first fluid canister containing the first fluid to the microfluidic mixer chip, a second fluid pathway providing fluid communication from a second fluid canister containing the second fluid to the microfluidic mixer chip, a third fluid pathway providing fluid communication from a third fluid canister containing the at least one third fluid to the microfluidic mixer chip, and a fourth fluid pathway providing fluid communication from the microfluidic mixer chip to the dispenser, the dispenser configured to receive metered microfluidic amounts of each of the first fluid, second fluid, and at least one third fluid from the microfluidic mixer chip for dispensing, the controlling the microfluidic mixer device including heating the first fluid pathway based on the viscosity of the first fluid; and
  dispensing the microfluidic blend from the dispenser.

2. The method of claim 1, wherein the mix controller communicates with the blend software application and receives the instruction associated with the blend recipe.

3. The method of claim 1, wherein the microfluidic mixer device further includes a microfluidic mixer chip heater, disposed within the microfluidic mixer device housing and configured to heat the removable microfluidic mixer chip, the method further comprising:
  controlling the microfluidic mixer chip heater such that the mix temperature is between 100 degrees F. and 300 degrees F.

4. The method of claim 1, wherein the microfluidic mixer device further includes a microfluidic mixer chip heater disposed within the microfluidic mixer device housing, the method further comprising: changing the viscosity of at least one of the fluids by controlling the microfluidic mixer chip heater according to the blend recipe and feedback from at least one temperature sensor.

5. The method of claim 1, wherein the microfluidic mixer device further includes a canister heater block disposed within the device housing and configured to replaceably receive fluid canisters and heat received fluid canisters, the method further comprising:
  decreasing the viscosity of at least one of the fluids by heating at least one fluid canister via the canister heater block according to the blend recipe and feedback from at least one sensor.

6. The method of claim 1, further comprising: controlling each of the plurality of microfluidic pumps and controlling each of the plurality of valves according to the blend recipe and at least one pressure sensor.

7. The method of claim 1, further comprising: controlling each of the plurality of microfluidic pumps and each of the plurality of valves according to the blend recipe and feedback from at least one pressure sensor to provide a system pressure within the microfluidic mixer device, the system pressure being from about 0.1 PSI to about 10 PSI.

8. A processor-implemented method, comprising:
receiving, at an at least one processor of a microfluidic mixer device, an instruction to initiate a blend event at the microfluidic mixer device;
initiating the blend event at the microfluidic mixer device in response to receiving the instruction, the microfluidic mixer device including:
  a microfluidic mixer device housing;
  at least one microfluidic pump disposed within the microfluidic mixer device housing;
  a heater disposed within the microfluidic mixer device housing;
  one or more valves disposed within the microfluidic mixer device housing;
  a dispenser at least partially extending through the microfluidic mixer device housing; and
  a mixer manifold disposed within the microfluidic mixer device housing, the mixer manifold including a plurality of microfluidic channels therein and configured to receive and accurately microfluidically meter fluids;
  a plurality of fluid pathways defined within the microfluidic mixer device, the plurality of fluid pathways including: a first fluid pathway providing fluid communication from a first fluid reservoir containing a first fluid to the mixer manifold, a second fluid pathway providing fluid communication from a second fluid reservoir containing a second fluid to the mixer manifold, and a third fluid pathway providing fluid communication from a microfluidic mixer chip to the dispenser, the first fluid having a dependence of viscosity on temperature different from a dependence of viscosity on temperature of the second fluid; and
microfluidically metering each of at least the first fluid and the second fluid by controlling, via the at least one processor and in response to the received instruction and feedback from at least one sensor: the at least one microfluidic pump, the heater, and the one or more valves to provide a microfluidic blend comprising the first fluid and the second fluid, the controlling the heater including heating the first fluid pathway based on the dependence of viscosity on temperature of the first fluid; and
dispensing the microfluidic blend from the dispenser.

9. The method of claim 8, wherein the error tolerance is less than +/−10%.

10. The method of claim 8, wherein the first fluid comprises a cannabinoid.

11. The method of claim 8, wherein the second fluid comprises a terpene.

12. The method of claim 1, wherein a flow resistance of the first fluid pathway is different from a flow resistance of the second fluid pathway.

13. The method of claim 8, wherein the first fluid is wax-like at room temperature.

14. The method of claim 1, further comprising reading information from EEPROM to retrieve information about the contents of at least one of the first fluid canister, the second fluid canister, or the third fluid canister.

* * * * *